(12) United States Patent
Ukrainsky et al.

(10) Patent No.: US 11,317,804 B2
(45) Date of Patent: May 3, 2022

(54) MULTIPURPOSE DIAGNOSTIC EXAMINATION APPARATUS AND SYSTEM

(71) Applicant: Comprehensive Telemedicine, NY, NY (US)

(72) Inventors: Gennady Ukrainsky, NY, NY (US); Boris Sagalovich, NY, NY (US); Danny Kopit, Brooklyn, NY (US)

(73) Assignee: COMPREHENSIVE TELEMEDICINE, New York, NY (US)

( * ) Notice: Subject to any disclaimer, the term of this patent is extended or adjusted under 35 U.S.C. 154(b) by 142 days.

(21) Appl. No.: 16/043,179

(22) Filed: Jul. 24, 2018

(65) Prior Publication Data
US 2018/0344160 A1 Dec. 6, 2018

Related U.S. Application Data

(62) Division of application No. 14/716,892, filed on May 20, 2015, now Pat. No. 10,058,247.

(51) Int. Cl.
*A61B 5/00* (2006.01)
*A61B 7/04* (2006.01)
(Continued)

(52) U.S. Cl.
CPC ........ *A61B 5/0022* (2013.01); *A61B 1/00006* (2013.01); *A61B 1/00009* (2013.01); *A61B 1/00066* (2013.01); *A61B 1/045* (2013.01); *A61B 1/051* (2013.01); *A61B 1/053* (2013.01); *A61B 1/0676* (2013.01);
(Continued)

(58) Field of Classification Search
CPC ......... A61B 13/00; A61B 8/00; A61B 8/4477; A61B 8/54; A61B 5/0022; A61B 5/0013; A61B 5/0035; A61B 5/0077; A61B 5/0082; A61B 5/441; A61B 5/7282;
(Continued)

(56) References Cited

U.S. PATENT DOCUMENTS 6,106,457 A    8/2000   Perkins et al.
6,790,178 B1 *   9/2004   Mault ................ A61B 5/02055
                                                                             600/300
(Continued)

*Primary Examiner* — Lynsey C Eiseman
*Assistant Examiner* — Amanda L Steinberg
(74) *Attorney, Agent, or Firm* — Ashok Tankha

(57) ABSTRACT

A multipurpose diagnostic examination apparatus includes a diagnosis control unit (DCU), an attachment unit, and an image capture device (ICD). The attachment unit is detachably connected to and extends from a front end of the DCU. A microcontroller of the DCU receives and processes actuation signals from trigger elements of the DCU to indicate actions to be performed by the ICD removably connected to a camera module of the DCU, and/or by a medical diagnostic device (MDD) connected to the DCU via the attachment unit. The microcontroller facilitates transmission of diagnostic image data captured by the ICD and processed by the camera module, and diagnostic examination data from the MDD, to a medical diagnostic examination system (MDES) accessible on a local user device via a connector interface of the DCU. The MDES, in communication with a remote user device over a communication network, facilitates remote viewing, selection, and diagnostic examinations.

19 Claims, 88 Drawing Sheets

(51) Int. Cl.
- A61B 8/00 (2006.01)
- A61B 13/00 (2006.01)
- A61B 1/227 (2006.01)
- A61B 3/12 (2006.01)
- A61B 3/14 (2006.01)
- A61B 90/30 (2016.01)
- A61B 34/00 (2016.01)
- A61B 90/00 (2016.01)
- A61B 1/00 (2006.01)
- A61B 1/06 (2006.01)
- A61B 1/07 (2006.01)
- A61B 1/05 (2006.01)
- A61B 1/045 (2006.01)
- G16H 40/67 (2018.01)
- G16H 30/40 (2018.01)
- G16H 40/63 (2018.01)

(52) U.S. Cl.
CPC .............. *A61B 1/0684* (2013.01); *A61B 1/07* (2013.01); *A61B 1/227* (2013.01); *A61B 3/12* (2013.01); *A61B 3/14* (2013.01); *A61B 5/0013* (2013.01); *A61B 5/0035* (2013.01); *A61B 5/0077* (2013.01); *A61B 5/441* (2013.01); *A61B 7/04* (2013.01); *A61B 8/00* (2013.01); *A61B 8/4477* (2013.01); *A61B 8/54* (2013.01); *A61B 13/00* (2013.01); *A61B 34/25* (2016.02); *A61B 90/30* (2016.02); *A61B 90/37* (2016.02); *G16H 30/40* (2018.01); *G16H 40/63* (2018.01); *G16H 40/67* (2018.01); *A61B 5/68* (2013.01); *A61B 5/682* (2013.01); *A61B 5/6817* (2013.01); *A61B 5/6823* (2013.01); *A61B 5/7435* (2013.01); *A61B 2560/045* (2013.01); *A61B 2560/0443* (2013.01); *A61B 2562/0233* (2013.01); *A61B 2562/227* (2013.01); *A61B 2576/00* (2013.01)

(58) Field of Classification Search
CPC ........... A61B 5/7285; A61B 3/12; A61B 3/14; A61B 7/04; A61B 1/227
See application file for complete search history.

(56) References Cited

U.S. PATENT DOCUMENTS

| | | | |
|---|---|---|---|
| 10,130,244 B2* | 11/2018 | Patel | G03B 17/48 |
| 10,524,675 B2* | 1/2020 | Ellis | A61B 5/02438 |
| 2004/0073455 A1* | 4/2004 | McConnochie | G06Q 50/22 705/2 |
| 2009/0248924 A1* | 10/2009 | Melin | H04L 12/66 710/63 |
| 2009/0312638 A1 | 12/2009 | Bartlett | |
| 2013/0345625 A1* | 12/2013 | Causey, III | A61B 5/7475 604/66 |
| 2015/0087926 A1* | 3/2015 | Raz | G16H 40/67 600/301 |
| 2015/0199783 A1* | 7/2015 | Cashman | E04H 1/1222 705/2 |
| 2018/0000336 A1* | 1/2018 | Gilad-Gilor | A61B 1/0011 |

* cited by examiner

MULTIPURPOSE DIAGNOSTIC EXAMINATION APPARATUS AND SYSTEM

CROSS REFERENCE TO RELATED APPLICATIONS

This application is a divisional application of non-provisional patent application Ser. No. 14/716,892, titled "Multipurpose Diagnostic Examination Apparatus And System", filed May 20, 2015 in the United States Patent and Trademark Office. The specification of the above referenced patent application is incorporated herein by reference in its entirety.

BACKGROUND

Telemedicine is designed to provide medical diagnosis and treatment to patients remotely. Telemedicine also provides patients with access to healthcare in restricted areas and difficult to access areas, and to rural communities. Telemedicine also reduces cost and resource consumption for providing healthcare. In telemedicine applications, medical information is collected from medical devices and transferred through a media communication network to a remote location for the purpose of remote consultations, medical examinations, medical procedures, etc. Situations where a medical examination of a distant patient is required comprise, for example, when healthcare facility access to a patient is restricted due to multiple reasons such as remote location, military environment, home patients, etc., emergency situations where time restriction calls for immediate diagnostic examination of the patient, situations when a patient cannot be frequently mobilized to a hospital and requires regular checkups, etc. It is difficult to carry and move bulky or heavy diagnostic equipment to remote locations or into emergency situation environments. Anatomical examination in these situations is therefore difficult unless the patient is rushed to the nearest hospital with the required facilities and equipment.

Major concerns while performing virtual diagnostic examination are safety, efficiency, and cost effectiveness. For example, conventional virtual diagnostic systems typically need to be compliant with the Health Insurance Portability and Accountability act (HIPAA) standards. Efficiency and cost effectiveness, however, are not as clearly defined and depend significantly on a diagnostician's requirements. For a medical device such as a stethoscope or a dermatoscope, the effectiveness of the medical device depends not only on the efficiency of the medical device in recording diagnostic data, but also on the ability of the medical device to provide useful information in a timely, usable, and appropriate manner. Medical devices with a poor user interface or inadequate controls are unlikely to be used for telemedicine applications when the information requirements are time critical. Moreover, conventional medical devices that are used in telemedicine applications communicate data using universal serial bus (USB) 2.0 communication standards that use substantially low speed data communication, for example, at a speed of about 480 megabits per second (Mbit/s). Even a telemedicine device compatible with a high quality image processing technology or a video digital signal processing technology is not sufficient for processing high quality image data using USB 2.0 communication standards. Conventional telemedicine devices typically use outdated technology that is now superseded by updated technology that allows faster data transmission. Conventional telemedicine devices are not equipped with the updated technology that allows clarity and significantly fast communication of diagnostic data collected using the telemedicine devices.

Conventional telemedicine techniques also lack interactivity between patients and healthcare providers. Moreover, in conventional diagnostic examination procedures, observations are subjectively recorded from an examining doctor's perspective. The examining doctor records the observations and stores the recorded observations digitally or in a written form. However, if the doctor's observations are incorrect, the patient has to undergo examination again by another physician. A doctor typically creates transcripts for a large number of patient records in a day that can wear out the doctor. In such situations, the doctor may end up recording incorrect observation data. In such cases patient records are not reliable. Hence, there is a need for a computer implemented system that records and stores diagnostic data in real time, for example, in an audio file format, a video file format, an image file format, etc., instead of relying on subjective observations of one doctor, thereby allowing another doctor to perform accurate medical evaluations and examinations using the recorded diagnostic data.

Hence, there is a long felt but unresolved need for a multipurpose diagnostic examination apparatus that facilitates medical imaging and remote diagnostic examination of a patient in real time via a communication network, while ensuring clarity of diagnostic data recorded by medical diagnostic devices, and providing diagnostic data in a timely, usable, and appropriate format for accurate remote medical diagnosis. Moreover, there is a need for a method and system that facilitates medical imaging and remote diagnostic examinations using the multipurpose diagnostic examination apparatus implemented with an updated data communication standard, thereby ensuring safety, efficiency, and cost effectiveness of medical diagnostic examinations.

SUMMARY OF THE INVENTION

This summary is provided to introduce a selection of concepts in a simplified form that are further disclosed in the detailed description of the invention. This summary is not intended to identify key or essential inventive concepts of the claimed subject matter, nor is it intended for determining the scope of the claimed subject matter.

The multipurpose diagnostic examination apparatus disclosed herein addresses the above stated needs for facilitating medical imaging and remote diagnostic examination of a patient in real time via a communication network, while ensuring clarity of diagnostic data recorded by medical diagnostic devices, and providing diagnostic data in a timely, usable, and appropriate format for accurate remote medical diagnosis. The method and system disclosed herein address the above stated needs for facilitating medical imaging and remote diagnostic examinations using the multipurpose diagnostic examination apparatus implemented with an updated data communication standard, thereby ensuring safety, efficiency, and cost effectiveness of medical diagnostic examinations.

The multipurpose diagnostic examination apparatus disclosed herein communicates with a medical diagnostic examination system accessible on a local user device via a connector interface of a diagnosis control unit of the multipurpose diagnostic examination apparatus. The multipurpose diagnostic examination apparatus comprises the diagnosis control unit, an attachment unit, and an image capture device. The diagnosis control unit comprises a microcontroller. The microcontroller detects an operable connection of the image capture device and/or a medical diagnostic device, for example, a stethoscope device, a dermatoscope device, an otoscope device, etc., to the diagnosis control unit via the attachment unit. The microcontroller receives actuation signals from one or more of multiple trigger elements positioned on a predefined section of the diagnosis control unit. The microcontroller processes the received actuation signals to generate action control signals. The action control signals indicate one or more actions to be performed by the image capture device and/or multiple medical diagnostic devices interchangeably connected to the diagnosis control unit via the attachment unit.

The attachment unit is detachably connected to and extends from a connector slot configured at a front end of the diagnosis control unit. The attachment unit comprises a receptacle for accommodating the image capture device and operably connects a medical diagnostic device to the diagnosis control unit. The image capture device removably connects to a camera module positioned at a front section of the diagnosis control unit. The image capture device is supported within the receptacle of the attachment unit. The image capture device captures diagnostic image data during medical imaging and diagnostic examinations. The camera module processes the captured diagnostic image data. The microcontroller of the diagnosis control unit facilitates transmission of the processed diagnostic image data from the camera module and diagnostic examination data of multiple formats from the medical diagnostic device to the medical diagnostic examination system accessible on the local user device via the connector interface configured at a rear section of the diagnosis control unit. The connector interface is in communication with the camera module and the operably connected medical diagnostic device via the attachment unit to receive and transmit the processed diagnostic image data and the diagnostic examination data to the medical diagnostic examination system. In an embodiment, the connector interface is in communication with the operably connected medical diagnostic device via the connector slot configured at the front end of the diagnosis control unit to receive and transmit the diagnostic examination data to the medical diagnostic examination system. The medical diagnostic examination system on the local user device is in communication with a remote user device over a communication network to facilitate remote viewing, remote selection, and remote diagnostic examinations of multiple anatomical examination areas via the communication network.

In one or more embodiments, related systems include but are not limited to circuitry and/or programming for effecting the methods disclosed herein; the circuitry and/or programming can be any combination of hardware, software, and/or firmware configured to effect the methods disclosed herein depending upon the design choices of a system designer. Also, various structural elements may be employed depending on the design choices of the system designer.

BRIEF DESCRIPTION OF THE DRAWINGS

The foregoing summary, as well as the following detailed description of the invention, is better understood when read in conjunction with the appended drawings. For the purpose of illustrating the invention, exemplary constructions of the invention are shown in the drawings. However, the invention is not limited to the specific methods, structures, and components disclosed herein. The description of a method step or a structure or a component referenced by a numeral in a drawing is applicable to the description of that method step or structure or component shown by that same numeral in any subsequent drawing herein.

DETAILED DESCRIPTION OF THE INVENTION

Figure 1A:
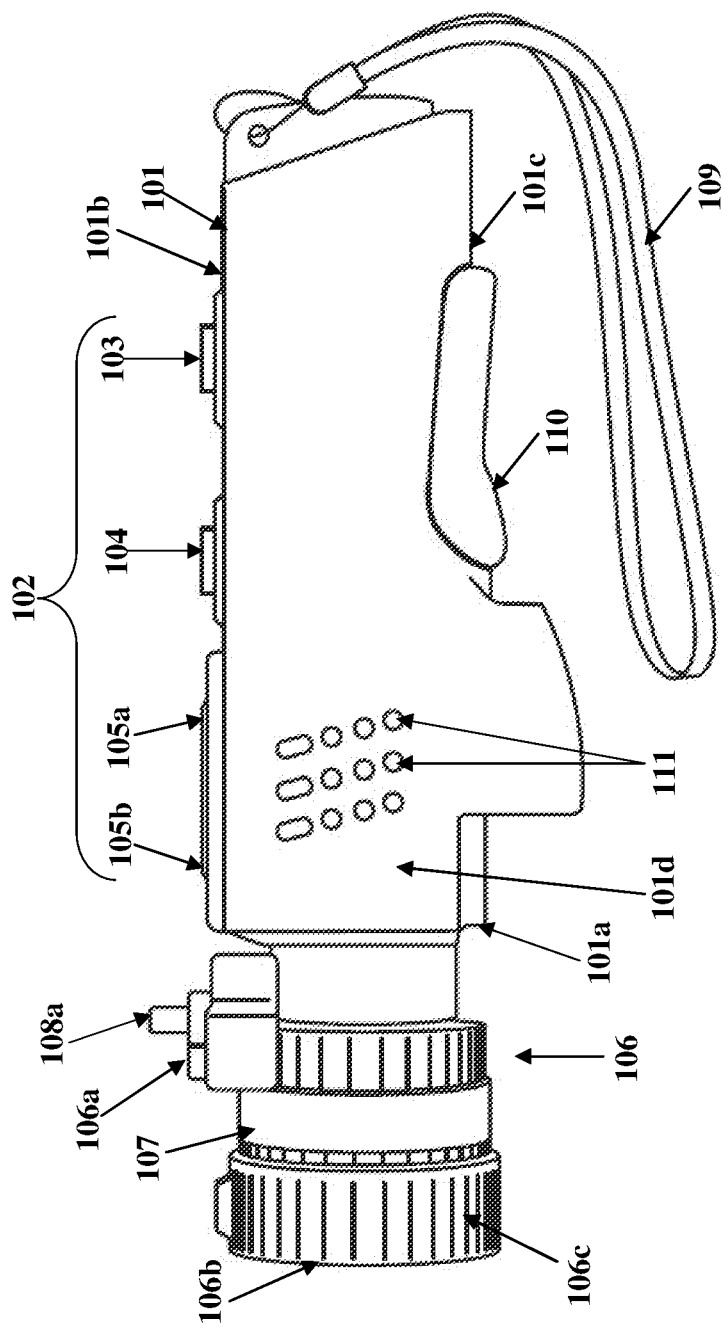
FIG. 1A exemplarily illustrates a right side elevation view showing an image capture device removably connected to a front section of a diagnosis control unit of a multipurpose diagnostic examination apparatus.
Figure 3:
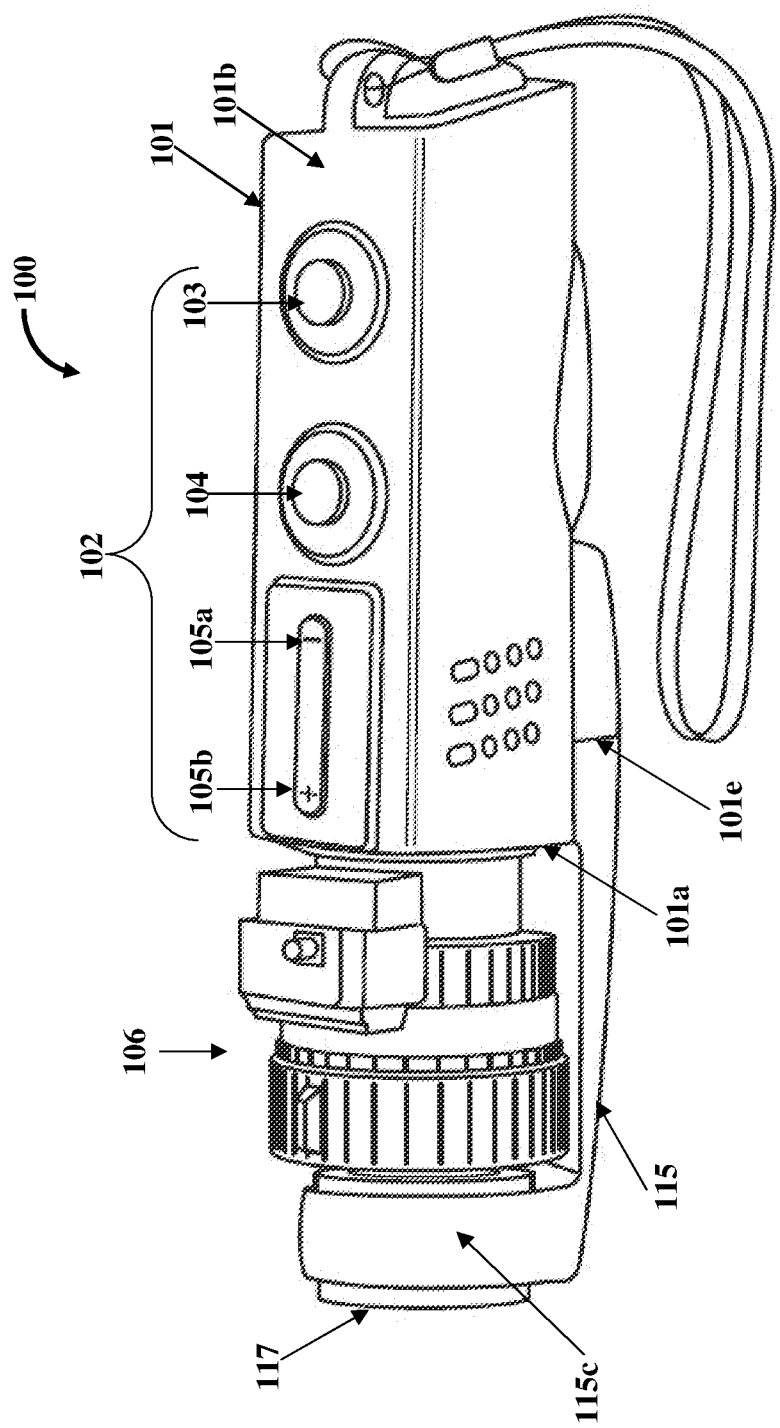
FIG. 3 exemplarily illustrates a top perspective view of the multipurpose diagnostic examination apparatus, showing the image capture device removably connected to the front section of the diagnosis control unit, and the attachment unit detachably connected to and extending from a front end of the diagnosis control unit.

FIG. 1A exemplarily illustrates a right side elevation view showing an image capture device 106 removably connected to a front section 101*a* of a diagnosis control unit 101 of a multipurpose diagnostic examination apparatus 100 exemplarily illustrated in FIG. 3. The image capture device 106 comprises a universal serial bus (USB) 3.0 high definition (HD) camera. The image capture device 106 comprises an optical lens 107 in operable communication with a camera module 124 exemplarily illustrated in FIG. 5F. The optical lens 107 has multiple adjustable features comprising, for example, focus, zoom, and aperture. In an embodiment, a rubber cup 106*c* positioned on a front surface 106*b* of the image capture device 106 for protecting the optical lens 107. The rubber cup 106*c* together with the optical lens 107, when moved or rotated, adjusts the zoom of the optical lens 107. In another embodiment, a disposable cap (not shown) is removably attached to the front surface 106*b* of the image capture device 106 for protecting the optical lens 107 of the image capture device 106, for example, when the multipurpose diagnostic examination apparatus 100 is used for a throat diagnostic examination. In an embodiment, the disposable cap is a disposable clear cap compliant with Food and Drug Administration (FDA) standards. In an embodiment, a small handle 108*a* is positioned on an upper section 106*a* of the image capture device 106. The handle 108*a* allows a user, for example, a medical assistant to open and close the aperture of the image capture device 106. In an embodiment, the multipurpose diagnostic examination apparatus 100 comprises a hand holder wristband 109 for allowing a user to conveniently hold the multipurpose diagnostic examination apparatus 100 by the diagnosis control unit 101 in hand. In an embodiment as exemplarily illustrated in FIGS. 1A-1B, the diagnosis control unit 101 comprises heat dissipation cutouts 111 positioned on side surfaces 101*d* of the diagnosis control unit 101 to allow heat generated during the operation of the multipurpose diagnostic examination apparatus 100 to be dissipated. In an embodiment, a support element 110 is positioned on a lower surface 101*c* of the diagnosis control unit 101.

Figure 5A:
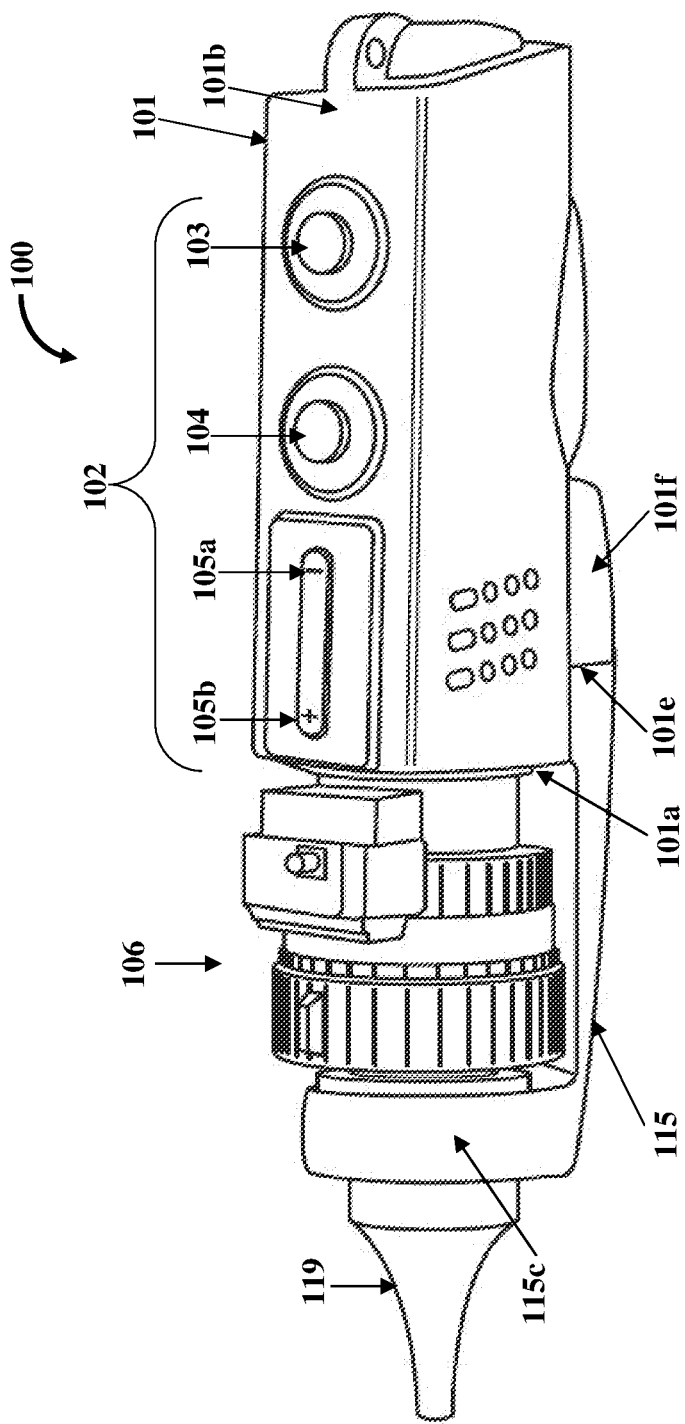
FIG. 5A exemplarily illustrates a top perspective view of the multipurpose diagnostic examination apparatus, showing the image capture device removably connected to the front section of the diagnosis control unit, and the otoscope device operably connected to the front section of the attachment unit.
Figure 5B:
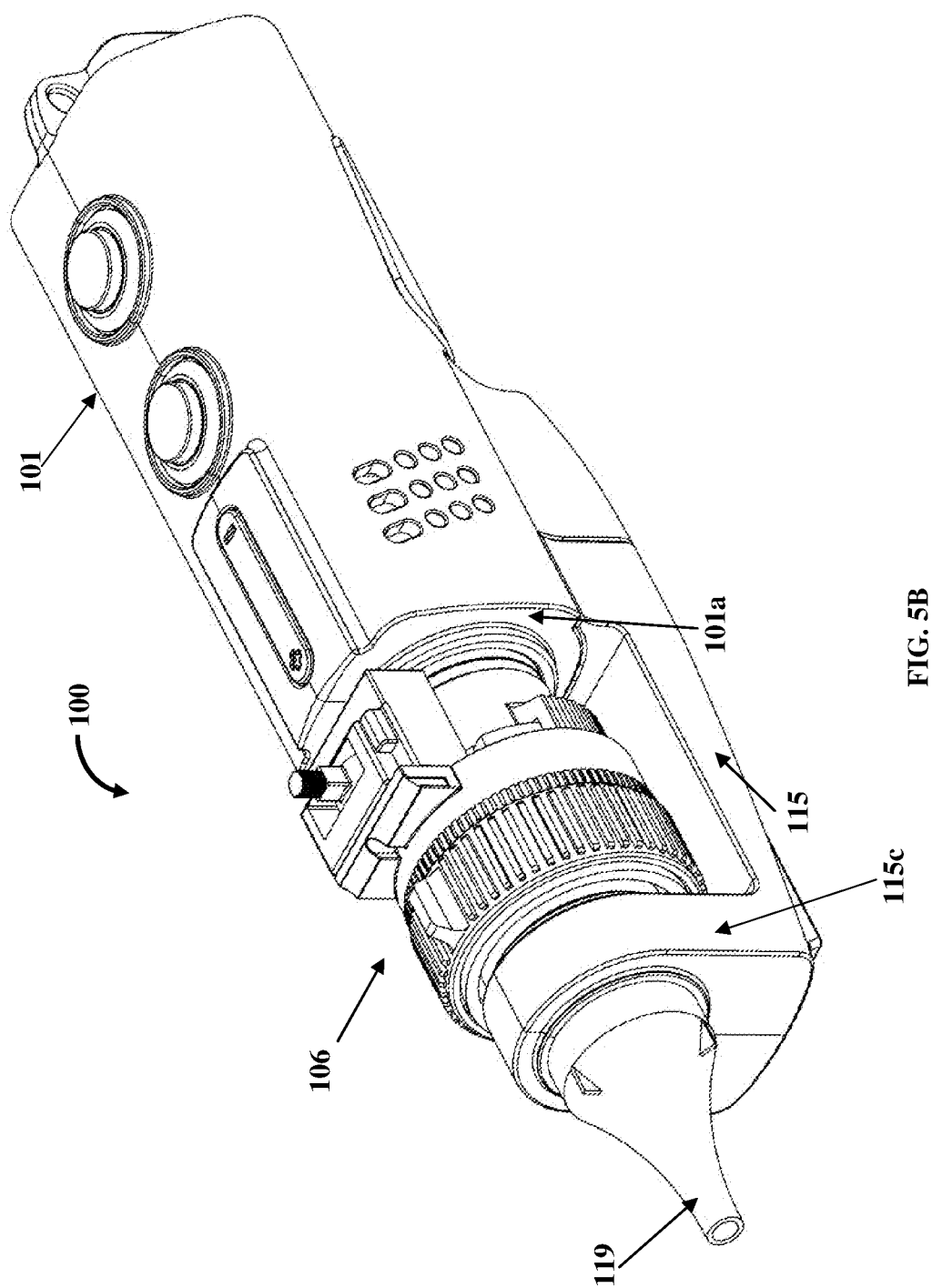
FIG. 5B exemplarily illustrates a right side perspective view of the multipurpose diagnostic examination apparatus, showing the image capture device removably connected to the front section of the diagnosis control unit, and the otoscope device operably connected to the front section of the attachment unit.
Figure 5C:
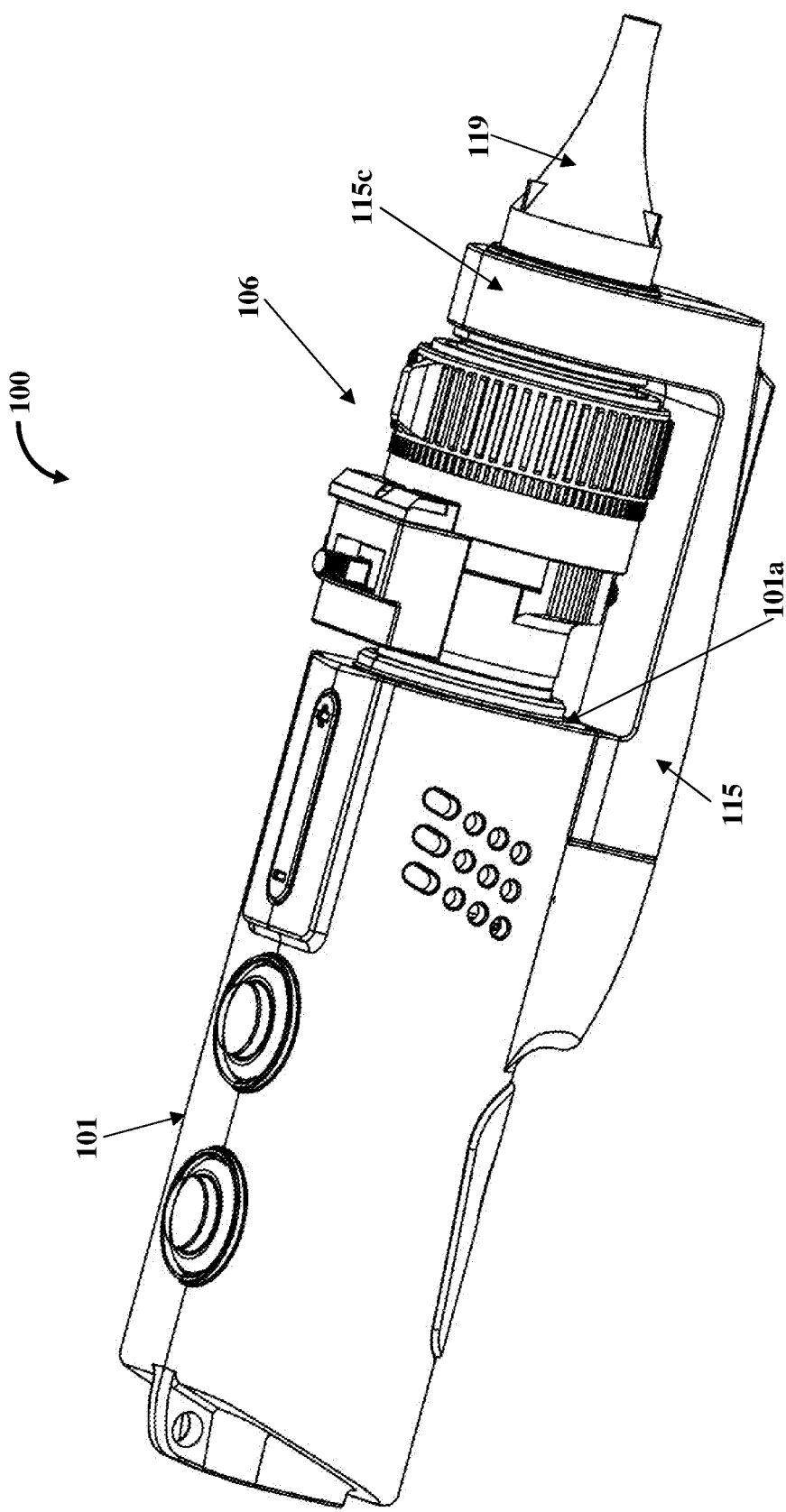
FIG. 5C exemplarily illustrates a left side perspective view of the multipurpose diagnostic examination apparatus, showing the image capture device removably connected to the front section of the diagnosis control unit, and the otoscope device operably connected to the front section of the attachment unit.
Figure 5D:
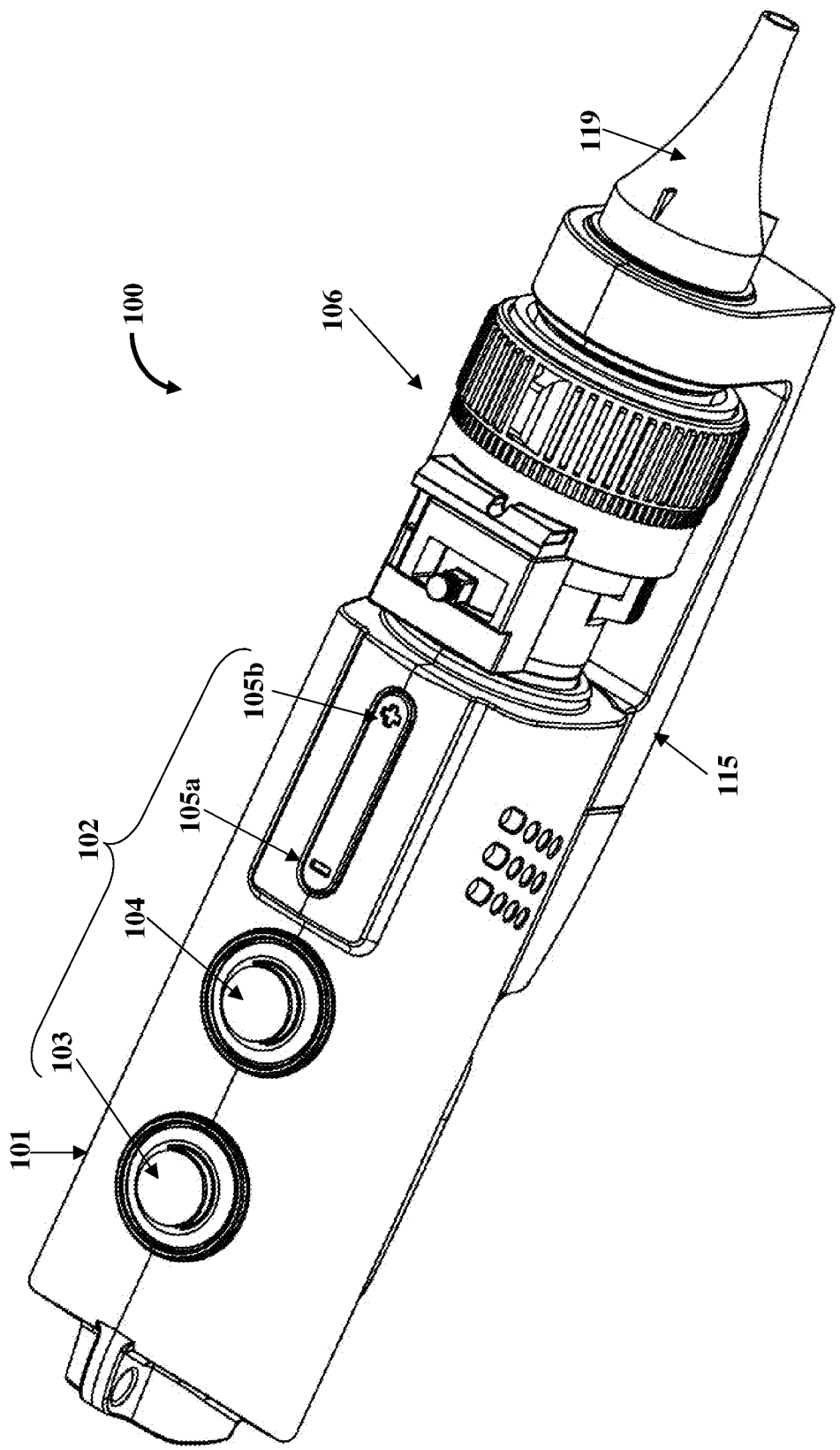
FIG. 5D exemplarily illustrates a top perspective view of the multipurpose diagnostic examination apparatus, showing the image capture device, the otoscope device connected to the attachment unit, and trigger elements.
Figure 5E:
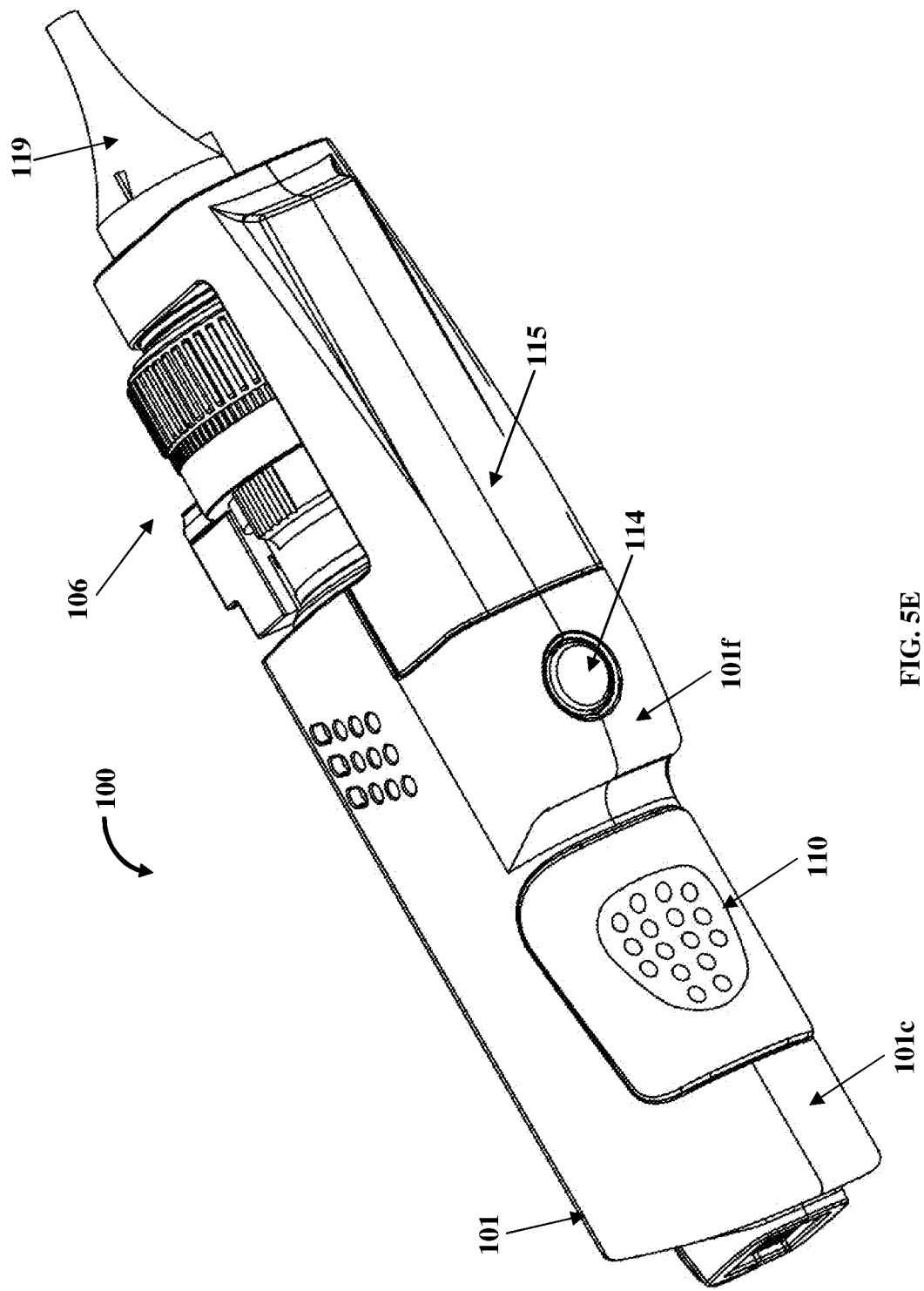
FIG. 5E exemplarily illustrates a bottom perspective view of the multipurpose diagnostic examination apparatus, showing the image capture device, the attachment unit, the otoscope device, a support element, and a release button.
Figure 5F:
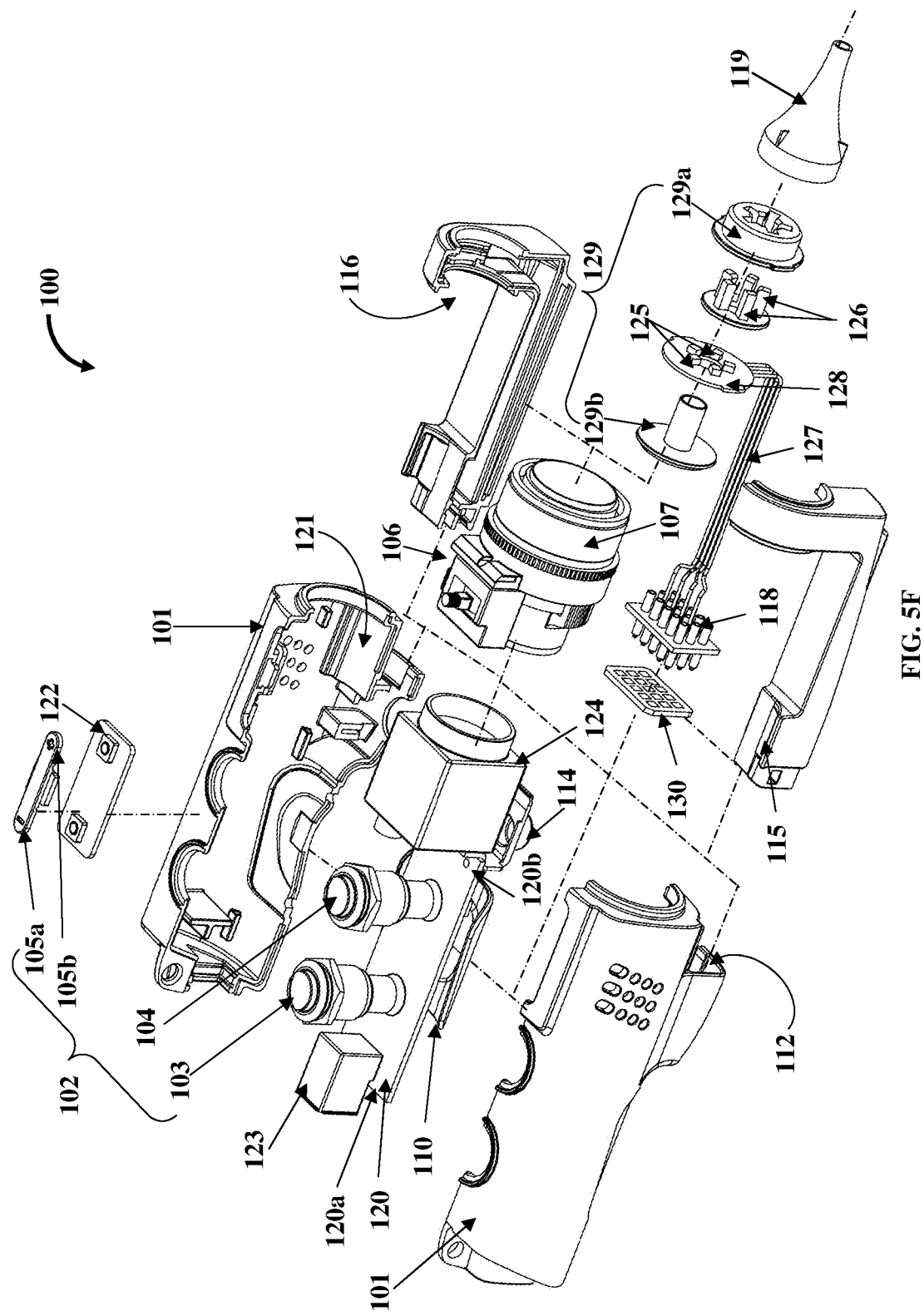
FIG. 5F exemplarily illustrates an exploded view of the multipurpose diagnostic examination apparatus comprising the diagnosis control unit, the attachment unit, the image capture device, and the otoscope device.

In an embodiment, the camera module 124 exemplarily illustrated in FIG. 5F, is, for example, a universal serial bus (USB) 3.0 compatible camera module comprising a complementary metal-oxide-semiconductor (CMOS) or a charge coupled device (CCD) image sensor, and a digital media processor for creating and producing high definition (HD) image data and/or HD video data with resolution, for example, 2080×1552 pixels at 60 frames per second (fps). The camera module 124 is manufactured, for example, by Point Grey Research, Inc. The image capture device 106 further comprises an integrated hardware platform. The integrated hardware platform facilitates multifunctional usage of the image capture device 106 for medical industry applications and telemedicine applications. The image capture device 106 of the multipurpose diagnostic examination apparatus 100 disclosed herein can be used for medical imaging during diagnostic examinations comprising, for example, a general medical examination, a cardiovascular examination, a lung examination, a bowel examination, a throat examination, an otoscopy, a dermatological examination, an ophthalmoscopy, an endoscopy of different organs, etc.

The image capture device 106 captures diagnostic image data during medical imaging and diagnostic examinations. In an embodiment, the image capture device 106 is configured as a video camera for performing medical imaging and remote diagnostic examinations. The camera module 124 processes the captured diagnostic image data. The processing of the captured diagnostic image data performed by the camera module 124 comprises, for example, color filtering, digitizing the captured diagnostic image data, etc. The diagnosis control unit 101 of the multipurpose diagnostic examination apparatus 100 exemplarily illustrated in FIG. 3, comprises a microcontroller 2004, for example, an 8 bit microcontroller exemplarily illustrated in FIG. 20. The microcontroller 2004 facilitates transmission of the processed diagnostic image data from the camera module 124 to a medical diagnostic examination system 2506 that is configured as an application software on a local user device 2505 as exemplarily illustrated in FIG. 25. In an embodiment, the microcontroller 2004 controls the camera module 124 for controlling, for example, a single image capture. In an embodiment, the image capture device 106 is enabled with universal serial bus (USB) 3.0 video capturing technology for allowing uncompressed video transmission, for example, in the SuperSpeed® transfer mode of SuperSpeed LLC, at a speed of, for example, about 5 gigabits per second (Gbit/s). The use of the USB 3.0 video capturing technology produces true color image quality of the diagnostic image data generated by the multipurpose diagnostic examination apparatus 100 that can be displayed on a display screen of the local user device 2505 compatible with USB 3.0 communication standards. In an embodiment, the image capture device 106 operates, for example, based on USB 3.0 protocols. The USB 3.0 protocol allows the image capture device 106 to create true color images that can be displayed on a display screen of a USB 3.0 compatible local user device 2505, for example, a computer monitor, a tablet monitor, a desktop monitor, a laptop monitor, etc. The image capture device 106 stores the captured diagnostic image data in a local memory of the image capture device 106. In an embodiment, the image capture device 106 erases the stored diagnostic image data from the local memory of the image capture device 106, for example, by simultaneous activation of a power control trigger element 103 and an action control trigger element 104 of the multipurpose diagnostic examination apparatus 100.

In an embodiment, the trigger elements 102 are positioned on a predefined section, for example, an upper section 101*b* of the diagnosis control unit 101 as exemplarily illustrated in FIG. 1A. The trigger elements 102 comprise, for example, the power control trigger element 103, the action control trigger element 104, and two output modification trigger elements 105*a* and 105*b* as exemplarily illustrated in FIG. 1A. On activation of the action control trigger element 104, the image capture device 106 creates an image from a real time video output of the USB 3.0 HD camera. In an embodiment, the power control trigger element 103 and the action control trigger element 104 can be used, for example, for activating or deactivating the image capture device 106, for activating or deactivating a medical diagnostic device, for example, an otoscope device 119 exemplarily illustrated in FIGS. 5A-5L, or an ophthalmoscope device (not shown), or a stethoscope device 134 exemplarily illustrated in FIGS. 11A-11G, or a dermatoscope device 131 exemplarily illustrated in FIG. 8, or an ultrasound device 141 exemplarily illustrated in FIGS. 13A-13H, or an endoscope device (not shown), etc., operably connected to the diagnosis control unit 101 for controlling an image capture and storage operation of the image capture device 106, for recording, transferring, or deleting diagnostic image data and diagnostic examination data via the image capture device 106 and/or the medical diagnostic device, etc.

Figure 1B:
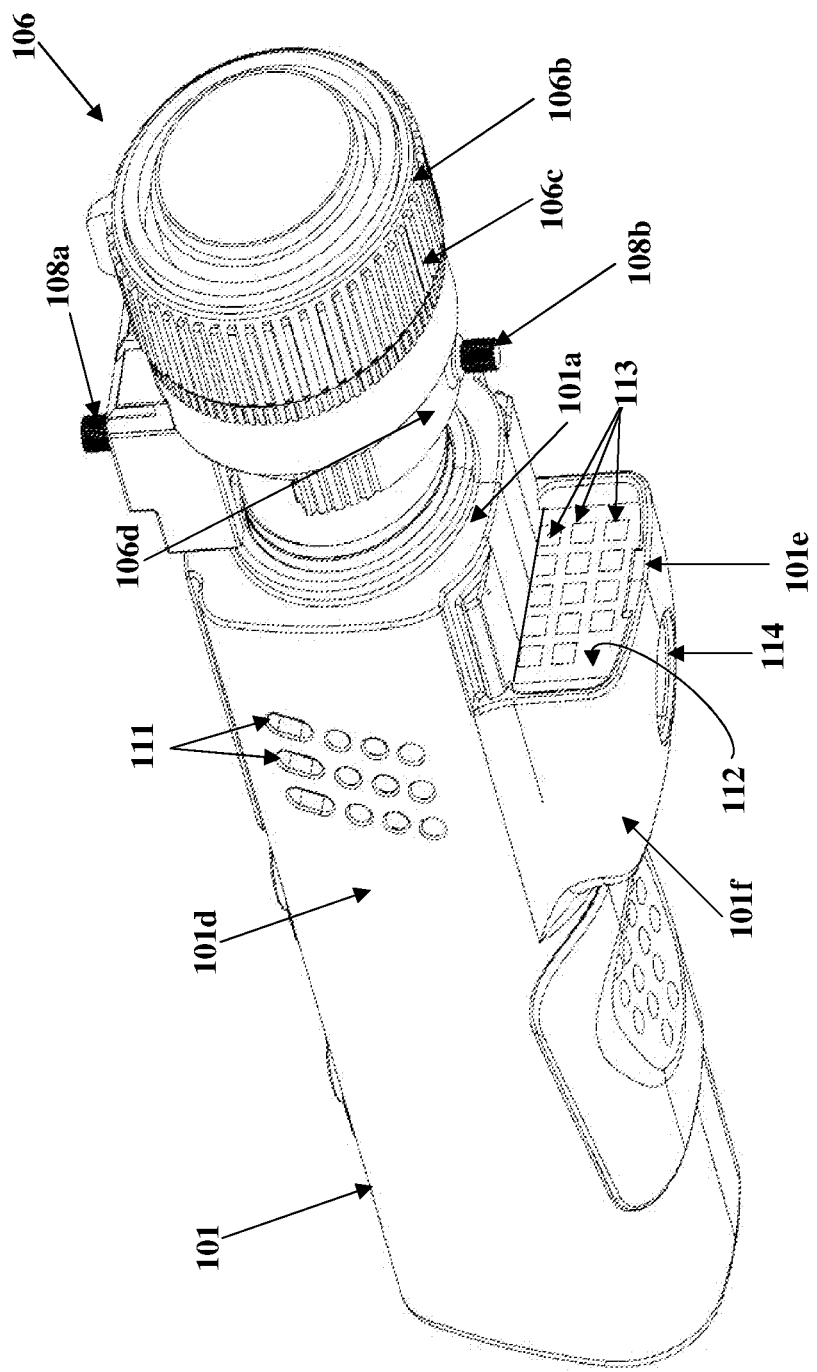
FIG. 1B exemplarily illustrates a front perspective view showing the image capture device removably connected to the front section of the diagnosis control unit and a connector slot configured at a front end of the diagnosis control unit for connecting an attachment unit of the multipurpose diagnostic examination apparatus.

FIG. 1B exemplarily illustrates a front perspective view showing the image capture device 106 removably connected to the front section 101*a* of the diagnosis control unit 101 and a connector slot 112 configured at a front end 101*e* of the diagnosis control unit 101 for connecting an attachment unit 115 of the multipurpose diagnostic examination apparatus 100 exemplarily illustrated in FIG. 3. As exemplarily illustrated in FIG. 1B, the connector slot 112 is configured on a lower section 101*f* extending below the front end 101*e* of the diagnosis control unit 101. The connector slot 112 comprises connector pads 113. In an embodiment, the connector slot 112 at the front end 101*e* of the diagnosis control unit 101 comprises, for example, 3×5 connector pads 113, that is, connector pads 113 on three rows and five columns of the connector slot 112 for receiving attachment signals from the attachment unit 115 exemplarily illustrated in FIGS. 2A-2B, connected to the diagnosis control unit 101. The connector pads 113 are configured to engage with spring contact connectors 118 positioned at a rear end 115*b* of the attachment unit 115 exemplarily illustrated in FIG. 2B, to allow electrical communication of light sources positioned on a light support 117 operably connected to a front section 115*c* of the attachment unit 115 exemplarily illustrated in FIG. 2A, or positioned on a predefined section along a length of the attachment unit 115, with the microcontroller 2004 of the diagnosis control unit 101 exemplarily illustrated in FIG. 20. Furthermore, the connector pads 113 are configured to engage with the spring contact connectors 118 positioned on the rear end 115b of the attachment unit 115 to allow electrical communication of a medical diagnostic device operably connected to the front end 115a of the attachment unit 115, with the microcontroller 2004 of the diagnosis control unit 101.

As exemplarily illustrated in FIG. 1B, the connector pads 113 are arranged, for example, in three rows. The top row comprises, for example, five connector pads 113 that receive and connect to the spring contact connectors 118 of the light sources, for example, light emitting diodes (LEDs) 125 exemplarily illustrated in FIG. 5F, positioned on the front section 115c of the attachment unit 115, for allowing control of a brightness level of light generated from the LEDs 125 used during medical imaging and diagnostic examinations. In an embodiment, the light source is a clear plastic LED attachment used as a light pipe for illuminating difficult to access areas comprising, for example, areas inside the throat, the ear, the nose, etc., during medical imaging and diagnostic examinations. The second row comprises, for example, five connector pads 113 that receive and connect to the spring contact connectors 118 of a stethoscope device 134 positioned at a front end 115a of the attachment unit 115 exemplarily illustrated in FIGS. 10A-10B and FIGS. 11A-11G, for controlling the operation of the stethoscope device 134 and for enabling communication with the stethoscope device 134. The third row comprises, for example, four connector pads 113 that receive and connect to spring contact connectors 118 of an ultrasound device 141 exemplarily illustrated in FIGS. 12A-12B and FIGS. 13A-13H, for controlling operation of the ultrasound device 141 and enabling communication with the ultrasound device 141. In an embodiment, the first and second connector pads of the first row are configured to provide power and ground connections to the image capture device 106 and the medical diagnostic device, for example, the stethoscope device 134 or the ultrasound device 141, or the image capture device 106 alone, depending on which medical diagnostic device is connected to the attachment unit 115 of the multipurpose diagnostic examination apparatus 100.

In an embodiment as exemplarily illustrated in FIG. 1B, the multipurpose diagnostic examination apparatus 100 further comprises a release button 114 positioned on the lower section 101f of the diagnosis control unit 101. The release button 114 allows removal of the attachment unit 115 from the diagnosis control unit 101 on application of pressure on the release button 114. In an embodiment, small handles 108a and 108b are positioned on the upper section 106a and the lower section 106d of the image capture device 106 respectively to allow a user, for example, a medical assistant to open and close the aperture of the image capture device 106.

Figure 2A:
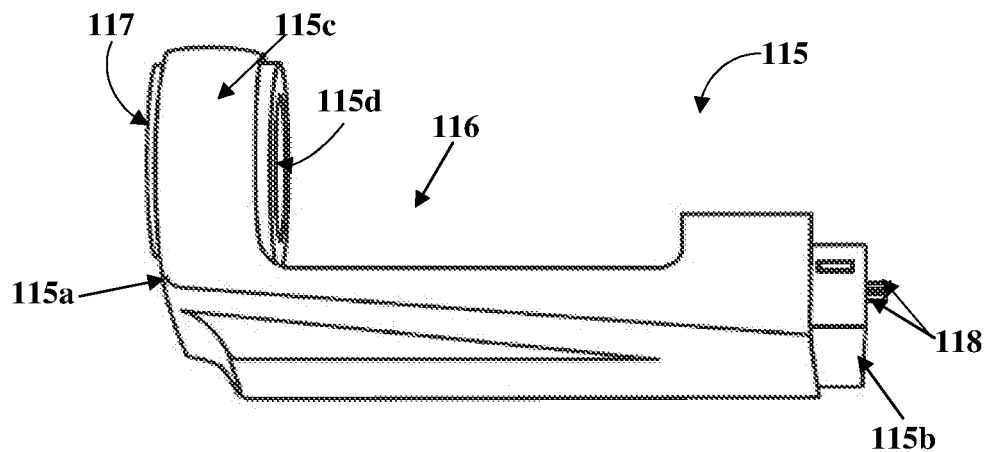
FIG. 2A exemplarily illustrates a right side perspective view of an attachment unit of the multipurpose diagnostic examination apparatus, showing a light support connected to a front section of the attachment unit.

FIG. 2A exemplarily illustrates a right side perspective view of an attachment unit 115 of the multipurpose diagnostic examination apparatus 100 exemplarily illustrated in FIG. 3, showing a light support 117 connected to a front section 115c of the attachment unit 115. The front section 115c extends, for example, in an upward perpendicular direction from the front end 115a of the attachment unit 115 as exemplarily illustrated in FIG. 2A. The front section 115c comprises an opening 115d for allowing the image capture device 106 exemplarily illustrated in FIG. 3, to view one or more anatomical examination areas of a patient. The attachment unit 115 comprises a receptacle 116 for accommodating the image capture device 106 as exemplarily illustrated in FIG. 3. The attachment unit 115 operably connects a medical diagnostic device, for example, an otoscope device 119 exemplarily illustrated in FIGS. 5A-5L, or an ophthalmoscope device (not shown), or a stethoscope device 134 exemplarily illustrated in FIGS. 11A-11G, or a dermatoscope device 131 exemplarily illustrated in FIG. 8, or an ultrasound device 141 exemplarily illustrated in FIGS. 13A-13H, or an endoscope device (not shown), etc., to the diagnosis control unit 101. The light support 117 houses light sources, for example, light emitting diodes (LEDs) 125 exemplarily illustrated in FIG. 5F. The LEDs 125 are positioned on the light support 117 on the front section 115c of the attachment unit 115. The attachment unit 115 is operably connected to the front end 101e of the diagnosis control unit 101 to create a receptacle 116 to accommodate the image capture device 106 as exemplarily illustrated in FIG. 3. The LEDs 125 attached to the front section 115c of the attachment unit 115 to allow the image capture device 106 removably connected to the front section 101a of the diagnosis control unit 101 exemplarily illustrated in FIGS. 1A-1B, and supported within the receptacle 116 of the attachment unit 115 to function as a general medical examination device.

Figure 2B:
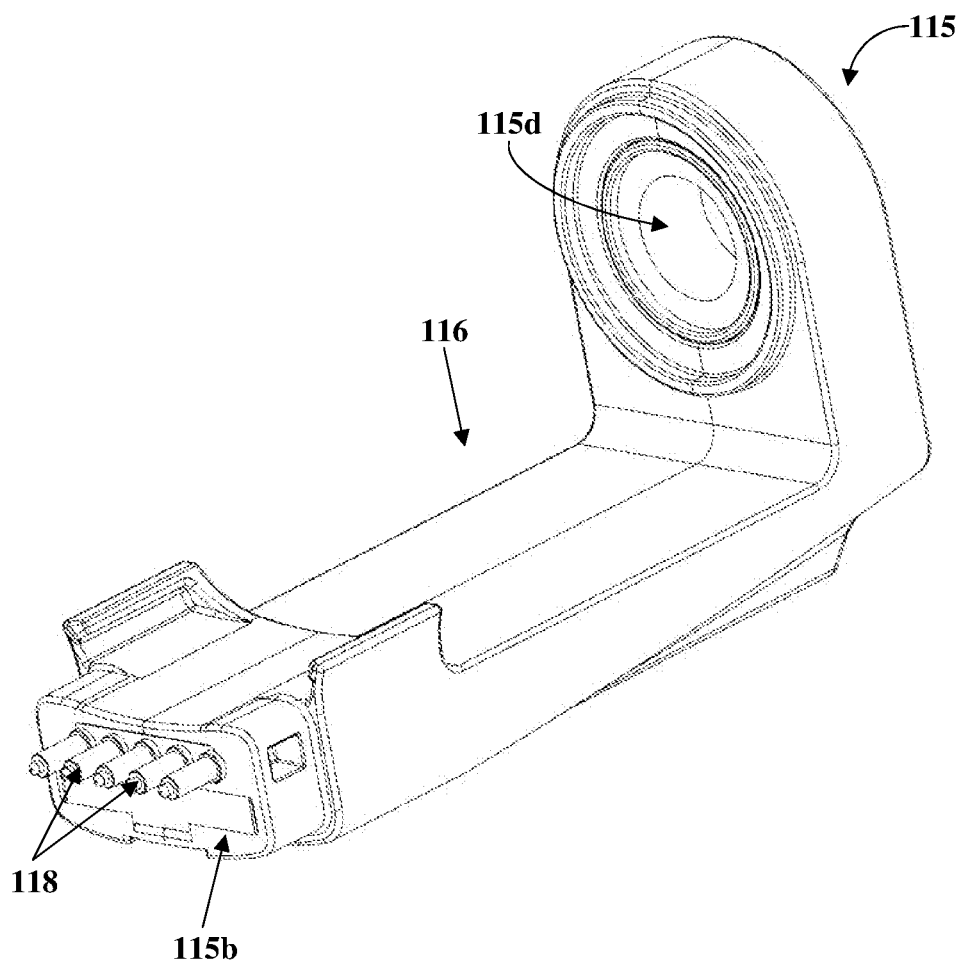
FIG. 2B exemplarily illustrates a rear perspective view of the attachment unit, showing spring contact connectors positioned at a rear end of the attachment unit for electrically connecting light sources positioned on the front section of the attachment unit to a microcontroller of the diagnosis control unit.
Figure 20:
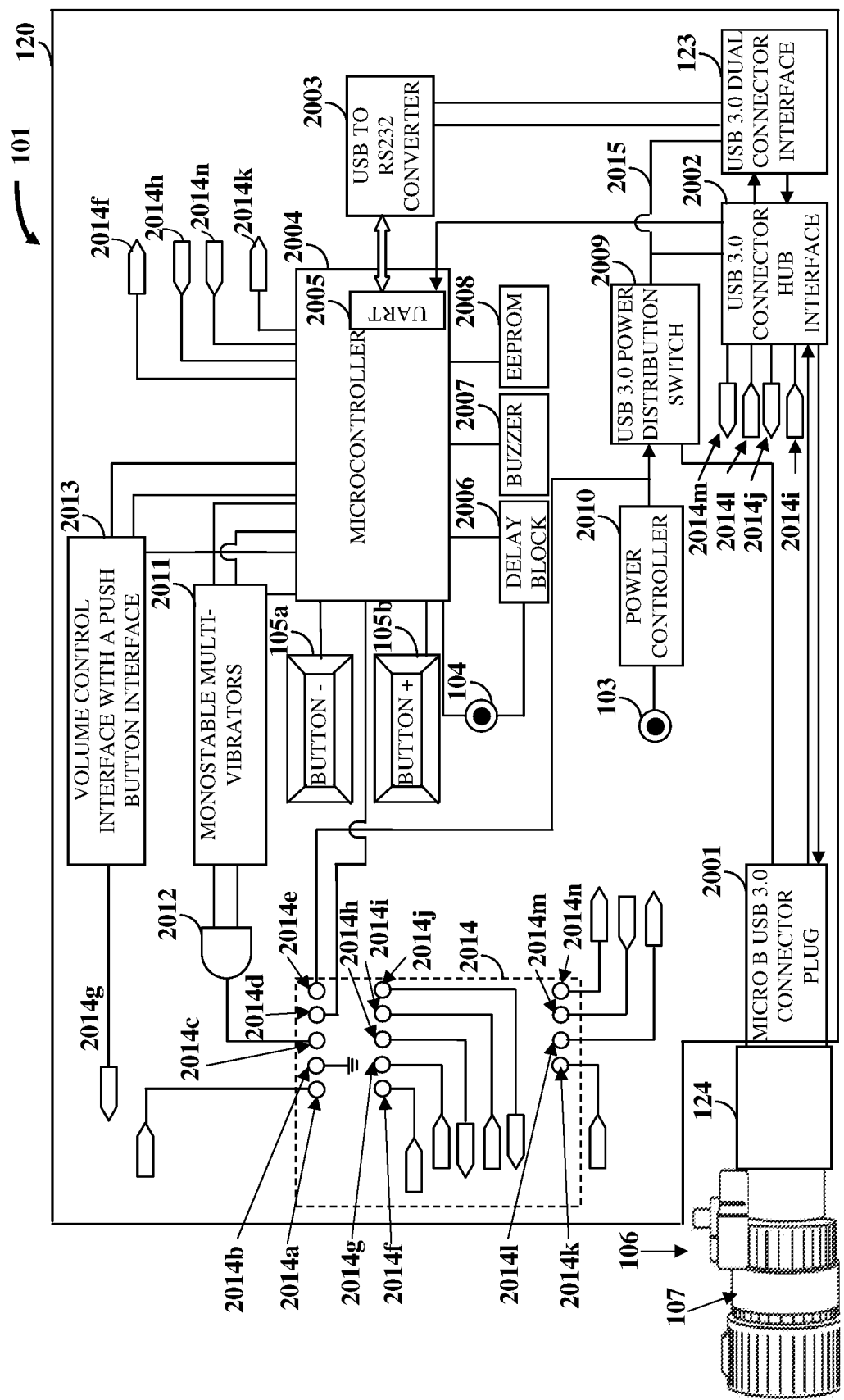
FIG. 20 exemplarily illustrates a block diagram of the diagnosis control unit of the multipurpose diagnostic examination apparatus.

FIG. 2B exemplarily illustrates a rear perspective view of the attachment unit 115, showing spring contact connectors 118 positioned at a rear end 115b of the attachment unit 115 for electrically connecting light sources, for example, the light emitting diodes (LEDs) 125 exemplarily illustrated in FIG. 5F, positioned on the front section 115c of the attachment unit 115 to the microcontroller 2004 of the diagnosis control unit 101 exemplarily illustrated in FIG. 20. The spring contact connectors 118 are, for example, Mill-Max® spring contact connectors of Mill-Max Mfg. Corp. In an embodiment, the attachment unit 115 comprises a row of five spring contact connectors 118 configured to connect to a row of five connector pads 113 of the diagnosis control unit 101 exemplarily illustrated in FIG. 1B.

FIG. 3 exemplarily illustrates a top perspective view of the multipurpose diagnostic examination apparatus 100, showing the image capture device 106 removably connected to the front section 101a of the diagnosis control unit 101, and the attachment unit 115 detachably connected to and extending from the front end 101e of the diagnosis control unit 101. The multipurpose diagnostic examination apparatus 100 with the image capture device 106 exemplarily illustrated in FIG. 3 can be used, for example, as a general examination device. The attachment unit 115 is configured as a removable and replicable attachment unit 115. The image capture device 106 is screwably connected to the front section 101a of the diagnosis control unit 101. As exemplarily illustrated in FIG. 3, the diagnosis control unit 101 comprises trigger elements 102 comprising, for example, the power control trigger element 103, the action control trigger element 104, and two output modification trigger elements 105a and 105b positioned on the upper section 101b of the diagnosis control unit 101. The light support 117 positioned on the front section 115c of the attachment unit 115 comprises one or more light sources, for example, light emitting diodes (LEDs) 125 exemplarily illustrated in FIG. 5F, that generate light of varied brightness levels for improving quality of medical imaging and remote diagnostic examinations. The LEDs 125 facilitate medical imaging performed by the image capture device 106. The brightness of light generated from the LEDs 125 can be controlled by a user, for example, a medical assistant, via the output modification trigger elements 105a and 105b configured, for example, as up or down push buttons. For example, the user can increase the brightness of light generated from the LEDs 125 by pressing the "+" output modification trigger element 105b, and decrease the brightness of light generated from the LEDs 125 by pressing the "−" output modification trigger element 105a.

Figure 4:
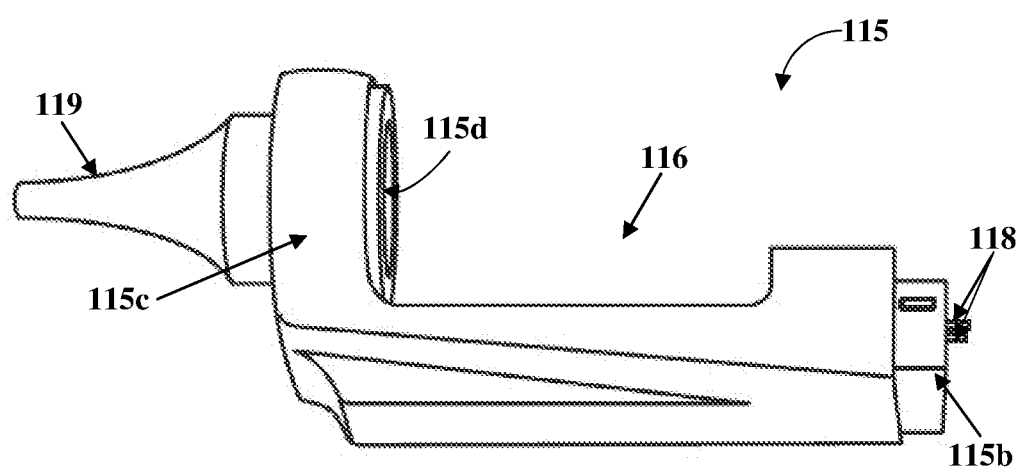
FIG. 4 exemplarily illustrates a right side perspective view of the attachment unit, showing an otoscope device operably connected to the front section of the attachment unit.

FIG. 4 exemplarily illustrates a right side perspective view of the attachment unit 115, showing an otoscope device 119 operably connected to the front section 115c of the attachment unit 115. The otoscope device 119 is a medical diagnostic device used for viewing inside a patient's ears. The otoscope device 119 is in fluid communication with the opening 115d configured in the front section 115c of the attachment unit 115. In an embodiment, light sources, for example, light emitting diodes (LEDs) 125 are housed inside the otoscope device 119 as exemplarily illustrated in FIG. 5F. A conventional otoscope device requires a smaller receptacle and hence centralization of the LEDs 125 in the multipurpose diagnostic examination apparatus 100 exemplarily illustrated in FIGS. 5A-5L, allows focusing of light during diagnostic examinations. The attachment unit 115 for the otoscope device 119 comprises a row of spring contact connectors 118 configured at the rear end 115b of the attachment unit 115 to connect to the connector pads 113 of the diagnosis control unit 101 exemplarily illustrated in FIG. 1B, for allowing control of the brightness levels of light generated from the LEDs 125 by the diagnosis control unit 101.

FIG. 5A exemplarily illustrates a top perspective view of the multipurpose diagnostic examination apparatus 100, showing the image capture device 106 removably connected to the front section 101a of the diagnosis control unit 101, and the otoscope device 119 operably connected to the front section 115c of the attachment unit 115. The attachment unit 115 with the otoscope device 119 is detachably connected to and extends from the front end 101e of the lower section 101f of the diagnosis control unit 101. The multipurpose diagnostic examination apparatus 100 further comprises trigger elements 102, for example, the power control trigger element 103, the action control trigger element 104, and the output modification trigger elements 105a and 105b positioned on the upper section 101b of the diagnosis control unit 101 for controlling operation of the otoscope device 119 and light sources, for example, a set of light emitting diodes (LEDs) 125 arranged in a circle inside the otoscope device 119 as exemplarily illustrated in FIG. 5F. The LEDs 125 inside the otoscope device 119 are activated and the otoscope device 119 is inserted into a patient's ears. The image capture device 106 records a video or captures an image of the patient's ear canal and tympanic membrane, or eardrum and stores the recorded video or the captured image in the local memory of the image capture device 106 as diagnostic image data prior to transmission to the medical diagnostic examination system 2506 exemplarily illustrated in FIG. 25.

FIGS. 5B-5C exemplarily illustrate a right side perspective view and a left side perspective view of the multipurpose diagnostic examination apparatus 100 respectively, showing the image capture device 106 removably connected to the front section 101a of the diagnosis control unit 101, and the otoscope device 119 operably connected to the front section 115c of the attachment unit 115.

FIG. 5D exemplarily illustrates a top perspective view of the multipurpose diagnostic examination apparatus 100, showing the image capture device 106, the otoscope device 119 connected to the attachment unit 115, and the trigger elements 102 comprising the power control trigger element 103, the action control trigger element 104, and the output modification trigger elements 105a and 105b.

FIG. 5E exemplarily illustrates a bottom perspective view of the multipurpose diagnostic examination apparatus 100, showing the image capture device 106, the attachment unit 115, the otoscope device 119, a support element 110, and a release button 114. The support element 110 is positioned on the lower surface 101c of the diagnosis control unit 101. The release button 114 is positioned on the lower section 101f of the diagnosis control unit 101.

FIG. 5F exemplarily illustrates an exploded view of the multipurpose diagnostic examination apparatus 100 comprising the diagnosis control unit 101, the attachment unit 115, the image capture device 106, and the otoscope device 119. The exploded view shows the trigger elements 102 comprising the power control trigger element 103, the action control trigger element 104, and the output modification trigger elements 105a and 105b. The exploded view also shows the support element 110 and the release button 114. The power control trigger element 103 and the action control trigger element 104 are positioned on a printed circuit board (PCB) 120 housed in a cavity 121 of the diagnosis control unit 101. The output modification trigger elements 105a and 105b are positioned on a PCB 122 housed in the cavity 121 of the diagnosis control unit 101. The exploded view also shows a connector interface 123 positioned on a rear section 120a of the PCB 120. The image capture device 106 is removably connected to the camera module 124 of the diagnosis control unit 101. The camera module 124 is operably connected to a front section 120b of the PCB 120. The camera module 124 is in operable communication with the optical lens 107 of the image capture device 106. The camera module 124 processes the diagnostic image data received from the image capture device 106 prior to transmission to the medical diagnostic examination system 2506 exemplarily illustrated in FIG. 25, via the connector interface 123. FIG. 5F exemplarily illustrates an electrical configuration of the light sources, for example, the LEDs 125. As exemplarily illustrated in FIG. 5F, wires 127 extending from a PCB 128 of the LEDs 125 are connected to the spring contact connectors 118 of the attachment unit 115. The spring contact connectors 118 of the attachment unit 115 operably connect to a connector pad PCB 130 housed in the connector slot 112 of the diagnosis control unit 101.

The PCB 128 of the LEDs 125, the LEDs 125, and light pipes 126 are housed in a light pipe holder 129. The light pipes 126 house the LEDs 125 and provide a path for the light emitted from the LEDs 125 to reach the otoscope device 119. The light pipes 126 are configured of a transparent material in one or more sizes. In an embodiment, the light pipes 126 are configured as short rectangular pipes as exemplarily illustrated in FIG. 5F, for use in conjunction with the otoscope device 119. In another embodiment, the light pipes 126 are configured as long cylindrical pipes exemplarily illustrated in FIG. 11G, FIG. 13H, and FIG. 14G, for use in general medical diagnostic examinations, for example, a throat diagnostic examination. A front portion 129a and a rear portion 129b of the light pipe holder 129 exemplarily illustrated in FIG. 5F, together house the PCB 128 of the LEDs 125, the LEDs 125, and the light pipes 126 therewithin.

Figure 5G:
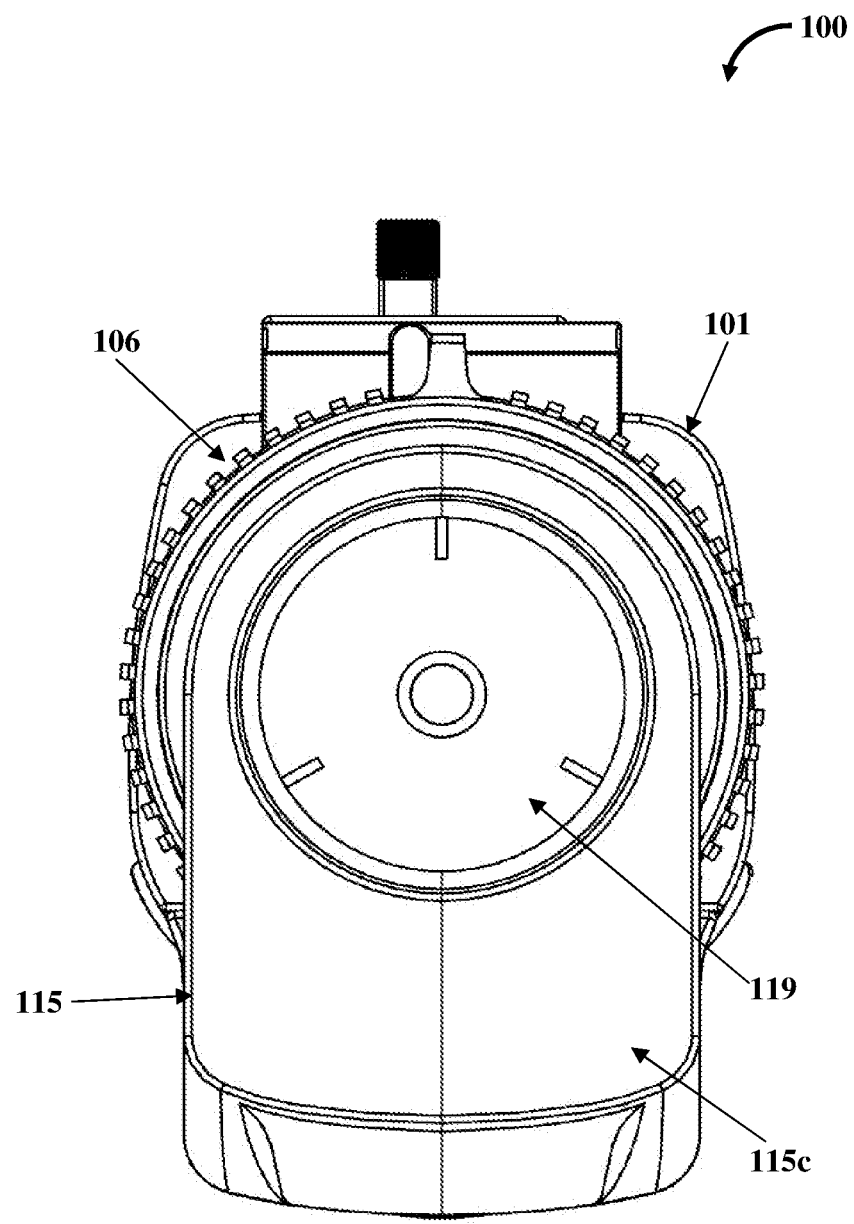
FIG. 5G exemplarily illustrates a front elevation view of the multipurpose diagnostic examination apparatus, showing the otoscope device connected to the front section of the attachment unit.

FIG. 5G exemplarily illustrates a front elevation view of the multipurpose diagnostic examination apparatus 100, showing the otoscope device 119 connected to the front section 115c of the attachment unit 115.

Figure 5H:
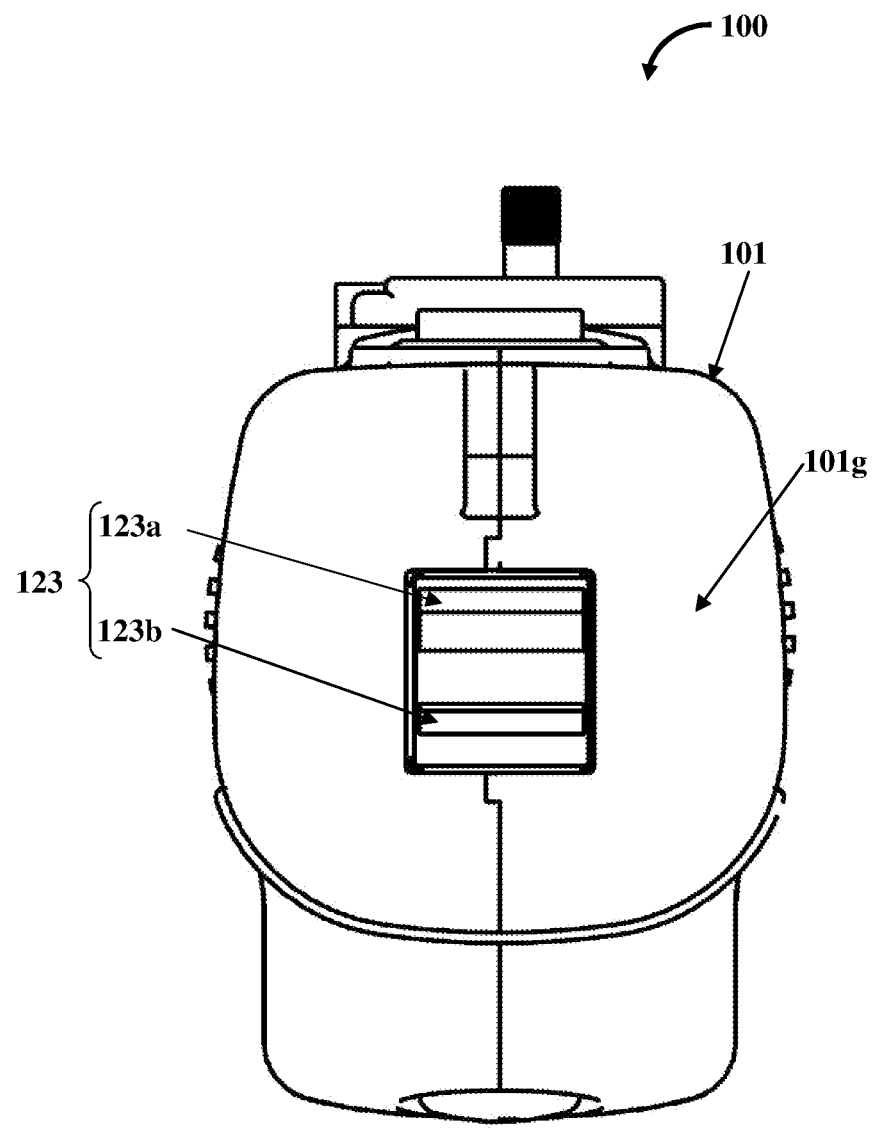
FIG. 5H exemplarily illustrates a rear elevation view of the multipurpose diagnostic examination apparatus, showing a connector interface configured at a rear section of the diagnosis control unit.

FIG. 5H exemplarily illustrates a rear elevation view of the multipurpose diagnostic examination apparatus 100, showing the connector interface 123, for example, a universal serial bus (USB) 3.0 connector interface configured at the rear section 101g of the diagnosis control unit 101. The connector interface 123 is in communication with the camera module 124 exemplarily illustrated in FIG. 5F, and the otoscope device 119 via the attachment unit 115. The connector interface 123 allows electronic communication between the multipurpose diagnostic examination apparatus 100 and the medical diagnostic examination system 2506 accessible on a local user device 2505 exemplarily illustrated in FIG. 25, for medical imaging and diagnostic examinations. The connector interface 123 receives and transmits the processed diagnostic image data of the patient's ear from the camera module 124 to the medical diagnostic examination system 2506. The connector interface 123 comprises, for example, at least two connector elements 123a and 123b configured, for example, as two USB 3.0 connecter ports. The connector element 123a or 123b allows communication of the processed diagnostic image data from the camera module 124 and/or the otoscope device 119 to the medical diagnostic examination system 2506 on receiving instructions from the microcontroller 2004 exemplarily illustrated in FIG. 20. For example, the connector element 123a or 123b allows video and/or audio data communication. The connector element 123a or 123b allows serial data communication between the microcontroller 2004 of the diagnosis control unit 101 and the medical diagnostic examination system 2506 for controlling operations of the image capture device 106 and/or the otoscope device 119 exemplarily illustrated in FIGS. 5A-5G, for medical imaging and diagnostic examinations. For example, the connector element 123a or 123b allows RS-232 communication with the medical diagnostic examination system 2506 accessible on the local user device 2505. In an embodiment, the connector interface 123 is, for example, a USB 3.0 connector interface, a hardware connector interface such as the Thunderbolt connector interface or a Thunderbolt 2 connector interface, etc.

In an embodiment, the connector interface 123 is a universal serial bus (USB) 3.0 connector interface configured to allow uncompressed, high speed, and high quality serial data communication between the camera module 124 of the diagnosis control unit 101 and the medical diagnostic examination system 2506. In an embodiment, the connector interface 123 allows storage of the diagnostic image data and the diagnostic examination data comprising, for example, images and audio files on the local user device 2505, a remote hard disk, a USB flash drive, or a dedicated server such as the data management server 2510 via a communication network 2509 exemplarily illustrated in FIG. 25. In an embodiment, the data storage performed is compliant with Health Insurance Portability and Accountability Act (HIPAA) standards.

Figure 5I:
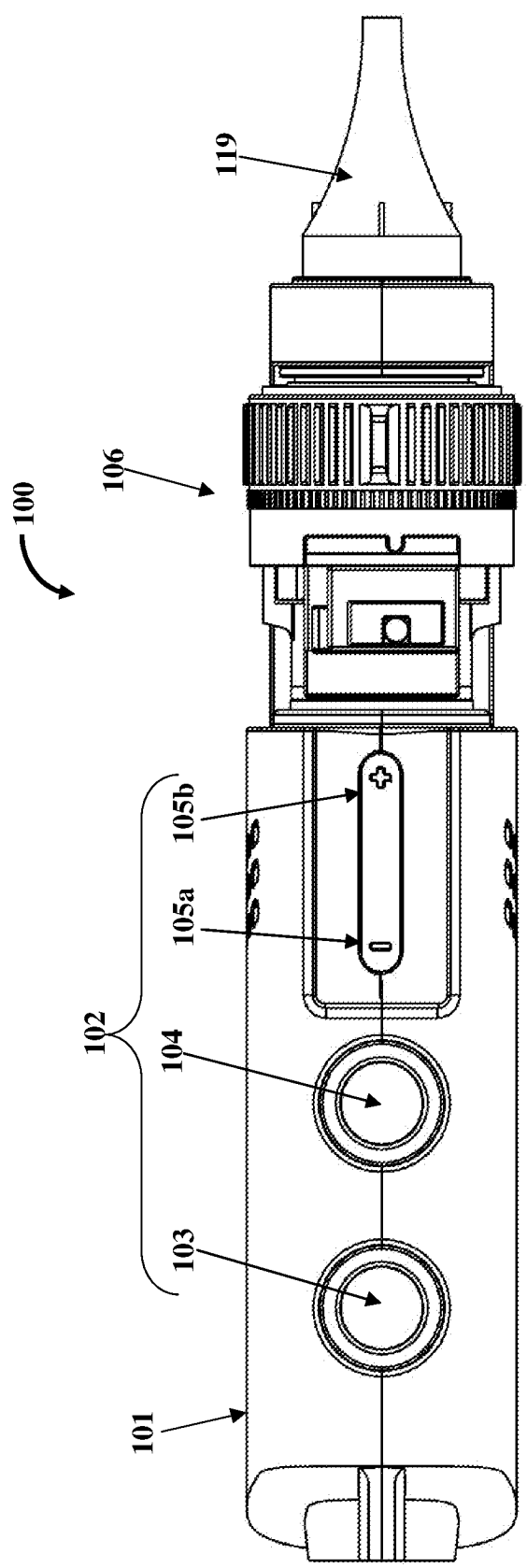
FIG. 5I exemplarily illustrates a top plan view of the multipurpose diagnostic examination apparatus, showing the image capture device, the trigger elements, and the otoscope device.

FIG. 5I exemplarily illustrates a top plan view of the multipurpose diagnostic examination apparatus 100, showing the image capture device 106, the trigger elements 102 comprising the power control trigger element 103, the action control trigger element 104, and the output modification trigger elements 105a and 105b, and the otoscope device 119.

Figure 5J:
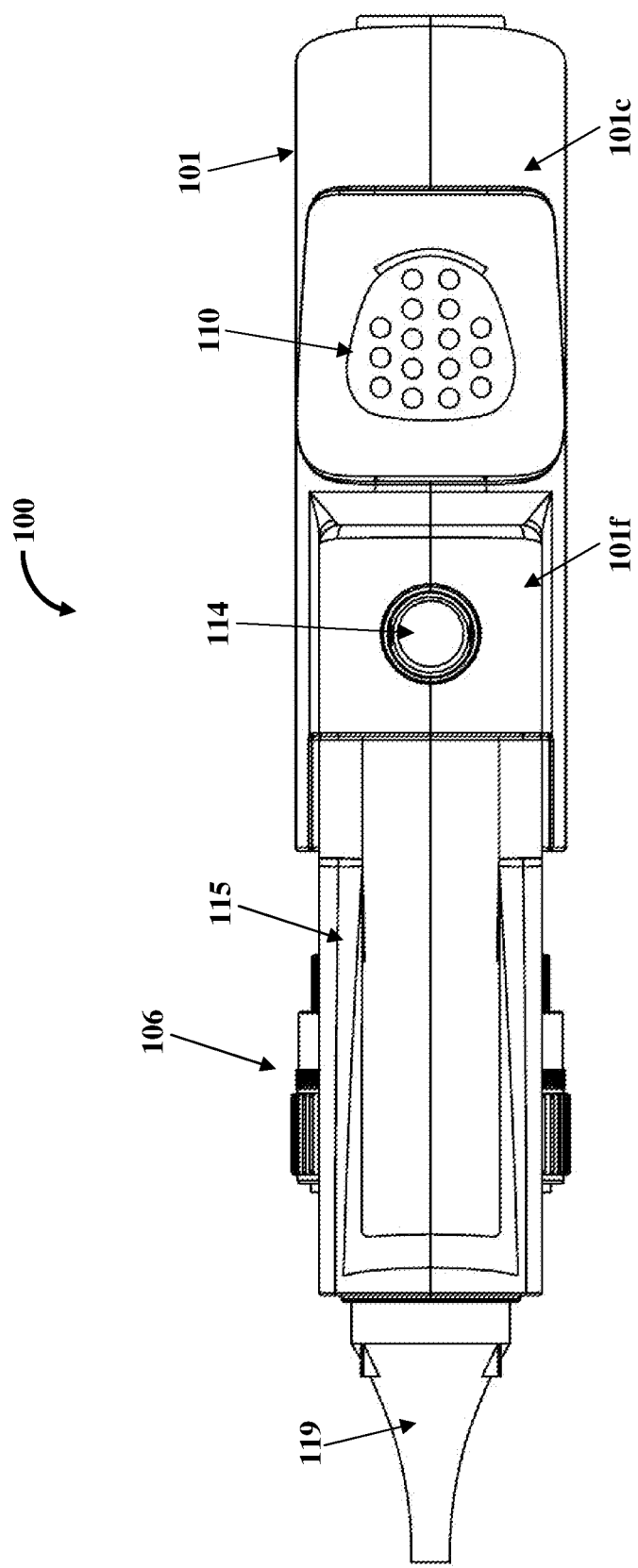
FIG. 5J exemplarily illustrates a bottom view of the multipurpose diagnostic examination apparatus, showing the attachment unit, the otoscope device, the support element, and the release button.

FIG. 5J exemplarily illustrates a bottom view of the multipurpose diagnostic examination apparatus 100, showing the attachment unit 115, the otoscope device 119, the support element 110, and the release button 114. The support element 110 positioned on the lower surface 101c of the diagnosis control unit 101 provides support to a user while holding the multipurpose diagnostic examination apparatus 100. In an embodiment, the support element 110 is a finger grip, for example, made of rubber material.

Figure 5K:
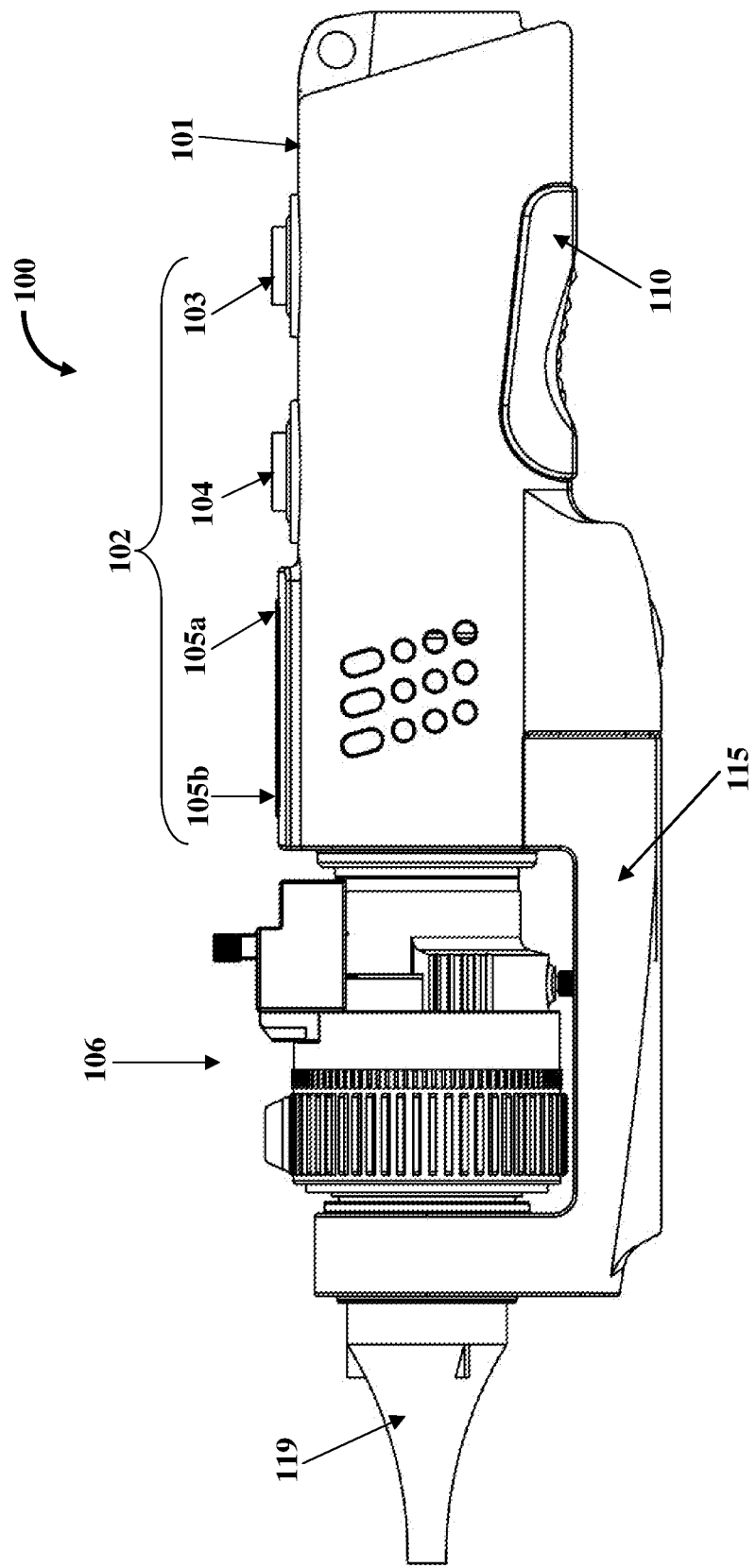
FIGS. 5K-5L exemplarily illustrate side elevation views of the multipurpose diagnostic examination apparatus, showing the attachment unit, the otoscope device, the image capture device, the trigger elements, and the support element.
Figure 5L:
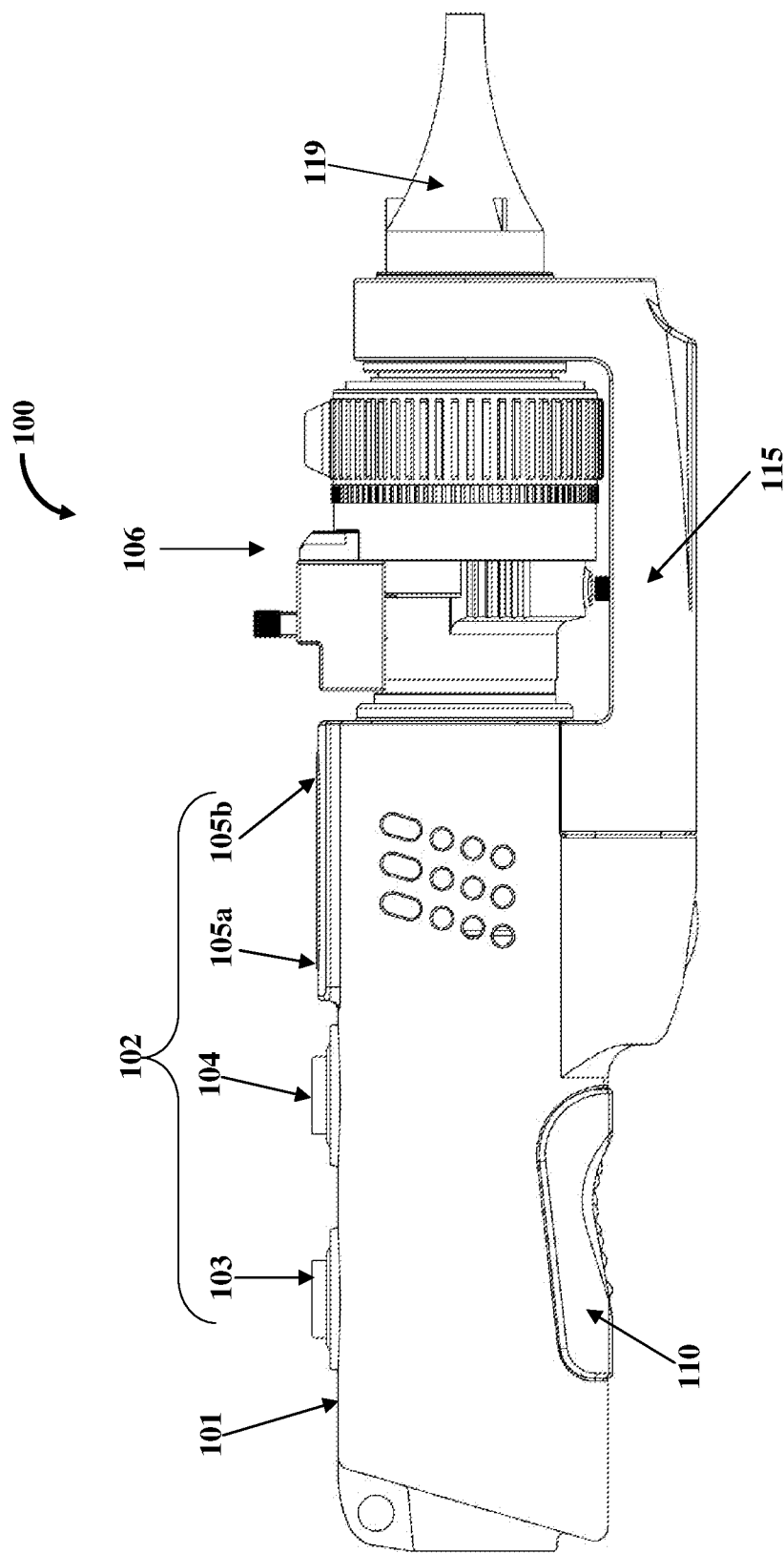

FIGS. 5K-5L exemplarily illustrate side elevation views of the multipurpose diagnostic examination apparatus 100, showing the attachment unit 115, the otoscope device 119, the image capture device 106, the trigger elements 102 comprising the power control trigger element 103, the action control trigger element 104, and the output modification trigger elements 105a and 105b, and the support element 110.

Figure 6A:
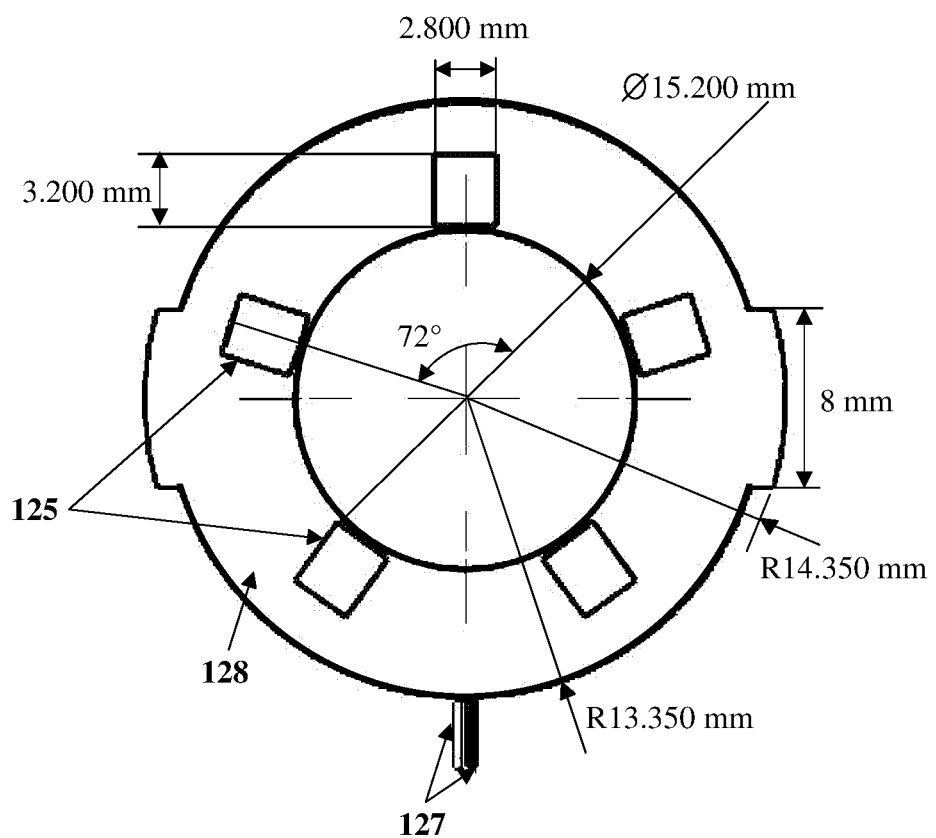
FIGS. 6A-6B exemplarily illustrate front elevation views of a printed circuit board connected to light sources.
Figure 6B:
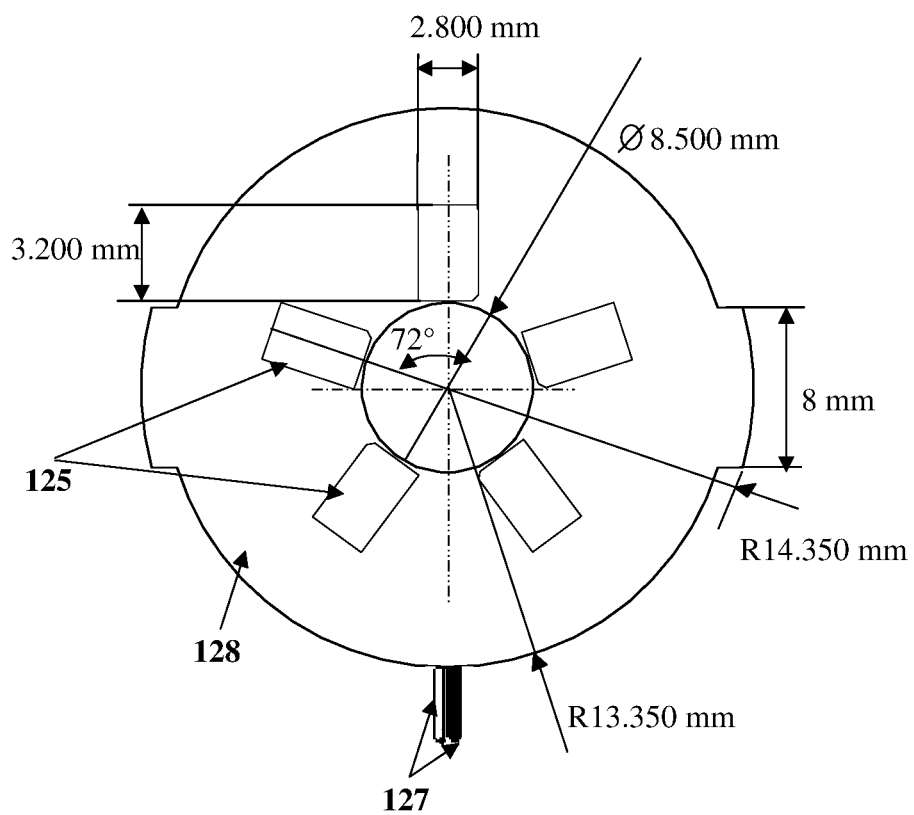

FIGS. 6A-6B exemplarily illustrate front elevation views of a printed circuit board (PCB) 128 connected to light sources, for example, a set of light emitting diodes (LEDs) 125. The microcontroller 2004 of the diagnosis control unit 101 exemplarily illustrated in FIG. 20, and a constant current light emitting diode (LED) driver 2101 exemplarily illustrated in FIG. 21, control the brightness of the LEDs 125. The constant current LED driver 2101 is positioned under the PCB 128. The PCB 128 comprises wires 127, for example, a red wire and a black wire configured to allow electrical connection of the LEDs 125 to the spring contact connectors 118 of the attachment unit 115 exemplarily illustrated in FIG. 2B and FIG. 5F. The LEDs 125 are used as light sources for illuminating anatomical examination areas to be examined FIG. 6A exemplarily illustrates geometrical specifications of the PCB 128 and the LEDs 125 connected to the PCB 128. The geometrical specifications comprise, for example, a diameter of a ring or a circle defined by the LEDs 125, a width and a height of each of the LEDs 125, etc. The diameter of the circle defined by the LEDs 125 is, for example, 15.2 mm as exemplarily illustrated in FIG. 6A, or 8.5 mm as exemplarily illustrated in FIG. 6B. The width of each LED 125 is, for example, about 2.8 mm. The height of each LED 125 is, for example, about 3.2 mm In an embodiment, a PCB 128 with the diameter of the circle of the LED ring equal to 8.5 mm is used with the otoscope device 119 to provide a centralized light source for examining areas inside the nose and the ears through the otoscope device 119 exemplarily illustrated in FIG. 4 and FIGS. 5A-5L.

Figure 7:
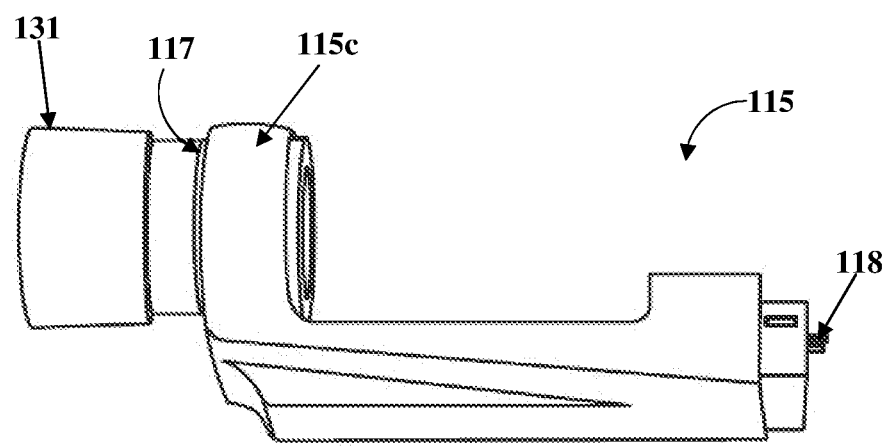
FIG. 7 exemplarily illustrates a right side perspective view of the attachment unit, showing a dermatoscope device operably connected to the front section of the attachment unit.

FIG. 7 exemplarily illustrates a right side perspective view of the attachment unit 115, showing a dermatoscope device 131 operably connected to the front section 115c of the attachment unit 115. The dermatoscope device 131 is, for example, a plastic attachment used for skin diagnostics. The attachment unit 115 for the dermatoscope device 131 comprises a row of spring contact connectors 118 configured to connect to the connector pads 113 of the diagnosis control unit 101 exemplarily illustrated in FIG. 1B, for controlling brightness levels of light generated from the light sources positioned on the light support 117.

Figure 8:
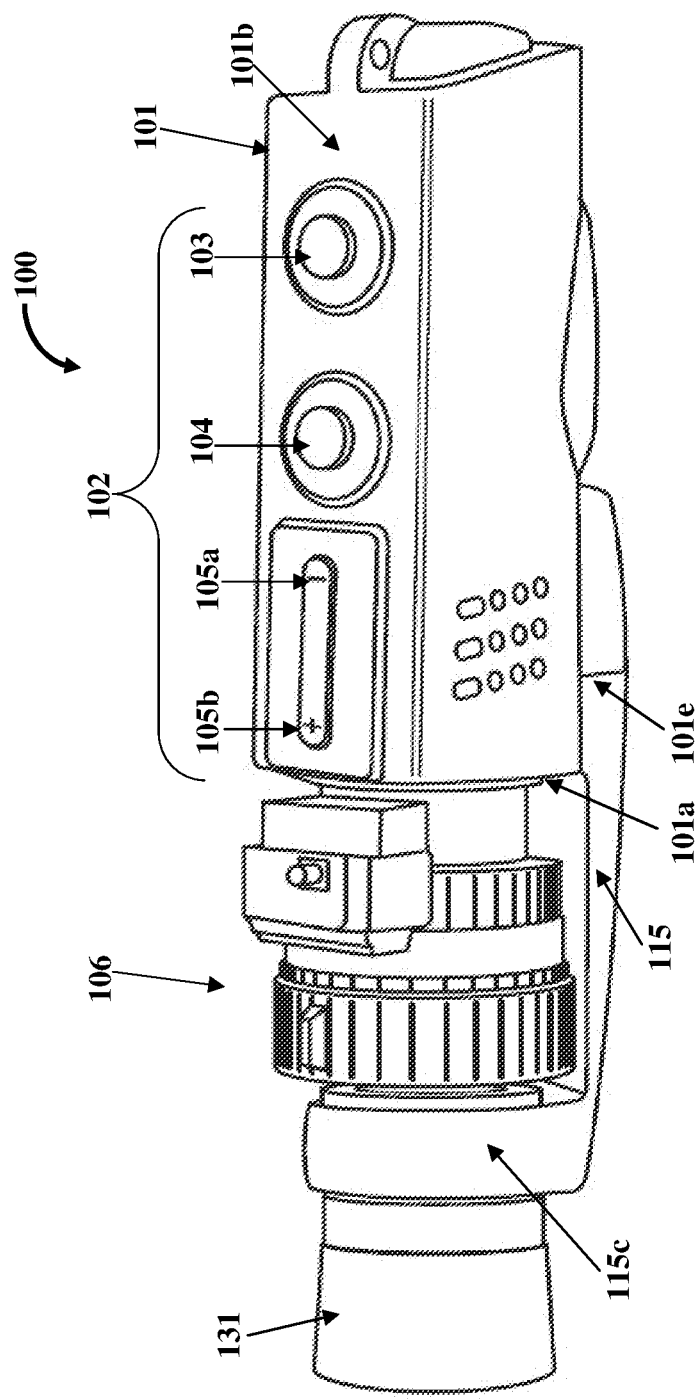
FIG. 8 exemplarily illustrates a top perspective view of the multipurpose diagnostic examination apparatus, showing the image capture device removably connected to the front section of the diagnosis control unit, and the dermatoscope device operably connected to the front section of the attachment unit.

FIG. 8 exemplarily illustrates a top perspective view of the multipurpose diagnostic examination apparatus 100, showing the image capture device 106 removably connected to the front section 101a of the diagnosis control unit 101, and the dermatoscope device 131 operably connected to the front section 115c of the attachment unit 115. The attachment unit 115 is detachably connected to and extends from the front end 101e of the diagnosis control unit 101. The trigger elements 102 comprising the power control trigger element 103, the action control trigger element 104, and two output modification trigger elements 105a and 105b are positioned on the upper section 101b of the diagnosis control unit 101 for controlling operation of the image capture device 106 and the dermatoscope device 131.

Figure 9:
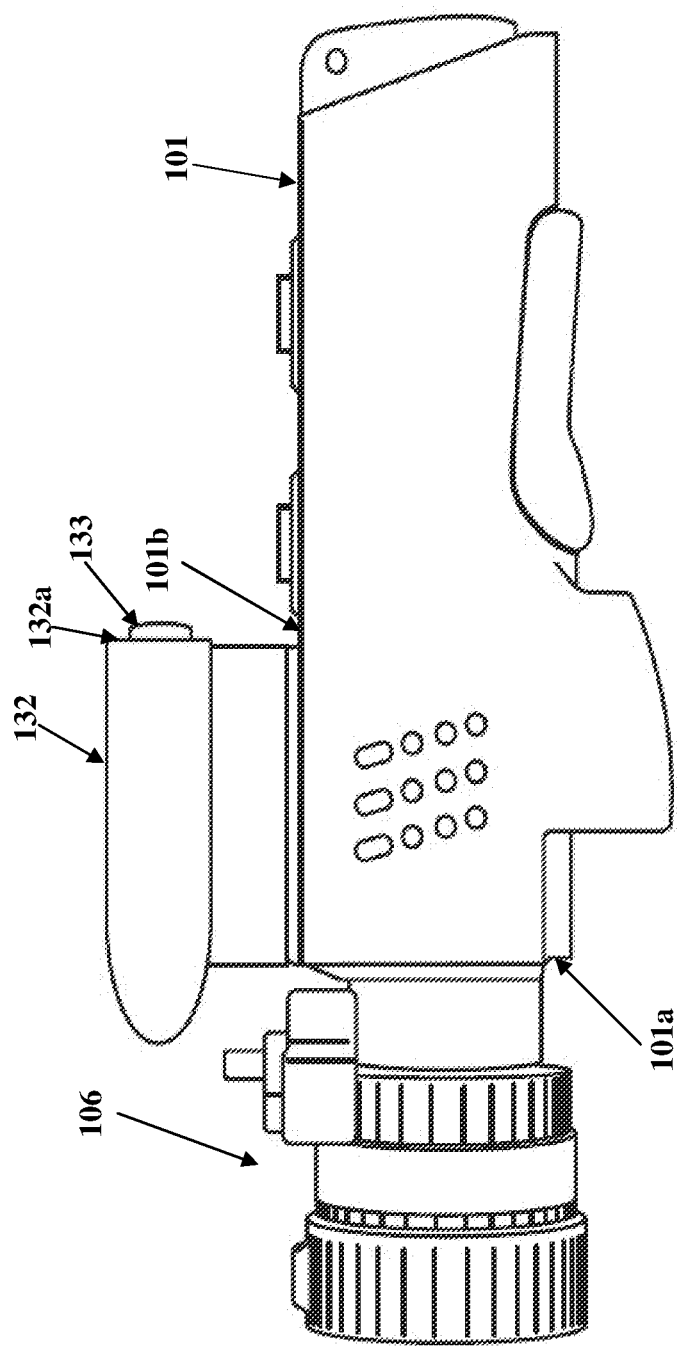
FIG. 9 exemplarily illustrates a right side elevation view showing the image capture device removably connected to the front section of the diagnosis control unit, and a light source operably connected to an upper section of the diagnosis control unit.

FIG. 9 exemplarily illustrates a right side elevation view, showing the image capture device 106 removably connected to the front section 101a of the diagnosis control unit 101, and a light source operably connected to the upper section 101b of the diagnosis control unit 101. In an embodiment, the light source is a laser pointer 132 as exemplarily illustrated in FIG. 9. The laser pointer 132 facilitates virtual diagnostic examination for a doctor. The laser pointer 132 indicates anatomical examination areas on a patient's body to allow a doctor to remotely verify that correct anatomical examination areas are examined. For example, to allow a doctor to verify proper functioning of a patient's heart, he/she should listen to five points on the heart. The laser pointer 132 exemplarily illustrated in FIG. 9, is used to ensure that the doctor is listening to the correct point. The laser pointer 132 comprises a power control push button 133 positioned, for example, on a rear section 132a of the laser pointer 132 for activating and deactivating the laser pointer 132.

Figure 10A:
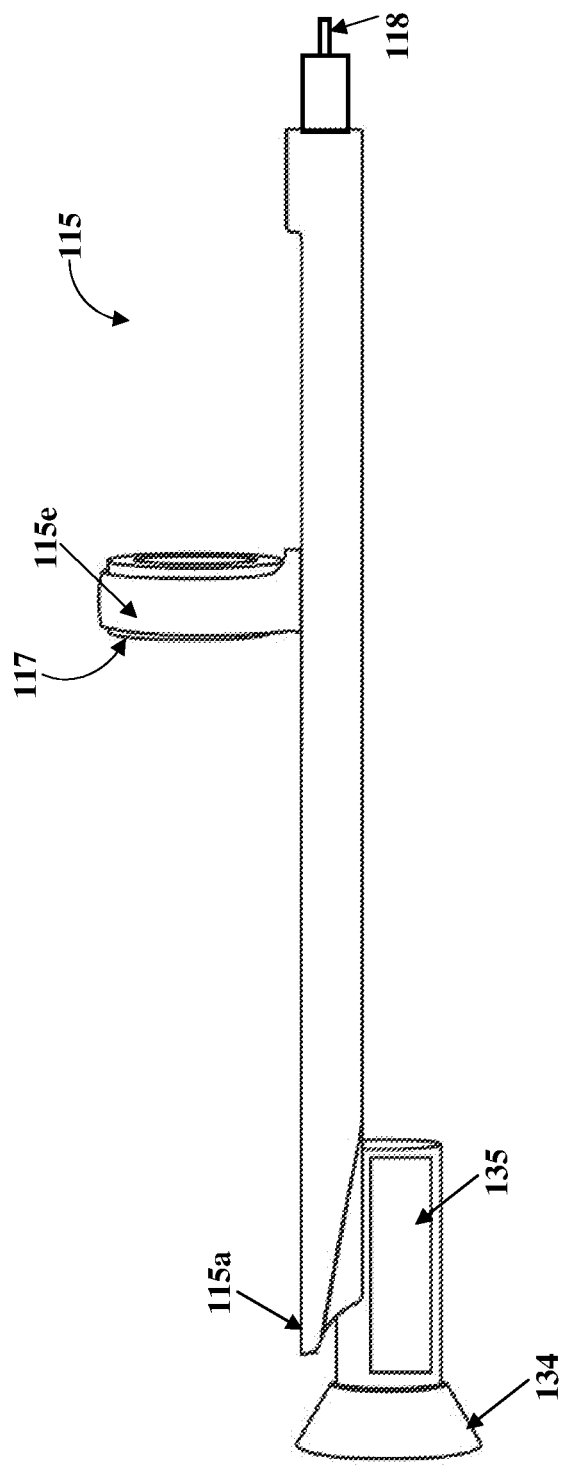
FIG. 10A exemplarily illustrates a right side perspective view of an embodiment of the attachment unit, showing a stethoscope device operably connected to a front end of the attachment unit.

FIG. 10A exemplarily illustrates a right side perspective view of an embodiment of the attachment unit 115, showing a stethoscope device 134 operably connected to the front end 115a of the attachment unit 115. The stethoscope device 134 is an acoustic medical diagnostic device for auscultation or listening to internal sounds of a patient's body. The stethoscope device 134 is, for example, an electronic stethoscope device. In this embodiment, the attachment unit 115 comprises a light support 117 housing light sources, for example, light emitting diodes (LEDs) 125 exemplarily illustrated in FIGS. 11A-11B and FIGS. 11F-11G, positioned on a predefined section along the length of the attachment unit 115, for example, on a section 115e proximal to the rear end 115b of the attachment unit 115 as exemplarily illustrated in FIG. 10A. As exemplarily illustrated in FIG. 10A, the attachment unit 115 for the stethoscope device 134 is of a substantially longer length, that is, a length sufficient to permit medical imaging of anatomical examination areas, and to allow a doctor to view a patient's body through the image capture device 106 exemplarily illustrated in FIG. 11A. The stethoscope device 134 comprises an array of piezoelectric microphones 2201 exemplarily illustrated in FIG. 22, and a touchscreen 135, for example, a liquid crystal display (LCD) touchscreen as exemplarily illustrated in FIG. 10A. The piezoelectric microphones 2201 of the stethoscope device 134 convert internal sounds from the patient's body to electrical signals that are transmitted to the diagnosis control unit 101 through the spring contact connectors 118 connected to the connector slot 112 of the diagnosis control unit 101 exemplarily illustrated in FIG. 1B. The touchscreen 135 displays information associated with operations and controls of the stethoscope device 134.

Figure 10B:
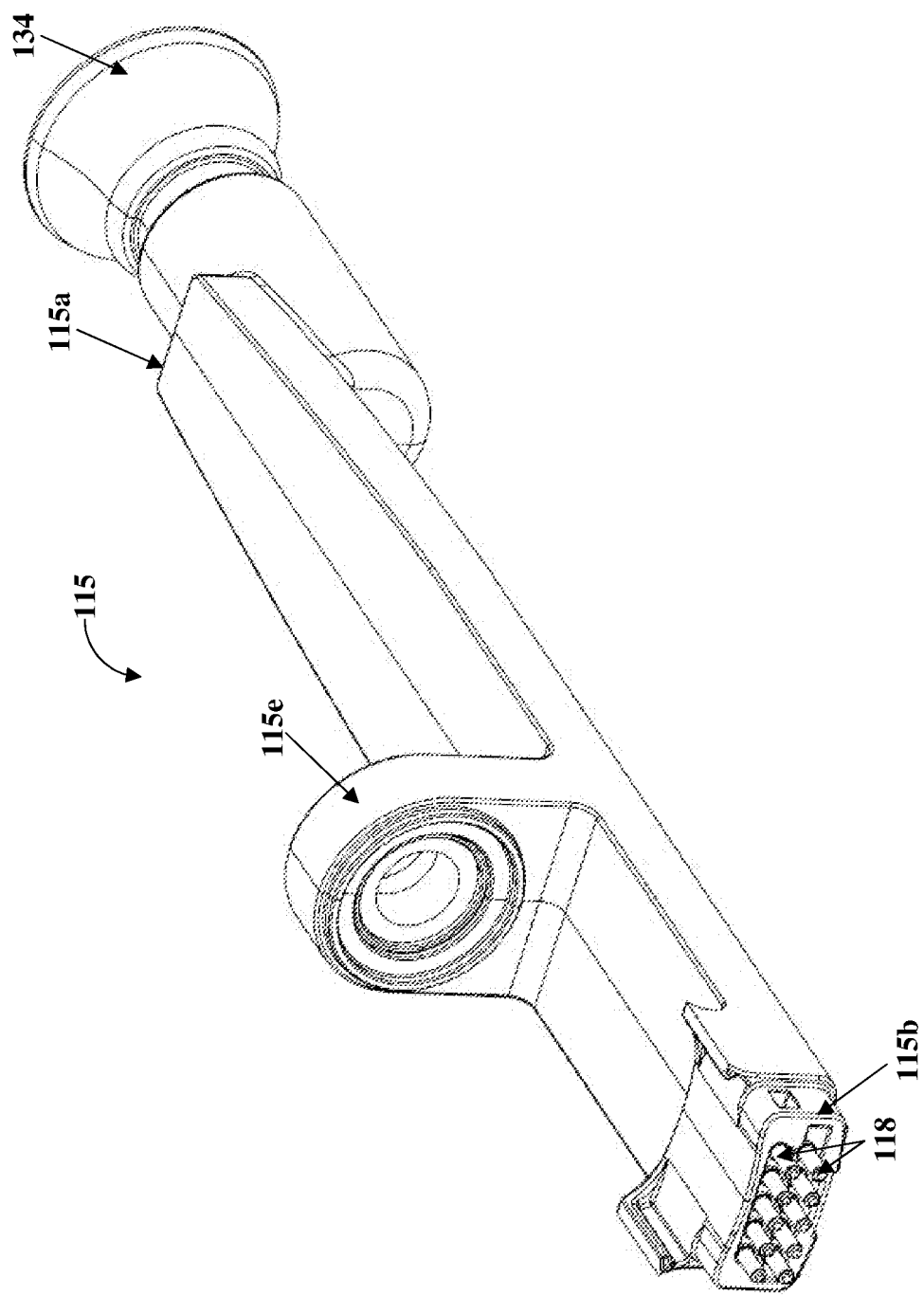
FIG. 10B exemplarily illustrates a rear perspective view of the embodiment of the attachment unit shown in FIG. 10A, showing spring contact connectors positioned at the rear end of the attachment unit for electrically connecting the stethoscope device positioned at the front end of the attachment unit to the microcontroller of the diagnosis control unit.

FIG. 10B exemplarily illustrates a rear perspective view of the embodiment of the attachment unit 115 shown in FIG. 10A, showing the spring contact connectors 118 positioned at the rear end 115b of the attachment unit 115 for electrically connecting the stethoscope device 134 positioned at the front end 115a of the attachment unit 115 to the microcontroller 2004 exemplarily illustrated in FIG. 20. If a user, for example, a medical assistant wants to use the stethoscope device 134 with the multipurpose diagnostic examination apparatus 100 exemplarily illustrated in FIGS. 11A-11G, the user can connect the spring contact connectors 118 of the attachment unit 115 comprising the stethoscope device 134 exemplarily illustrated in FIGS. 10A-10B, to the connector pads 113 positioned in the connector slot 112 of the diagnosis control unit 101 exemplarily illustrated in FIG. 1B. The stethoscope device 134 connects to the connector pads 113 of the diagnosis control unit 101 via the spring contact connectors 118 of the attachment unit 115. The spring contact connectors 118 are, for example, Mill-Max® spring contact connectors of Mill-Max Mfg. Corp. The stethoscope device 134 communicates diagnostic acoustic data with the medical diagnostic examination system 2506 on a local user device 2505 exemplarily illustrated in FIG. 25, by transmitting the electrical signals generated by the piezoelectric microphones 2201 exemplarily illustrated in FIG. 22, of the stethoscope device 134 to the medical diagnostic examination system 2506 via the connector interface 123, for example, the universal serial bus (USB) connector interface of the diagnosis control unit 101 exemplarily illustrated in FIG. 11G. The stethoscope device 134 requires a substantially small opening and hence centralization of the light sources at the section 115e proximal to the rear end 115b of the attachment unit 115 allows focusing light during diagnostic examination using the stethoscope device 134.

Figure 11A:
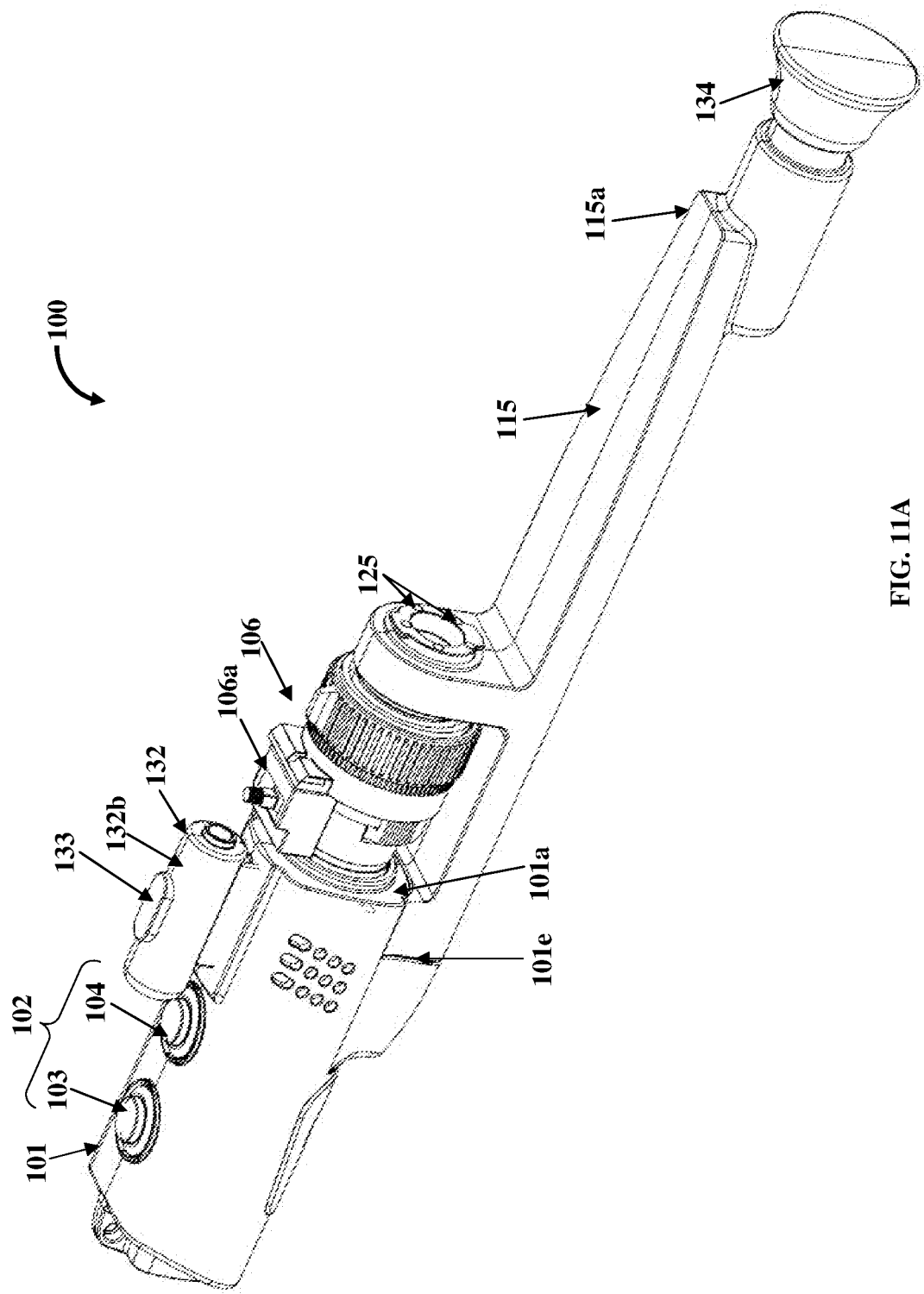
FIG. 11A exemplarily illustrates a left side perspective view of the multipurpose diagnostic examination apparatus, showing light sources, the image capture device removably connected to the front section of the diagnosis control unit, and the stethoscope device operably connected to the front end of the embodiment of the attachment unit shown in FIGS. 10A-10B.

FIG. 11A exemplarily illustrates a left side perspective view of the multipurpose diagnostic examination apparatus 100, showing the light sources comprising, for example, light emitting diodes (LEDs) 125 and a laser pointer 132, the image capture device 106 removably connected to the front section 101a of the diagnosis control unit 101, and the stethoscope device 134 operably connected to the front end 115a of the embodiment of the attachment unit 115 shown in FIGS. 10A-10B. The multipurpose diagnostic examination apparatus 100 comprises trigger elements 102, for example, a power control trigger element 103 and an action control trigger element 104. The power control trigger element 103 and the action control trigger element 104 control activation and deactivation of the stethoscope device 134 and initiation and termination of audio file generation and storage. The laser pointer 132 comprises a power control push button 133 positioned on the upper section 132b of the laser pointer 132 for activating or deactivating the laser pointer 132. The laser pointer 132 is configured to indicate anatomical examination areas on a patient's body to allow a doctor to remotely verify that correct anatomical examination areas are examined. The stethoscope device 134 records and transmits the diagnostic acoustic data to the diagnosis control unit 101 via the attachment unit 115.

Figure 11B:
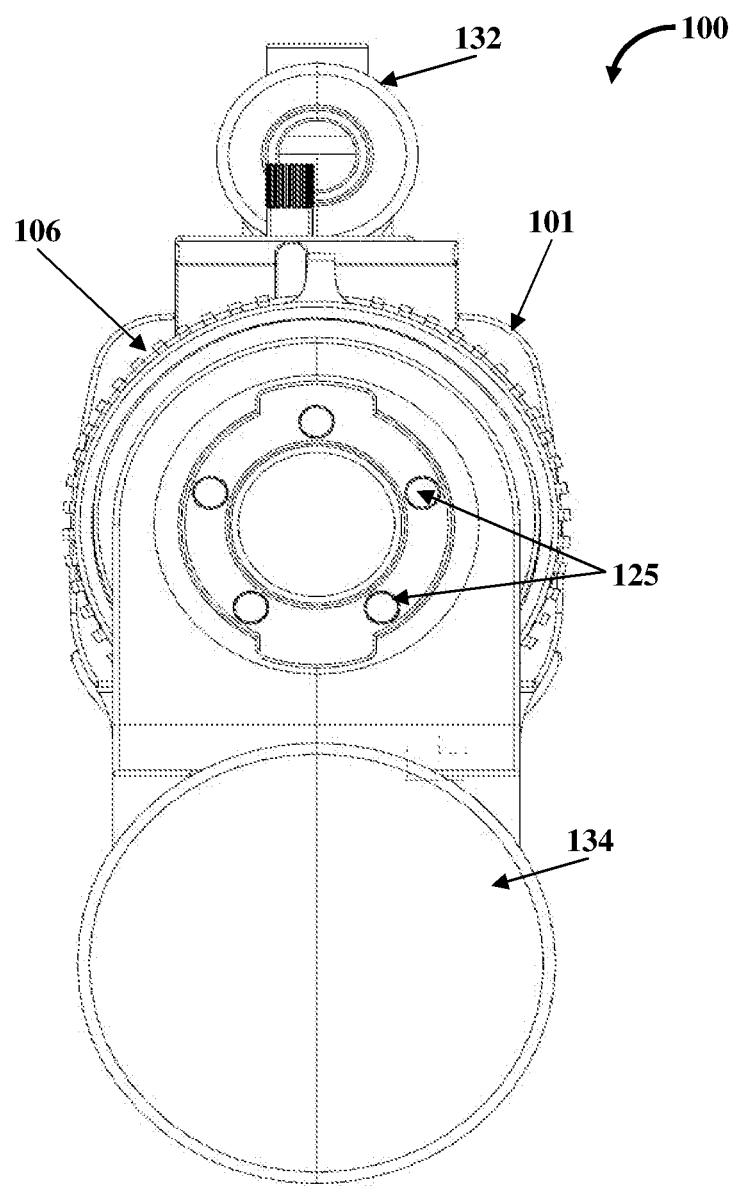
FIG. 11B exemplarily illustrates a front elevation of the multipurpose diagnostic examination apparatus, showing light sources and the stethoscope device.

FIG. 11B exemplarily illustrates a front elevation of the multipurpose diagnostic examination apparatus 100, showing the light sources comprising, for example, the light emitting diodes (LEDs) 125 and the laser pointer 132, and the stethoscope device 134.

Figure 11C:
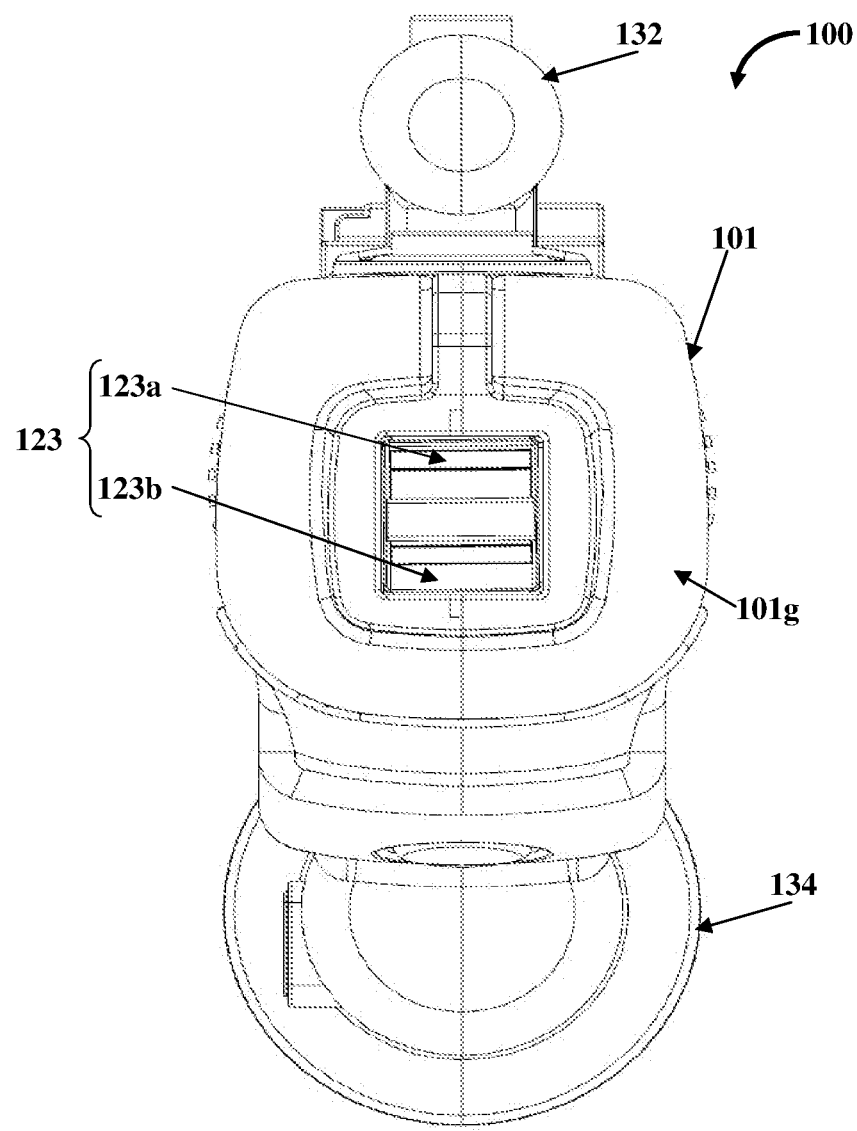
FIG. 11C exemplarily illustrates a rear elevation view of the multipurpose diagnostic examination apparatus, showing the connector interface configured at the rear section of the diagnosis control unit.

FIG. 11C exemplarily illustrates a rear elevation view of the multipurpose diagnostic examination apparatus 100, showing the connector interface 123 configured at the rear section 101g of the diagnosis control unit 101. The connector interface 123 comprising at least two connector elements 123a and 123b is in communication with the stethoscope device 134 connected to the front end 115a of the attachment unit 115 exemplarily illustrated in FIG. 11A, via the connector slot 112 configured at the front end 101e of the diagnosis control unit 101 exemplarily illustrated in FIG. 1B, to receive the diagnostic examination data, for example, the diagnostic acoustic data recorded by the stethoscope device 134. The connector elements 123a and 123b of the connector interface 123 allow communication of the diagnostic acoustic data to the medical diagnostic examination system 2506 exemplarily illustrated in FIG. 25. The connector element 123a or 123b allows serial data communication between the microcontroller 2004 of the diagnosis control unit 101 exemplarily illustrated in FIG. 20, and the medical diagnostic examination system 2506 for controlling operations of the image capture device 106 and/or the stethoscope device 134 exemplarily illustrated in FIGS. 11A-11B, for medical imaging and diagnostic examinations.

Figure 11D:
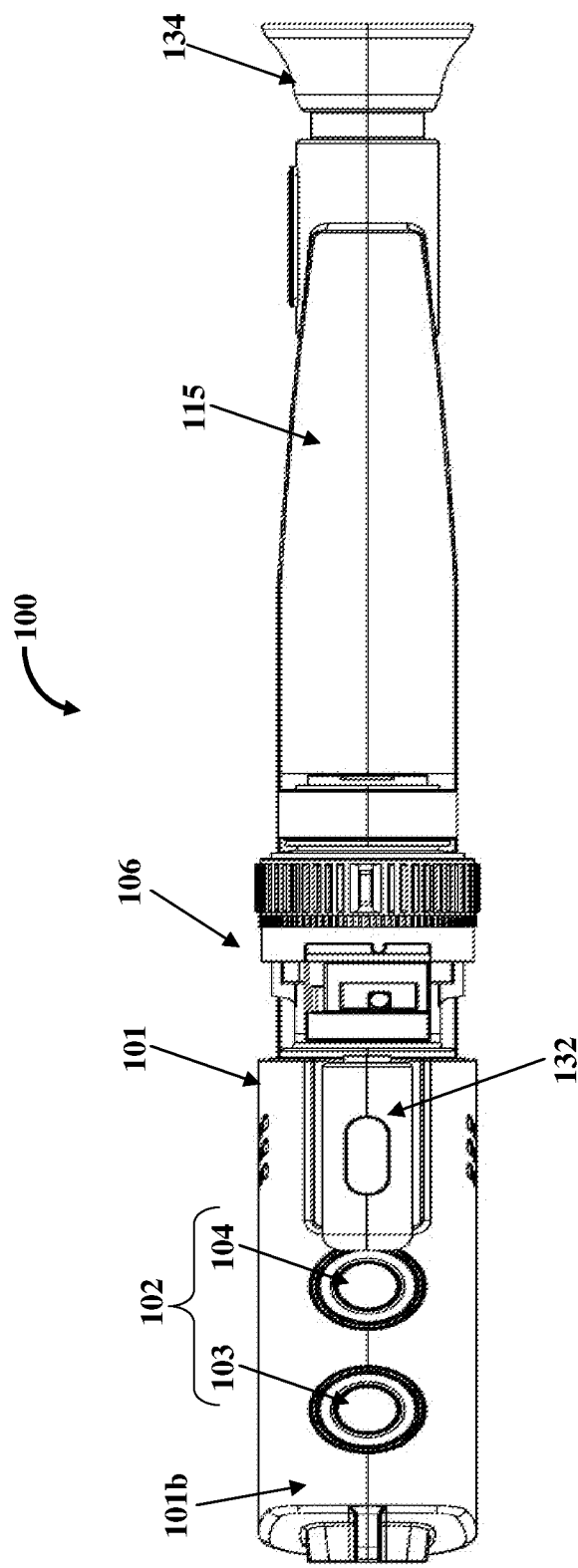
FIG. 11D exemplarily illustrates a top plan view of the multipurpose diagnostic examination apparatus, showing the stethoscope device connected to the embodiment of the attachment unit shown in FIGS. 10A-10B, and the trigger elements positioned on the upper section of the diagnosis control unit.

FIG. 11D exemplarily illustrates a top plan view of the multipurpose diagnostic examination apparatus 100, showing the stethoscope device 134 connected to the embodiment of the attachment unit 115 shown in FIGS. 10A-10B, and the trigger elements 102 comprising the power control trigger element 103 and the action control trigger element 104 positioned on the upper section 101b of the diagnosis control unit 101. The trigger elements 102 control the operation of the stethoscope device 134, the laser pointer 132, and the image capture device 106.

Figure 11E:
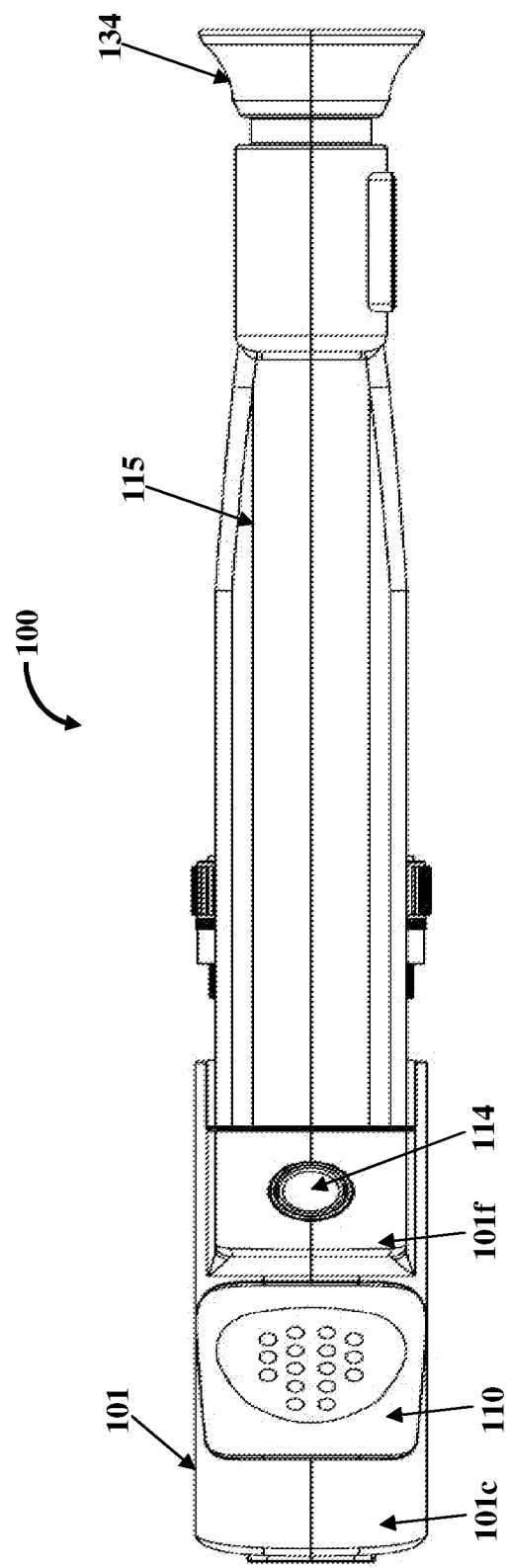
FIG. 11E exemplarily illustrates a bottom view of the multipurpose diagnostic examination apparatus, showing the support element, the release button, and the stethoscope device.

FIG. 11E exemplarily illustrates a bottom view of the multipurpose diagnostic examination apparatus 100, showing the support element 110 on the lower surface 101c of the diagnosis control unit 101, the release button 114 positioned on the lower section 101f of the diagnosis control unit 101, and the stethoscope device 134 connected to the attachment unit 115.

Figure 11F:
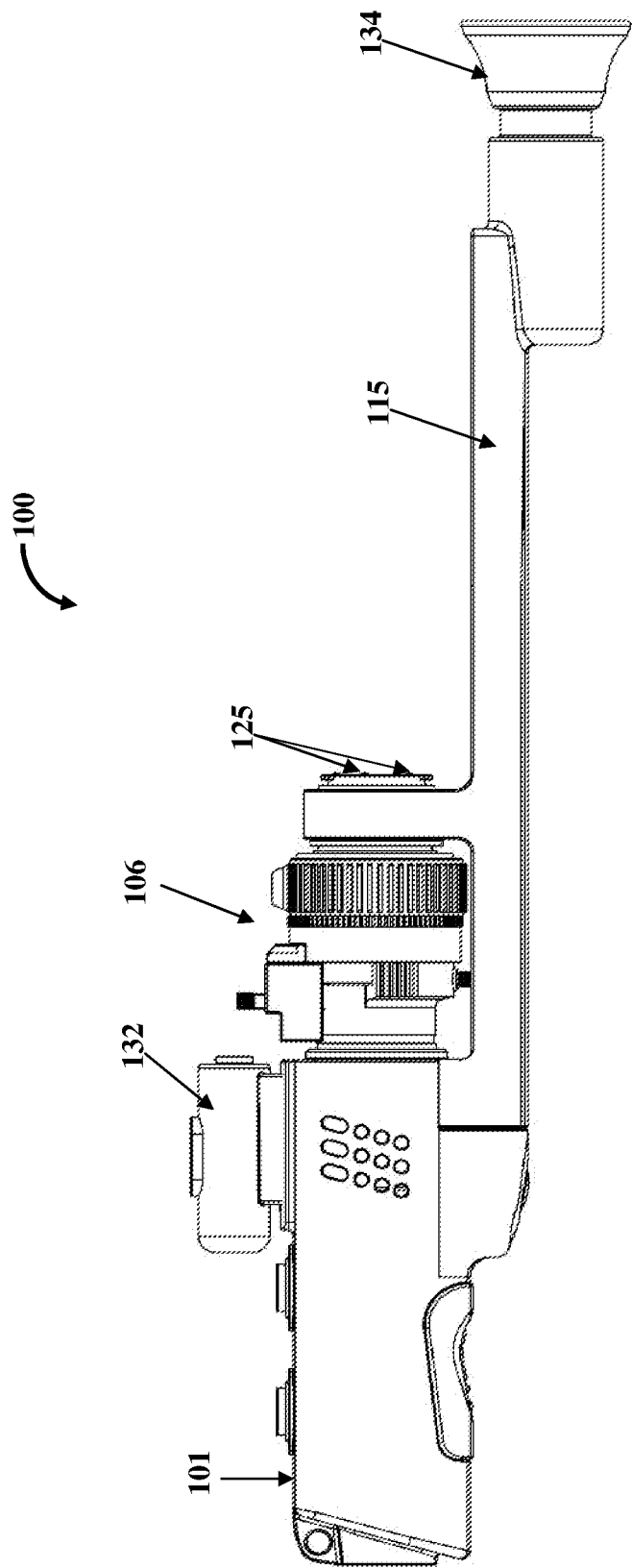
FIG. 11F exemplarily illustrates a left side elevation view of the multipurpose diagnostic examination apparatus, showing the image capture device, light sources, and the stethoscope device.

FIG. 11F exemplarily illustrates a left side elevation view of the multipurpose diagnostic examination apparatus 100, showing the image capture device 106, the light sources comprising, for example, the light emitting diodes (LEDs) 125 and the laser pointer 132, and the stethoscope device 134. The attachment unit 115 for the stethoscope device 134 is of a length sufficient to permit medical imaging of anatomical examination areas, and to allow a doctor to view a patient's body through the image capture device 106. In an embodiment, the attachment unit 115 is configured to have one of different lengths. In an embodiment, the length of the attachment unit 115 is selected based on a function of a focal length of the optical lens 107 of the image capture device 106 to facilitate medical imaging.

Figure 11G:
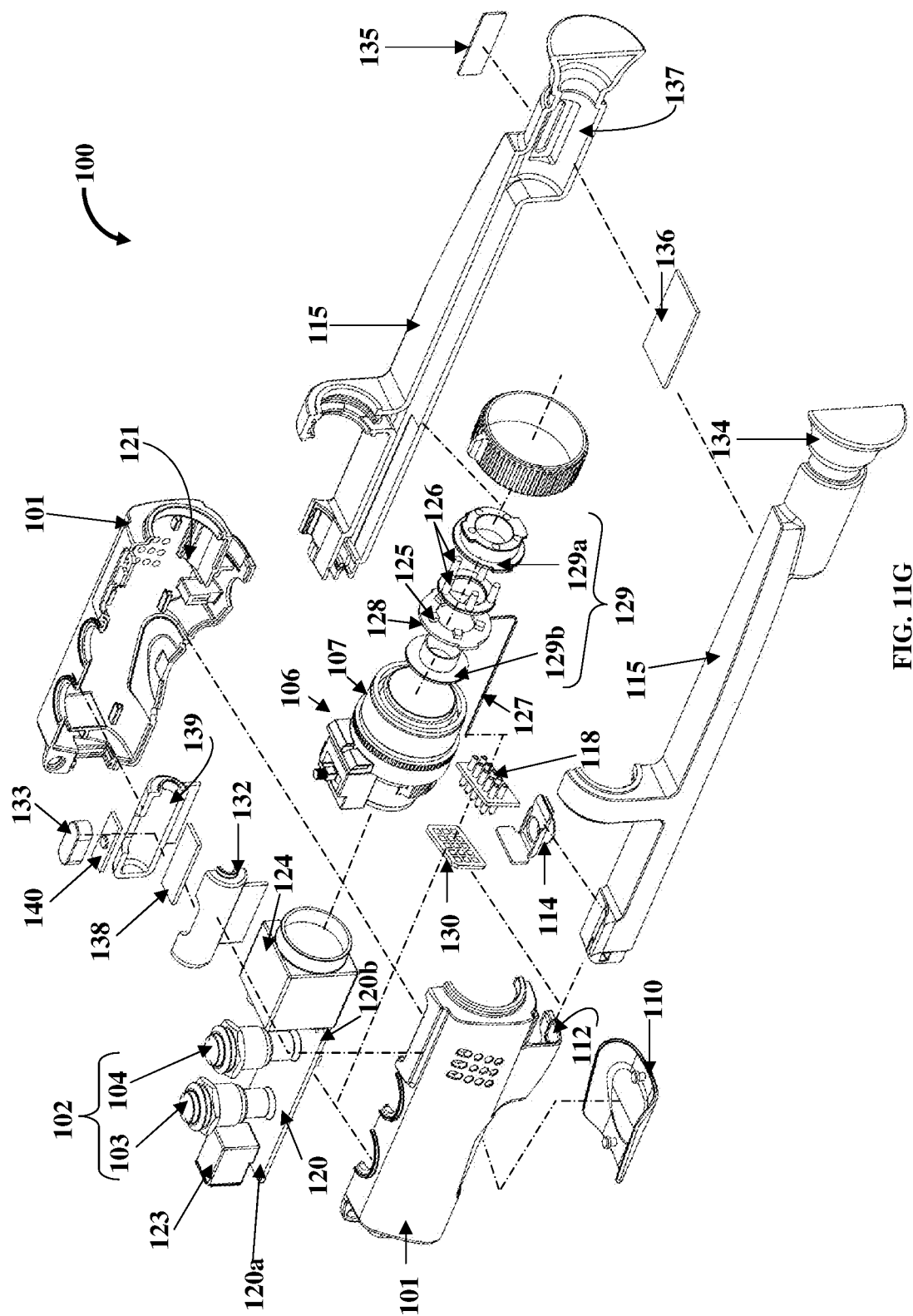
FIG. 11G exemplarily illustrates an exploded view of the multipurpose diagnostic examination apparatus comprising the diagnosis control unit, the attachment unit, the image capture device, the stethoscope device, and light sources.

FIG. 11G exemplarily illustrates an exploded view of the multipurpose diagnostic examination apparatus 100 comprising the diagnosis control unit 101, the attachment unit 115, the image capture device 106, the stethoscope device 134, and the light sources, for example, the light emitting diodes (LEDs) 125 and the laser pointer 132. The exploded view shows the trigger elements 102, for example, the power control trigger element 103 and the action control trigger element 104. The exploded view also shows the support element 110 and the release button 114. The power control trigger element 103 and the action control trigger element 104 are positioned on a printed circuit board (PCB) 120 housed in a cavity 121 of the diagnosis control unit 101. The exploded view also shows the connector interface 123 positioned on the rear section 120a of the PCB 120 and the camera module 124 positioned on the front section 120b of the PCB 120. The image capture device 106 is removably connected to the camera module 124 of the diagnosis control unit 101. The camera module 124 is in operable communication with the optical lens 107 of the image capture device 106. The stethoscope device 134 comprises the touchscreen 135 configured to display information associated with operations and controls of the stethoscope device 134. A PCB 136 of the stethoscope device 134 is positioned inside a cavity 137 of the stethoscope device 134.

FIG. 11G also exemplarily illustrates an electrical configuration of the LEDs 125. As exemplarily illustrated in FIG. 11G, wires 127 extending from the PCB 128 of the LEDs 125 are connected to the spring contact connectors 118 of the attachment unit 115. The spring contact connectors 118 of the attachment unit 115 operably connect to the connector pad PCB 130 housed in the connector slot 112 of the diagnosis control unit 101. The PCB 128 of the LEDs 125, the LEDs 125, and the light pipes 126 are housed within the front portion 129a and the rear portion 129b of the light pipe holder 129. The exploded view also shows a PCB 138 and the power control push button 133 of the laser pointer 132. The PCB 138 of the laser pointer 132 is housed in a cavity 139 of the laser pointer 132. The power control push button 133 is connected to a power control push button PCB 140 that is housed in the cavity 139 of the laser pointer 132.

Figure 12A:
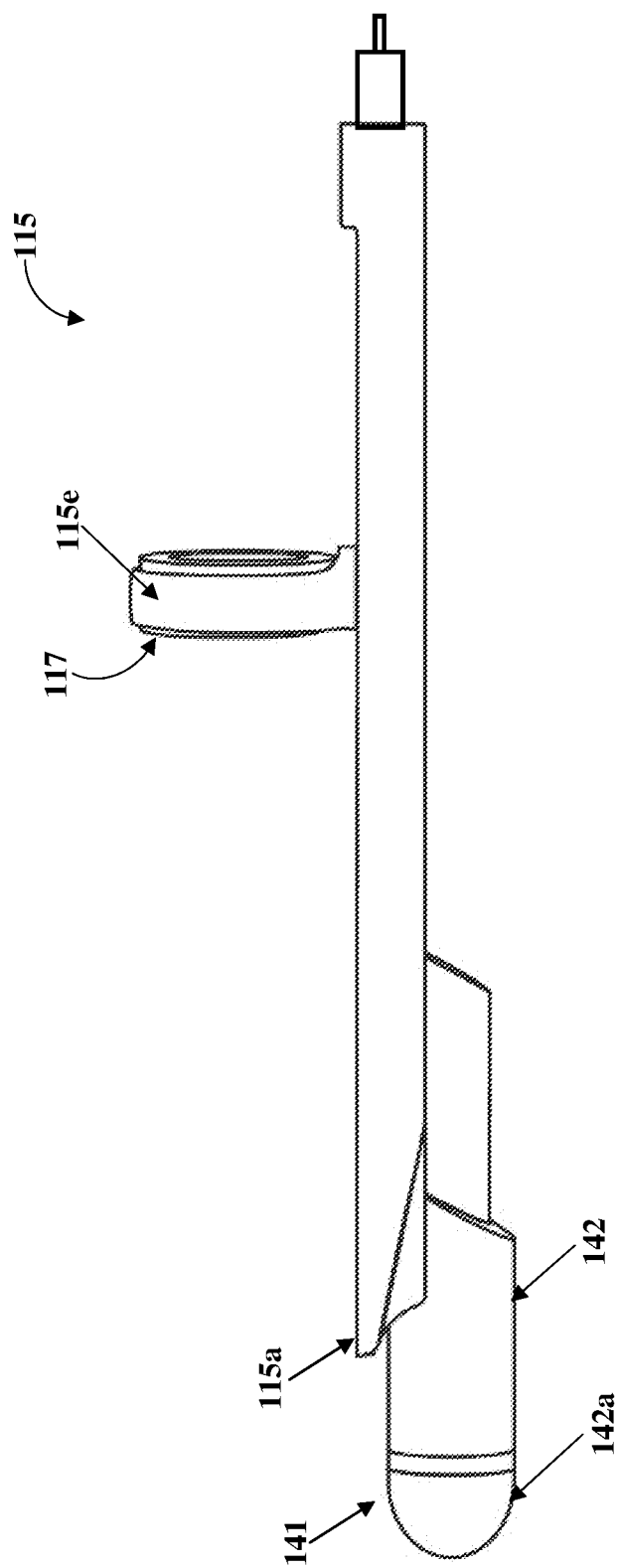
FIG. 12A exemplarily illustrates a right side perspective view of an embodiment of the attachment unit, showing an ultrasound device operably connected to a front end of the attachment unit.

FIG. 12A exemplarily illustrates a right side perspective view of an embodiment of the attachment unit 115, showing an ultrasound device 141 operably connected to a front end 115a of the attachment unit 115. The ultrasound device 141 uses high frequency sound waves to create an image of a body part, for example, stomach, liver, heart, tendons, muscles, joints and blood vessels inside a patient's body. In this embodiment, the attachment unit 115 comprises a light support 117 housing the light sources, for example, light emitting diodes (LEDs) 125 exemplarily illustrated in FIGS. 13A-13B and FIGS. 13F-13H, on a predefined section along the length of the attachment unit 115, for example, on a section 115e proximal to the rear end 115b of the attachment unit 115. The attachment unit 115 for the ultrasound device 141 is of a length sufficient to permit medical imaging of anatomical examination areas, and to allow a doctor to view a patient's body through the image capture device 106 exemplarily illustrated in FIG. 13A. The length of the attachment unit 115 is determined based on the focal length of the optical lens 107 of the image capture device 106 exemplarily illustrated in FIG. 13H.

The ultrasound device 141 comprises a configurable ultrasound probe 142, that is, a replaceable transducer ultrasound probe. The ultrasound probe 142 is selected based on diagnostics required. The ultrasound device 141 further comprises ultrasonic transducer sensors 142a positioned on the ultrasound probe 142. The ultrasonic transducer sensors 142a are configured to receive diagnostic examination data, when the ultrasound device 141 is placed in contact with anatomical examination areas. The ultrasound device 141 requires a relatively small opening and hence centralization of the light emitting diodes (LEDs) 125 at the section 115e proximal to the rear end 115b of the attachment unit 115 helps in focusing light during a diagnostic examination using the ultrasound device 141.

Figure 12B:
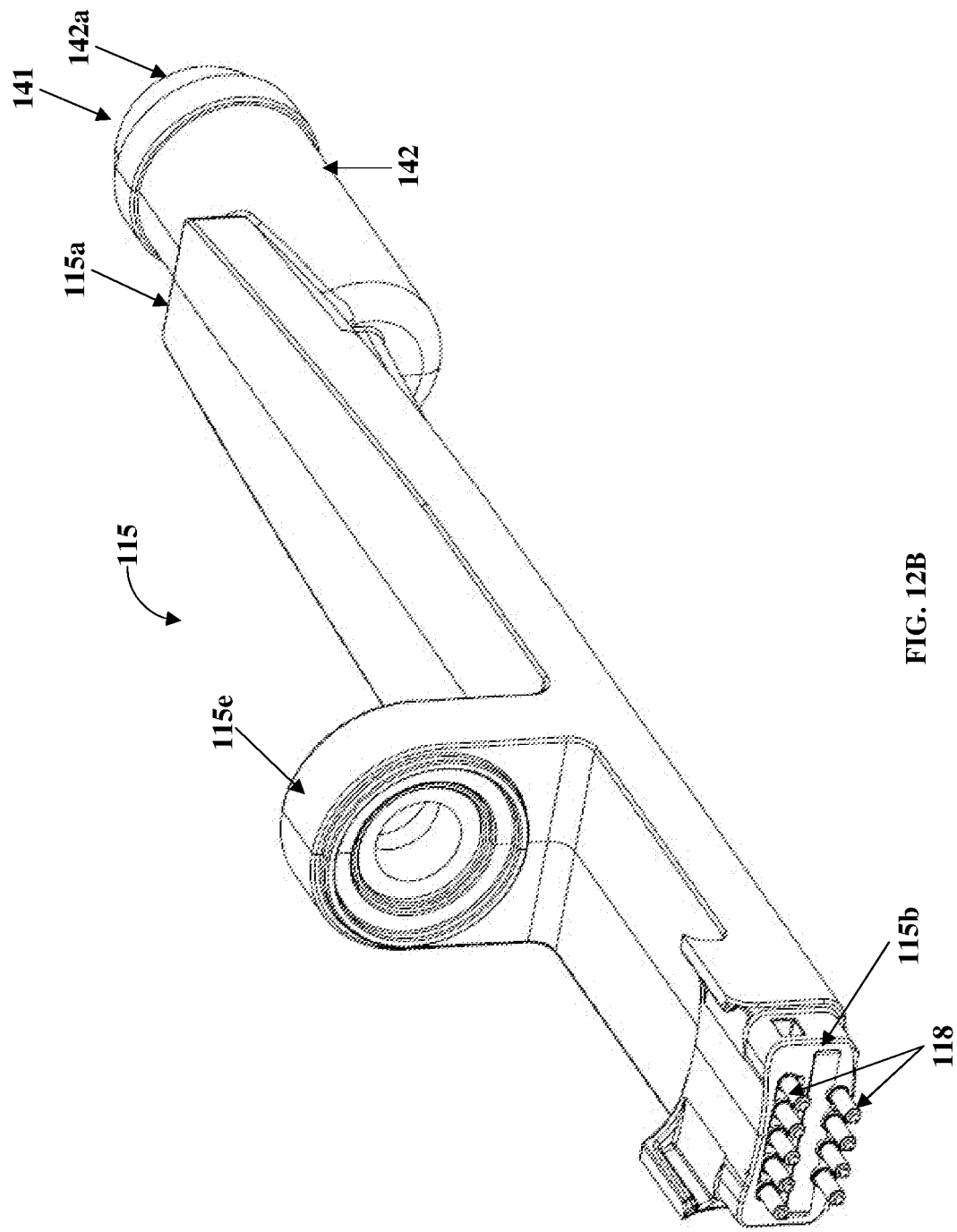
FIG. 12B exemplarily illustrates a rear perspective view of the embodiment of the attachment unit shown in FIG. 12A, showing spring contact connectors positioned at the rear end of the attachment unit for electrically connecting the ultrasound device positioned at the front end of the attachment unit to the microcontroller of the diagnosis control unit.

FIG. 12B exemplarily illustrates a rear perspective view of the embodiment of the attachment unit 115 shown in FIG. 12A, showing the spring contact connectors 118 positioned at the rear end 115b of the attachment unit 115 for electrically connecting the ultrasound device 141 positioned at the front end 115a of the attachment unit 115 to the microcontroller 2004 of the diagnosis control unit 101 exemplarily illustrated in FIG. 20. If a user, for example, a medical assistant wants to use the ultrasound device 141 with the multipurpose diagnostic examination apparatus 100 exemplarily illustrated in FIGS. 13A-13H, the user can connect the spring contact connectors 118 of the attachment unit 115 comprising the ultrasound device 141 exemplarily illustrated in FIGS. 12A-12B, to the connector pads 113 positioned in the connector slot 112 of the diagnosis control unit 101 exemplarily illustrated in FIG. 1B. The ultrasound device 141 connects to the connector pads 113 of the diagnosis control unit 101 via the spring contact connectors 118 of the attachment unit 115. The spring contact connectors 118 are, for example, Mill-Max® spring contact connectors of Mill-Max Mfg. Corp. The ultrasonic transducer sensors 142a of the ultrasound device 141 transmit the diagnostic examination data through the ultrasound probe 142 and to the diagnosis control unit 101 via the attachment unit 115 exemplarily illustrated in FIGS. 13A-13H. The ultrasound device 141 communicates the diagnostic examination data with the medical diagnostic examination system 2506 on a local user device 2505 exemplarily illustrated in FIG. 25, by transmitting the electrical signals generated by the ultrasonic transducer sensors 142a of the ultrasound device 141 to the medical diagnostic examination system 2506 via the connector interface 123, for example, the universal serial bus (USB) connector interface of the diagnosis control unit 101 exemplarily illustrated in FIG. 13H.

Figure 13A:
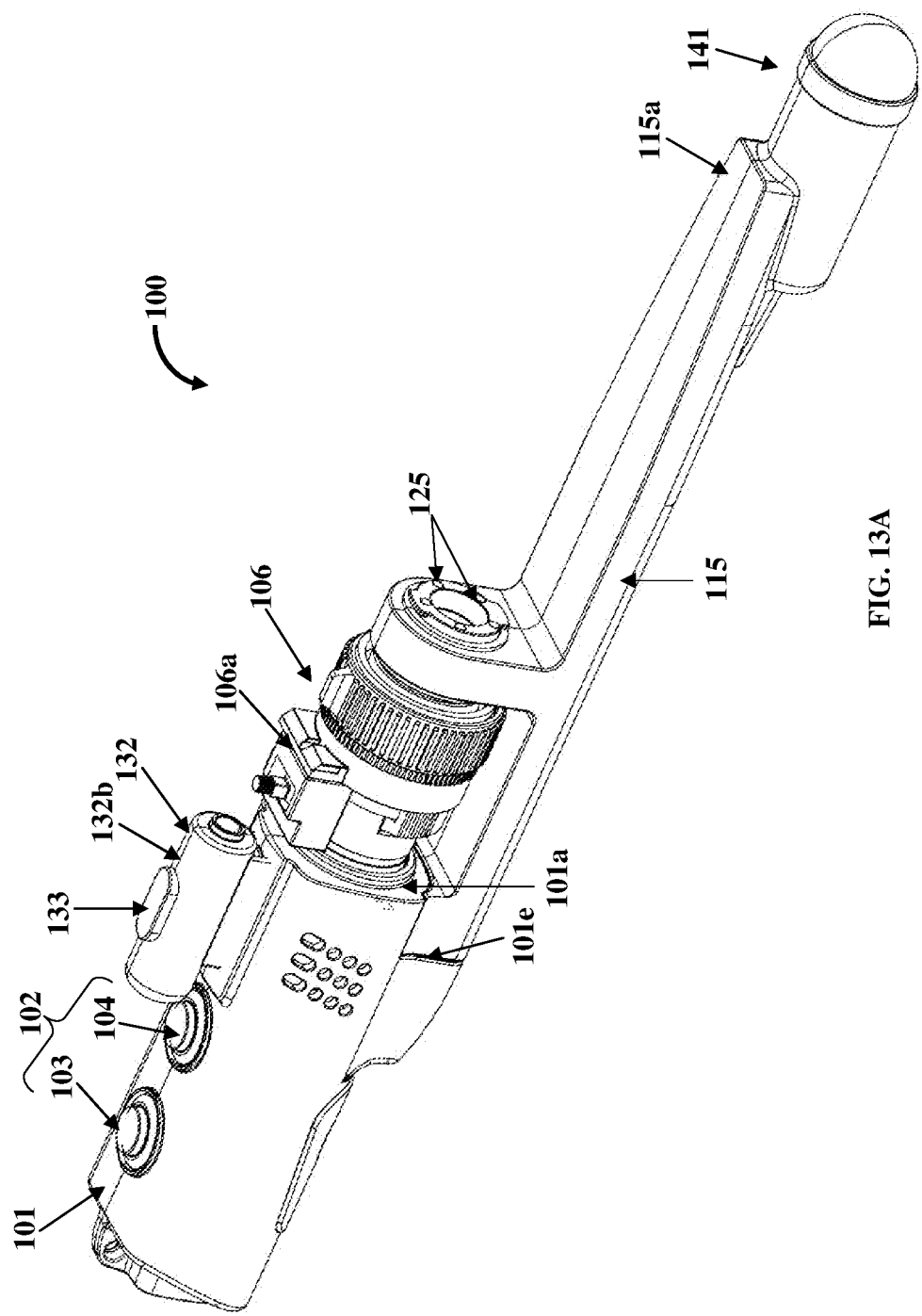
FIG. 13A exemplarily illustrates a left side perspective view of the multipurpose diagnostic examination apparatus, showing the image capture device removably connected to the front section of the diagnosis control unit, light sources operably connected to the diagnosis control unit, and the ultrasound device operably connected to the front end of the embodiment of the attachment unit shown in FIGS. 12A-12B.

FIG. 13A exemplarily illustrates a left side perspective view of the multipurpose diagnostic examination apparatus 100, showing the image capture device 106 removably connected to the front section 101a of the diagnosis control unit 101, light sources comprising light emitting diodes (LEDs) 125 and a laser pointer 132 operably connected to the diagnosis control unit 101, and the ultrasound device 141 operably connected to the front end 115a of the embodiment of the attachment unit 115 shown in FIGS. 12A-12B. The attachment unit 115 is detachably connected to and extends from the front end 101e of the diagnosis control unit 101. The multipurpose diagnostic examination apparatus 100 comprises trigger elements 102, for example, a power control trigger element 103 and an action control trigger element 104. The power control trigger element 103 and the action control trigger element 104 activate and deactivate the ultrasound device 141 connected to the attachment unit 115, and control initiation and termination of ultrasound image capturing and storage. The laser pointer 132 comprises a power control push button 133 positioned on the upper section 132b of the laser pointer 132 for activating or deactivating the laser pointer 132. The laser pointer 132 is configured to indicate anatomical examination areas on a patient's body to allow a doctor to remotely verify that correct anatomical examination areas are examined. The ultrasound device 141 records and transmits the diagnostic examination data, for example, the ultrasound image data to the diagnosis control unit 101 via the attachment unit 115.

Figure 13B:
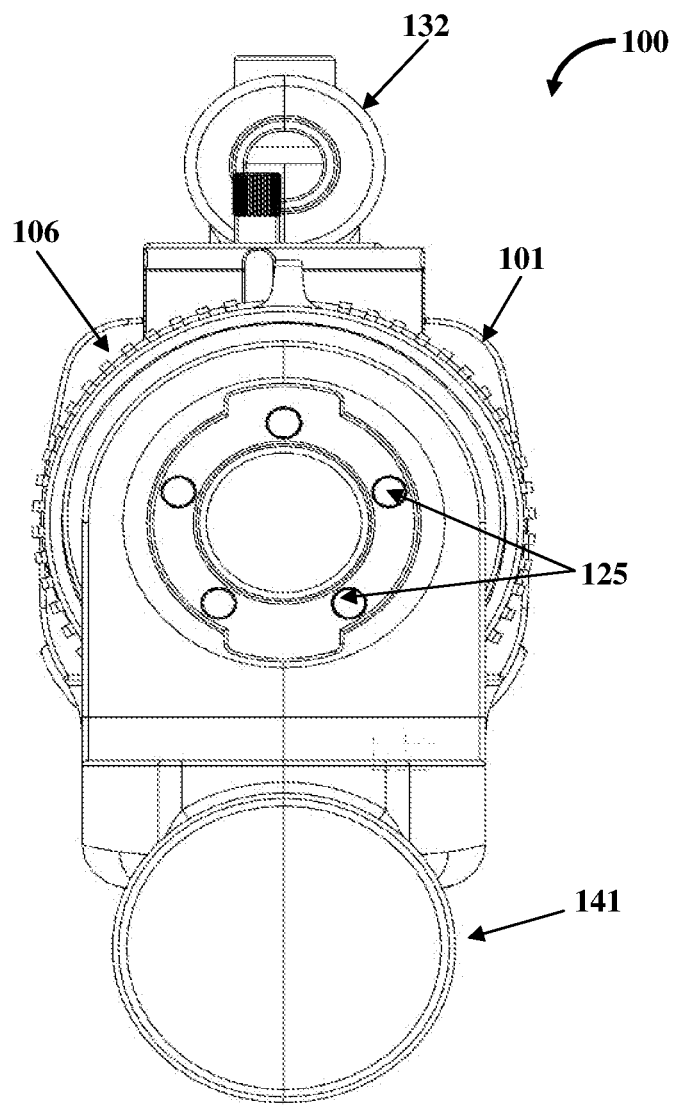
FIG. 13B exemplarily illustrates a front elevation of the multipurpose diagnostic examination apparatus, showing light sources and the ultrasound device.

FIG. 13B exemplarily illustrates a front elevation of the multipurpose diagnostic examination apparatus 100, showing the light sources comprising the light emitting diodes (LEDs) 125 and the laser pointer 132, and the ultrasound device 141.

Figure 13C:
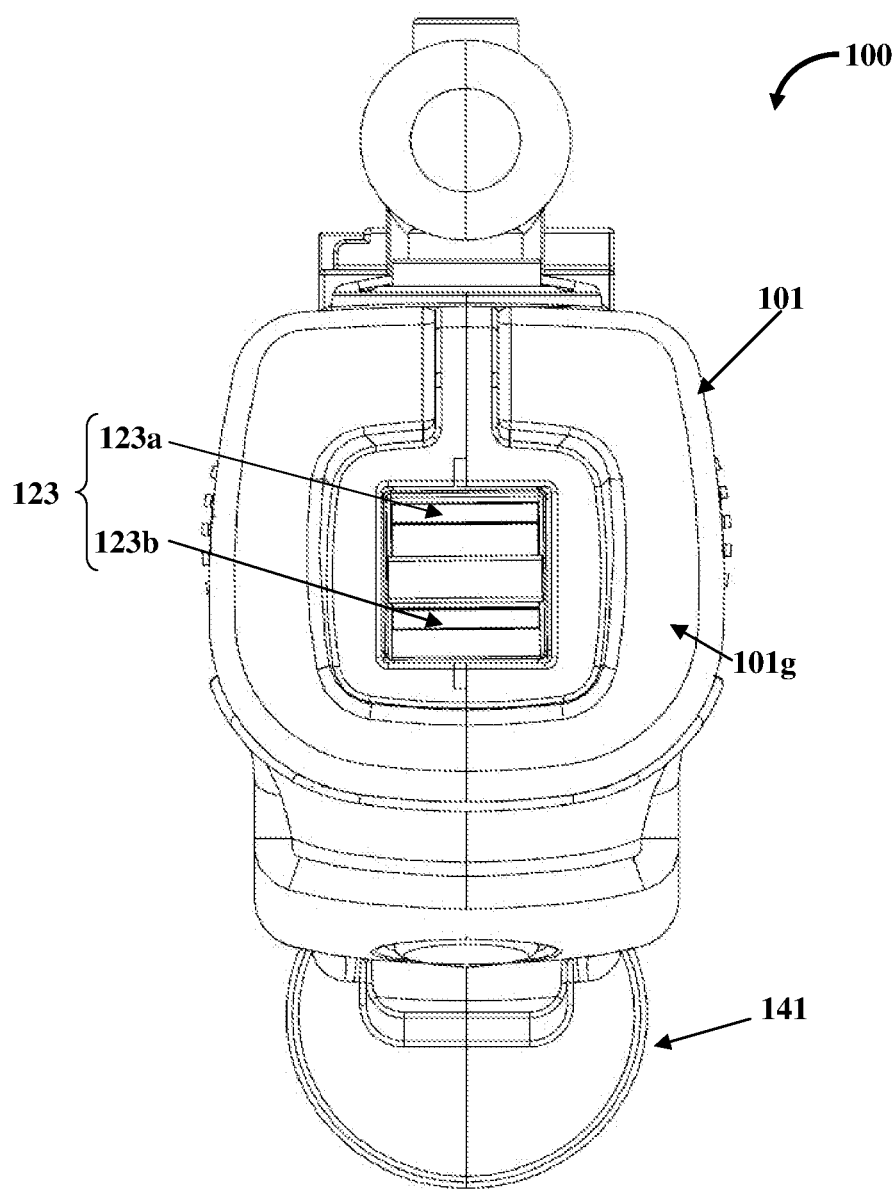
FIG. 13C exemplarily illustrates a rear elevation view of the multipurpose diagnostic examination apparatus, showing the connector interface configured at the rear section of the diagnosis control unit.

FIG. 13C exemplarily illustrates a rear elevation view of the multipurpose diagnostic examination apparatus 100, showing the connector interface 123 configured at the rear section 101g of the diagnosis control unit 101. The connector interface 123 comprising at least two connector elements 123a and 123b is in communication with the ultrasound device 141 connected to the front end 115a of the attachment unit 115 exemplarily illustrated in FIG. 12A, via the connector slot 112 configured at the front end 101e of the diagnosis control unit 101 exemplarily illustrated in FIG. 1B, to receive the diagnostic examination data, for example, the ultrasound image data recorded by the ultrasound device 141. The connector elements 123a and 123b of the connector interface 123 allow communication of the ultrasound image data to the medical diagnostic examination system 2506 exemplarily illustrated in FIG. 25. The connector element 123a or 123b allows serial data communication between the microcontroller 2004 of the diagnosis control unit 101 exemplarily illustrated in FIG. 20, and the medical diagnostic examination system 2506 for controlling operations of the image capture device 106 and/or the ultrasound device 141 exemplarily illustrated in FIGS. 13A-13B, for medical imaging and diagnostic examinations.

Figure 13D:
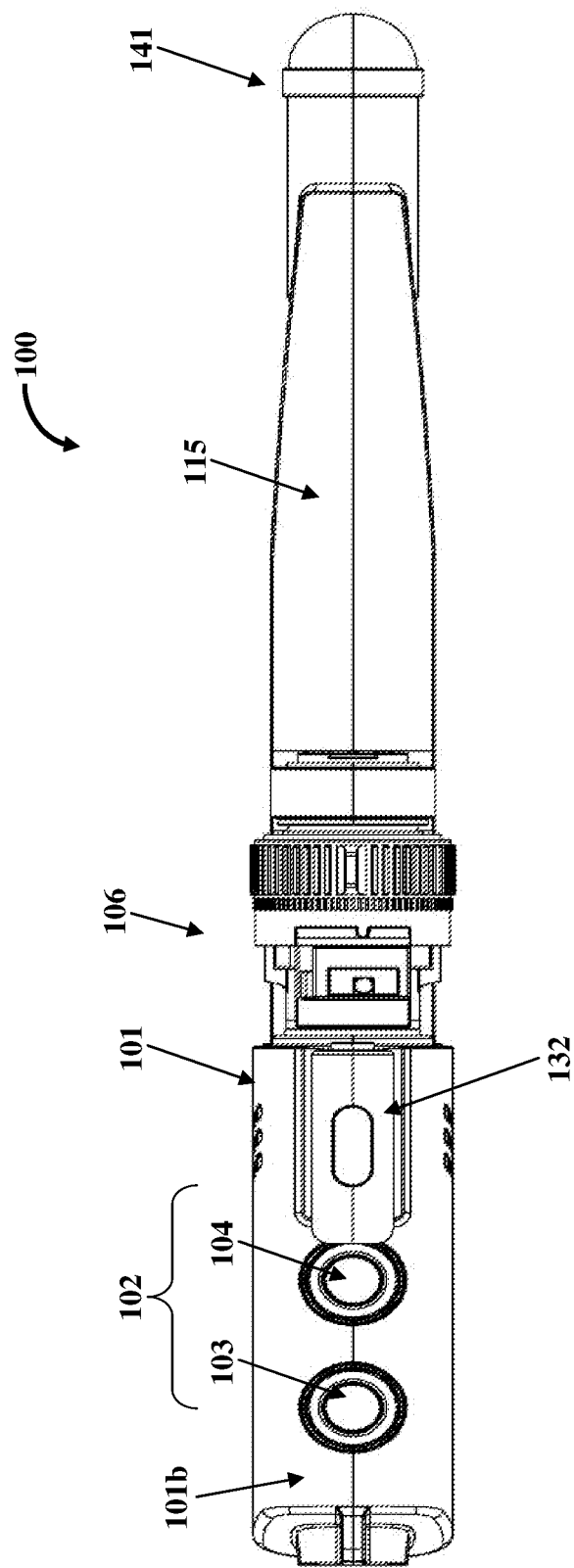
FIG. 13D exemplarily illustrates a top plan view of the multipurpose diagnostic examination apparatus, showing trigger elements positioned on the upper section of the diagnosis control unit, light sources, the image capture device, and the ultrasound device.

FIG. 13D exemplarily illustrates a top plan view of the multipurpose diagnostic examination apparatus 100, showing trigger elements 102 comprising the power control trigger element 103 and the action control trigger element 104 positioned on the upper section 101b of the diagnosis control unit 101, a light source, for example, the laser pointer 132, the image capture device 106, and the ultrasound device 141. The trigger elements 102 control the operation of the ultrasound device 141, the laser pointer 132, and the image capture device 106.

Figure 13E:
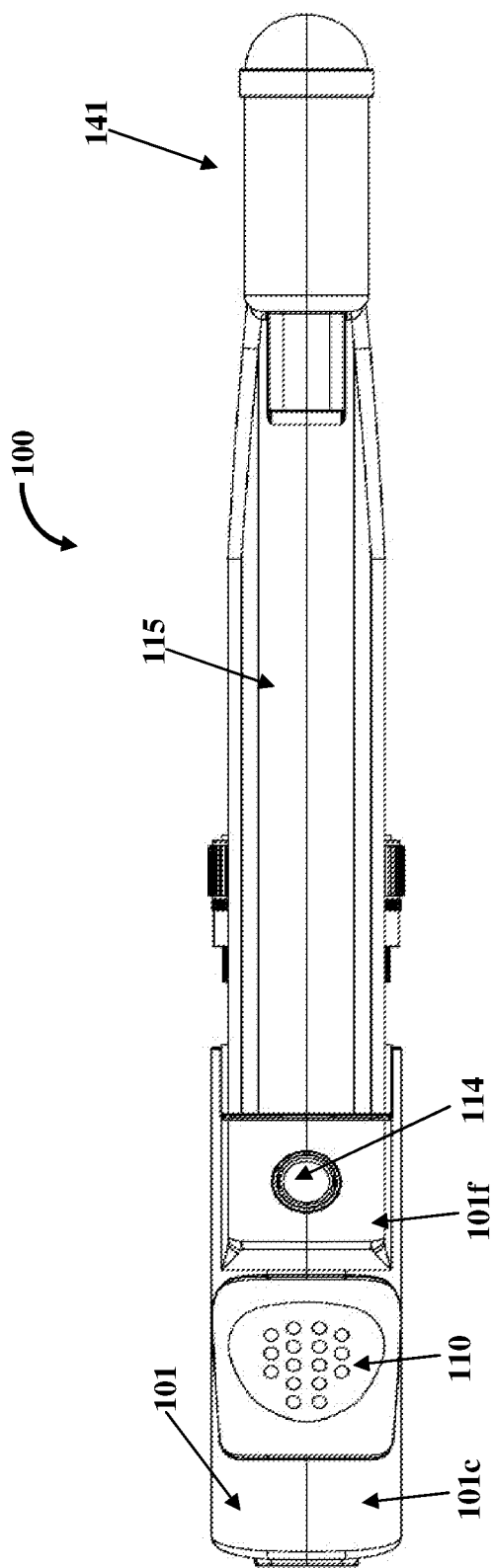
FIG. 13E exemplarily illustrates a bottom view of the multipurpose diagnostic examination apparatus, showing the support element, the release button, and the ultrasound device.

FIG. 13E exemplarily illustrates a bottom view of the multipurpose diagnostic examination apparatus 100, showing the support element 110 on the lower surface 101c of the diagnosis control unit 101, the release button 114 positioned on the lower section 101f of the diagnosis control unit 101, and the ultrasound device 141 connected to the attachment unit 115.

Figure 13F:
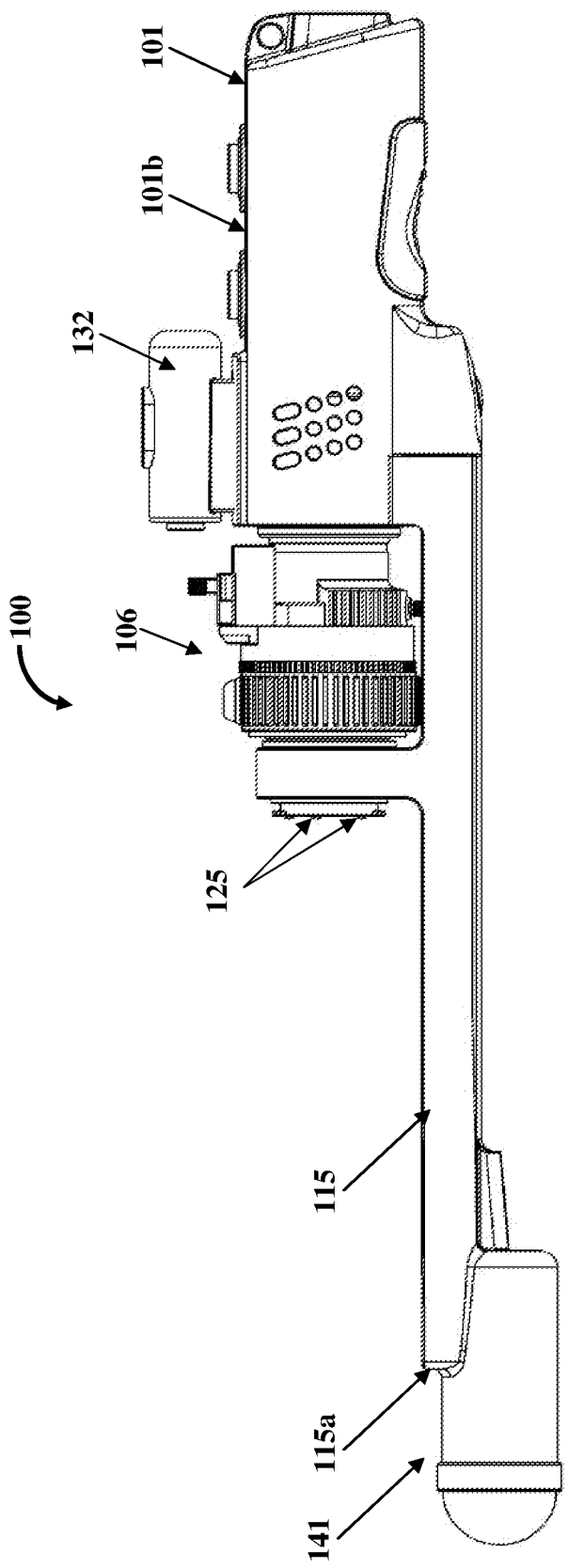
FIGS. 13F-13G exemplarily illustrate side elevation views of the multipurpose diagnostic examination apparatus, showing the image capture device, a light source, and the ultrasound device.
Figure 13G:
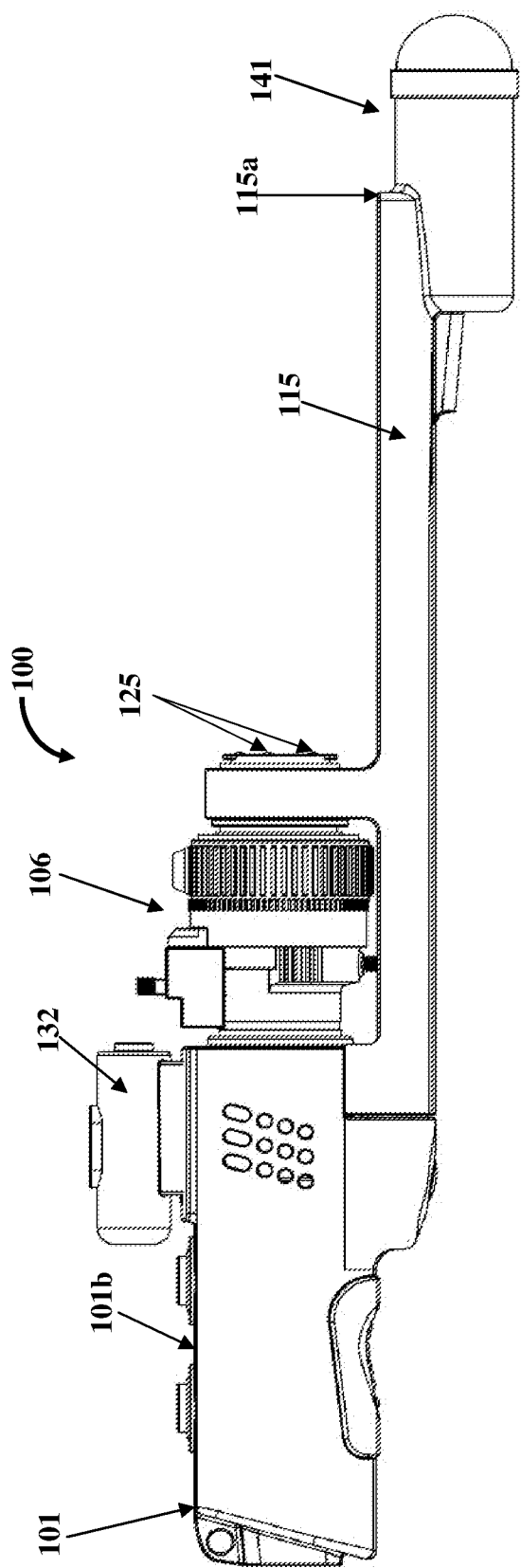

FIGS. 13F-13G exemplarily illustrate side elevation views of the multipurpose diagnostic examination apparatus 100, showing the image capture device 106, the light source, for example, the laser pointer 132 operably connected to the upper section 101b of the diagnosis control unit 101, and the ultrasound device 141 operably connected to the front end 115a of the attachment unit 115.

Figure 13H:
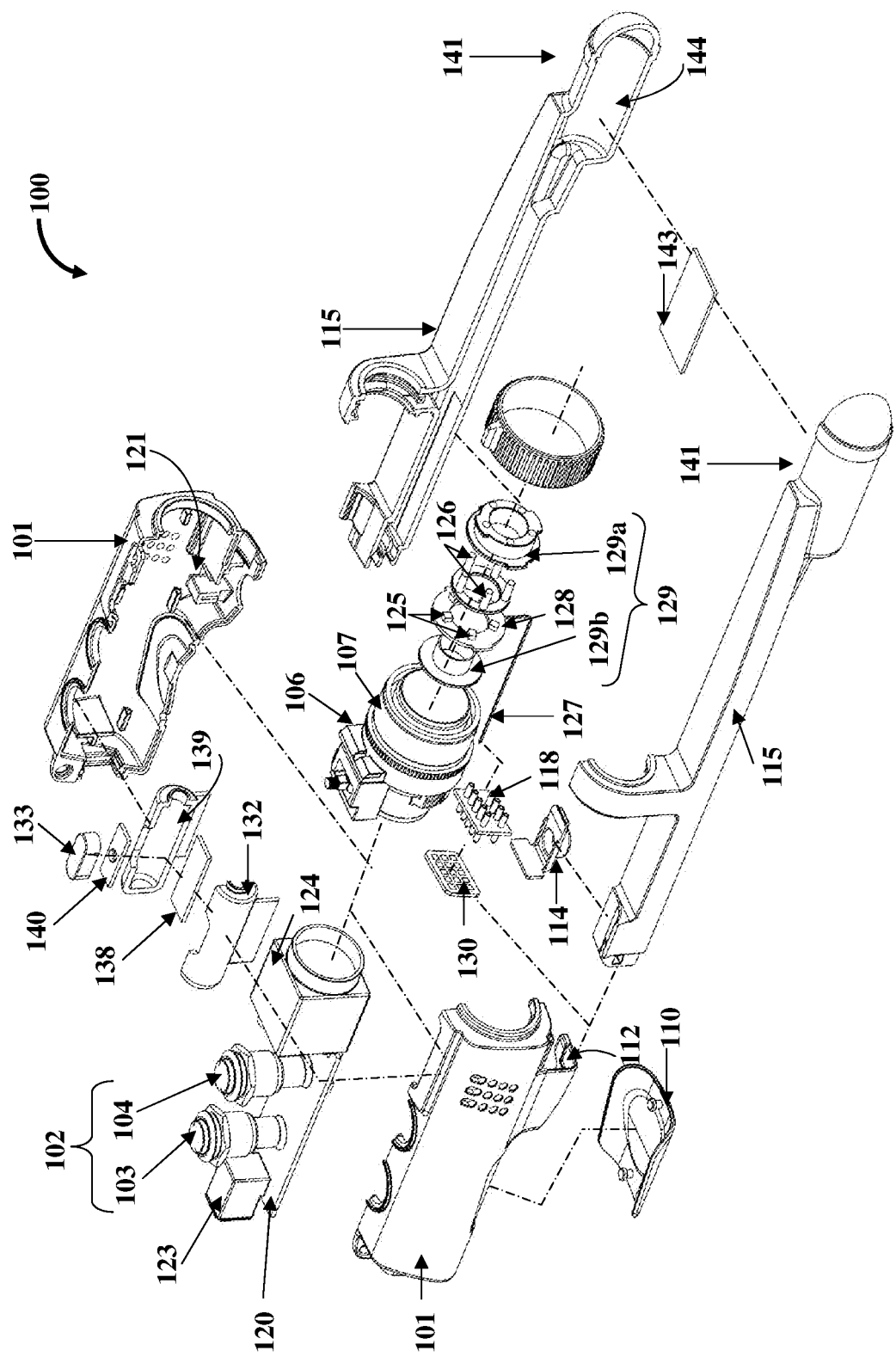
FIG. 13H exemplarily illustrates an exploded view of the multipurpose diagnostic examination apparatus comprising the diagnosis control unit, the attachment unit, the image capture device, the ultrasound device, and light sources.

FIG. 13H exemplarily illustrates an exploded view of the multipurpose diagnostic examination apparatus 100 comprising the diagnosis control unit 101, the attachment unit 115, the image capture device 106, the ultrasound device 141, and the light sources, for example, the light emitting diodes (LEDs) 125 and the laser pointer 132. The exploded view shows the trigger elements 102, for example, the power control trigger element 103 and the action control trigger element 104. The exploded view also shows the support element 110 and the release button 114. The power control trigger element 103 and the action control trigger element 104 are positioned on a printed circuit board (PCB) 120 housed in a cavity 121 of the diagnosis control unit 101. The exploded view also shows the connector interface 123 positioned on the rear section 120a of the PCB 120 and the camera module 124 positioned on the front section 120b of the PCB 120. The image capture device 106 is removably connected to the camera module 124 of the diagnosis control unit 101. The camera module 124 is in operable communication with the optical lens 107 of the image capture device 106. A PCB 143 of the ultrasound device 141 is positioned inside a cavity 144 of the ultrasound device 141.

FIG. 13H also exemplarily illustrates an electrical configuration of the light emitting diodes (LEDs) 125. As exemplarily illustrated in FIG. 13H, wires 127 extending from the PCB 128 of the LEDs 125 are connected to the spring contact connectors 118 of the attachment unit 115. The spring contact connectors 118 of the attachment unit 115 operably connect to the connector pad PCB 130 housed in the connector slot 112 of the diagnosis control unit 101. The PCB 128 of the LEDs 125, the LEDs 125, and the light pipes 126 are housed within the front portion 129a and the rear portion 129b of the light pipe holder 129. The exploded view also shows a PCB 138 and the power control push button 133 of the laser pointer 132. The PCB 138 of the laser pointer 132 is housed in a cavity 139 of the laser pointer 132. The power control push button 133 is connected to a power control push button PCB 140 that is housed in the cavity 139 of the laser pointer 132.

Figure 14A:
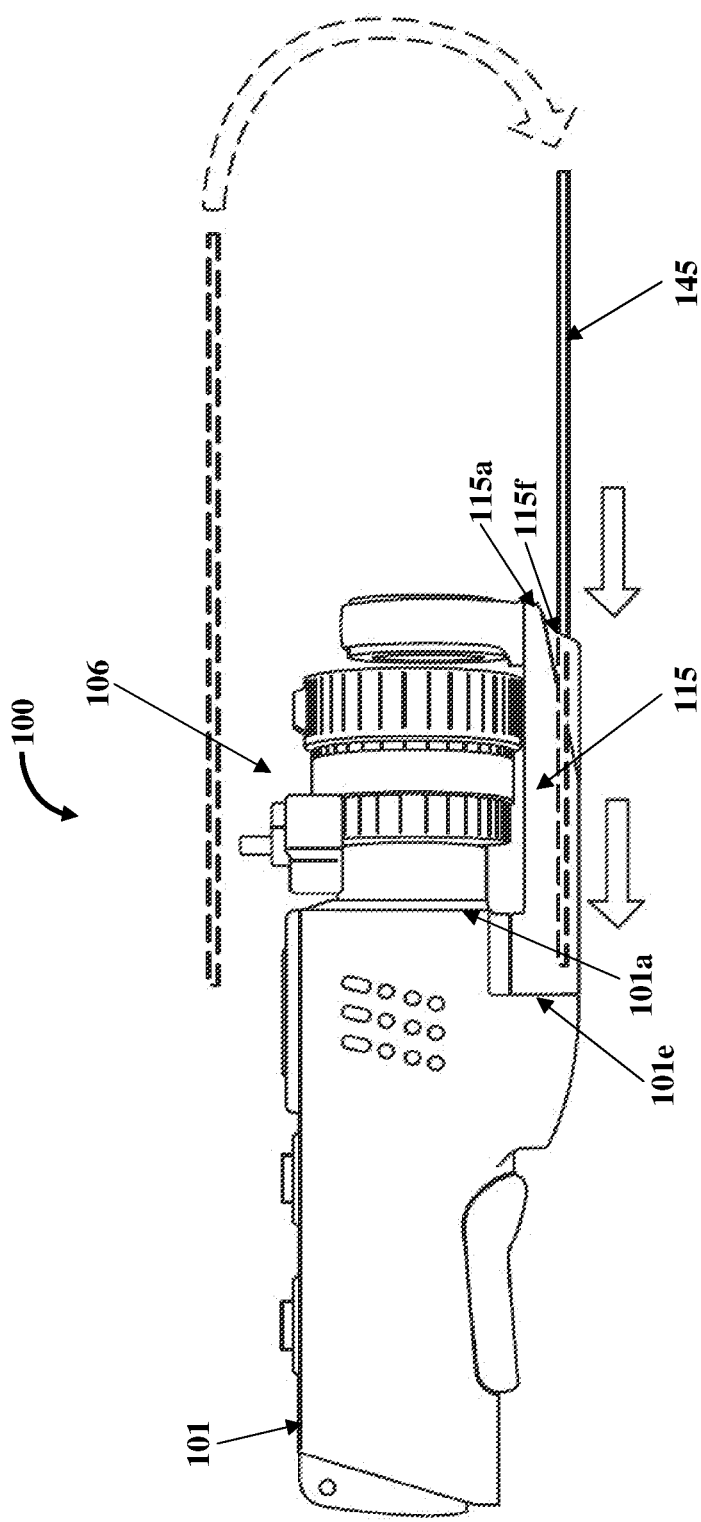
FIG. 14A exemplarily illustrates a left side elevation view of the multipurpose diagnostic examination apparatus, showing an embodiment where a diagnosis assistance element is removably connected to a lower section of the attachment unit.

FIG. 14A exemplarily illustrates a left side elevation view of the multipurpose diagnostic examination apparatus 100, showing an embodiment where a diagnosis assistance element 145 is removably connected to a lower section 115f of the attachment unit 115. In an embodiment, the diagnosis assistance element 145 is a conventional tongue depressor of a predetermined length that can be used, for example, for throat diagnostic examination. The image capture device 106 is removably connected to the front section 101a of the diagnosis control unit 101 to capture images of, for example, a patient's throat during the throat diagnostic examination.

Figure 14B:
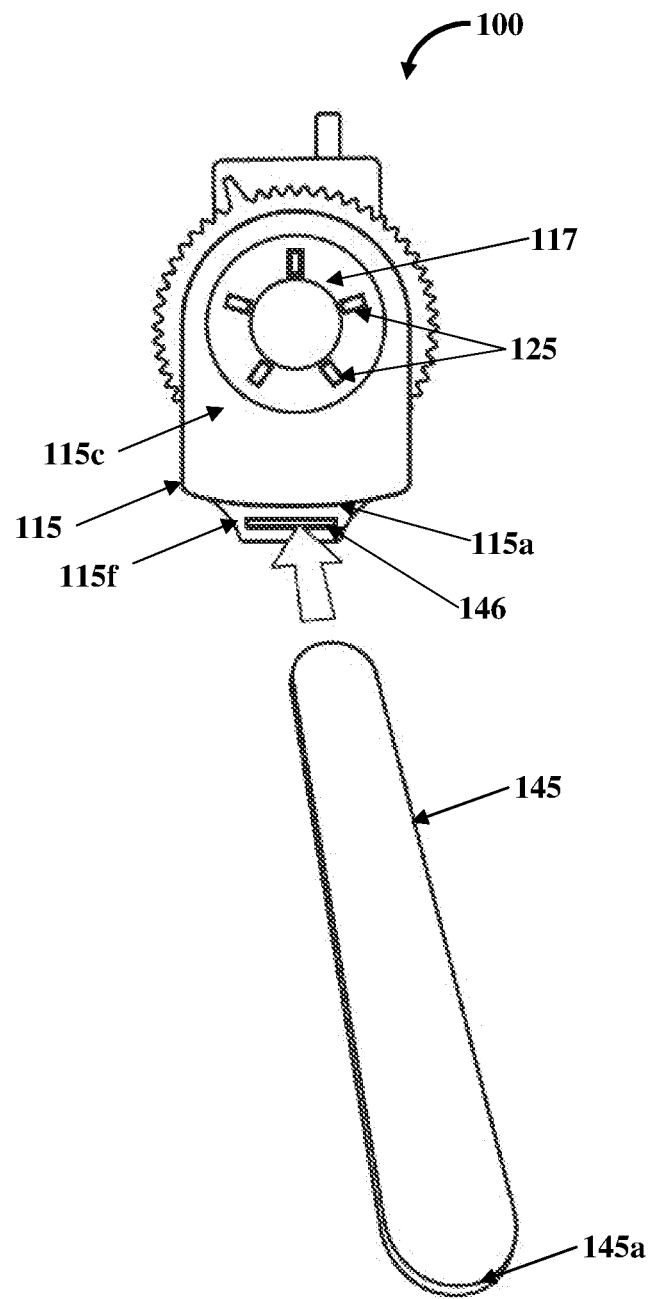
FIG. 14B exemplarily illustrates a front elevation view of the multipurpose diagnostic examination apparatus, showing an embodiment where a supplementary attachment slot is positioned on the lower section of the attachment unit for inserting the diagnosis assistance element.

FIG. 14B exemplarily illustrates a front elevation view of the multipurpose diagnostic examination apparatus 100, showing an embodiment where a supplementary attachment slot 146 is positioned on the lower section 115f of the attachment unit 115 below the front end 115a of the attachment unit 115, for inserting the diagnosis assistance element 145. In an embodiment, the supplementary attachment slot 146 accommodates the diagnosis assistance element 145, for example, a tongue depressor of a predefined length exemplarily illustrated in FIGS. 14A-14G and FIGS. 14J-14M, for facilitating the diagnostic examinations. In an embodiment, the supplementary attachment slot 146 for the diagnosis assistance element 145 is, for example, about 75% of the length of the diagnosis assistance element 145 for facilitating adjustable positioning of the diagnosis assistance element 145 in the supplementary attachment slot 146. In an embodiment, the diagnosis assistance element 145 is configured as a standard disposable tongue depressor.

As exemplarily illustrated in FIG. 14B, a light support 117 positioned on the front section 115c of the attachment unit 115 houses the light sources, for example, light emitting diodes (LEDs) 125. In an embodiment, the light sources are, for example, set of five LEDs 125 arranged in a circle on the front section 115c of the attachment unit 115 of the multipurpose diagnostic examination apparatus 100. The LEDs 125 are configured to illuminate and indicate one or more anatomical examination areas during medical imaging and diagnostic examinations. In an embodiment, light sources, for example, LEDs (not shown) are positioned on the edge 145a of the diagnosis assistance element 145. In this embodiment, the positioning of the light sources at the edge 145a of the diagnosis assistance element 145 improves viewing and examination of hidden items inside a patient's oral cavity that are not visible to a doctor during a typical medical diagnostic examination such as a dental checkup. In this embodiment, a clear plastic sheet can be attached to the edge 145a of the diagnosis assistance element 145 for covering and protecting the light sources.

Figure 14C:
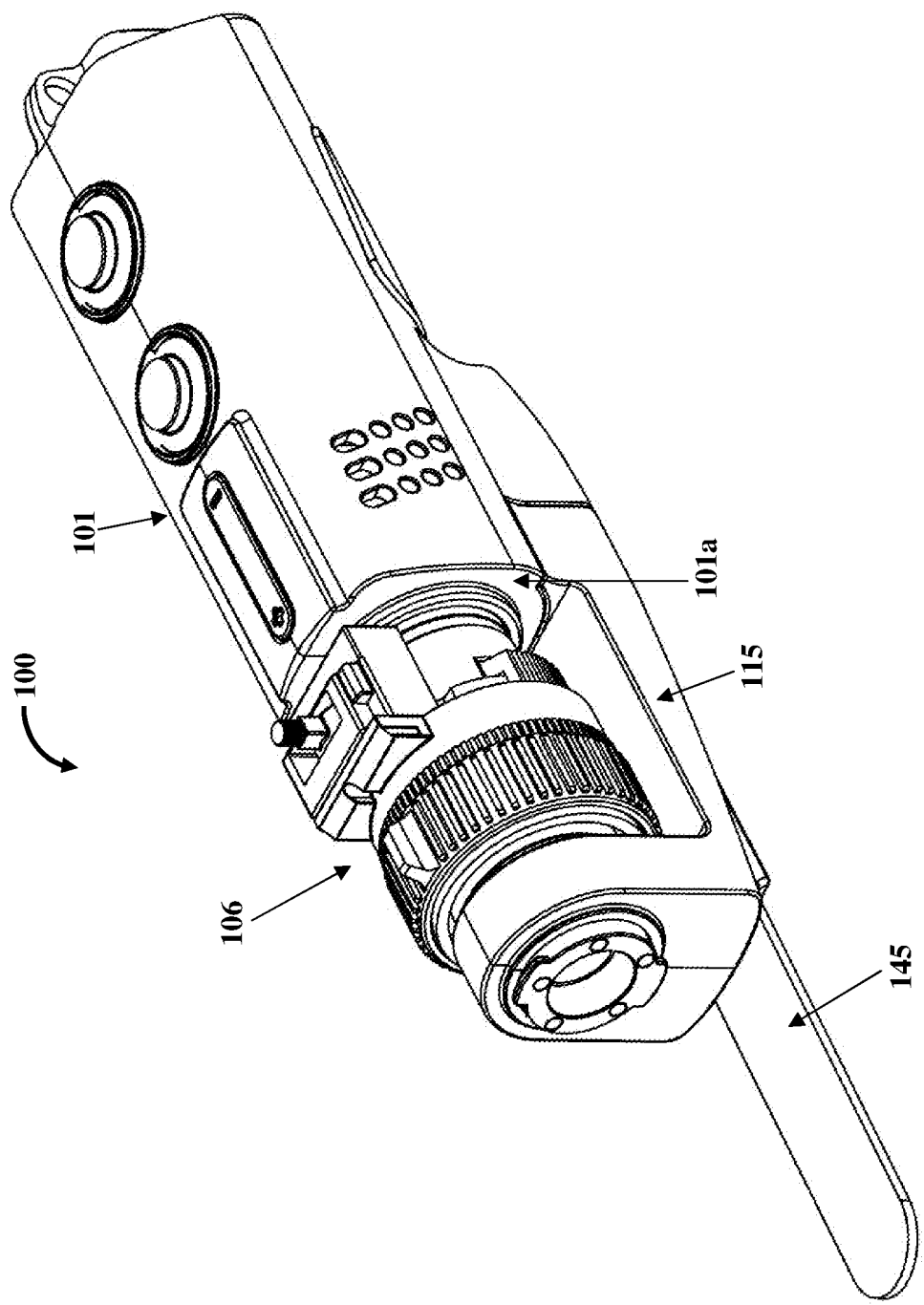
FIG. 14C exemplarily illustrates a right side perspective view of the multipurpose diagnostic examination apparatus, showing the image capture device removably connected to the front section of the diagnosis control unit and the diagnosis assistance element connected to the attachment unit.

FIG. 14C exemplarily illustrates a right side perspective view of the multipurpose diagnostic examination apparatus 100, showing the image capture device 106 removably connected to the front section 101a of the diagnosis control unit 101 and the diagnosis assistance element 145 connected to the attachment unit 115.

Figure 14D:
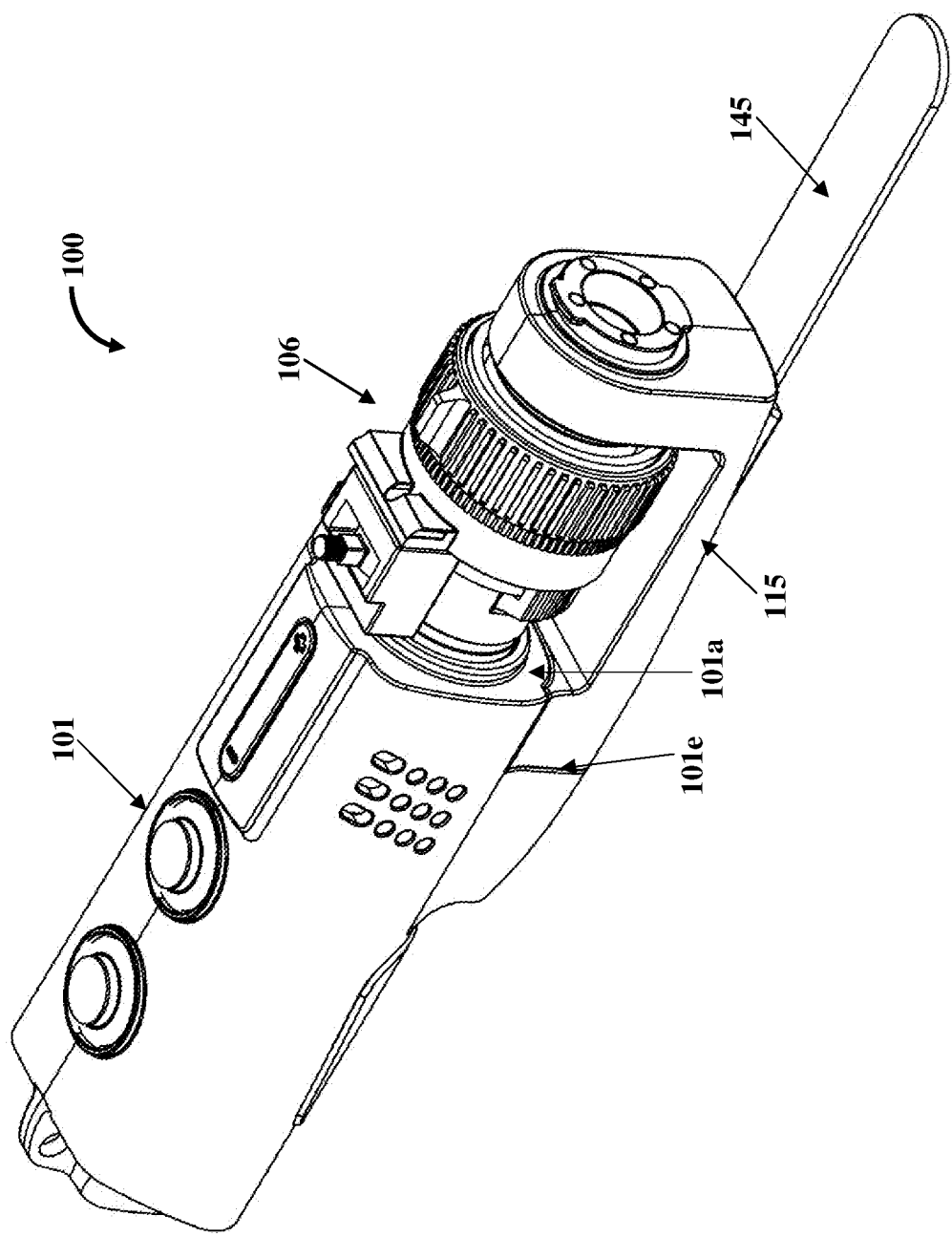
FIG. 14D exemplarily illustrates a left side perspective view of the multipurpose diagnostic examination apparatus, showing the image capture device removably connected to the front section of the diagnosis control unit and the diagnosis assistance element connected to the attachment unit.

FIG. 14D exemplarily illustrates a left side perspective view of the multipurpose diagnostic examination apparatus 100, showing the image capture device 106 removably connected to the front section 101a of the diagnosis control unit 101 and the diagnosis assistance element 145 connected to the attachment unit 115.

Figure 14E:
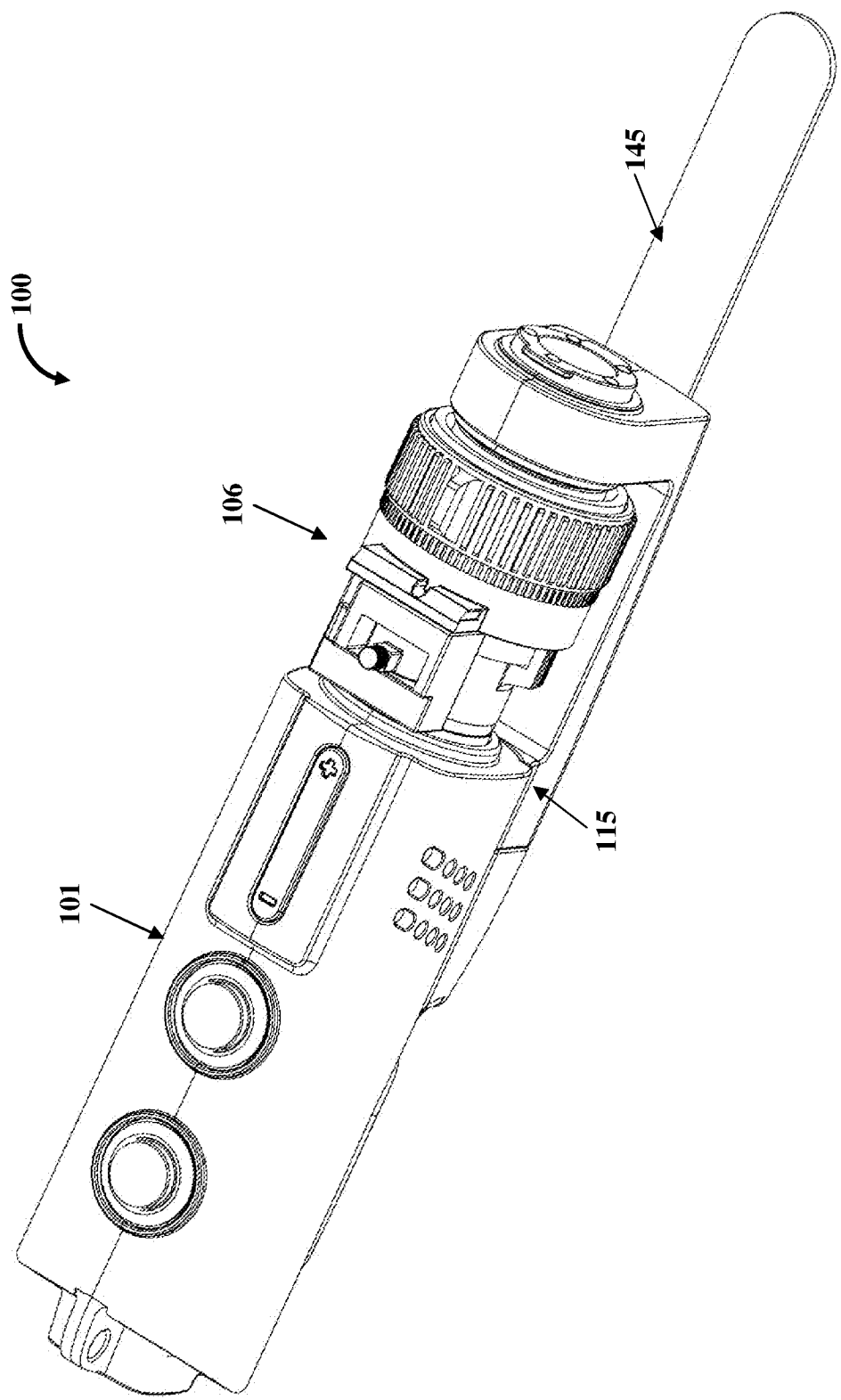
FIG. 14E exemplarily illustrates a top perspective view of the multipurpose diagnostic examination apparatus, showing the image capture device and the diagnosis assistance element.

FIG. 14E exemplarily illustrates a top perspective view of the multipurpose diagnostic examination apparatus 100, showing the image capture device 106 and the diagnosis assistance element 145.

Figure 14F:
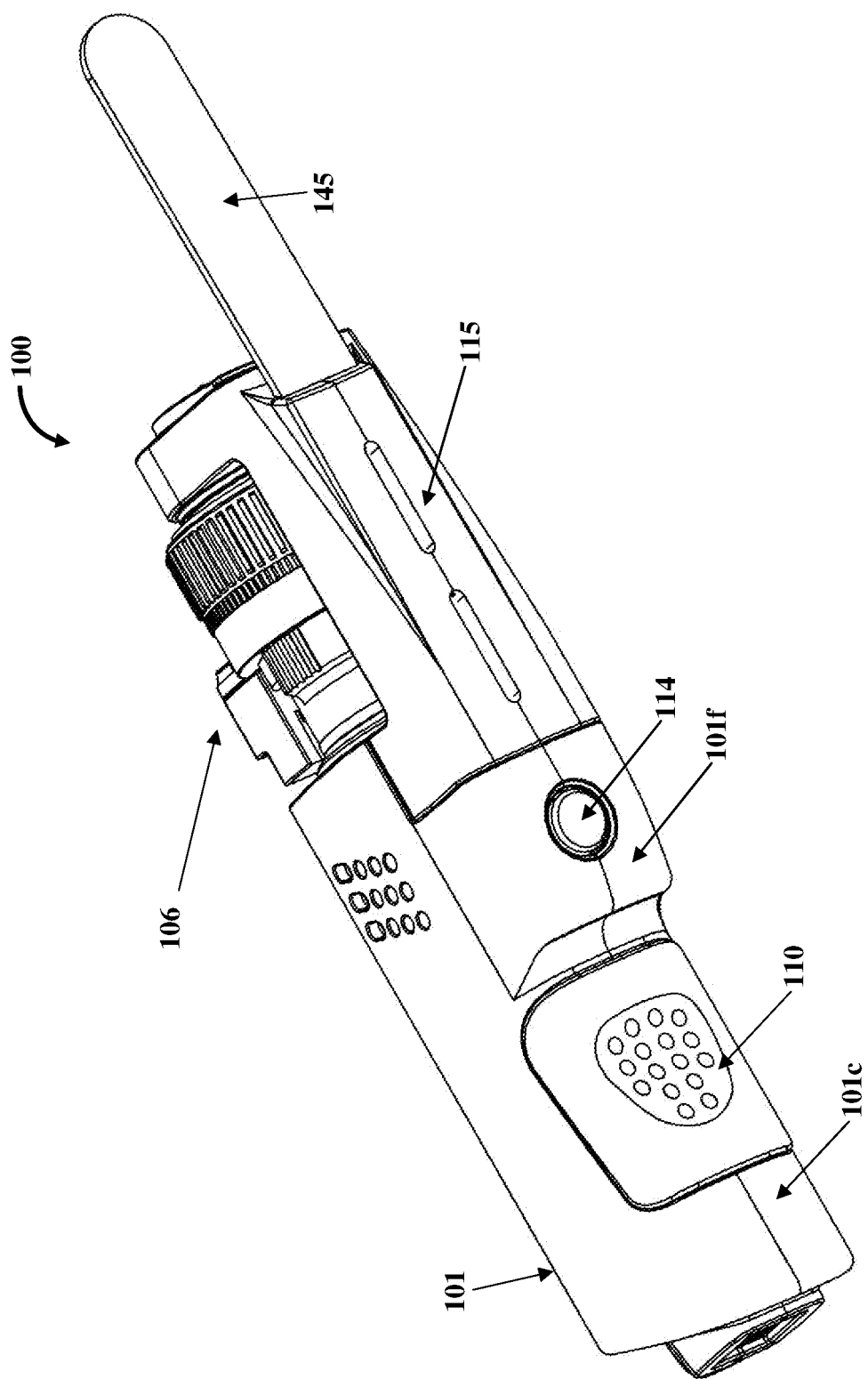
FIG. 14F exemplarily illustrates a bottom perspective view of the multipurpose diagnostic examination apparatus, showing the image capture device, the diagnosis assistance element, the support element, and the release button.

FIG. 14F exemplarily illustrates a bottom perspective view of the multipurpose diagnostic examination apparatus 100, showing the image capture device 106, the diagnosis assistance element 145, the support element 110, and the release button 114. The support element 110 is positioned on the lower surface 101c of the diagnosis control unit 101. The release button 114 is positioned on the lower section 101f of the diagnosis control unit 101.

Figure 14G:
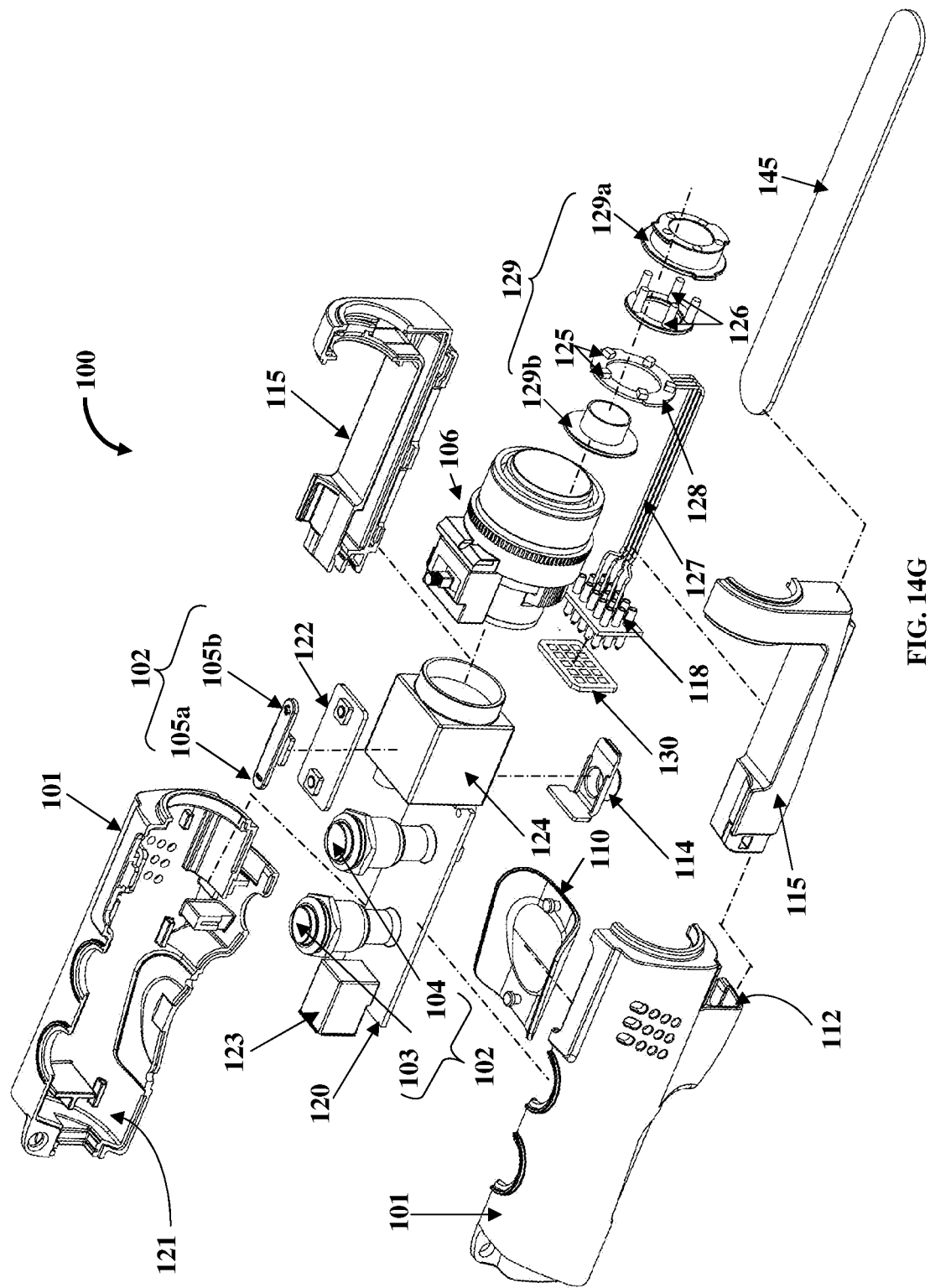
FIG. 14G exemplarily illustrates an exploded view of the multipurpose diagnostic examination apparatus comprising the diagnosis control unit, the attachment unit, the image capture device, and the diagnosis assistance element.

FIG. 14G exemplarily illustrates an exploded view of the multipurpose diagnostic examination apparatus 100 comprising the diagnosis control unit 101, the attachment unit 115, the image capture device 106, and the diagnosis assistance element 145. The exploded view shows the trigger elements 102 comprising, for example, the power control trigger element 103, the action control trigger element 104, and two output modification trigger elements 105a and 105b. The exploded view also shows the support element 110 and the release button 114. The power control trigger element 103 and the action control trigger element 104 are positioned on a printed circuit board (PCB) 120 housed in a cavity 121 of the diagnosis control unit 101. The exploded view also shows the connector interface 123 positioned on the rear section 120a of the PCB 120 and the camera module 124 positioned on the front section 120b of the PCB 120. The image capture device 106 is removably connected to the camera module 124 of the diagnosis control unit 101. The camera module 124 is in operable communication with the optical lens 107 of the image capture device 106. FIG. 14G also exemplarily illustrates an electrical configuration of the light sources, for example, the light emitting diodes (LEDs) 125. As exemplarily illustrated in FIG. 14G, wires 127 extending from the PCB 128 of the LEDs 125 are connected to the spring contact connectors 118 of the attachment unit 115. The spring contact connectors 118 of the attachment unit 115 operably connect to the connector pad PCB 130 housed in the connector slot 112 of the diagnosis control unit 101. The PCB 128 of the LEDs 125, the LEDs 125, and the light pipes 126 are housed within the front portion 129a and the rear portion 129b of the light pipe holder 129.

Figure 14H:
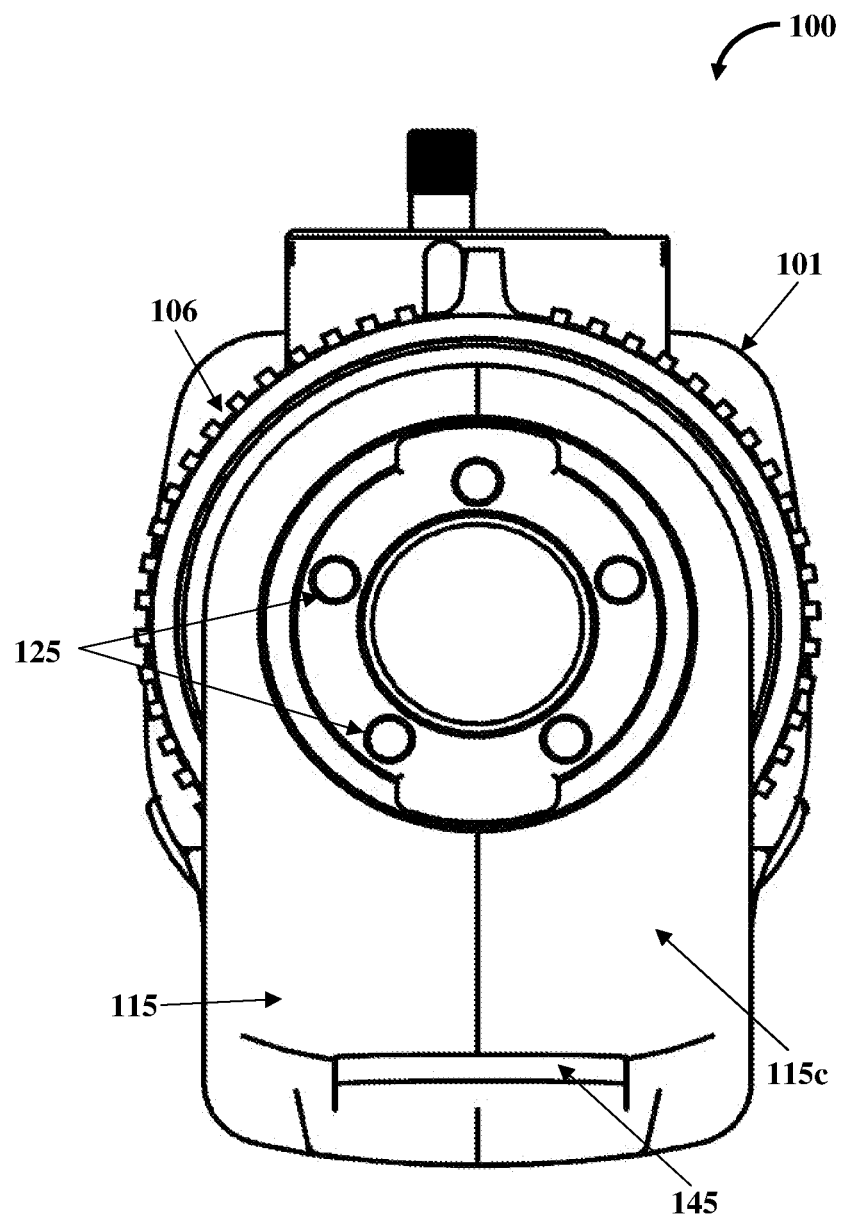
FIG. 14H exemplarily illustrates a front elevation view of the multipurpose diagnostic examination apparatus, showing the diagnosis assistance element extending from the front section of the attachment unit, and the light sources.

FIG. 14H exemplarily illustrates a front elevation view of the multipurpose diagnostic examination apparatus 100, showing the diagnosis assistance element 145 extending from the front section 115c of the attachment unit 115, and the light sources comprising, for example, the light emitting diodes (LEDs) 125.

Figure 14I:
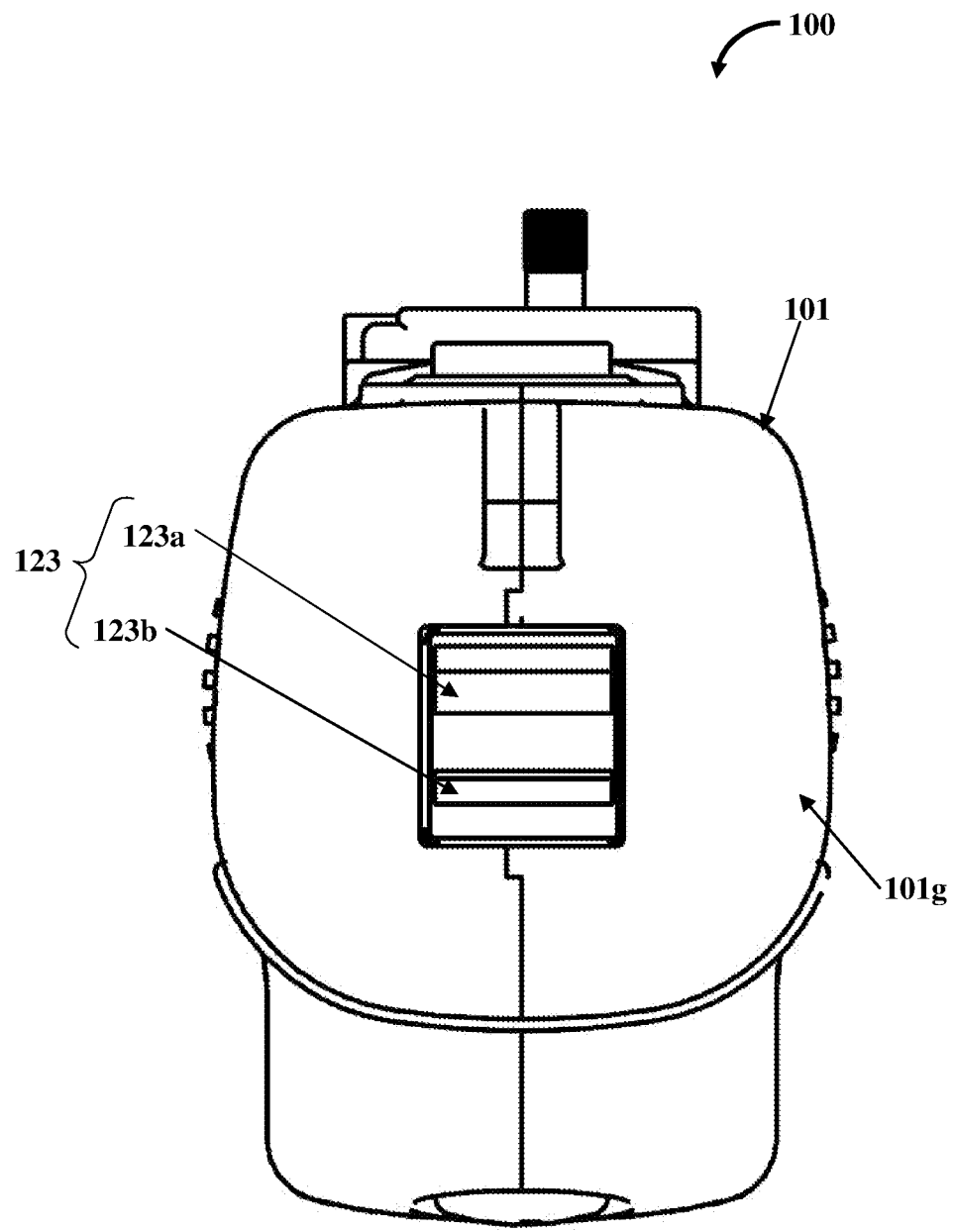
FIG. 14I exemplarily illustrates a rear elevation view of the multipurpose diagnostic examination apparatus, showing the connector interface configured at the rear section of the diagnosis control unit.

FIG. 14I exemplarily illustrates a rear elevation view of the multipurpose diagnostic examination apparatus 100, showing the connector interface 123 configured at the rear section 101g of the diagnosis control unit 101. As exemplarily illustrated in FIG. 14I, the connector interface 123 comprises at least two connector elements 123a and 123b. The connector interface 123 is in communication with the image capture device 106 connected to the front section 101a of the diagnosis control unit 101 exemplarily illustrated in FIGS. 14C-14D, to receive diagnostic image data, for example, images of a patient's throat captured by the image capture device 106. The connector elements 123a and 123b of the connector interface 123 allow communication of the diagnostic image data to the medical diagnostic examination system 2506 exemplarily illustrated in FIG. 25. The connector element 123a or 123b allows serial data communication between the microcontroller 2004 of the diagnosis control unit 101 exemplarily illustrated in FIG. 20, and the medical diagnostic examination system 2506 for controlling operations of the image capture device 106 exemplarily illustrated in FIGS. 14A-14H, for medical imaging and diagnostic examinations.

Figure 14J:
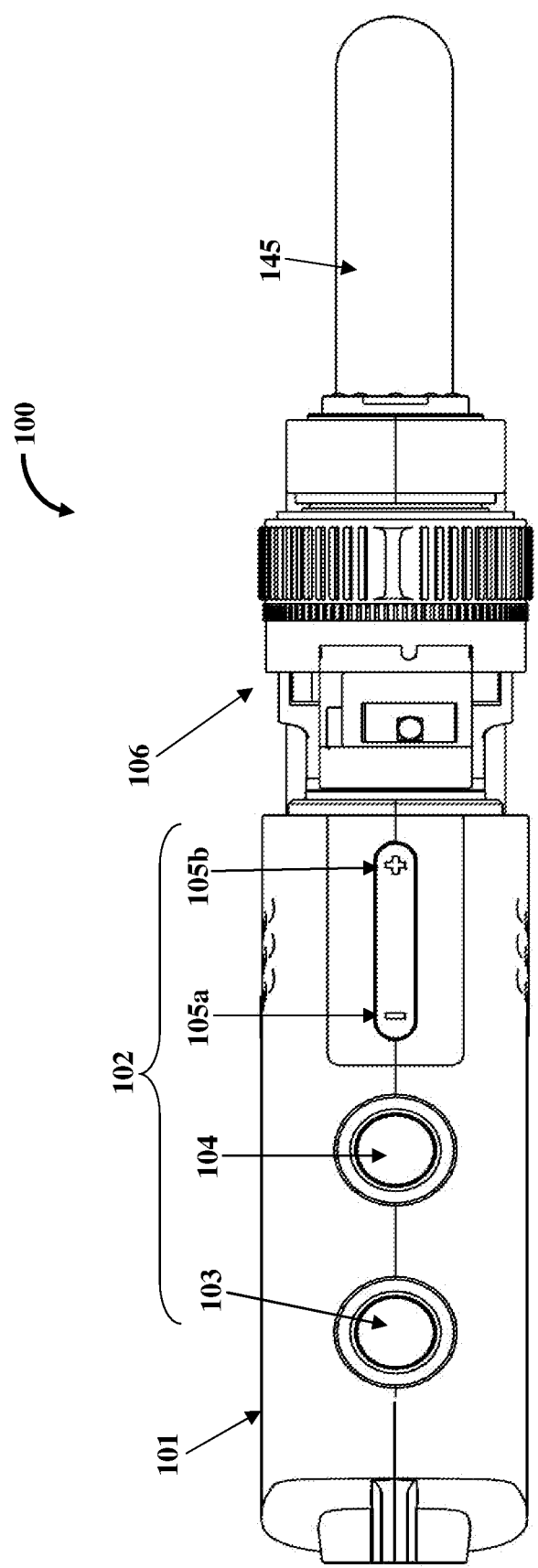
FIG. 14J exemplarily illustrates a top plan view of the multipurpose diagnostic examination apparatus, showing the image capture device, the trigger elements, and the diagnosis assistance element.

FIG. 14J exemplarily illustrates a top plan view of the multipurpose diagnostic examination apparatus 100, showing the image capture device 106, the trigger elements 102 comprising the power control trigger element 103, the action control trigger element 104, and the output modification trigger elements 105a and 105b, and the diagnosis assistance element 145.

Figure 14K:
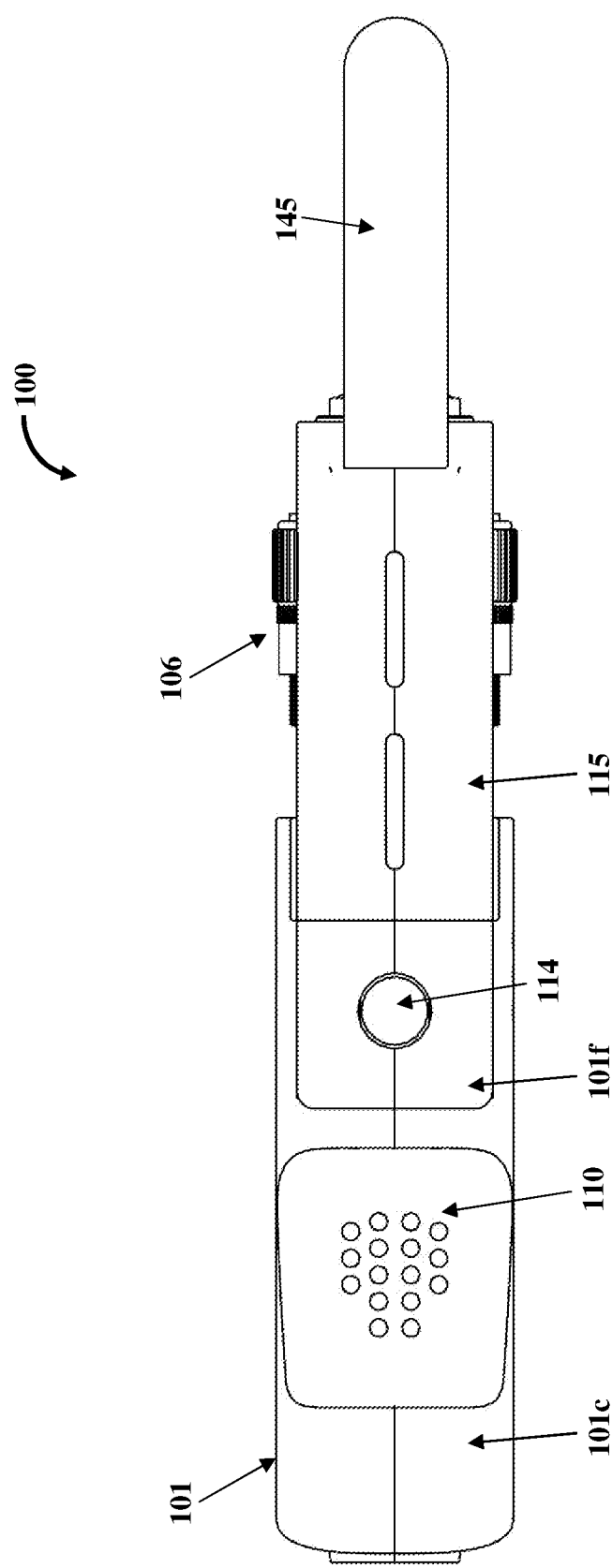
FIG. 14K exemplarily illustrates a bottom view of the multipurpose diagnostic examination apparatus, showing the diagnosis assistance element, the support element, and the release button.

FIG. 14K exemplarily illustrates a bottom view of the multipurpose diagnostic examination apparatus 100, showing the diagnosis assistance element 145, the support element 110 on the lower surface 101c of the diagnosis control unit 101, and the release button 114 on the lower section 101f of the diagnosis control unit 101.

Figure 14L:
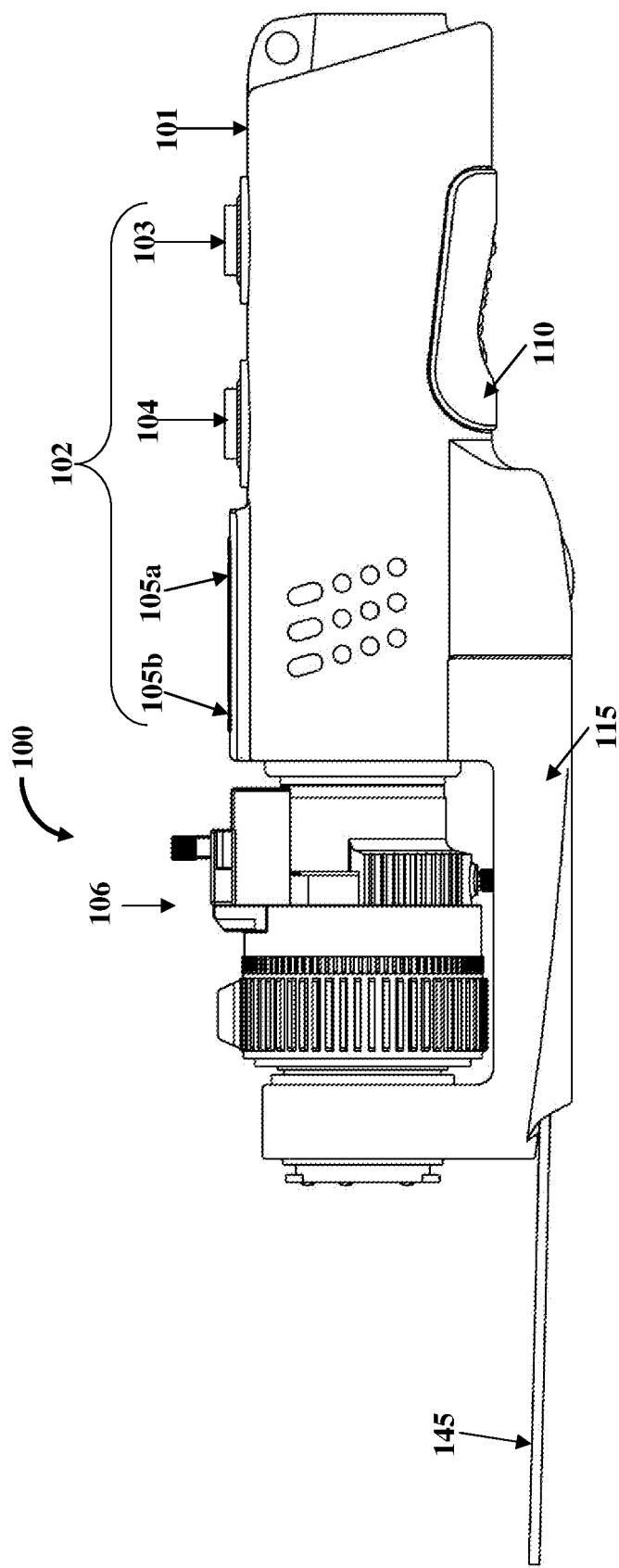
FIGS. 14L-14M exemplarily illustrate side elevation views of the multipurpose diagnostic examination apparatus, showing the image capture device, the trigger elements, the diagnosis assistance element, and the support element.
Figure 14M:
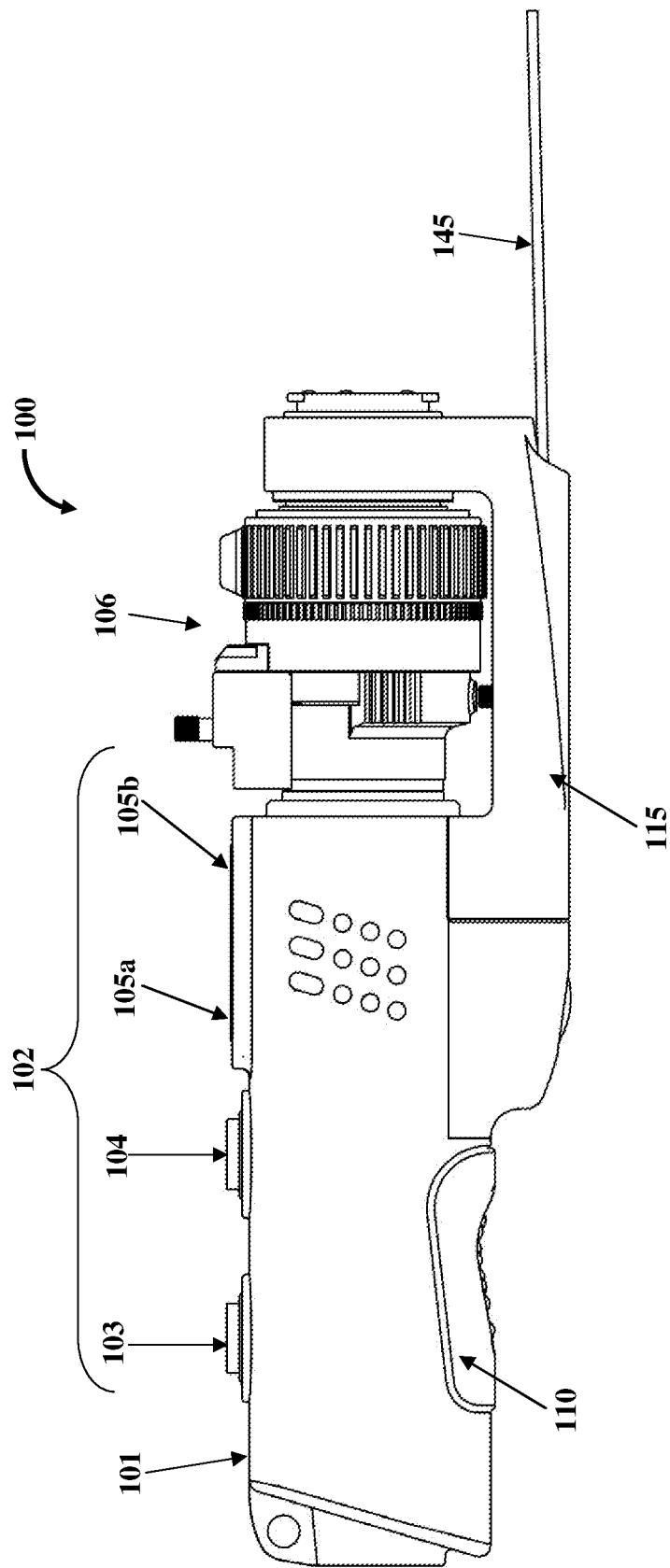

FIGS. 14L-14M exemplarily illustrate side elevation views of the multipurpose diagnostic examination apparatus 100, showing the image capture device 106, the trigger elements 102 comprising the power control trigger element 103, the action control trigger element 104, and the output modification trigger elements 105a and 105b, the diagnosis assistance element 145, and the support element 110.

Figure 15:
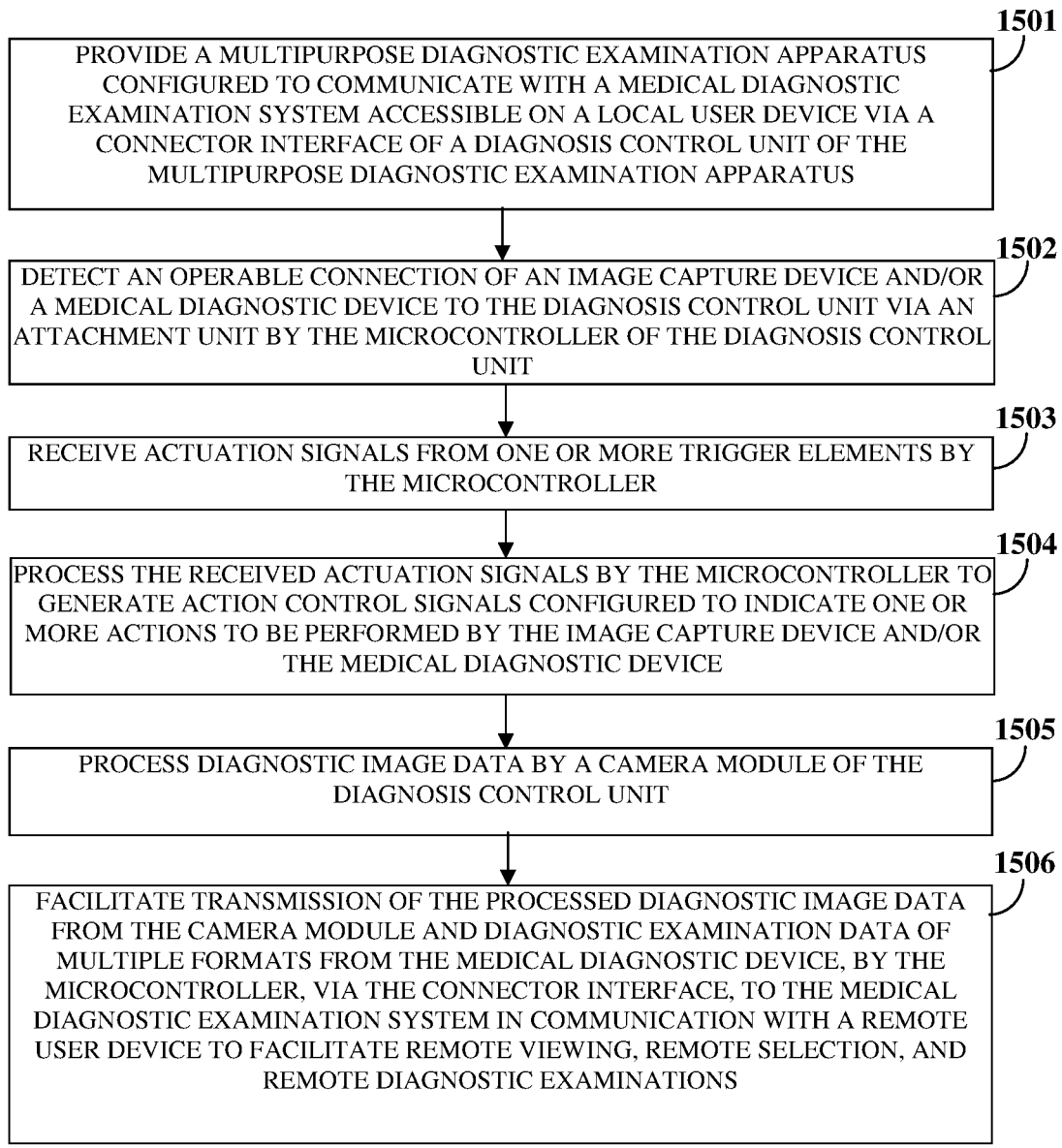
FIG. 15 illustrates a method for facilitating medical imaging and remote diagnostic examinations.

FIG. 15 illustrates a method for facilitating medical imaging and remote diagnostic examinations. In the method disclosed herein, the multipurpose diagnostic examination apparatus 100 configured to communicate with the medical diagnostic examination system 2506 accessible on a local user device 2505 exemplarily illustrated in FIG. 25, via a connector interface 123 configured at the rear section 101g of the diagnosis control unit 101 exemplarily illustrated in FIG. 5F, FIG. 11G, FIG. 13H, and FIG. 14G, is provided 1501. In an embodiment, the multipurpose diagnostic examination apparatus 100 is configured to wirelessly communicate with the medical diagnostic examination system 2506 accessible on the local user device 2505 via a communication network 2509 exemplarily illustrated in FIG. 25, for example, a Bluetooth® communication network of Bluetooth Sig, Inc., a Wi-Fi® communication network of the Wi-Fi Alliance Corporation, etc. In this embodiment, the multipurpose diagnostic examination apparatus 100 is configured as a wireless multipurpose diagnostic examination apparatus 100, for example, a Bluetooth® enabled multipurpose diagnostic examination apparatus, or a Wi-Fi® enabled multipurpose diagnostic examination apparatus. The method disclosed herein provides a fast and easy way of activating and controlling the multipurpose diagnostic examination apparatus 100 via the medical diagnostic examination system 2506 accessible on the local user device 2505.

The multipurpose diagnostic examination apparatus 100 comprises the diagnosis control unit 101, the attachment unit 115, and the image capture device 106 as disclosed in the detailed description of FIGS. 1A-14M. The diagnosis control unit 101 comprises the microcontroller 2004 exemplarily illustrated in FIG. 20, in operable communication with multiple trigger elements 102 positioned on a predefined section, for example, an upper section 101b of the diagnosis control unit 101, and with the medical diagnostic examination system 2506 via the connector interface 123. The attachment unit 115 operably connects different medical diagnostic devices, for example, the otoscope device 119 exemplarily illustrated in FIGS. 5A-5L, an ophthalmoscope device (not shown), the stethoscope device 134 exemplarily illustrated in FIGS. 11A-11G, the dermatoscope device 131 exemplarily illustrated in FIG. 8, the ultrasound device 141 exemplarily illustrated in FIGS. 13A-13H, an endoscope device (not shown), etc., interchangeably to the diagnosis control unit 101. In an embodiment, a different attachment unit 115 is provided for each medical diagnostic device. By changing the attachment unit 115 with a particular medical diagnostic device, a user, for example, a medical assistant can modify the multipurpose diagnostic examination apparatus 100 comprising the image capture device 106 for four different diagnostic examinations. For example, when the medical assistant wants to use the otoscope device 119 and then an ophthalmoscope, the user can replace the attachment unit 115 comprising the otoscope device 119 with an attachment unit 115 comprising an ophthalmoscope device, and adjust brightness levels of the light emitted by the light sources, for example, the light emitting diodes (LEDs) 125 that are operably connected to the front section 115c of the respective attachment unit 115.

The microcontroller 2004 detects 1502 an operable connection of the image capture device 106 and/or a medical diagnostic device to the diagnosis control unit 101 via the attachment unit 115. The microcontroller 2004 receives 1503 actuation signals from one or more of the trigger elements 102. In an embodiment, the actuation signals are generated by a simultaneous activation or a subsequent activation of one or more of the trigger elements 102 positioned on the upper section 101b of the diagnosis control unit 101. As used herein, "simultaneous activation" refers to activation of two trigger elements 103 and 104 at the same time for generating actuation signals. Also, as used herein, "subsequent activation" refers to activation of one trigger element 103 or 104 after another for generating actuation signals. The microcontroller 2004 processes 1504 the received actuation signals to generate action control signals configured to indicate one or more actions to be performed by the image capture device 106 and/or the medical diagnostic device interchangeably connected to the diagnosis control unit 101 via the attachment unit 115.

In an embodiment, the microcontroller 2004 generates and transmits action control signals to one or more of multiple light sources, for example, light emitting diodes (LEDs) 125 operably connected to the front section 115c of the attachment unit 115, a predefined section such as the section 115e along the length of the attachment unit 115, and/or the upper section 101b of the diagnosis control unit 101, for illuminating and indicating one or more anatomical examination areas during medical imaging and remote diagnostic examinations. The illuminated and indicated anatomical examination areas are viewed and selected remotely on a remote user device 2511 via the communication network 2509 exemplarily illustrated in FIG. 25, for the remote diagnostic examinations.

Figure 22:
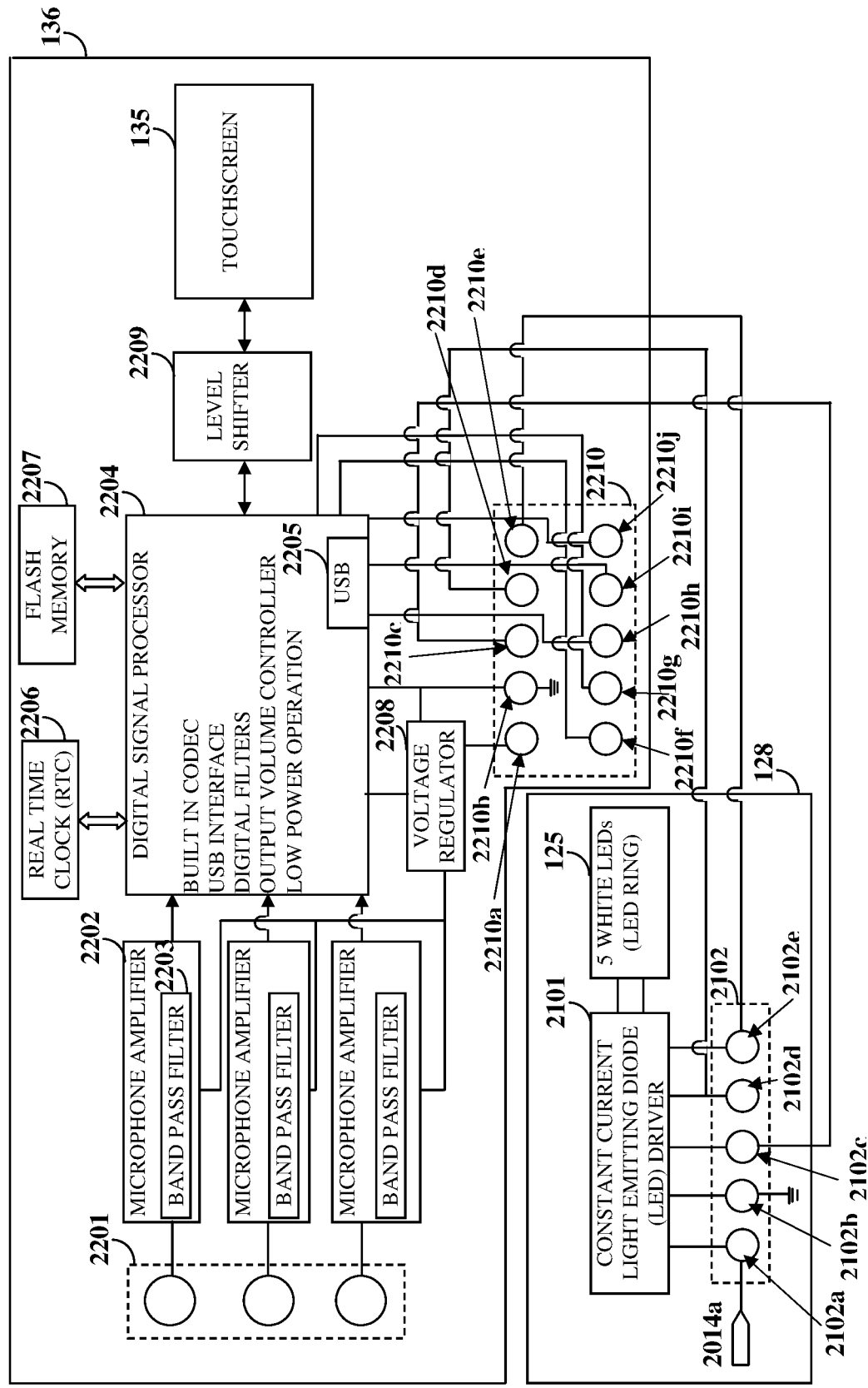
FIG. 22 exemplarily illustrates a block diagram of the printed circuit board of the stethoscope device and the light sources operably connected to the attachment unit.
Figure 23A:
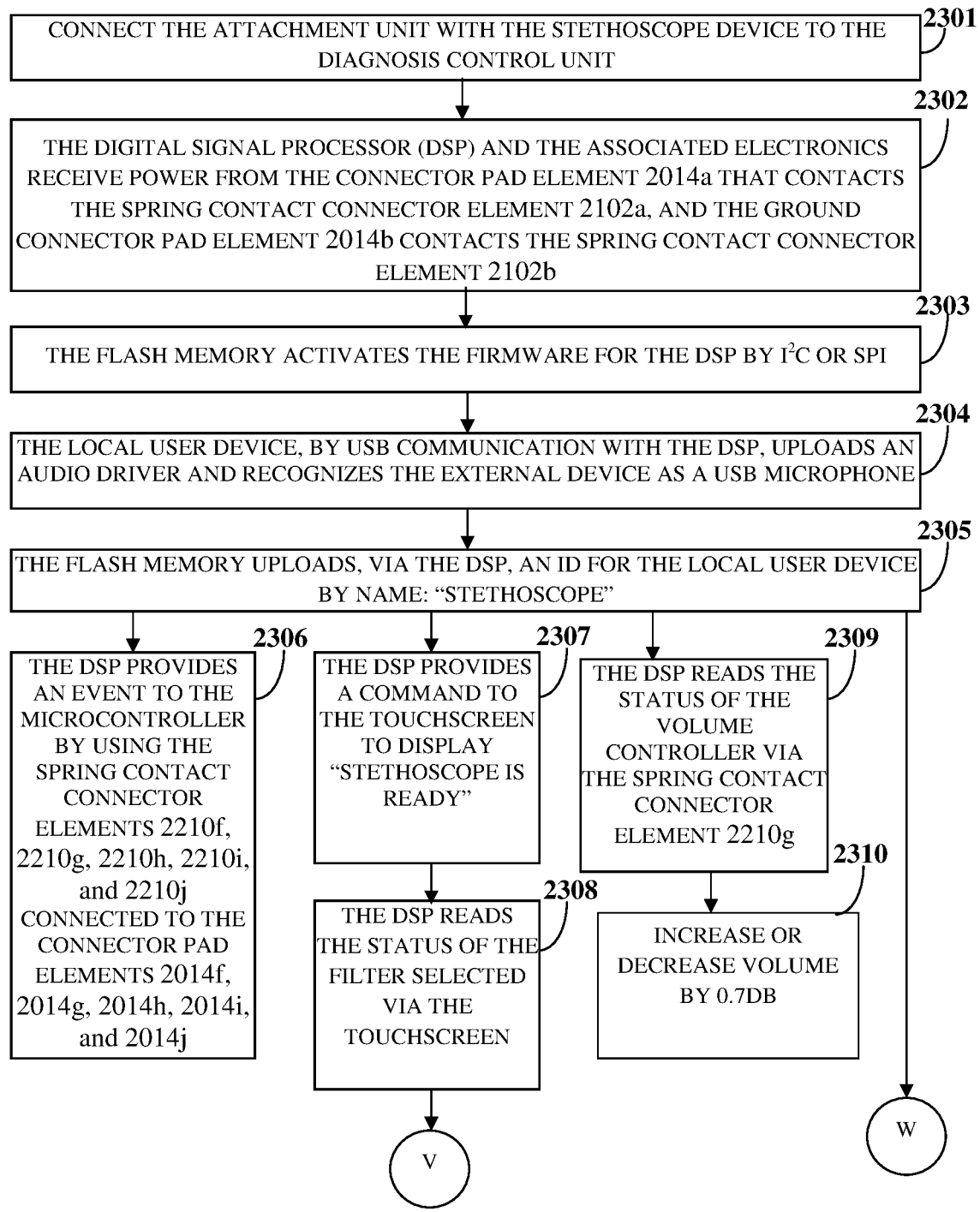
FIGS. 23A-23D exemplarily illustrate a flowchart comprising the steps performed by a digital signal processor of the stethoscope device for recording and transmitting audio data to the medical diagnostic examination system on a local user device.
Figure 23B:
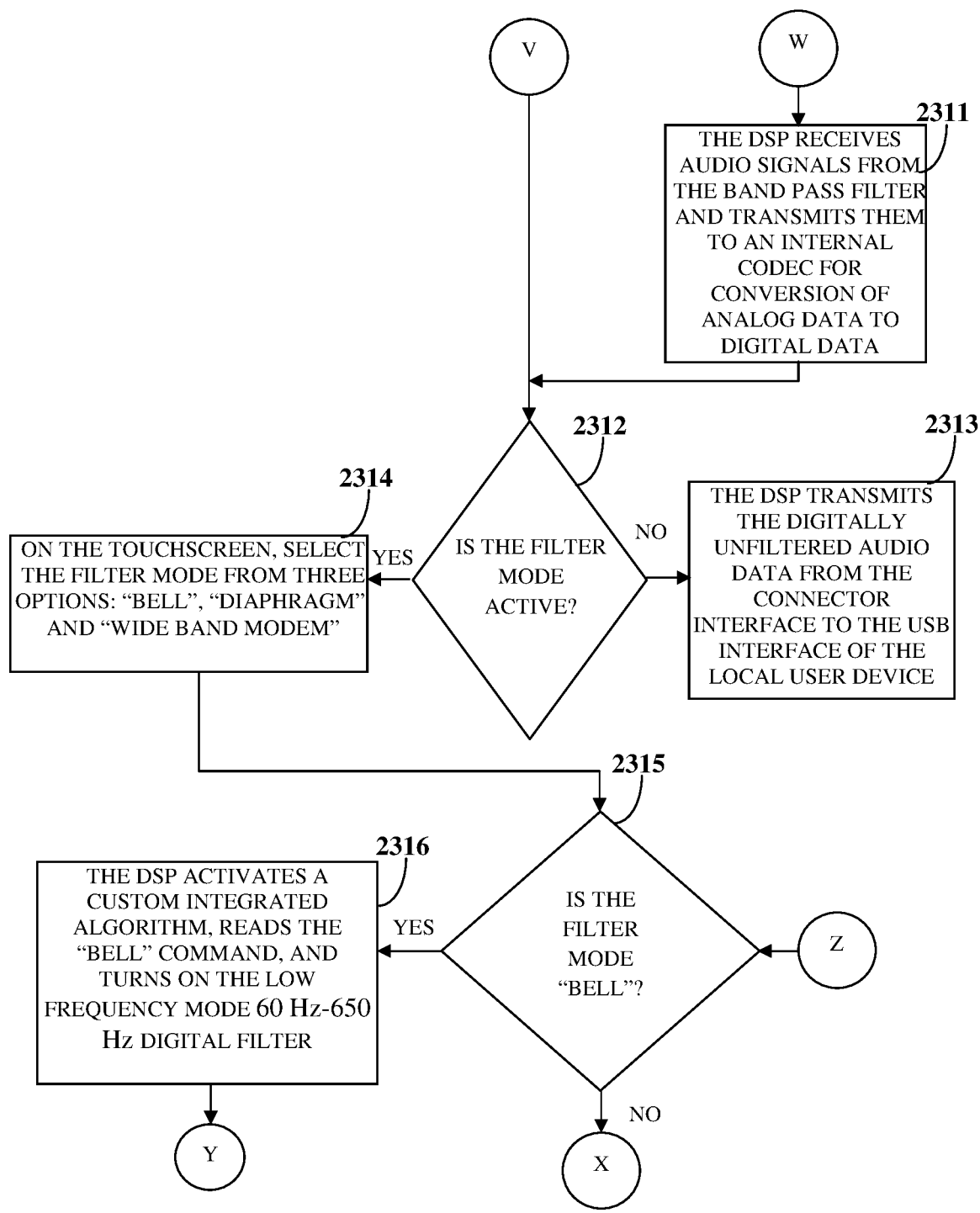
Figure 23C:
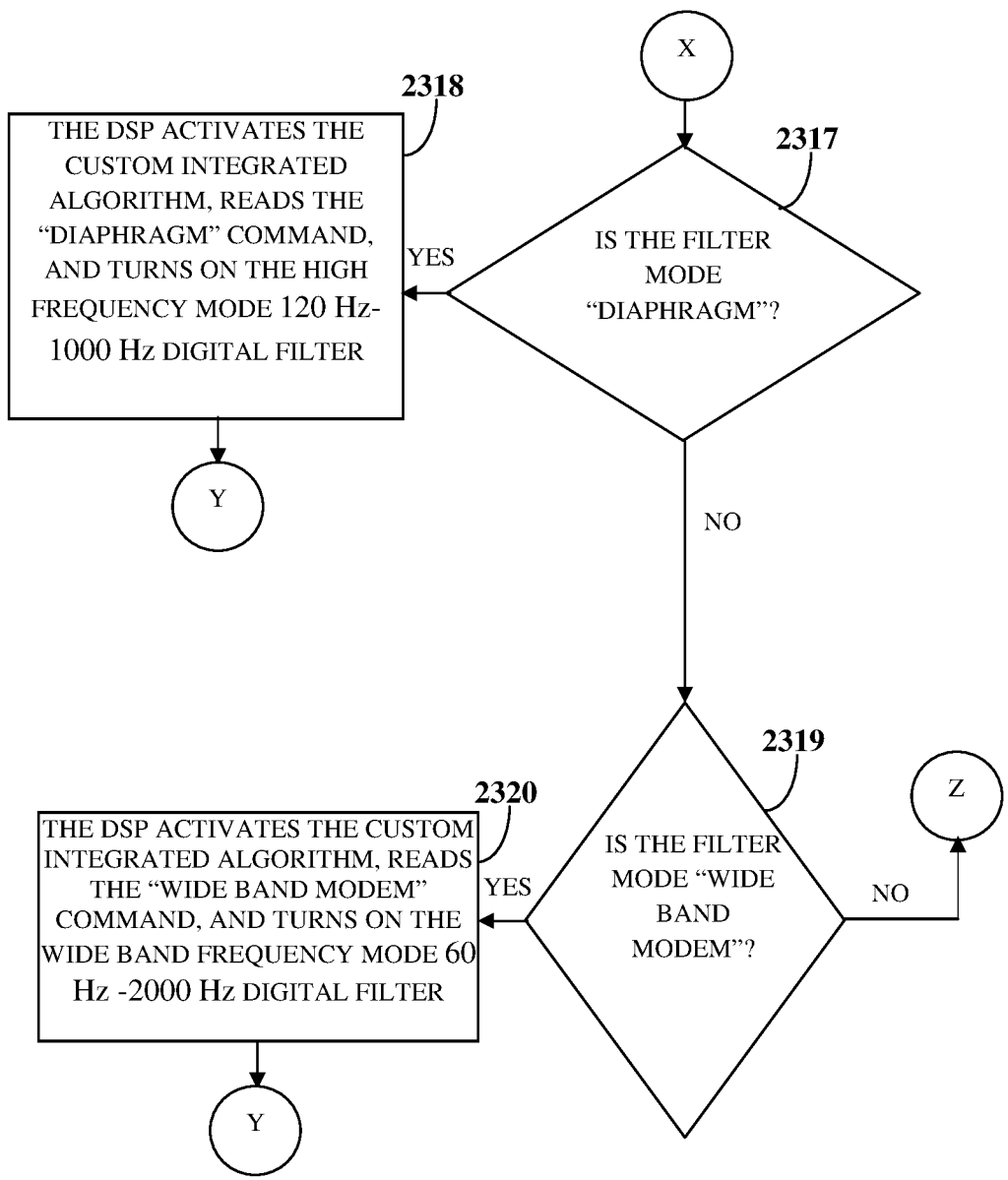
Figure 23D:
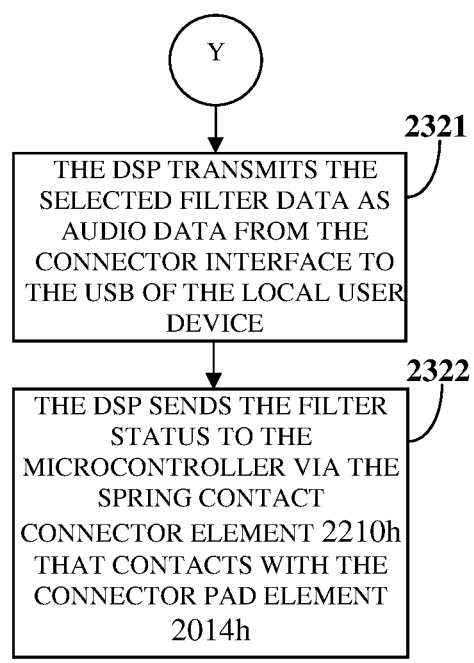

In an embodiment, the medical diagnostic device is a stethoscope device 134 comprising a digital signal processor 2204 exemplarily illustrated in FIG. 22. In an embodiment, the microcontroller 2004 generates and transmits action control signals to the digital signal processor 2204 of the stethoscope device 134 for actuating the stethoscope device 134 to perform the actions indicated by the generated action control signals. In an embodiment, the stethoscope device 134 comprises one or more microphones 2201 exemplarily illustrated in FIG. 22. In an embodiment, the microcontroller 2004 generates and transmits action control signals to the digital signal processor 2204 of the stethoscope device 134 for actuating the microphones 2201 to receive diagnostic acoustic data from one or more anatomical examination areas. In an embodiment, the stethoscope device 134 comprises a touchscreen 135. In an embodiment, the microcontroller 2004 generates and transmits action control signals to the digital signal processor 2204 of the stethoscope device 134 for actuating the touchscreen 135 to display information, for example, associated with the diagnostic acoustic data received by the stethoscope device 134, a connection status of the stethoscope device 134 to the diagnosis control unit 101, an activation status of the stethoscope device 134, etc. In an embodiment, the stethoscope device 134 comprises a real time clock 2206 exemplarily illustrated in FIG. 22. In an embodiment, the microcontroller 2004 generates and transmits action control signals to the digital signal processor 2204 of the stethoscope device 134 for actuating the real time clock 2206 to control recording of the diagnostic acoustic data by the stethoscope device 134 for a predefined time period.

Figure 24:
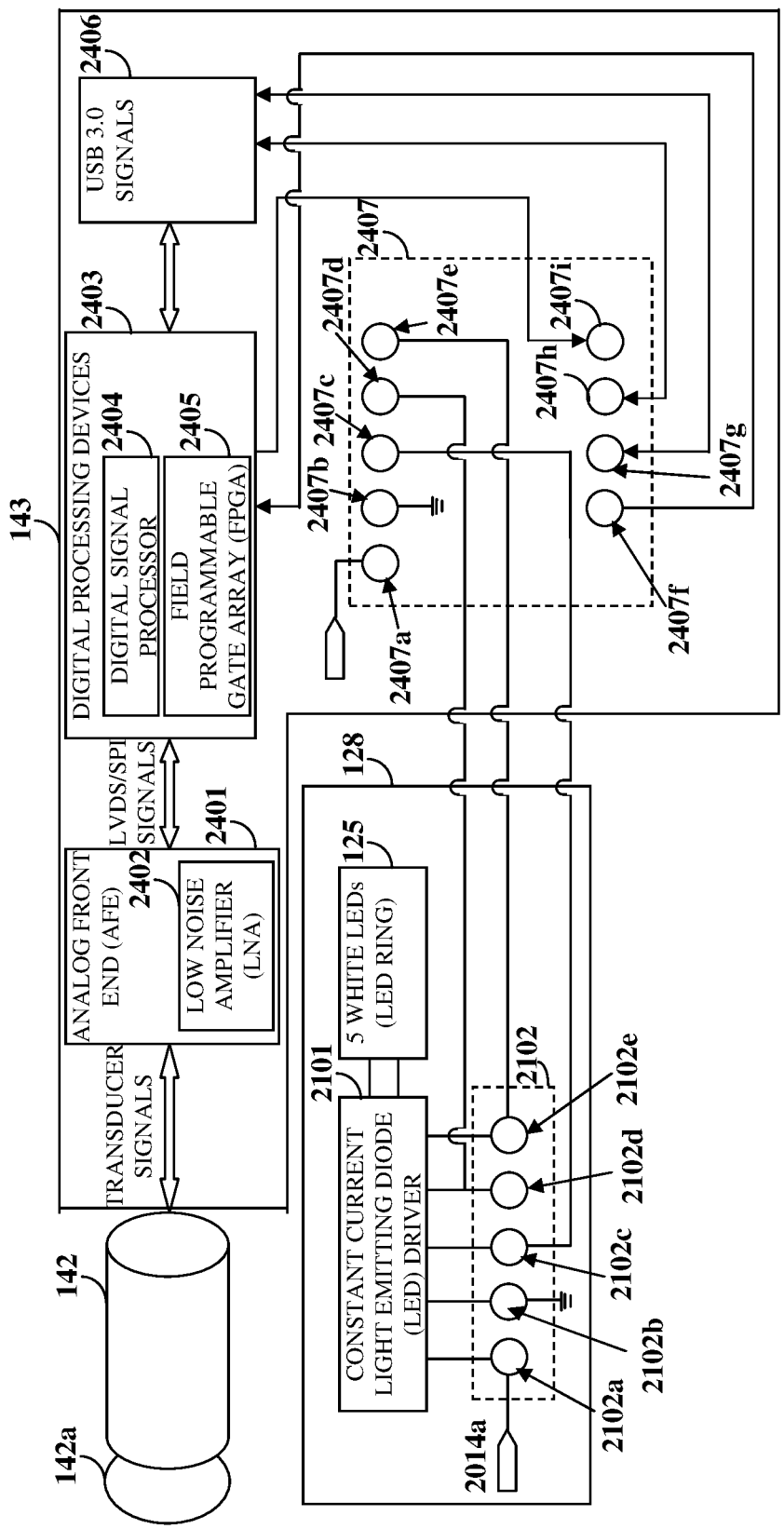
FIG. 24 exemplarily illustrates a block diagram of the printed circuit board of the ultrasound device and the light sources operably connected to the attachment unit.

In an embodiment, the medical diagnostic device is an ultrasound device 141 comprising an ultrasound digital signal processor 2404 exemplarily illustrated in FIG. 24. In an embodiment, the microcontroller 2004 generates and transmits action control signals to the ultrasound digital signal processor 2404 of the ultrasound device 141 for actuating the ultrasound device 141 to perform the actions indicated by the generated action control signals. In an embodiment, the ultrasound device 141 comprises one of multiple interchangeable ultrasound probes 142 operably connected to the attachment unit 115. In an embodiment, the microcontroller 2004 generates and transmits action control signals to the ultrasound digital signal processor 2404 of the ultrasound device 141 for actuating an interchangeable ultrasound probe 142 of the ultrasound device 141 to detect and receive ultrasonic sounds from one or more anatomical examination areas for remote diagnostic examinations.

The camera module 124 of the diagnosis control unit 101 exemplarily illustrated in FIG. 5F, FIG. 11G, FIG. 13H, and FIG. 14G, processes 1505 the diagnostic image data captured by the image capture device 106. The microcontroller 2004 facilitates 1506 transmission of the processed diagnostic image data from the camera module 124 and the diagnostic examination data of multiple formats from the medical diagnostic device, to the medical diagnostic examination system 2506 accessible on the local user device 2505 via the connector interface 123 of the diagnosis control unit 101. The diagnostic examination data comprises, for example, audio data, video data, image data, etc., and any combination thereof. The connector interface 123 is in communication with the camera module 124 and the medical diagnostic device via the attachment unit 115 to receive and transmit the processed diagnostic image data and the diagnostic examination data to the medical diagnostic examination system 2506. The medical diagnostic examination system 2506 on the local user device 2505 is in communication with a remote user device 2511 over the communication network 2509 to facilitate remote viewing, remote selection, and remote diagnostic examinations of the anatomical examination areas via the communication network 2509. In an embodiment, the microcontroller 2004 transmits diagnostic data management signals to the medical diagnostic examination system 2506 accessible on the local user device 2505 via the connector interface 123 of the diagnosis control unit 101 for managing the transmitted diagnostic image data and the transmitted diagnostic examination data.

Consider an example where a user, for example, a medical assistant connects the image capture device 106 to the diagnosis control unit 101 of the multipurpose diagnostic examination apparatus 100 and the microcontroller 2004 detects the connection of the image capture device 106 to the diagnosis control unit 101. The medical assistant who is operating the multipurpose diagnostic examination apparatus 100 activates the action control trigger element 104. On detecting activation of the action control trigger element 104, the microcontroller 2004 generates an action control signal indicating an action of capturing diagnostic image data by the image capture device 106. The diagnostic image data that the image capture device 106 captures comprises, for example, one or more images of an anatomical examination area of a patient. The camera module 124 processes the diagnostic image data. The microcontroller 2004 verifies whether a connector hub interface 2002 exemplarily illustrated in FIG. 20, is active for processing transmission of the diagnostic image data from the image capture device 106 to the medical diagnostic examination system 2506 deployed, for example, on the medical assistant's local user device 2505 exemplarily illustrated in FIG. 25, for example, a computing device such as a laptop or a tablet computing device. If the microcontroller 2004 verifies that the connector hub interface 2002 is active, the microcontroller 2004 sends a diagnostic data management signal to the medical diagnostic examination system 2506, for example, via a RS-232 port for recording the diagnostic image data captured by the image capture device 106. The camera module 124 transmits the processed diagnostic image data to the medical diagnostic examination system 2506 via the connector interface 123. The medical diagnostic examination system 2506 comprises a graphical diagnostic examination interface (GDEI) 2507 exemplarily illustrated in FIG. 25. The medical diagnostic examination system 2506 renders the diagnostic image data received as camera output from the camera module 124 on the GDEI 2507. For example, the medical diagnostic examination system 2506 renders high definition (HD) images of the anatomical examination area being recorded by the image capture device 106 in real time on the GDEI 2507. The medical assistant captures, for example, a screenshot of the rendered diagnostic image data and saves the screenshot in a local memory of the local user device 2505 or shares the captured screenshots with another user, for example, a doctor at a remote location in real time via an audio/video conference set up between the local user device 2505 of the medical assistant and a remote user device 2511 of the doctor, for remote diagnostic examinations.

Figure 16:
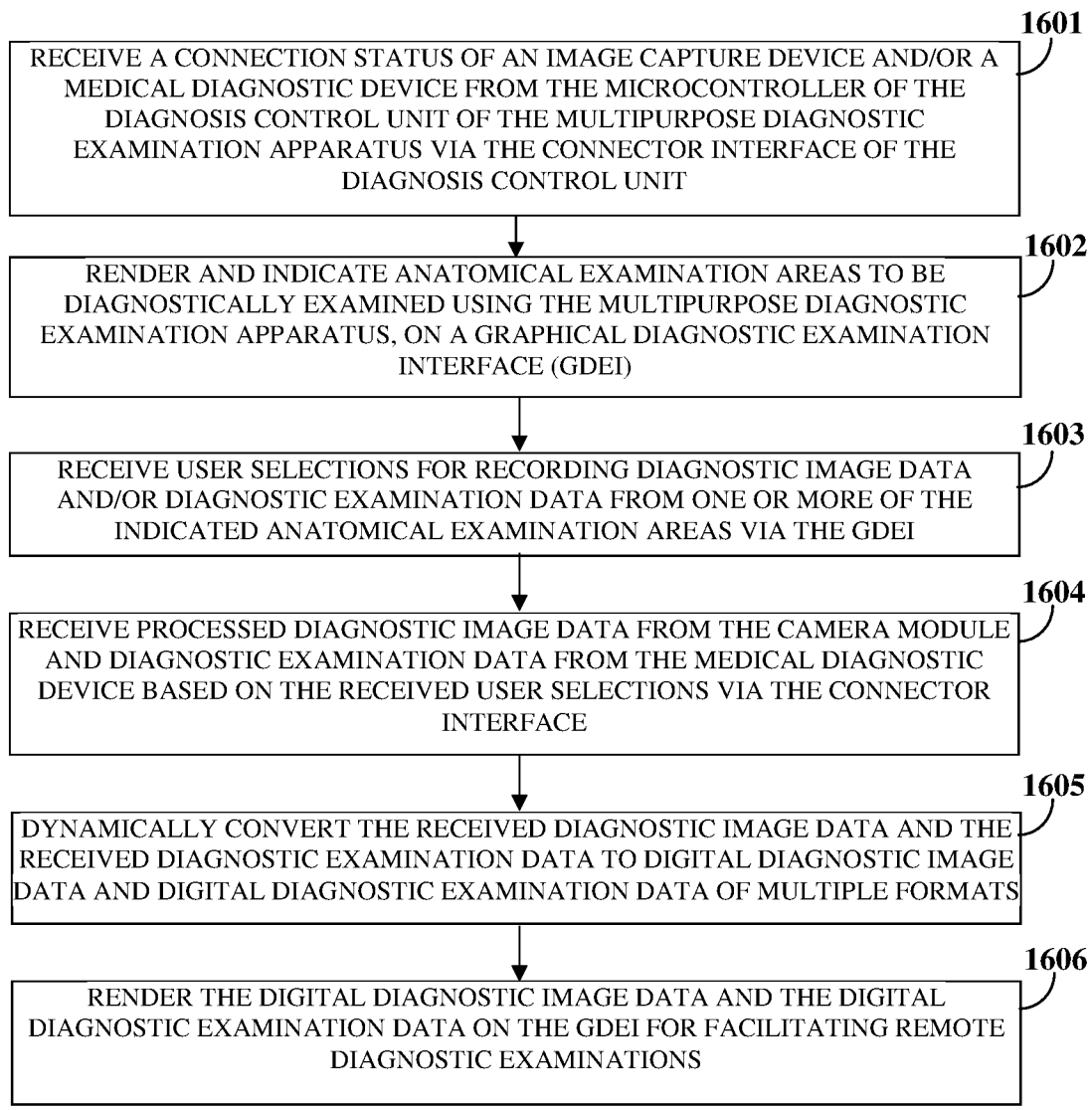
FIG. 16 illustrates a computer implemented method for performing medical imaging and remote diagnostic examinations, in communication with a medical diagnostic examination system.
Figure 25:
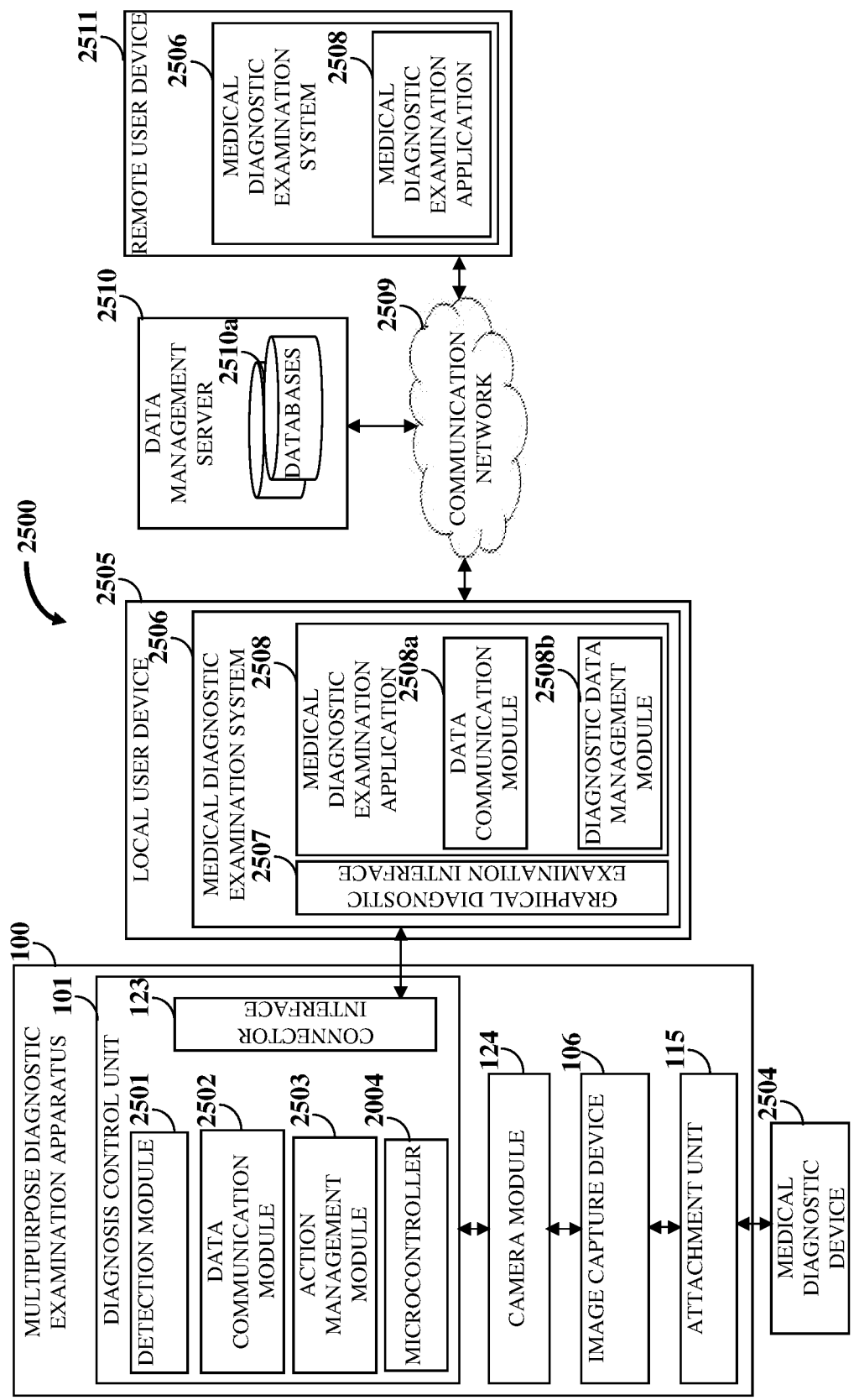
FIG. 25 exemplarily illustrates a system for facilitating medical imaging and remote diagnostic examinations.

FIG. 16 illustrates a computer implemented method for performing medical imaging and remote diagnostic examinations, in communication with the medical diagnostic examination system 2506 exemplarily illustrated in FIG. 25. The computer implemented method disclosed herein employs the medical diagnostic examination system 2506 accessible on a local user device 2505 exemplarily illustrated in FIG. 25. The medical diagnostic examination system 2506 communicates with the multipurpose diagnostic examination apparatus 100 exemplarily illustrated in FIGS. 1A-14M, via the connector interface 123 of the multipurpose diagnostic examination apparatus 100 or the communication network 2509 exemplarily illustrated in FIG. 25. The medical diagnostic examination system 2506 comprises at least one processor configured to execute computer program instructions for performing medical imaging and remote diagnostic examinations. The medical diagnostic examination system 2506 receives 1601 a connection status of the image capture device 106 and/or a medical diagnostic device, for example, an otoscope device 119 exemplarily illustrated in FIGS. 5A-5L, or an ophthalmoscope device (not shown), or a stethoscope device 134 exemplarily illustrated in FIGS. 11A-11G, or a dermatoscope device 131 exemplarily illustrated in FIG. 8, or an ultrasound device 141 exemplarily illustrated in FIGS. 13A-13H, or an endoscope device (not shown), etc., from the microcontroller 2004 of the diagnosis control unit 101 exemplarily illustrated in FIG. 20, via the connector interface 123.

The medical diagnostic examination system 2506 renders and indicates 1602 anatomical examination areas to be diagnostically examined using the multipurpose diagnostic examination apparatus 100, on the graphical diagnostic examination interface (GDEI) 2507 provided by the medical diagnostic examination system 2506 exemplarily illustrated in FIG. 25, based on the received connection status of the image capture device 106 and/or the medical diagnostic device. The medical diagnostic examination system 2506 receives 1603 user selections for recording diagnostic image data and/or diagnostic examination data from one or more of the indicated anatomical examination areas via the GDEI 2507. The medical diagnostic examination system 2506 receives 1604 the processed diagnostic image data from the camera module 124 and diagnostic examination data from the medical diagnostic device based on the received user selections via the connector interface 123.

The medical diagnostic examination system 2506 dynamically converts 1605 the received diagnostic image data and the received diagnostic examination data to digital diagnostic image data and digital diagnostic examination data of multiple formats respectively. The medical diagnostic examination system 2506 renders 1606 the digital diagnostic image data and the digital diagnostic examination data on the graphical diagnostic examination interface (GDEI) 2507 for facilitating remote diagnostic examinations. In an embodiment, the digital diagnostic examination data is in a format comprising, for example, audio file formats, video file formats, image file formats, etc. In an embodiment, the medical diagnostic examination system 2506 dynamically updates the digital diagnostic image data and the digital diagnostic examination data based on the received diagnostic image data and the received diagnostic examination data at a predefined time period, and displays the updated digital diagnostic image data and the digital diagnostic examination data on the GDEI 2507. In an embodiment, the medical diagnostic examination system 2506 transmits the digital diagnostic image data and the digital diagnostic examination data to a dedicated server such as the data management server 2510 exemplarily illustrated in FIG. 25, based on user inputs received via the GDEI 2507 for storing the digital diagnostic image data and the digital diagnostic examination data on the data management server 2510.

The graphical diagnostic examination interface (GDEI) 2507 is configured as a Health Insurance Portability and Accountability Act (HIPAA) compliant interface for media based conferencing. In this embodiment, the GDEI is configured as a video conferencing application programming interface (API) that is compliant with the HIPAA standards for media based conferencing, for example, audio and/or video conferencing. This GDEI 2507 is configured similar to an API of the Skype® software application of Skype Corporation or Adobe® connect of Adobe Systems Incorporated, but in compliance to the HIPAA standards. A user, for example, a doctor using the medical diagnostic examination system 2506 can remotely view the diagnostic image data and the diagnostic examination data in real time via this GDEI 2507 through a video/audio conference with a patient or a medical assistant. A user, for example, a medical assistant who operates the image capture device 106 of the multipurpose diagnostic examination apparatus 100 has to activate a screen sharing mode on the GDEI 2507 for facilitating medical imaging and remote diagnostic examinations of one or more anatomical examination areas of the patient. For example, a medical assistant activates the screen sharing mode on the GDEI 2507 to enable a doctor using the medical diagnostic examination system 2506 to remotely view the diagnostic image data and the diagnostic examination data in real time via a video/audio conference configured over a high speed network, for example, Google Fiber® of Google Inc., that offers a data speed of about 1 gigabit per second (Gbps). The data speed that Google Fiber® offers is faster than the data speed of about 25 Megabits per second (Mbps) that conventional internet providers typically offer. The image capture device 106 used in this video/audio conference, comprises a high speed universal serial bus (USB) 3.0 camera, for example, a 5 Gbps USB 3.0 camera, for facilitating medical imaging and remote diagnostic examinations of the anatomical examination areas with an enhanced image quality. The user activates the screen sharing mode on the GDEI 2507 typically during diagnostic examinations performed with the medical diagnostic devices, for example, the stethoscope device 134 exemplarily illustrated in FIGS. 11A-11G, the ultrasound device 141 exemplarily illustrated in FIGS. 13A-13H, etc. In another embodiment, the image capture device 106 comprises a web camera, for example, a USB 3.0 web camera for facilitating medical imaging and remote diagnostic examinations of the anatomical examination areas of a patient without activating the screen sharing mode on the GDEI 2507. The user activates the web camera mode typically during diagnostic examinations performed with the medical diagnostic devices, for example, the otoscope device 119 exemplarily illustrated in FIGS. 5A-5L, the dermatoscope device 131 exemplarily illustrated in FIG. 8, the diagnosis assistance element 145 such as a tongue depressor exemplarily illustrated in FIGS. 14A-14H and FIGS. 14J-14M, etc.

Figure 17:
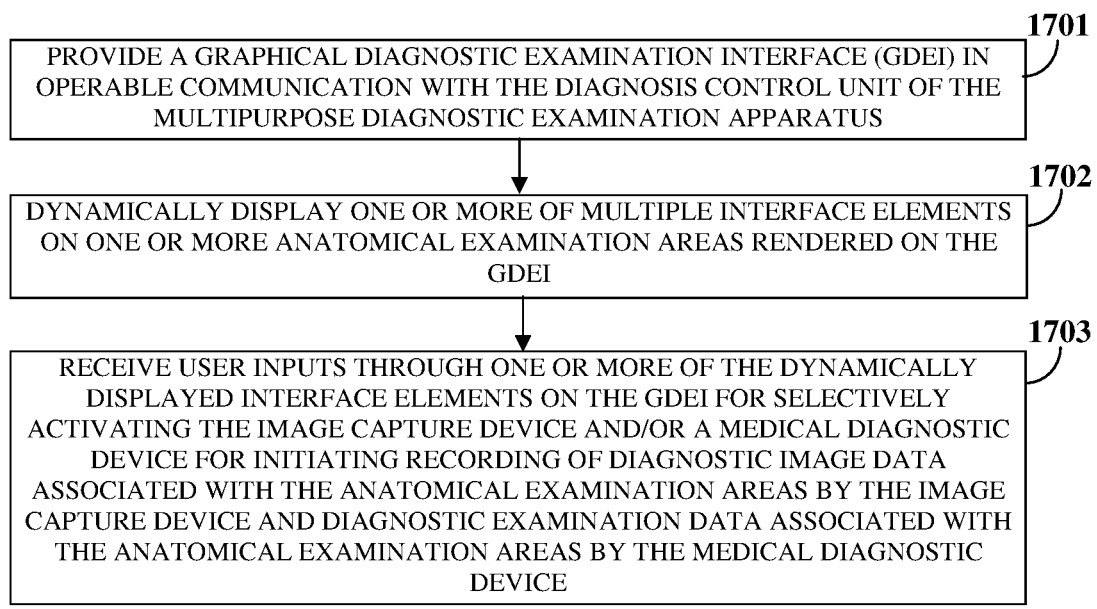
FIG. 17 illustrates a computer implemented method for facilitating medical imaging and remote diagnostic examinations of one or more anatomical examination areas via a graphical diagnostic examination interface.
Figure 18A:
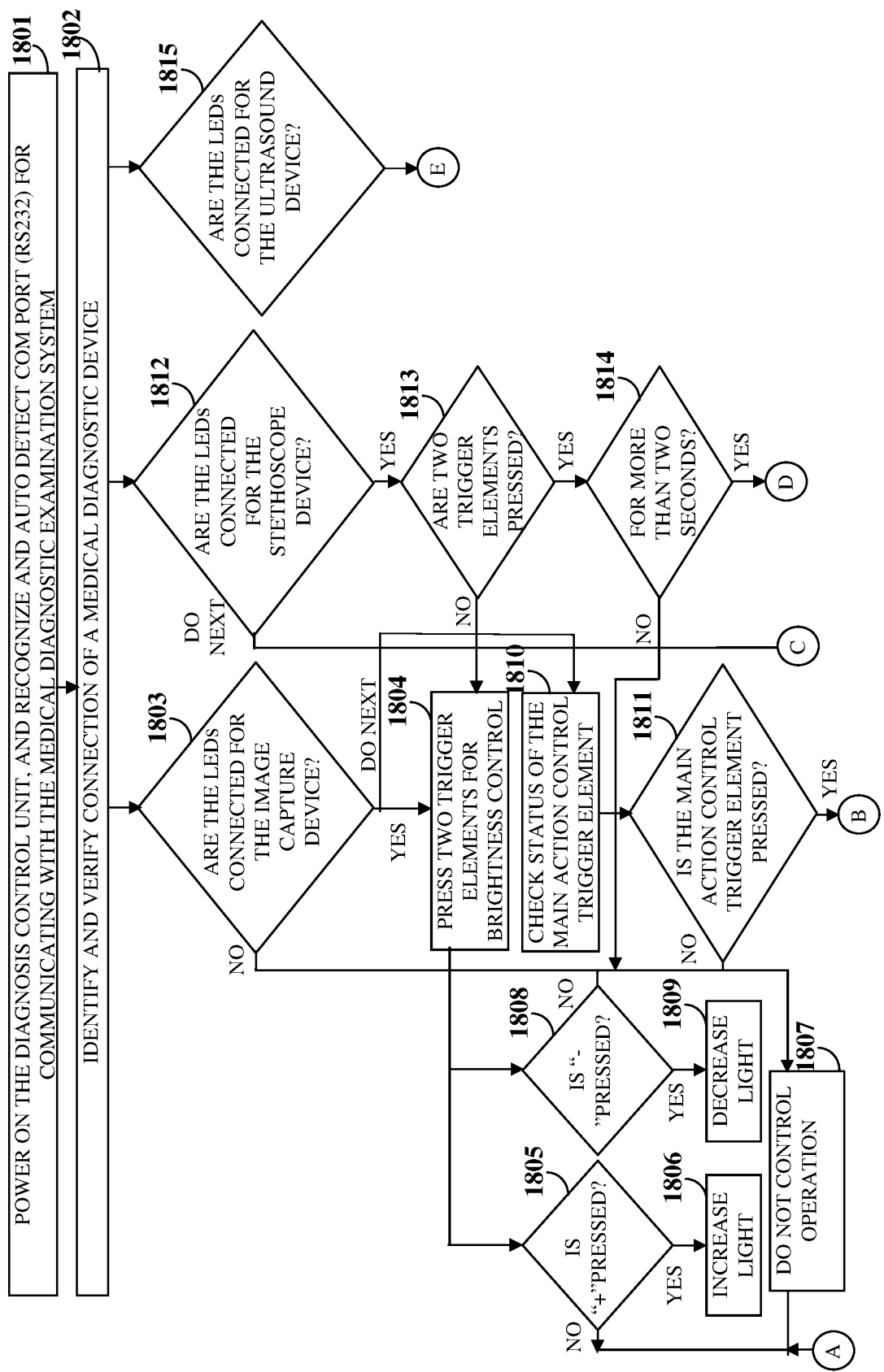
FIGS. 18A-18E exemplarily illustrate a flowchart comprising the steps performed by the microcontroller of the diagnosis control unit for facilitating medical imaging and remote diagnostic examinations.
Figure 18B:
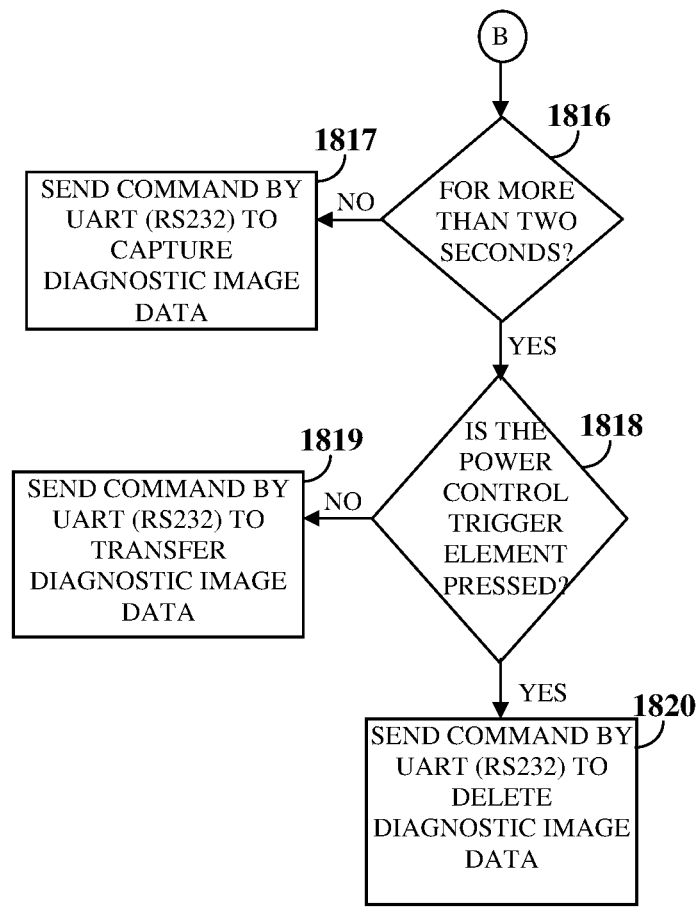
Figure 18C:
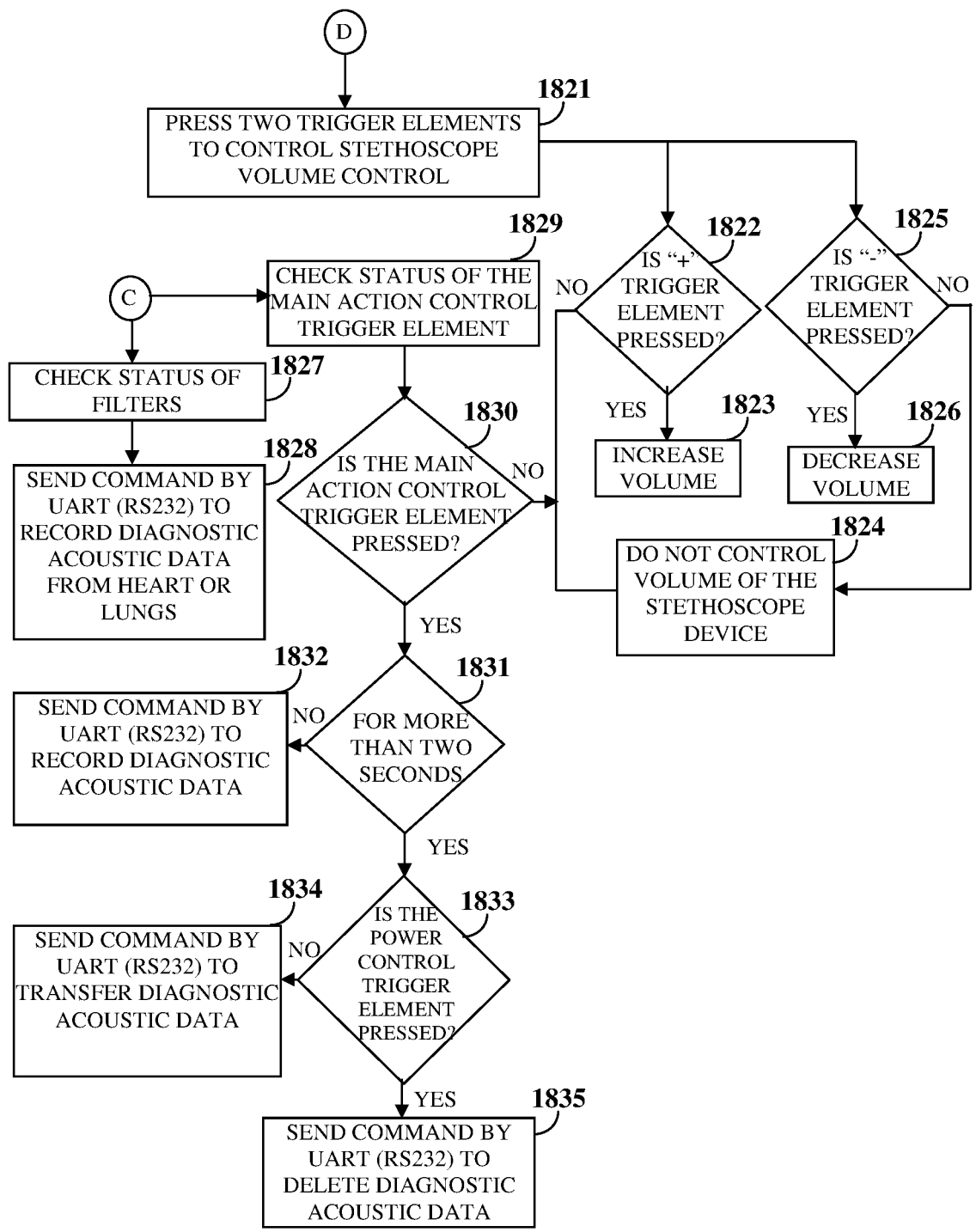
Figure 18D:
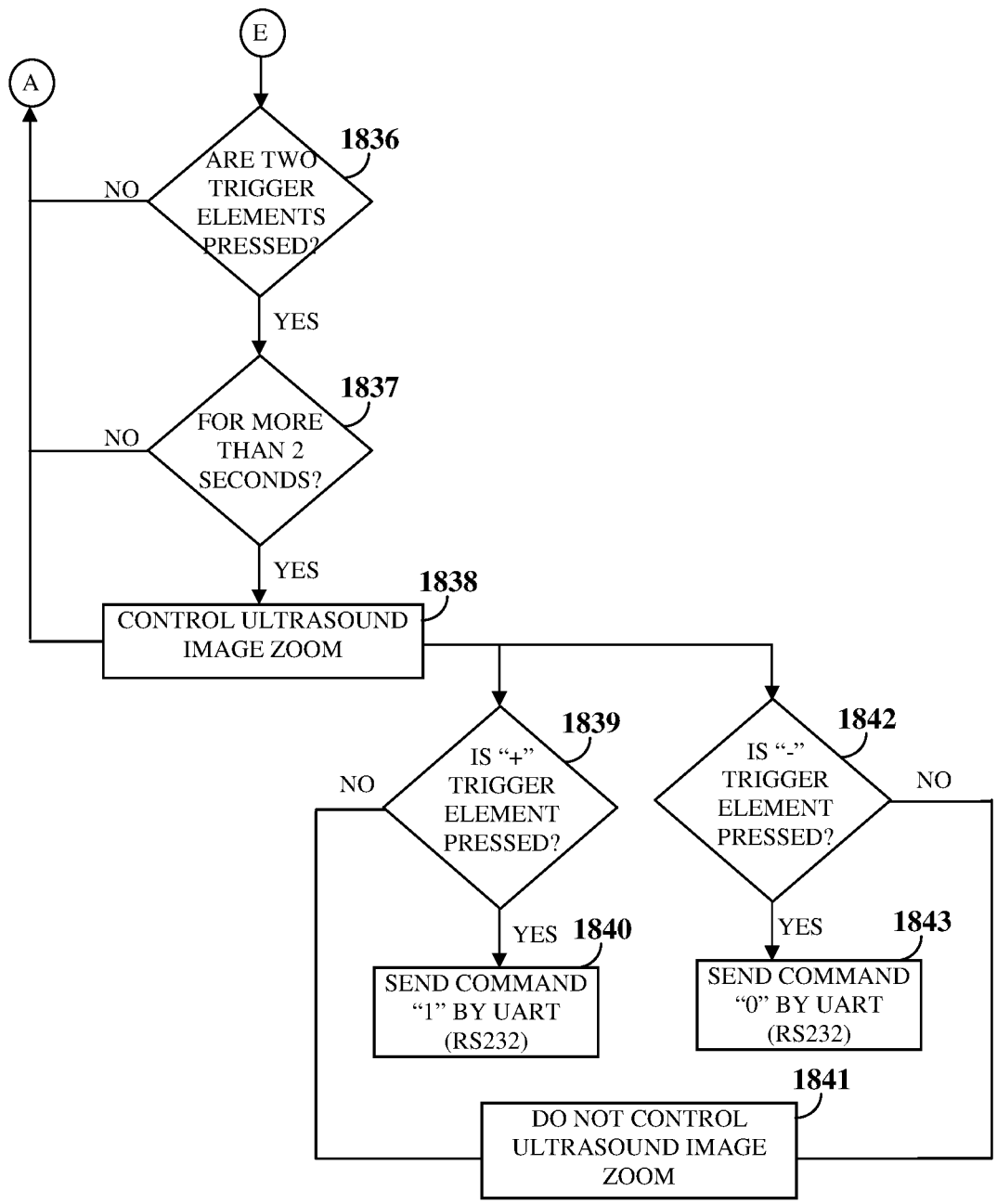
Figure 18E:
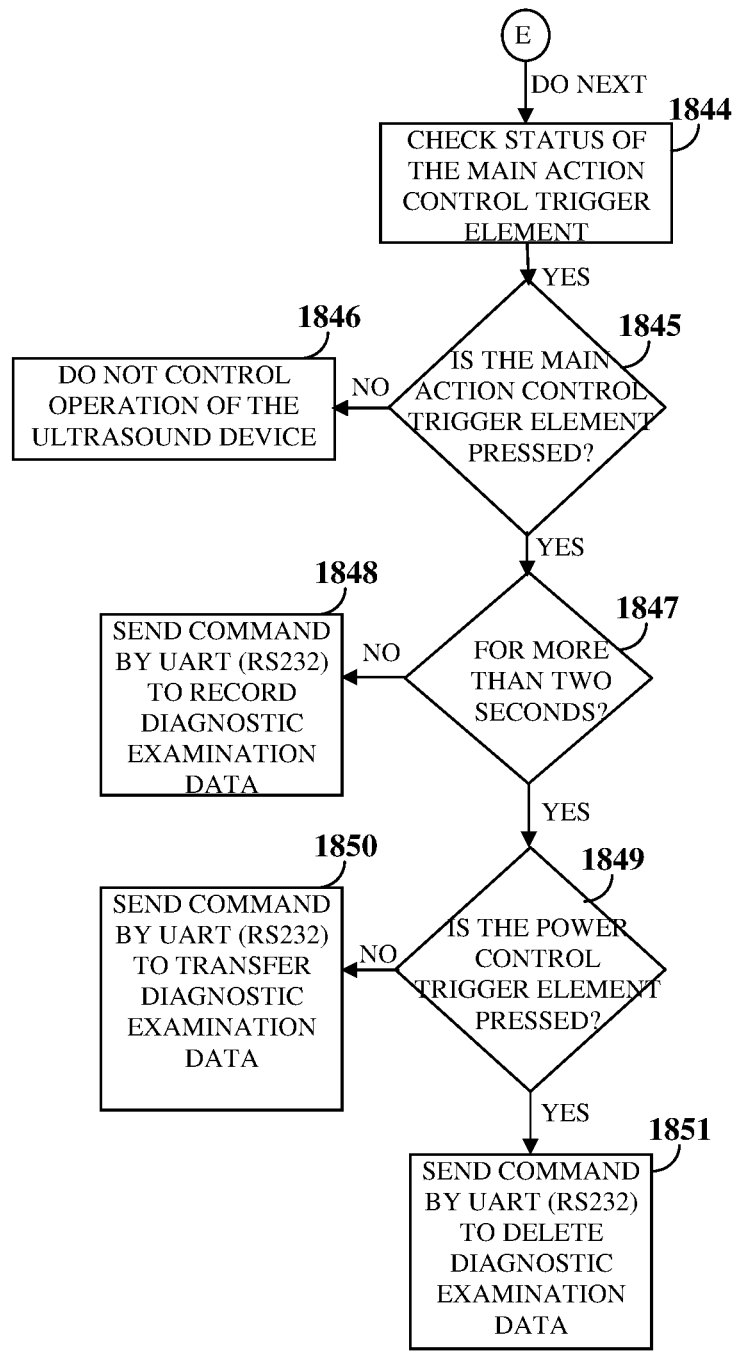

FIG. 17 illustrates a computer implemented method for facilitating medical imaging and remote diagnostic examinations of one or more anatomical examination areas via the graphical diagnostic examination interface (GDEI) 2507 exemplarily illustrated in FIG. 25. The method disclosed herein employs the medical diagnostic examination system 2506 exemplarily illustrated in FIG. 25, comprising at least one processor configured to execute computer program instructions for facilitating medical imaging and remote diagnostic examinations of one or more anatomical examination areas. The medical diagnostic examination system 2506, in operable communication with the diagnosis control unit 101 of the multipurpose diagnostic examination apparatus 100 exemplarily illustrated in FIGS. 1A-14M, provides 1701 the GDEI 2507. The GDEI 2507 of the medical diagnostic examination system 2506 is in operable communication with the diagnosis control unit 101 of the multipurpose diagnostic examination apparatus 100 exemplarily illustrated in FIGS. 1A-14M. The GDEI 2507 is configured to render and indicate one or more anatomical examination areas to be diagnostically examined using the multipurpose diagnostic examination apparatus 100 based on the connection status of the image capture device 106 and a medical diagnostic device, for example, an otoscope device 119 exemplarily illustrated in FIGS. 5A-5L, or an ophthalmoscope device (not shown), or a stethoscope device 134 exemplarily illustrated in FIGS. 11A-11G, or a dermatoscope device 131 exemplarily illustrated in FIG. 8, or an ultrasound device 141 exemplarily illustrated in FIGS. 13A-13H, or an endoscope device (not shown), etc., to the diagnosis control unit 101. The GDEI 2507 dynamically displays 1702 one or more of multiple interface elements on the rendered anatomical examination areas.

The graphical diagnostic examination interface (GDEI) 2507 receives 1703 user inputs through one or more of the dynamically displayed interface elements for selectively activating the image capture device 106 and/or the medical diagnostic device for initiating recording of diagnostic image data associated with the anatomical examination areas by the image capture device 106 and diagnostic examination data associated with the anatomical examination areas by the medical diagnostic device. In an embodiment, the medical diagnostic examination system 2506 stores the recorded diagnostic image data and the recorded diagnostic examination data in one or more formats. In an embodiment, the GDEI dynamically displays an updated status of diagnostic examination data based on subsequent diagnostic image data and subsequent diagnostic examination data received from the multipurpose diagnostic examination apparatus 100 by the medical diagnostic examination system 2506.

Consider an example where a user, for example, a medical assistant connects the stethoscope device 134 to the diagnosis control unit 101 of the multipurpose diagnostic examination apparatus 100 via the attachment unit 115. The medical assistant selects a microphone option or a stethoscope option on the graphical diagnostic examination interface (GDEI) 2507 to allow the medical diagnostic examination system 2506 to recognize the stethoscope device 134 as an audio/sound device, for example, a microphone on his/her local user device 2505 exemplarily illustrated in FIG. 25. The medical assistant selects an interface element 2702 exemplarily illustrated in FIG. 27A, followed by an interface element 2708 or 2709 exemplarily illustrated in FIG. 27C, for recording the diagnostic examination data at the heart or the lungs of a patient respectively, using the stethoscope device 134. Consider that the medical assistant is in an audio/video conference with a doctor at a remote location who is using the medical diagnostic examination system 2506 on his/her remote user device 2511. The doctor therefore, in real time views the anatomical examination areas on the GDEI 2507 exemplarily illustrated in FIG. 27D and FIG. 27F, and requests the medical assistant to record diagnostic examination data at one of the anatomical examination areas. The medical assistant activates the action control trigger element 104 of the multipurpose diagnostic examination apparatus 100 to start recording the diagnostic examination data at the anatomical examination areas indicated by the doctor. On detecting activation of the action control trigger element 104 and connection of the stethoscope device 134 to the diagnosis control unit 101, the microcontroller 2004 generates an action control signal indicating an action of recording diagnostic examination data by the stethoscope device 134. The diagnostic examination data recorded by the stethoscope device 134 comprises, for example, audio data of the anatomical examination areas such as the heart, the lungs, or the bowel, of the patient.

The microcontroller 2004 verifies whether the connector hub interface 2002 exemplarily illustrated in FIG. 20, is active for allowing transmission of the diagnostic examination data from the stethoscope device 134 to the medical diagnostic examination system 2506 on the medical assistant's local user device 2505. If the microcontroller 2004 verifies that the connector hub interface 2002 is active, the microcontroller 2004 sends a diagnostic data management signal to the medical diagnostic examination system 2506, for example, via a RS-232 port for recording the diagnostic examination data. The medical diagnostic examination system 2506 starts recording the audio data from the stethoscope device 134 in real time.

The medical diagnostic examination system 2506 records the audio data, converts the recorded audio data to a waveform (WAV) audio file format, creates a .WAV file of a configurable recording duration of about 1 minute, and stores the created .WAV file on a Health Insurance Portability and Accountability Act (HIPAA) compliant hard drive, or a HIPAA compliant dedicated server, or a HIPAA compliant server in a cloud computing environment. As used herein, "cloud computing environment" refers to a processing environment comprising configurable computing physical and logical resources, for example, networks, servers, storage, applications, services, etc., and data distributed over a communication network 2509, for example, the internet. The cloud computing environment provides on-demand network access to a shared pool of the configurable computing physical and logical resources. The medical assistant stores and/or shares the created .WAV files with the doctor via the audio/video conference for remote diagnostic examination. The doctor listens to audio output, that is, the audio data recorded by the stethoscope device 134 at the patient's heart, lungs, and/or bowel in real time. Similarly, the medical assistant can replace the stethoscope device 134 with an ultrasound device 141 and select another interface element 2706 on the graphical diagnostic examination interface (GDEI) 2507 exemplarily illustrated in FIG. 27A, for recording the diagnostic examination data using the ultrasound device 141. The microcontroller 2004 detects the connection of the ultrasound device 141 to the diagnosis control unit 101 and the activation of the action control trigger element 104 and allows the medical diagnostic examination system 2506 to record and store the ultrasound image data on a HIPAA compliant hard drive, or a HIPAA compliant dedicated server, or a HIPAA compliant server in a cloud computing environment for remote diagnostic examination.

FIGS. 18A-18E exemplarily illustrate a flowchart comprising the steps performed by the microcontroller 2004 of the diagnosis control unit 101 exemplarily illustrated in FIG. 20, for facilitating medical imaging and remote diagnostic examinations. When a user, for example, a medical assistant powers on 1801 the diagnosis control unit 101, the microcontroller 2004 recognizes and auto detects a communication (COM) port, for example, a RS-232 port for communicating with the medical diagnostic examination system 2506 accessible on a local user device 2505 exemplarily illustrated in FIG. 25. The microcontroller 2004 identifies and verifies 1802 which one of multiple medical diagnostic devices, for example, the otoscope device 119 exemplarily illustrated in FIGS. 5A-5L, an ophthalmoscope device (not shown), the stethoscope device 134 exemplarily illustrated in FIGS. 11A-11G, the dermatoscope device 131 exemplarily illustrated in FIG. 8, the ultrasound device 141 exemplarily illustrated in FIGS. 13A-13H, an endoscope device (not shown), etc., is connected to the diagnosis control unit 101 via the attachment unit 115. The microcontroller 2004 checks 1803 whether the light sources, for example, the light emitting diodes (LEDs) 125 are connected to the attachment unit 115, and whether the image capture device 106 is connected to the diagnosis control unit 101. The multipurpose diagnostic examination apparatus 100 comprising the image capture device 106 exemplarily illustrated in FIGS. 1A-14M can be used, for example, as a general examination device, an otoscope device 119, a stethoscope device 134, or a dermatoscope device 131, or an ultrasound device 141.

If the light emitting diodes (LEDs) 125 are not connected, the microcontroller 2004 does not control 1807 the operation of the LEDs 125. When only the light emitting diodes (LEDs) 125 and the image capture device 106 are connected to the multipurpose diagnostic examination apparatus 100, the two trigger elements 105a and 105b, for example, push buttons positioned on the upper section 101b of the diagnosis control unit 101 are used to control brightness levels of the LEDs 125. The user presses 1804 the output modification trigger elements 105a and 105b for controlling brightness of the LEDs 125, and the microcontroller 2004 receives actuation signals from the output modification trigger elements 105a and 105b. The microcontroller 2004 checks 1805 whether a "+" output modification trigger element 105b is pressed by the user. If the "+" output modification trigger element 105b is pressed, then the microcontroller 2004 increases 1806 the brightness of light emitted from the LEDs 125. If the "+" output modification trigger element 105b is not pressed, then the microcontroller 2004 does not control 1807 the operation of the LEDs 125. The microcontroller 2004 checks 1808 whether a "−" output modification trigger element 105a is pressed by the user. If the "−" output modification trigger element 105a is pressed, then the microcontroller 2004 decreases 1809 the brightness of light emitted from the LEDs 125. If the "−" output modification trigger element 105a is not pressed, then the microcontroller 2004 does not control 1807 the operation of the LEDs 125.

The microcontroller 2004 also checks 1810 the status of the action control trigger element 104 positioned on the upper section 101b of the diagnosis control unit 101 for controlling operation of the image capture device 106. The user can activate the image capture device 106 by applying a momentary press on the action control trigger element 104. The microcontroller 2004 checks 1811 whether the action control trigger element 104 is pressed. If the action control trigger element 104 is not pressed, then the microcontroller 2004 does not control 1807 operation of the image capture device 106. If the action control trigger element 104 is pressed, then the microcontroller 2004 checks 1816 whether the action control trigger element 104 is pressed for more than two seconds. If the action control trigger element 104 is not pressed for more than two seconds, then a universal asynchronous receiver/transmitter (UART) 2005 of the microcontroller 2004 exemplarily illustrated in FIG. 20, sends 1817 a command through a diagnostic data management signal to the medical diagnostic examination system 2506, for example, via a RS-232 port to capture diagnostic image data received from the image capture device 106 via the connector interface 123 of the multipurpose diagnostic examination apparatus 100. The microcontroller 2004 checks 1818 whether the power control trigger element 103 is pressed along with pressing the action control trigger element 104 for more than two seconds. If the power control trigger element 103 is not pressed and the action control trigger element 104 is pressed for more than two seconds, then the UART 2005 of the microcontroller 2004 sends 1819 a command through a diagnostic data management signal to the medical diagnostic examination system 2506 to transfer the diagnostic image data to a data management server 2510 for storage, to another local user device via the connector interface 123, or to a remote user device 2511 over a communication network 2509 exemplarily illustrated in FIG. 25, for facilitating medical imaging and remote diagnostic examination. If the action control trigger element 104 is pressed for more than two seconds and the power control trigger element 103 is also pressed, then the UART 2005 of the microcontroller 2004 sends 1820 a command through a diagnostic data management signal to the medical diagnostic examination system 2506 to delete the diagnostic image data. The medical diagnostic examination system 2506 receives the diagnostic data management signals from the multipurpose diagnostic examination apparatus 100, for example, via RS-232 ports of the local user device 2505 that deploys the medical diagnostic examination system 2506 and performs data management comprising, for example, recording, transferring, or deletion of the diagnostic image data based on the received diagnostic data management signals.

The microcontroller 2004 then checks 1812 whether the stethoscope device 134 is connected to the attachment unit 115 along with the LEDs 125. If the stethoscope device 134 is connected, the microcontroller 2004 checks 1827 the status of filters of the stethoscope device 134 for filtering diagnostic acoustic data received by the stethoscope device 134. After filtering the diagnostic acoustic data, the universal asynchronous receiver/transmitter (UART) 2005 of the microcontroller 2004 sends 1828 a command through a diagnostic data management signal to the medical diagnostic examination system 2506 to record the diagnostic acoustic data, for example, from the heart or lungs of a patient. In an embodiment, the microcontroller 2004 checks whether another light source, for example, a laser pointer 132 is connected on the upper section 101b of the diagnosis control unit 101. The microcontroller 2004 checks 1829 the status of the action control trigger element 104. The microcontroller 2004 then checks 1830 whether the action control trigger element 104 is pressed. The microcontroller 2004 then checks 1831 whether the action control trigger element 104 is pressed for more than two seconds. If the action control trigger element 104 is not pressed for more than two seconds, then the UART 2005 of the microcontroller 2004 sends 1832 a command through a diagnostic data management signal to the medical diagnostic examination system 2506 to record diagnostic acoustic data received from the stethoscope device 134.

The microcontroller 2004 also checks 1833 whether the power control trigger element 103 is pressed along with the action control trigger element 104 for more than two seconds. If the action control trigger element 104 is pressed for more than two seconds and the power control trigger element 103 is not pressed, then the UART 2005 of the microcontroller 2004 sends 1834 a command through a diagnostic data management signal to the medical diagnostic examination system 2506 to transfer the diagnostic acoustic data to the data management server 2510 for storage, and/or to a local user device 2505 that is in communication with a remote user device 2511 over a communication network 2509 for facilitating remote diagnostic examination. If the action control trigger element 104 is pressed for more than two seconds along with the power control trigger element 103, then the UART 2005 of the microcontroller 2004 sends 1835 a command through a diagnostic data management signal to the medical diagnostic examination system 2506 to delete the diagnostic acoustic data. The medical diagnostic examination system 2506 receives the diagnostic data management signals from the multipurpose diagnostic examination apparatus 100, for example, via RS-232 ports of the local user device 2505 that deploys the medical diagnostic examination system 2506 and performs data management comprising, for example, recording, transferring, or deletion of the diagnostic acoustic data from the multipurpose diagnostic examination apparatus 100 comprising the stethoscope device 134 based on the received diagnostic data management signals.

In an embodiment, the multipurpose diagnostic examination apparatus 100 with the stethoscope device 134 exemplarily illustrated in FIGS. 11A-11G, comprises output modification trigger elements (not shown) similar to the output modification trigger elements 105a and 105b positioned on the upper section 101b of the diagnosis control unit 101 exemplarily illustrated in FIG. 3. The microcontroller 2004 checks 1813 whether two output modification trigger elements are pressed simultaneously. If the output modification trigger elements are pressed 1804 subsequently, then the output modification trigger elements are used for adjusting and controlling the brightness of light from the LEDs 125. The microcontroller 2004 checks 1814 whether the output modification trigger elements are pressed simultaneously for more than two seconds. If the output modification trigger elements are not pressed simultaneously for more than two seconds, then the microcontroller 2004 does not control 1807 volume of diagnostic acoustic data received from the stethoscope device 134. If the output modification trigger elements are pressed simultaneously, then the output modification trigger elements control 1821 audio volume of the stethoscope device 134. The microcontroller 2004 checks 1822 whether the "+" output modification trigger element is pressed. If the "+" output modification trigger element is pressed, then the stethoscope device 134 increases 1823 volume of the diagnostic acoustic data received by the stethoscope device 134. If the "+" output modification trigger element is not pressed, then the microcontroller 2004 does not control 1824 the volume of the stethoscope device 134. The microcontroller 2004 checks 1825 whether the "−" output modification trigger element is pressed. If the "−" output modification trigger element is pressed, then the stethoscope device 134 decreases 1826 the volume of the diagnostic acoustic data received by the stethoscope device 134. If the "−" output modification trigger element is not pressed, then the microcontroller 2004 does not control 1824 the volume of the stethoscope device 134.

The microcontroller 2004 then checks 1815 whether the ultrasound device 141 is connected to the attachment unit 115 along with the LEDs 125. In an embodiment, the microcontroller 2004 checks whether another light source, for example, a laser pointer 132 is connected on the upper section 101b of the diagnosis control unit 101. In an embodiment, the multipurpose diagnostic examination apparatus 100 with the ultrasound device 141 exemplarily illustrated in FIGS. 13A-13H, comprises output modification trigger elements (not shown) similar to the output modification trigger elements 105a and 105b positioned on the upper section 101b of the diagnosis control unit 101 exemplarily illustrated in FIG. 3. The microcontroller 2004 checks 1836 whether two output modification trigger elements are pressed simultaneously. If the output modification trigger elements are pressed 1804 subsequently, then the output modification trigger elements are used for adjusting and controlling brightness of light from the LEDs 125. If the output modification trigger elements are pressed simultaneously, then the output modification trigger elements are used for image zooming control. The microcontroller 2004 checks 1837 whether the output modification trigger elements are pressed simultaneously for more than two seconds. If the output modification trigger elements are not pressed simultaneously for more than two seconds, then the microcontroller 2004 does not control 1807 image zoom of diagnostic examination data comprising, for example, ultrasound image data received from the ultrasound device 141. If the output modification trigger elements are pressed simultaneously for more than two seconds, then the output modification trigger elements control 1838 image zooming of the diagnostic examination data. The microcontroller 2004 checks 1839 whether a "+" output modification trigger element is pressed. If the "+" output modification trigger element is pressed, then the universal asynchronous receiver/transmitter (UART) 2005 of the microcontroller 2004 sends 1840 a command "1" to the medical diagnostic examination system 2506 to increase zoom of the diagnostic examination data displayed on the graphical diagnostic examination interface (GDEI) 2507 of the medical diagnostic examination system 2506 exemplarily illustrated in FIG. 25. If the "+" output modification trigger element is not pressed, then the microcontroller 2004 does not control 1841 ultrasound image zooming. The microcontroller 2004 checks 1842 whether a "−" output modification trigger element is pressed. If the "−" output modification trigger element is pressed, then the UART 2005 of the microcontroller 2004 sends 1843 a command "0" to the medical diagnostic examination system 2506 to decrease zoom of the diagnostic examination data displayed on the GDEI 2507 of the medical diagnostic examination system 2506. If the "−" output modification trigger element is not pressed, then the microcontroller 2004 does not control 1841 ultrasound image zooming.

The microcontroller 2004 then checks 1844 the status of the action control trigger element 104. If the action control trigger element 104 is active, then the microcontroller 2004 checks 1845 whether the action control trigger element 104 is pressed. If the action control trigger element 104 is not pressed, then the microcontroller 2004 does not control 1846 operation of the ultrasound device 141. The microcontroller 2004 then checks 1847 whether the action control trigger element 104 is pressed for more than two seconds. If the action control trigger element 104 is not pressed for more than two seconds, then the universal asynchronous receiver/transmitter (UART) 2005 of the microcontroller 2004 sends 1848 a command through a diagnostic data management signal to the medical diagnostic examination system 2506 to record the diagnostic examination data from the ultrasound device 141. The microcontroller 2004 then checks 1849 whether the power control trigger element 103 is pressed along with the action control trigger element 104 being pressed for more than two seconds. If the action control trigger element 104 is pressed for more than two seconds and the power control trigger element 103 is not pressed, then the UART 2005 of the microcontroller 2004 sends 1850 a command through a diagnostic data management signal to the medical diagnostic examination system 2506 to transfer the diagnostic examination data to the data management server 2510 for storage and/or to a local user device 2505 for facilitating remote diagnostic examination. If the action control trigger element 104 is pressed for more than two seconds along with the power control trigger element 103, then the UART 2005 of the microcontroller 2004 sends 1851 a command through a diagnostic data management signal to the medical diagnostic examination system 2506 to delete the diagnostic examination data. The medical diagnostic examination system 2506 receives the diagnostic data management signals from the multipurpose diagnostic examination apparatus 100, for example, via RS-232 ports of the local user device 2505 that deploys the medical diagnostic examination system 2506 and performs data management comprising, for example, recording, transferring, or deletion of the diagnostic examination data from the multipurpose diagnostic examination apparatus 100 comprising the ultrasound device 141 based on the received diagnostic data management signals.

Figure 19A:
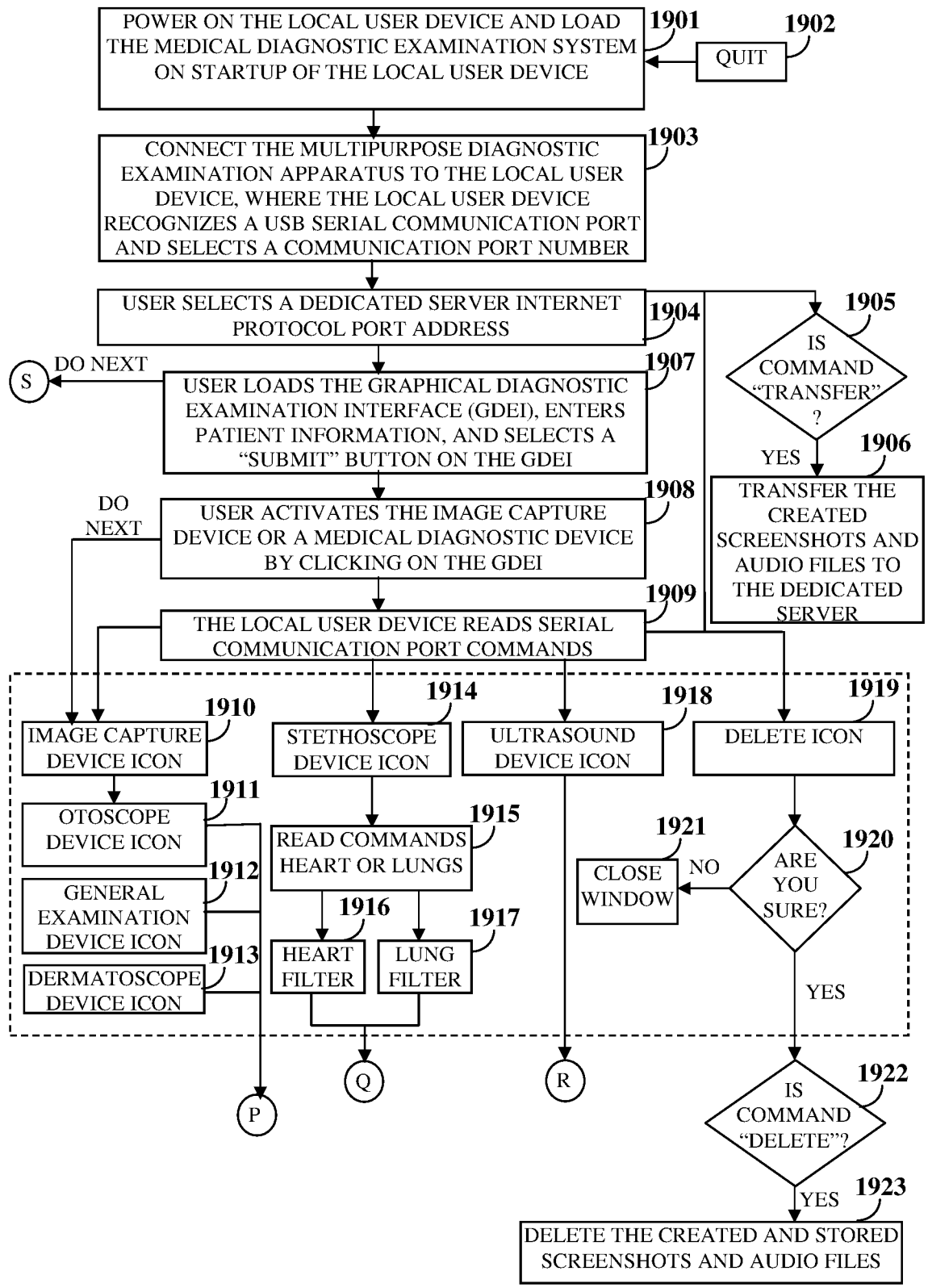
FIGS. 19A-19C exemplarily illustrate a flowchart comprising the steps performed by the medical diagnostic examination system for facilitating medical imaging and remote diagnostic examinations.
Figure 19B:
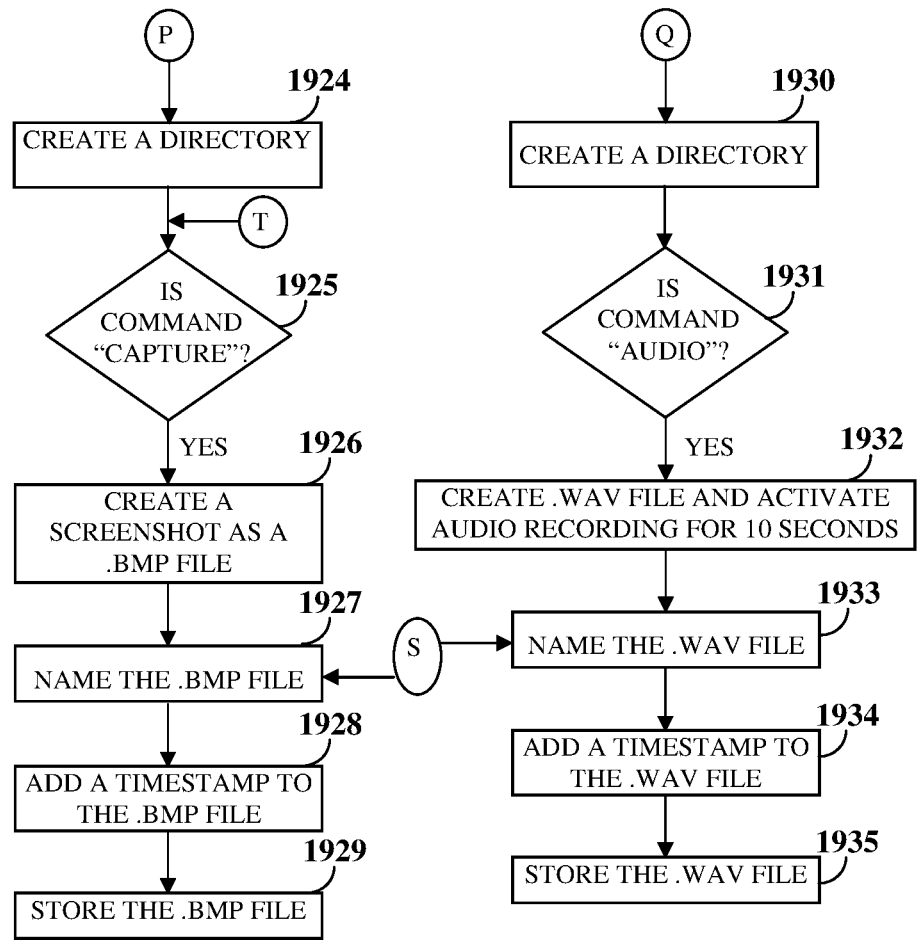
Figure 19C:
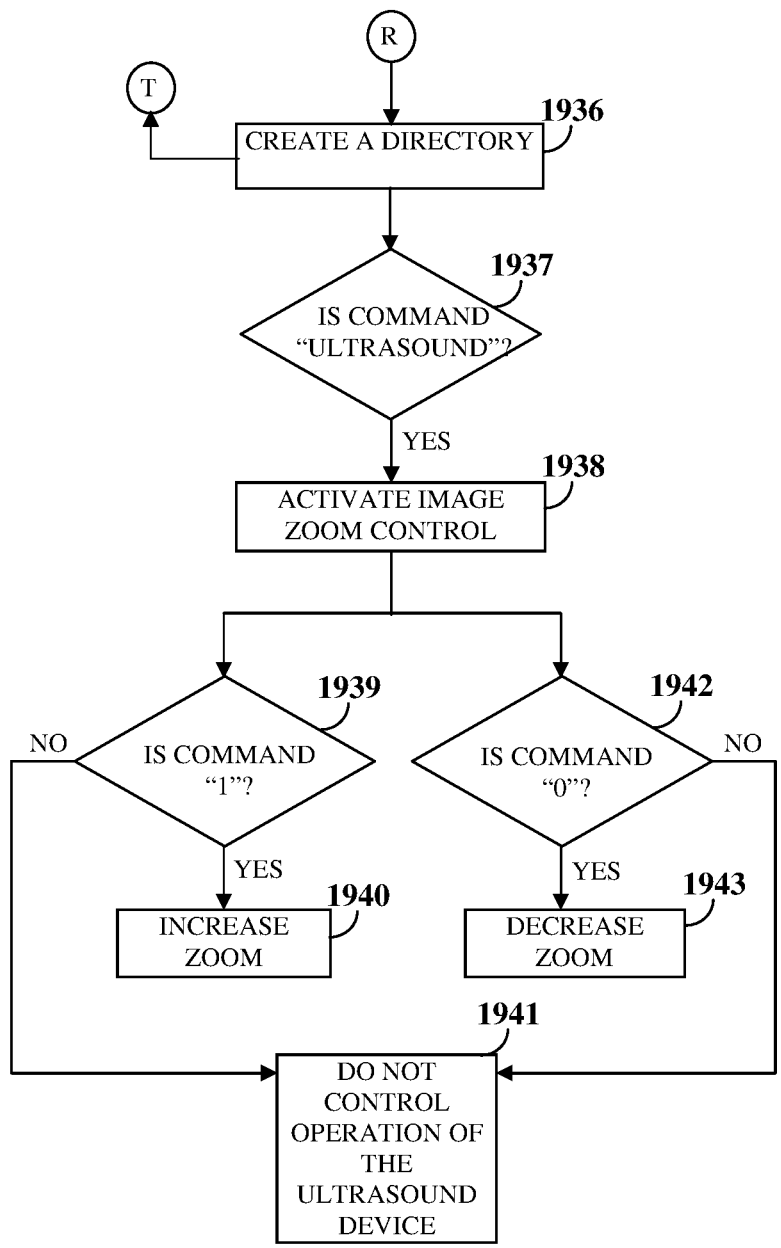

FIGS. 19A-19C exemplarily illustrate a flowchart comprising the steps performed by the medical diagnostic examination system 2506 exemplarily illustrated in FIG. 25, for facilitating medical imaging and remote diagnostic examinations. A user, for example, a medical assistant can activate the multipurpose diagnostic examination apparatus 100 comprising, for example, the image capture device 106 to be used as a general medical examination device, an otoscope device 119 exemplarily illustrated in FIGS. 5A-5L, or a dermatoscope device 131 exemplarily illustrated in FIG. 8, or comprising the image capture device 106 with the laser pointer 132 and the stethoscope device 134 exemplarily illustrated in FIGS. 11A-11G, or comprising the image capture device 106 with the laser pointer 132 and the ultrasound device 141 exemplarily illustrated in FIGS. 13A-

13H, by one click on the graphical diagnostic examination interface (GDEI) 2507 provided by the medical diagnostic examination system 2506 exemplarily illustrated in FIG. 25. A user first powers on 1901 a local user device 2505 exemplarily illustrated in FIG. 25, for example, a computer, a tablet computing device, a laptop, a notebook, etc., and downloads the medical diagnostic examination system 2506 on the local user device 2505. On startup of the local user device 2505, the medical diagnostic examination system 2506 is loaded. If the user does not want to access the medical diagnostic examination system 2506, the user can click 1902 on a "Quit" button provided on the GDEI 2507 of the medical diagnostic examination system 2506.

The user then connects 1903 the multipurpose diagnostic examination apparatus 100 to the local user device 2505 via the connector interface 123 of the multipurpose diagnostic examination apparatus 100. The local user device 2505 recognizes a universal serial bus (USB) serial communication port, for example, via low level drivers of the local user device 2505 and selects a communication (COM) port number for establishing serial communication between the multipurpose diagnostic examination apparatus 100 on the local user device 2505 and the multipurpose diagnostic examination apparatus 100. The connector interface 123 of the multipurpose diagnostic examination apparatus 100 comprises two connector elements 123a and 123b, for example, two USB ports. In an embodiment, one of the USB ports of the connector interface 123 is used for serial port communication between the local user device 2505 and the multipurpose diagnostic examination apparatus 100 for providing operational system support and automatically defining a COM port for communication between the local user device 2505 and the multipurpose diagnostic examination apparatus 100.

In this embodiment, the other USB port connects the microcontroller 2004 of the diagnosis control unit 101, through an internal connector hub interface 2002 of the diagnosis control unit 101 exemplarily illustrated in FIG. 20, to the image capture device 106 and/or a medical diagnostic device, for example, the otoscope device 119 exemplarily illustrated in FIGS. 5A-5L, or an ophthalmoscope device (not shown), or the stethoscope device 134 exemplarily illustrated in FIGS. 11A-11G, or the dermatoscope device 131 exemplarily illustrated in FIG. 8, or the ultrasound device 141 exemplarily illustrated in FIGS. 13A-13H, or an endoscope device (not shown), etc. The microcontroller 2004 identifies which one or two of the image capture device 106 and the medical diagnostic device are connected. For example, the image capture device 106 can be connected without the stethoscope device 134 or the ultrasound device 141, or in another example, the image capture device 106 can be connected with the stethoscope device 134 or the ultrasound device 141. The connector interface 123 recognizes the connection of the image capture device 106, the stethoscope device 134, and the ultrasound device 141. In an embodiment, the medical diagnostic examination system 2506 comprises, for example, three different application programming interfaces (APIs) for the image capture device 106, the stethoscope device 134, and the ultrasound device 141.

The user selects 1904 a dedicated service internet protocol (IP) port address of the data management server 2510 for diagnostic data communication between the medical diagnostic examination system 2506, the multipurpose diagnostic examination apparatus 100, and the data management server 2510. The user can transfer the diagnostic image data and the diagnostic examination data to the dedicated server, for example, the Health Insurance Portability and Accountability Act (HIPAA) compliant data management server 2510 for ensuring the security of diagnostic data communication. The medical diagnostic examination system 2506 checks 1905 whether a "transfer" command is received from the microcontroller 2004 of the multipurpose diagnostic examination apparatus 100. If the medical diagnostic examination system 2506 receives the "transfer" command, the medical diagnostic examination system 2506 transfers 1906 the created screenshots and audio files received from the image capture device 106 and/or the medical diagnostic device to the dedicated server via the communication network 2509 exemplarily illustrated in FIG. 25.

The user loads 1907 the graphical diagnostic examination interface (GDEI) 2507 provided by the medical diagnostic examination system 2506 exemplarily illustrated in FIG. 25, enters patient information comprising, for example, a first name, a last name, a date of birth, a medical case number, etc., via the GDEI 2507, and selects a "submit" button 2507a provided on the GDEI 2507. The patient information is used by the medical diagnostic examination system 2506 to create data files such as .BMP files of a bitmap (BMP) image file format or .WAV files of a waveform (WAV) audio file format for storing diagnostic examination data. The data files comprise, for example, patient information such as the first name and the last name, the date of birth, etc., and a timestamp. The timestamp comprises, for example, date in a format such as a MMDDYY+M+S format that comprises date, minutes, and seconds. In an embodiment, the medical diagnostic examination system 2506 creates a timestamp for each data file based on an operational system preset calendar date and time of the local user device 2505.

The medical diagnostic examination system 2506 detects a communication port of the multipurpose diagnostic examination apparatus 100. The user selects one or more of the three devices, for example, the image capture device 106, the stethoscope device 134, and/or the ultrasound device 141 via the graphical diagnostic examination interface (GDEI) 2507 that he/she wishes to activate 1908 in the multipurpose diagnostic examination apparatus 100. The microcontroller 2004 of the multipurpose diagnostic examination apparatus 100 sends diagnostic data management signals via the connector interface 123 of the multipurpose diagnostic examination apparatus 100 to RS-232 ports of the local user device 2505 for indicating different functions to be performed by the medical diagnostic examination system 2506 for management of the diagnostic image data and the diagnostic examination data received from the multipurpose diagnostic examination apparatus 100. The medical diagnostic examination system 2506 on the local user device 2505 reads 1909 diagnostic data management signals configured as serial communication port commands received from the multipurpose diagnostic examination apparatus 100. The medical diagnostic examination system 2506 detects the serial communication port of the multipurpose diagnostic examination apparatus 100 and displays icons for the medical diagnostic devices, for example, the otoscope device 119 exemplarily illustrated in FIGS. 5A-5L, an ophthalmoscope device (not shown), the stethoscope device 134 exemplarily illustrated in FIGS. 11A-11G, the dermatoscope device 131 exemplarily illustrated in FIG. 8, the ultrasound device 141 exemplarily illustrated in FIGS. 13A-13H, an endoscope device (not shown), etc., connected to the multipurpose diagnostic examination apparatus 100 on the GDEI 2507.

If the user selects 1910 an image capture device icon on the graphical diagnostic examination interface (GDEI) 2507, then the medical diagnostic examination system 2506 further displays multiple icons, for example, an otoscope device icon 1911, a general examination device icon 1912, or a dermatoscope device icon 1913 on the GDEI 2507 for selecting a medical diagnostic device to perform diagnostic examination. The medical diagnostic examination system 2506 creates 1924 a directory for storing the diagnostic image data received from the image capture device 106, and the general medical examination device, or the otoscope device 119, or the dermatoscope device 131. The medical diagnostic examination system 2506 creates screenshots as .BMP files for the diagnostic image data and stores the created .BMP files in the directory. Consider an example where the user selects the otoscope device icon on the GDEI 2507 for activating use of the otoscope device 119 in the multipurpose diagnostic examination apparatus 100. If the user presses the action control trigger element 104 on the diagnosis control unit 101 of the multipurpose diagnostic examination apparatus 100, then the microcontroller 2004 sends a "capture" command to the local user device 2505. The medical diagnostic examination system 2506 checks 1925 whether the medical diagnostic examination system 2506 has received a "capture" command from the microcontroller 2004 of the multipurpose diagnostic examination apparatus 100. If the medical diagnostic examination system 2506 has received the "capture" command, the medical diagnostic examination system 2506 receives and processes the "capture" command, creates 1926 a screenshot of the diagnostic image data displayed on the GDEI 2507, and saves the screenshot as a .BMP file. The medical diagnostic examination system 2506 then names 1927 the .BMP file and adds 1928 a timestamp to the .BMP file. The medical diagnostic examination system 2506 then stores 1929 the .BMP file in the directory created for the image capture device 106, for example, in a secure hard drive, a HIPAA compliant secure flash memory, or the data management server 2510.

If the multipurpose diagnostic examination apparatus 100 connected to the local user device 2505 that deploys the medical diagnostic examination system 2506 comprises the image capture device 106 and the stethoscope device 134, the medical diagnostic examination system 2506 displays a stethoscope device icon on the graphical diagnostic examination interface (GDEI) 2507 to the user. When the user selects 1914 the stethoscope device icon, the local user device 2505 recognizes the image capture device 106 and the stethoscope device 134 connected via the connector interface 123 comprising, for example, universal serial bus (USB) ports. The medical diagnostic examination system 2506 reads 1915 heart or lung commands received from the user via the GDEI 2507. The user selects a heart filter 1916 or a lung filter 1917 on the GDEI 2507 if the user wishes to receive diagnostic acoustic data from the heart or the lungs of a patient respectively. The medical diagnostic examination system 2506 creates 1930 a directory for storing diagnostic acoustic data received from the stethoscope device 134. The microcontroller 2004 of the multipurpose diagnostic examination apparatus 100 sends a diagnostic data management signal configured as an "audio" command by RS-232 ports to the medical diagnostic examination system 2506 on the local user device 2505 to indicate the next function to be performed on the diagnostic acoustic data. If the user selects the action control trigger element 104 for recording the diagnostic acoustic data, the microcontroller 2004 transmits the "audio" command through a diagnostic data management signal to the medical diagnostic examination system 2506 on the local user device 2505 to record the received diagnostic acoustic data, for example, for 10 seconds and create, for example, a .WAV file. The medical diagnostic examination system 2506 checks 1931 whether the "audio" command is received from the multipurpose diagnostic examination apparatus 100. If the medical diagnostic examination system 2506 receives the "audio" command, the medical diagnostic examination system 2506 creates 1932 the .WAV file and activates audio recording for 10 seconds. The medical diagnostic examination system 2506 names 1933 the created .WAV file and adds 1934 a timestamp to the created .WAV file. The medical diagnostic examination system 2506 stores 1935 the created .WAV file in a directory created for diagnostic acoustic data received from heart or lungs.

If the user wants to receive diagnostic examination data comprising, for example, ultrasound image data from the ultrasound device 141, the user connects the image capture device 106 and the ultrasound device 141 to the multipurpose diagnostic examination apparatus 100. The user selects 1918 an ultrasound device icon on the graphical diagnostic examination interface (GDEI) 2507. The local user device 2505 recognizes and detects communication ports of the image capture device 106 and the ultrasound device 141. The medical diagnostic examination system 2506 launches an ultrasound application programming interface (API) to allow the user to view the ultrasound image data from the ultrasound device 141 on the GDEI 2507. The medical diagnostic examination system 2506 creates 1936 a directory for storing the ultrasound image data received from the ultrasound device 141. The microcontroller 2004 of the multipurpose diagnostic examination apparatus 100 sends diagnostic data management signals to the medical diagnostic examination system 2506 on the local user device 2505 via serial communication ports, indicating next functions to be performed on the ultrasound image data. If the user presses both the "+" output modification trigger element and the "−" output modification trigger element of the multipurpose diagnostic examination apparatus 100, then the microcontroller 2004 sends an "ultrasound" command to the medical diagnostic examination system 2506. The medical diagnostic examination system 2506 checks 1937 whether an "ultrasound" command is received from the multipurpose diagnostic examination apparatus 100. The two output modification trigger elements function as ultrasound zoom controllers. If the medical diagnostic examination system 2506 receives the "ultrasound" command from the multipurpose diagnostic examination apparatus 100, the medical diagnostic examination system 2506 activates 1938 image zoom control. If the user presses the "+" output modification trigger element, the communication port of the medical diagnostic examination system 2506 receives a command "1" 1939 from the microcontroller 2004 for increasing 1940 zoom of the image displayed on the GDEI 2507. If the user presses the "−" output modification trigger element, the communication port of the medical diagnostic examination system 2506 receives a command "0" 1942 from the microcontroller 2004 for decreasing 1943 zoom of the image displayed on the GDEI 2507. If the medical diagnostic examination system 2506 receives no command from the microcontroller 2004 of the multipurpose diagnostic examination apparatus 100, then the medical diagnostic examination system 2506 does not control 1941 zoom of the ultrasound image data from the ultrasound device 141. If the user presses the action control trigger element 104, then the microcontroller 2004 sends a "capture" command to the medical diagnostic examination system 2506. The medical diagnostic examination system 2506 creates a screenshot of the image displayed on the GDEI 2507, names the screenshot, adds a timestamp, and stores the created image file.

If the user selects 1919 a "delete" icon on the graphical diagnostic examination interface (GDEI) 2507, the medical diagnostic examination system 2506 prompts 1920 the user to confirm the delete command via the GDEI 2507. If the user indicates that he/she does not want to delete the ultrasound image data, then the medical diagnostic examination system 2506 closes 1921 a "delete" window on the GDEI 2507. The medical diagnostic examination system 2506 checks 1922 whether the "delete" command is received from the microcontroller 2004 of the multipurpose diagnostic examination apparatus 100. If the medical diagnostic examination system 2506 receives the "delete" command, then the medical diagnostic examination system 2506 deletes 1923 the created and stored screenshots and audio files.

FIG. 20 exemplarily illustrates a block diagram of the diagnosis control unit 101 of the multipurpose diagnostic examination apparatus 100 exemplarily illustrated in FIGS. 1A-14M, showing the image capture device 106 connected to the diagnosis control unit 101. FIG. 20 exemplarily illustrates a configuration of the printed circuit board (PCB) 120 to be incorporated in the diagnosis control unit 101. The PCB 120 of the diagnosis control unit 101 is connected to a universal serial bus (USB) 3.0 compatible camera module 124 as exemplarily illustrated in FIG. 20. The optical lens 107 for the camera module 124 comprises a manual adjustable zoom functionality along with an image focusing functionality. The camera module 124 interconnects with a supplementary connector interface, for example, a micro B USB 3.0 connector plug 2001. In an embodiment, the micro B USB 3.0 connector plug 2001 is configured, for example, as two removable adapters configured to allow the multipurpose diagnostic examination apparatus 100 to function as the image capture device 106 along with the stethoscope device 134 exemplarily illustrated in FIGS. 11A-11G, or with the ultrasound device 141 exemplarily illustrated in FIGS. 13A-13H. The micro B USB 3.0 connector plug 2001 is accommodated in the PCB 120 of the diagnosis control unit 101. The micro B USB 3.0 connector plug 2001 plugs in directly to the camera module 124.

The diagnosis control unit 101 further comprises a universal serial bus (USB) 3.0 connector hub interface 2002 configured to allow simultaneous operation of the image capture device 106 with a medical diagnostic device, for example, the stethoscope device 134 or the ultrasound device 141. For example, the connector hub interface 2002 can allow a simultaneous operation of the image capture device 106 and the stethoscope device 134 or a simultaneous operation of the image capture device 106 and the ultrasound device 141. When two devices, for example, the image capture device 106 and the stethoscope device 134 or the image capture device 106 and the ultrasound device 141 connect through one USB port on a local user device 2505 exemplarily illustrated in FIG. 25, the operating system of the local user device 2505, for example, Windows® XP, 7, 8/8.1, etc., of Microsoft corporation, the Mac operating system (OS) of Apple Inc., the Linux® operating system, the Android operating system of Google Inc., etc., recognizes the image capture device 106 and the connected medical diagnostic device, for example, 134, 141, etc., as two separate devices via device drivers installed in the local user device 2505. When a medical diagnostic device such as the ultrasound device 141 or the stethoscope device 134 is not connected to the multipurpose diagnostic examination apparatus 100, the local user device 2505 recognizes only the image capture device 106. The communication signals, for example, the USB 3.0 communication signals between the image capture device 106 and the connector hub interface 2002 comprise, for example, D-_a, D+_a, SSRX-_a, SSRX+_a, SSTX-_a, SSTX+_a, GND, etc. The connector hub interface 2002 transmits acknowledge signals to the microcontroller 2004 to indicate connection of the image capture device 106 and/or a medical diagnostic device, for example, 134, 141, etc., to the diagnosis control unit 101.

In an embodiment, the microcontroller 2004 is configured to verify whether the connector hub interface 2002 is active and can process transmission of the diagnostic image data to the local user device 2505. The microcontroller 2004 is configured to receive actuation signals from one or more of multiple trigger elements 102 positioned on a predefined section, for example, the upper section 101*b* of the diagnosis control unit 101 exemplarily illustrated in FIG. 1A. The microcontroller 2004 processes the received actuation signals to generate action control signals for indicating one or more actions to be performed by the image capture device 106, and/or multiple medical diagnostic devices for example, the otoscope device 119 exemplarily illustrated in FIGS. 5A-5L, an ophthalmoscope device (not shown), the stethoscope device 134 exemplarily illustrated in FIGS. 11A-11G, the dermatoscope device 131 exemplarily illustrated in FIG. 8, the ultrasound device 141 exemplarily illustrated in FIGS. 13A-13H, an endoscope device (not shown), etc., interchangeably connected to the diagnosis control unit 101 via the attachment unit 115. The actions to be performed by the image capture device 106 and the medical diagnostic devices comprise, for example, one or more of power control of the image capture device 106 and the medical diagnostic devices, power control of one or more of multiple light sources, for example, the light emitting diodes 125, the laser pointer 132, etc., capture of the diagnostic image data by the image capture device 106, recording of the diagnostic examination data by the medical diagnostic devices, recording of the diagnostic image data and the diagnostic examination data for a predefined time period, managing storage of the diagnostic image data and the diagnostic examination data, managing deletion of the stored diagnostic image data and the stored diagnostic examination data, light generation and brightness control by the light sources, image scaling by the image capture device 106, audio volume control, creation of audio files in multiple audio file formats, etc., and any combination thereof. The medical diagnostic devices record diagnostic examination data comprising, for example, audio data, video data, image data, etc., and any combination thereof. The camera module 124 processes the captured diagnostic image data and the recorded diagnostic examination data. The microcontroller 2004 facilitates transmission of the processed diagnostic image data and the diagnostic examination data of multiple formats from the medical diagnostic devices to the medical diagnostic examination system 2506 accessible on the local user device 2505 exemplarily illustrated in FIG. 25, via the universal serial bus (USB) 3.0 connector interface 123.

The connector interface 123 comprises at least two connector elements 123*a* and 123*b* configured, for example, as connector plugs exemplarily illustrated in FIG. 5H. The communication signals between the camera module 124 and a top connector element 123*a* of the connector interface 123 comprise, for example, D-_MAIN, D+_MAIN, SSRX-_MAIN, SSRX+_MAIN, SSTX-_MAIN, SSTX+_MAIN, GND, GND_DRAIN, etc. The top connector element 123*a* of the connector interface 123 connects to and communicates with the camera module 124 and the bottom connector element 123b connects to and communicates with the microcontroller 2004 of the diagnosis control unit 101. In an embodiment, the connector interface 123 configured as a USB 3.0 dual connector plug can be used as a USB 2.0 dual connector plug. If a USB 2.0 dual connector plug is used as the connector interface 123 for facilitating communication of the camera module 124 with the microcontroller 2004 of the diagnosis control unit 101, then only bottom connector element signals, for example, D− and D+ are utilized for the communication.

The connector interface 123 communicates with a data converter, for example, a universal serial bus (USB) to RS-232 converter 2003. The USB to RS-232 converter 2003 converts, for example, D− and D+ signals from the connector interface 123 to transmitter and receiver signals, for example, Tx and Rx to allow the camera module 124 to communicate with a universal asynchronous receiver or transmitter (UART) 2005 of the microcontroller 2004. In an embodiment, the microcontroller 2004 is, for example, an 8 bit microcontroller. In an embodiment, the microcontroller 2004 comprises, for example, the UART 2005, a serial peripheral interface (SPI), an inter-integrated circuit (I²C), and three ports with ten external interrupt support pins, for example, INT0 to INT9.

As exemplarily illustrated in FIG. 20, the power control trigger element 103 and the action control trigger element 104 are internally connected to the microcontroller 2004. In an embodiment, the power control trigger element 103 is configured to generate one or more outputs on occurrence of a single push or press on the power control trigger element 103. In an embodiment, the power control trigger element 103 is configured as an external momentary push button with double connects. In this embodiment, one push of the power control trigger element 103 creates dual events. The diagnosis control unit 101 further comprises a delay block 2006 configured as an integrated chip configured to function as a debouncer. The delay block 2006 is configured to provide pulses with a delay to the microcontroller 2004. For example, when the action control trigger element 104 is pressed and held for two seconds, the delay block 2006 provides an interrupt to the microcontroller 2004, thereby allowing the microcontroller 2004 to transmit diagnostic data management signals to the medical diagnostic examination system 2506, for example, via RS-232 communication ports of the local user device 2505 that deploys the medical diagnostic examination system 2506. In another example, when the action control trigger element 104 is pressed, the delay block 2006 provides an interrupt to the microcontroller 2004 to facilitate transfer of the recorded diagnostic examination data to the medical diagnostic examination system 2506. In another example, when both the action control trigger element 104 and the power control trigger element 103 are pressed and held simultaneously, the delay block 2006 provides an interrupt to the microcontroller 2004 to transmit diagnostic data management signals to the medical diagnostic examination system 2506, for example, via the RS-232 communication ports for indicating deletion of diagnostic examination data.

The diagnosis control unit 101 further comprises a buzzer 2007, for example, a small sized magnetic buzzer. The buzzer 2007 determines and provides better use experience of the multipurpose diagnostic examination apparatus 100 to a user. The buzzer 2007 enables transfer of the created diagnostic examination data files, for example, .WAV files of a waveform (WAV) audio file format or .PNG files of a portable network graphics (PNG) format to a directory created by the medical diagnostic examination system 2506, when a user presses and holds the action control trigger element 104. The buzzer 2007 also enables deletion of the created diagnostic examination data files by the medical diagnostic examination system 2506, when the user presses and holds the action control trigger element 104 and the power control trigger element 103. In an embodiment, the microcontroller 2004 is in communication with a 1024 kilobyte (kb) serial complementary metal-oxide-semiconductor (CMOS) electrically erasable programmable read only memory (EEPROM) 2008.

A VBUS connector pin 2015 of the top connector element 123a of the connector interface 123 provides a voltage supply of, for example, about 5 volts (V) to the connector hub interface 2002. The VBUS connector pin 2015 of the top connector element 123a of the connector interface 123 connects to a power distribution switch 2009, for example, a universal serial bus (USB) 3.0 power distribution switch. The VBUS connector pin 2015 of the top connector element 123a provides a voltage supply of, for example, about 5 V from the connector interface 123 to the power distribution switch 2009. The power distribution switch 2009 provides a power output comprising, for example, a voltage of about 5 V and a current of about 900 milliamperes (mA) to the camera module 124 via the micro B USB 3.0 connector plug 2001 to allow activation or deactivation of the camera module 124. The activation or deactivation of the power supply to the camera module 124 can be controlled by the power control trigger element 103. The power control trigger element 103 transmits control signals to a power controller 2010 configured as an on/off controller and accommodated on the PCB 120. The power controller 2010 is configured to control activation and deactivation of the camera module 124 based on the control signals received from the power control trigger element 103. Each time the power control trigger element 103 is pushed or pressed, the power controller 2010 sends high or low power enabling control signals to the power distribution switch 2009 for providing power supply to the camera module 124 and the PCB 128 of the light sources, for example, the light emitting diodes (LEDs) 125 exemplarily illustrated in FIG. 5F, FIGS. 6A-6B, FIG. 11G, FIG. 13H, and FIG. 14G, to control powering of the LEDs 125 on the attachment unit 115.

In an embodiment, the action control trigger element 104 comprises, for example, a green LED (not shown). In an embodiment, the action control trigger element 104 allows a user to trigger the capture of diagnostic image data via the image capture device 106, for example, when a general medical examination device, the otoscope device 119 exemplarily illustrated in FIGS. 5A-5L, or the dermatoscope device 131 exemplarily illustrated in FIG. 8, is connected to the diagnosis control unit 101 via the attachment unit 115. For example, when only the image capture device 106 exemplarily illustrated in FIGS. 11A-11G, is connected to the diagnosis control unit 101, the action control trigger element 104 allows a user to trigger the capture of one image per click of the action control trigger element 104. In an embodiment, the action control trigger element 104 allows a user to trigger generation of audio files comprising diagnostic acoustic data recorded from anatomical examination areas such as heart or lungs, for example, in a .WAV file format, when the stethoscope device 134 along with the image capture device 106 is connected to the diagnosis control unit 101 via the attachment unit 115. For example, the action control trigger element 104 allows the user to trigger the capture of one image per click via the image capture device 106 and trigger recording and generation of a .WAV file for diagnostic acoustic data recorded from the lungs via the stethoscope device 134. In an embodiment, when the image capture device 106 and the ultrasound device 141 exemplarily illustrated in FIGS. 13A-13H, are connected to the diagnosis control unit 101 via the attachment unit 115, the action control trigger element 104 allows a user to trigger the capture of an image per click via the image capture device 106 and trigger the capture of ultrasound images via the ultrasound device 141. In an embodiment, the action control trigger element 104 allows transfer of the recorded diagnostic examination data to the data management server 2510 via the communication network 2509 exemplarily illustrated in FIG. 25. In an embodiment, the action control trigger element 104 allows deletion of the recorded diagnostic examination data by simultaneously pressing the power control trigger element 103 along with the action control trigger element 104.

The diagnosis control unit 101 further comprises one or more monostable multivibrators 2011. The microcontroller 2004 transmits enabling and disabling signals to the monostable multivibrators 2011 for activation and deactivation of the monostable multivibrators 2011. The monostable multivibrators 2011 control the brightness of light emitted from the light emitting diodes (LEDs) 125. The monostable multivibrators 2011 are configured to create manual pulse width modulation (PWM). The monostable multivibrators 2011 create output pulses based on inputs received from the microcontroller 2004 and generate output pulses that are transmitted to a constant current LED driver 2101 exemplarily illustrated in FIG. 21. The output pulses received from the microcontroller 2004 are used as inputs to the constant current LED driver 2101 that defines a retriggering time of pulse for changing brightness levels of light emitted from the LEDs 125.

Figure 21:
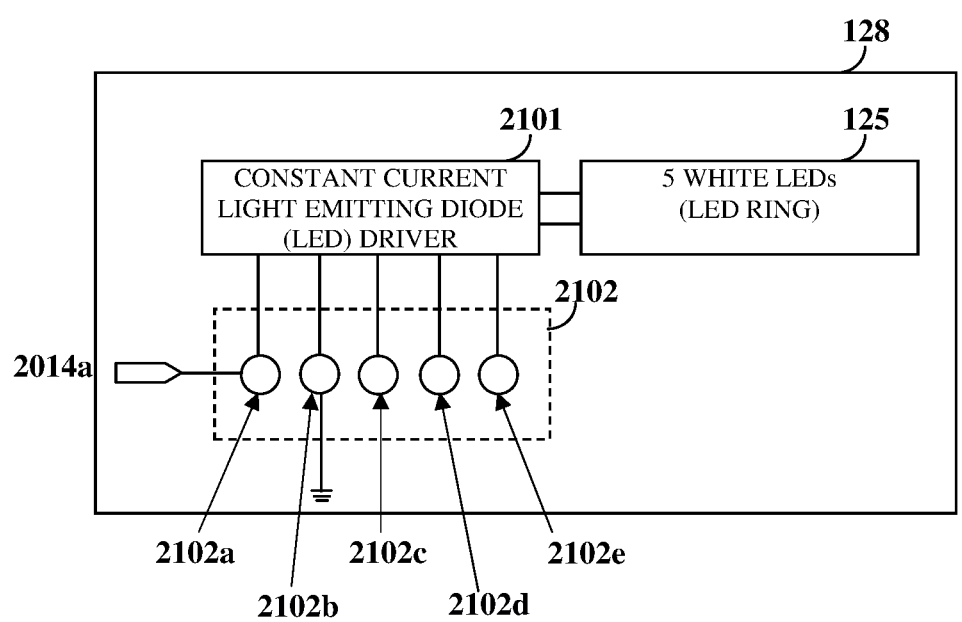
FIG. 21 exemplarily illustrates a block diagram of the printed circuit board of the light sources configured to be operably connected to the attachment unit for illuminating and indicating anatomical examination areas during medical imaging and remote diagnostic examinations.

The diagnosis control unit 101 further comprises an AND gate 2012 configured to generate a correct logic status input pulse to the constant current light emitting diode (LED) driver 2101 exemplarily illustrated in FIG. 21. The AND gate 2012 generates and provides an input signal to an ILED pin of the constant current LED driver 2101. The constant current LED driver 2101 is, for example a TPS61061 driver with digital brightness control. The ILED pin of the constant current LED driver 2101 provides a digital interface to allow digital brightness control; that is, input at the ILED pin controls the brightness. By controlling the voltage input to the constant current LED driver 2101, the brightness level of the LEDs 125 can be controlled. For example, the ILED pin is programmed to receive a voltage input in a flat band voltage (VFB) of about 15.6 millivolts (mV) to about 500 mV.

The output modification trigger elements 105a and 105b exemplarily illustrated in FIGS. 1A-1B, can be used to adjust brightness levels of light generated from the light emitting diodes (LEDs) 125, adjust image scaling, perform volume control, etc. In an embodiment, the output modification trigger elements 105a and 105b are configured to control brightness of the LEDs 125, when the image capture device 106 configured as a general medical examination device, the otoscope device 119 exemplarily illustrated in FIGS. 5A-5L, or the dermatoscope device 131 exemplarily illustrated in FIG. 8, is connected to the diagnosis control unit 101. The output modification trigger elements 105a and 105b are configured to modify the output of the medical diagnostic devices, for example, the otoscope device 119, an ophthalmoscope device (not shown), the stethoscope device 134 exemplarily illustrated in FIGS. 11A-11G, the dermatoscope device 131, the ultrasound device 141 exemplarily illustrated in FIGS. 13A-13H, an endoscope device (not shown), etc. For example, the output modification trigger elements (not shown) can be used to control ultrasound image zooming in the multipurpose diagnostic examination apparatus 100 comprising the ultrasound device 141. In another example, the output modification trigger elements (not shown) can be configured as stethoscope volume controllers in the multipurpose diagnostic examination apparatus 100 comprising the stethoscope device 134. In an embodiment, the output modification trigger elements are configured to control audio output of the stethoscope device 134 and brightness of the LEDs 125, when the multipurpose diagnostic examination apparatus 100 comprises the image capture device 106 and the stethoscope device 134. For example, the "−" output modification trigger element decreases volume of the audio output from the stethoscope device 134 and the "+" output modification trigger element increases volume of the audio output from the stethoscope device 134. The two output modification trigger elements can be simultaneously pressed and held to switch from volume control to brightness control or vice versa. On pressing the two output modification trigger elements simultaneously, the volume control interface with the push button interface 2013 is enabled and the monostable multivibrators 2011 are disabled or vice versa.

The microcontroller 2004 activates the volume control interface with the push button interface 2013 by transmitting an enable signal to the volume control interface with the push button interface 2013. The microcontroller 2004 receives signals from a digital signal processor 2204 exemplarily illustrated in FIG. 22, of the stethoscope device 134 that indicate that the stethoscope device 134 is connected. When both the "+" and "−" output modification trigger elements are pressed and held, the two output modification trigger elements are configured as volume controllers. The volume control interface with the push button interface 2013 operates by receiving high or low signals from the microcontroller 2004 based on actuation signals received from the two output modification trigger elements 105a and 105b.

The microcontroller 2004 transmits signals to the volume control interface with the push button interface 2013 for volume control of the stethoscope device 134. The microcontroller 2004 transmits another signal to the volume control interface with the push button interface 2013 for enabling or disabling the volume control interface with the push button interface 2013. The volume control interface with the push button interface 2013 transmits a volume control status signal to the stethoscope device 134 for decreasing or increasing the volume of diagnostic acoustic data received by the digital signal processor 2204 of the stethoscope device 134. The volume control status signal provides a status of audio filtering output received by the microcontroller 2004 from the stethoscope device 134.

In an embodiment, the output modification trigger elements control image scaling of diagnostic examination data recorded by ultrasound probes 142 of the ultrasound device 141, when the multipurpose diagnostic examination apparatus 100 comprises the image capture device 106 and the ultrasound device 141. For example, the "−" output modification trigger element decreases zoom and the "+" output modification trigger element increases zoom. By pressing and holding the output modification trigger elements simultaneously, brightness control is switched to ultrasound image scaling or vice versa.

The printed circuit board (PCB) 120 of the diagnosis control unit 101 further accommodates a connector pad circuitry 2014 comprising connector pad elements 2014a to 2014n. The connector pad element 2014a transmits a power control signal of, for example, about 5 V and 500 mA from the bottom connector element 123b of the connector interface 123 to the image capture device 106, the light emitting diodes (LEDs) 125, the stethoscope device 134, or the ultrasound device 141 connected to the diagnosis control unit 101. The connector pad element 2014b provides a ground connection to the image capture device 106, the LEDs 125, the stethoscope device 134, or the ultrasound device 141 connected to the diagnosis control unit 101. The AND gate 2012 provides the ILED input signal to the constant current LED driver 2101 via the connector pad element 2014c. The microcontroller 2004 receives a high acknowledge signal via the connector pad element 2014d of the diagnosis control unit 101 when the image capture device 106 is connected to the diagnosis control unit 101. The microcontroller 2004 transmits a power enabling signal to the image capture device 106 and the LEDs 125 via the connector pad element 2014e.

The microcontroller 2004 receives a high acknowledge signal via the connector pad element 2014f, when the stethoscope device 134 is connected to the diagnosis control unit 101 via the attachment unit 115. The microcontroller 2004 transmits a volume control signal to the digital signal processor 2204 of the stethoscope device 134 via the connector pad element 2014g. The microcontroller 2004 receives an audio filtering output status from the digital signal processor 2204 of the stethoscope device 134 via the connector pad element 2014h. The connector pad elements 2014i and 2014j are used to transmit universal serial bus (USB) D− and D+ signals for the digital signal processor 2204 of the stethoscope 134. The microcontroller 2004 receives, for example, a universal serial bus (USB) 2.0 communication signals via the connector pad elements 2014i and 2014j to allow communication of the stethoscope device 134 with the connector hub interface 2002.

The microcontroller 2004 transmits a control signal to the digital signal processor 2404 exemplarily illustrated in FIG. 24, of the ultrasound device 141 for activating zoom functionality via the connector pad element 2014k. The microcontroller 2004 receives, for example, universal serial bus (USB) 2.0 D− and D+ communication signals via the connector pad elements 2014l and 2014m to allow communication of the ultrasound device 141 with the connector hub interface 2002. The microcontroller 2004 receives a high acknowledge signal via the connector pad element 2014n of the diagnosis control unit 101, when the ultrasound device 141 is connected to the diagnosis control unit 101 via the attachment unit 115.

FIG. 21 exemplarily illustrates a block diagram of the printed circuit board 128 of the light sources, for example, the light emitting diodes (LEDs) 125 configured to be operably connected to the attachment unit 115 exemplarily illustrated in FIG. 5F, FIG. 11G, FIG. 13H, and FIG. 14G, for illuminating and indicating anatomical examination areas during medical imaging and remote diagnostic examinations. The spring contact connectors 118 positioned on the rear end 115b of the attachment unit 115 exemplarily illustrated in FIGS. 2A-2B, facilitate an electrical communication of the LEDs 125 that are operably connected, for example, to the front section 115c or the section 115e proximal to the rear end 115b of the attachment unit 115 exemplarily illustrated in FIGS. 2A-2B, FIGS. 10A-10B, and FIGS. 12A-12B, with the microcontroller 2004 of the diagnosis control unit 101. The spring contact connectors 118 connect to the connector pads 113 housed in the connector slot 112 configured at the front end 101e of the diagnosis control unit 101 exemplarily illustrated in FIG. 1B. The communication of action control signals, the diagnostic image data, and the diagnostic examination data is facilitated by the connections between the connector pads 113 of the connector slot 112 and the spring contact connectors 118 of the attachment unit 115.

The printed circuit board (PCB) 128 comprises a constant current light emitting diode (LED) driver 2101 configured to drive the light sources, for example, five LEDs 125 arranged in the form of a LED ring. The PCB 128 further comprises a spring contact connector circuitry 2102 with spring contact connector elements 2102a, 2102b, 2102c, 2102d, and 2102e that connect to the spring contact connectors 118 at the rear end 115b of the attachment unit 115. The spring contact connector element 2102a receives a power control signal of, for example, about 5 V and 500 mA from the bottom connector element 123b of the connector interface 123 exemplarily illustrated in FIG. 5H, FIG. 11C, FIG. 13C, FIG. 14I, and FIG. 20, for activating the LEDs 125. The spring contact connector element 2102b provides a ground connection to the LEDs 125. The spring contact connector element 2102c receives an ILED input signal from the AND gate 2012 of the diagnosis control unit 101 exemplarily illustrated in FIG. 20, for brightness control of the LEDs 125. The spring contact connector element 2102d transmits, for example, a high acknowledge signal to the microcontroller 2004 indicating connection of the image capture device 106 and the LEDs 125 to the diagnosis control unit 101 exemplarily illustrated in FIG. 11A, FIG. 11F, FIG. 13A, and FIGS. 13F-13G. The spring contact connector element 2102e receives power enabling signals from the microcontroller 2004 to control activation and deactivation of the image capture device 106 and the LEDs 125.

FIG. 22 exemplarily illustrates a block diagram of the printed circuit board (PCB) 136 of the stethoscope device 134 and the light sources, for example, the light emitting diodes (LEDs) 125 operably connected to the attachment unit 115 exemplarily illustrated in FIGS. 10A-10B and FIGS. 11A-11G. In an embodiment, the stethoscope device 134 comprises an array of three microphones 2201, for example, piezoelectric contact microphones for receiving high quality diagnostic acoustic data from human organs such as heart, lungs, bowel, etc. Each microphone 2201 transmits signals to a microphone amplifier 2202 comprising a band pass filter 2203. The microphone amplifier 2202 increases analog audio signal amplitude. The band pass filter 2203 is used to eliminate static and environment noise, for example, of a frequency range of about 60 hertz (Hz) to about 2 kilohertz (kHz).

The stethoscope device 134 comprises, for example, two main operational modes comprising a bell mode and a diaphragm mode. The bell mode and the diaphragm mode operate in two different frequencies ranges. In the bell mode, the stethoscope device 134 receives diagnostic acoustic data from the lungs. The bell mode operates in a predetermined frequency range for enabling reception of the diagnostic acoustic data from the lungs. In the bell mode, the stethoscope device 134 implements a filter operating in a frequency range of, for example, about 100 Hz to about 1000 Hz for lung sounds. In the diaphragm mode, the stethoscope device 134 receives diagnostic acoustic data from the heart or the bowel. The diaphragm mode operates in a predetermined frequency range for enabling reception of the diagnostic acoustic data from the heart or the bowel. In the diaphragm mode, the stethoscope device 134 implements a filter operating in a frequency range of, for example, about 60 Hz to about 650 Hz for heart sounds. The digital signal processor 2204 of the stethoscope device 134 processes action control signals received from the microcontroller 2004 exemplarily illustrated in FIG. 20, for actuating the stethoscope device 134 to perform one or more actions indicated by the action control signals. When the frequency range is changed on the touchscreen 135 of the stethoscope device 134, the signal received from the digital signal processor 2204 of the stethoscope device 134 changes a state from high to low or vice versa. If the stethoscope device 134 is not connected to the diagnosis control unit 101 via the attachment unit 115, then the microcontroller 2004 reads the signal as a floating pin signal.

FIG. 22 also exemplarily illustrates spring contact connector circuitry 2210 of the stethoscope device 134 comprising spring contact connector elements 2210a, 2210b, 2210c, 2210d, 2210e, 2210f, 2210g, 2210h, 22101, and 2210j. The signal received from the digital signal processor 2204 of the stethoscope device 134 via the spring contact connector element 2210a is a power signal received from the bottom connector element 123b, for example, a universal serial bus (USB) plug of the connector interface 123. The power signal received, for example, from a VBUS connector pin of the bottom connector element 123b provides, for example, a voltage of about 5 volts (V) and current of about 500 milliamperes (mA). The spring contact connector element 2210b provides a ground connection to the stethoscope device 134. The spring contact connector elements 2210c, 2210d, and 2210e of the stethoscope device 134 are connected to the spring contact connector elements 2102c, 2102d, and 2102e of the spring contact connector circuitry 2102 respectively, on the printed circuit board 128 of the light emitting diodes (LEDs) 125, to allow operable communication between the LEDs 125 and the stethoscope device 134 connected to the attachment unit 115 of the multipurpose diagnostic examination apparatus 100 exemplarily illustrated in FIGS. 11A-11G.

The digital signal processor 2204 of the stethoscope device 134 transmits a high acknowledge signal to the microcontroller 2004 of the diagnosis control unit 101 exemplarily illustrated in FIG. 20, via the spring contact connector element 2210f for indicating that the stethoscope device 134 is connected to the diagnosis control unit 101. The spring contact connector element 2210g transmits a volume control status signal to the digital signal processor 2204 of the stethoscope device 134, received from the microcontroller 2004 for increasing or decreasing volume of the diagnostic acoustic data received by the stethoscope device 134. The digital signal processor 2204 transmits a status of audio filtering via the spring contact connector element 2210h to the microcontroller 2004 of the diagnosis control unit 101. The stethoscope device 134 is configured with a built-in light emitting diode (LED) controller, for example, the constant current LED driver 2101. The signals received from the digital signal processor 2204 of the stethoscope device 134 via the spring contact connector elements 22101 and 2210j are, for example, universal serial bus (USB) 2.0 communication signals such as D−_b and D+_b communication signals that are transmitted to the connector hub interface 2002 of the diagnosis control unit 101 exemplarily illustrated in FIG. 20.

The digital signal processor 2204 of the stethoscope device 134 comprises, for example, a built-in codec, a universal serial bus (USB) interface 2205, digital filters, and an output volume controller. The built-in codec converts analog input from the microphone amplifiers 2202 comprising the band pass filters 2203 to digital data. The USB interface 2205 communicates with a driver support interface of the local user device 2505 comprising, for example, a Windows® operating system, the Mac OS of Apple Inc., a Linux® operating system, an Android operating system of Google Inc., etc. The local user device 2505 recognizes the stethoscope device 134 connected to the attachment unit 115, for example, as a USB microphone. The digital signal processor 2204 configures the digital filters. The output volume controller facilitates control of the volume of the output generated by the stethoscope device 134 based on inputs received from the volume control interface with the push button interface 2013 of the diagnosis control unit 101 exemplarily illustrated in FIG. 20. In an embodiment, the digital signal processor 2204 operates at low power values. For example, the stethoscope device 134, the LEDs 125, and the image capture device 106 exemplarily illustrated in FIGS. 11A-11G, operate at about 5 V received from the connector interface 123 comprising, for example, the USB ports that provide a USB 2.0 current of about 500 mA or a USB 3.0 current of about 900 mA. In an embodiment, the camera module 124 exemplarily illustrated in FIG. 11G, does not operate at low power.

The real time clock 2206 of the stethoscope device 134 controls recording of diagnostic acoustic data by the stethoscope device 134. The real time clock 2206 defines a time period, for example, number of seconds for recording an audio file comprising the diagnostic acoustic data. The stethoscope device 134 further comprises a flash memory 2207. The flash memory 2207 is used for booting the digital signal processor 2204 of the stethoscope device 134. The spring contact connector circuitry 2210 of the attachment unit 115 for the stethoscope device 134 connects to the connector pad circuitry 2014 of the diagnosis control unit 101 exemplarily illustrated in FIG. 20, for allowing electronic communication between the stethoscope device 134 connected to the front end 115a of the attachment unit 115 and the diagnosis control unit 101. That is, the spring contact connector elements 2210f, 2210g, 2210h, 22101, and 2210j of the spring contact connector circuitry 2210 of the attachment unit 115 contact the connector pad elements 2014f, 2014g, 2014h, 20141, and 2014j of the connector pad circuitry 2014 of the diagnosis control unit 101 respectively, exemplarily illustrated in FIG. 20.

The stethoscope device 134 further comprises a voltage regulator 2208, for example, a linear voltage regulator that provides a voltage supply of, for example, about 0.5 V to about 3.3 V, and a dual voltage output of, for example, about 1.2 V. In an example, a voltage supply of about 3.3 V from the voltage regulator 2208 can be used for powering internal parts and components of the digital signal processor 2204 of the stethoscope device 134. In an embodiment, the voltage regulator 2208 provides, for example, about 1.2 V for powering the digital signal processor 2204. The digital signal processor 2204 further communicates with a level shifter 2209 that communicates with the touchscreen 135 and controls red, green, and blue (RGB) color levels, for example, at about 1.8 V. The touchscreen 135 of the stethoscope device 134 is configured as a liquid crystal display (LCD) display screen. The touchscreen 135 functions as a user interface, for example, for displaying audio filtering information, a sleep mode of the stethoscope device 134, a connection status of the stethoscope device 134 with the diagnosis control unit 101 of the multipurpose diagnostic examination apparatus 100, time period of recording diagnostic acoustic data, a volume level, etc.

FIGS. 23A-23D exemplarily illustrate a flowchart comprising the steps performed by the digital signal processor (DSP) 2204 of the stethoscope device 134 exemplarily illustrated in FIGS. 10A-10B, FIGS. 11A-11G, and FIG. 22, for recording and transmitting audio data to the medical diagnostic examination system 2506 on a local user device 2505 exemplarily illustrated in FIG. 25. A user, for example, a medical assistant connects 2301 the attachment unit 115 with the stethoscope device 134 exemplarily illustrated in FIGS. 10A-10B, to the diagnosis control unit 101 of the multipurpose diagnostic examination apparatus 100 exemplarily illustrated in FIGS. 11A-11G. The digital signal processor 2204 and the associated electronics, for example, 2202, 2206, 2207, 2209, etc., exemplarily illustrated in FIG. 22, receives 2302 power of, for example, 5V, 500 mA, from the connector pad element 2014a that contacts the spring contact connector element 2102a, and the ground connector pad element 2014b contacts the spring contact connector element 2102b exemplarily illustrated in FIG. 20 and FIG. 22. The flash memory 2207 exemplarily illustrated in FIG. 22, activates 2303 firmware for the digital signal processor 2204 by using a serial peripheral interface (SPI) or an inter-integrated circuit ($I^2C$), The local user device 2505, for example, a personal computer, a laptop, a tablet computing device, etc., by a universal serial bus (USB) communication with the digital signal processor 2204 of the stethoscope device 134, uploads 2304 an audio driver and recognizes 2304 the external devices, for example, the microphones 2201 exemplarily illustrated in FIG. 22, as an audio input device. A device driver on the local user device 2505 supports multiple operating systems, for example, Windows® XP, 7, 8/8.1, etc., of Microsoft corporation, the Android operating system of Google Inc., the iOS operating system of Apple Inc., the Linux® operating system, etc.

The flash memory 2207, via the digital signal processor 2204, uploads 2305 an identifier (ID) for the local user device 2505 by a name, for example, "stethoscope". The digital signal processor 2204 provides 2306 an event, for example, a high digital signal to the microcontroller 2004 exemplarily illustrated in FIG. 20, by using the spring contact connector elements 2210f, 2210g, 2210h, 22101, and 2210j connected to the connector pad elements 2014f, 2014g, 2014h, 20141, and 2014j respectively, exemplarily illustrated in FIG. 20 and FIG. 22. The digital signal processor 2204 also receives 2311 audio signals from the band pass filter 2203 to an internal codec, for example, the SigmaDSP® Stereo ADAU1761 of Analog Devices, Inc. The internal codec converts analog data from the audio signals to digital data.

The digital signal processor 2204 also reads 2309 the status of a volume controller via the spring contact connector element 2210g exemplarily illustrated in FIG. 22. The volume control ranges, for example, from about −12 db to about +35.25 db. Each time the user activates the output modification trigger element, the volume increases or decreases 2310, for example, by about 0.7 db. The digital signal processor 2204 also provides 2307 a command to the touchscreen 135 to display "stethoscope is ready". The digital signal processor 2204 reads 2308 the status of the filter selected via the touchscreen 135. The digital signal processor 2204 checks 2312 the status of the filter mode. If the filter mode is not active, then the digital signal processor 2204 transmits 2313 the digitally unfiltered audio data from the bottom connector element 123b of the connector interface 123 of the diagnosis control unit 101 exemplarily illustrated in FIG. 11C, to a universal serial bus (USB) interface (not shown) of the local user device 2505. If the filter mode is active, then the digital signal processor 2204 allows 2314 a user to select the filter mode, for example, from three options, namely, "bell", "diaphragm", and "wide band modem" on the touchscreen 135.

The digital signal processor 2204 checks 2315 whether the option selected for the filter mode is "bell". If the selected option is "bell", then the digital signal processor 2204 activates 2316 a custom integrated algorithm developed, for example, using Matlab® of MathWorks, Inc., and converted into "C" code as a part of the firmware of the digital signal processor 2204. Based on the custom integrated algorithm, the digital signal processor 2204 reads 2316 the "bell" command, turns on the low frequency mode 60 Hz-650 Hz digital filter, and transmits 2321 the selected filter data as audio data from the connector interface 123 of the diagnosis control unit 101 to the universal serial bus (USB) interface of the local user device 2505. If the selected option is not "bell", the digital signal processor 2204 checks 2317 whether the option selected for the filter mode is "diaphragm". If the selected option is "diaphragm", then the digital signal processor 2204 activates 2318 the custom integrated algorithm, reads the "diaphragm" command, turns on the high frequency mode 120 Hz-1000 Hz digital filter, and transmits 2321 the selected filter data as audio data from the connector interface 123 of the diagnosis control unit 101 to the USB interface of the local user device 2505. If the selected option is not "diaphragm", then the digital signal processor 2204 checks 2319 whether the option selected for the filter mode is "wide band modem". If the selection option is "wide band modem", then the digital signal processor 2204 activates 2320 the custom integrated algorithm, reads the "wide band modem" command, turns on 2320 the wide band frequency mode 60 Hz-2000 Hz digital filter, and transmits 2321 the selected filter data as audio data from the connector interface 123 of the diagnosis control unit 101 to the USB interface of the local user device 2505. The digital signal processor 2204 then sends 2322 the status of the selected filter to the microcontroller 2004 of the diagnosis control unit 101 via the spring contact connector element 2210h that contacts with the connector pad element 2014h exemplarily illustrated in FIG. 20 and FIG. 22. If the selection option is not "wide band modem", then the digital signal processor 2204 repeats the process by checking 2315 whether the selected option is "bell".

FIG. 24 exemplarily illustrates a block diagram of the printed circuit board (PCB) 143 of the ultrasound device 141 and the light sources, for example, the light emitting diodes (LEDs) 125 operably connected to the attachment unit 115 exemplarily illustrated in FIGS. 13A-13H. The ultrasound device 141 comprises the ultrasonic transducer sensors 142a on the interchangeable ultrasound probe 142 that can be removed and replaced with a different ultrasound probe based on patient diagnostic requirements. The ultrasound probe 142 with the ultrasonic transducer sensors 142a is connected to the PCB 143 of the ultrasound device 141 exemplarily illustrated in FIG. 13H. In an embodiment, the ultrasound probe 142 is designed with a piezoelectric transducer array. The piezoelectric transducer array is configured to communicate, for example, about 8 to about 16 channels of analog signals from the ultrasonic transducer sensors 142a on the ultrasound probe 142. The ultrasound probe 142 is selected based on a focal zone of, for example, about 0.5 cm to about 20 cm, a depth range of about 0.5 cm to about 25 cm, and a pulse frequency of about 3.5 MHz to about 24 MHz. The ultrasound probe 142 is used for diagnostically examining anatomical examination areas comprising, for example, liver, kidney, aorta, heart, regional nerve blocks, pregnancy, urology, vascular areas, venous ablation, musculoskeletal areas, etc. A doctor can select which ultrasound probe 142 he/she wishes to connect to the ultrasound device 141 at the front end 115a of the attachment unit 115 exemplarily illustrated in FIGS. 12A-12B, for medical diagnostics. For example, a Doppler ultrasound probe 142 can be connected to the ultrasound device 141 at the front end 115a of the attachment unit 115 to allow a doctor to view dynamic images.

The printed circuit board (PCB) 143 of the ultrasound device 141 comprises an analog front end (AFE) electronic system 2401 configured for ultrasound applications. The AFE electronic system 2401 comprises a low noise amplifier (LNA) 2402 configured to receive transducer signals from the ultrasound probe 142. In an embodiment, the low noise amplifier 2402 receives a dynamic range of channels of transducer signals comprising, for example, about 8 channels to about 16 channels from the ultrasound probe 142. The digital processing devices 2403 of the ultrasound device 141 comprise a digital signal processor 2404 and a field programmable gate array (FPGA) 2405. In an embodiment, the digital processing devices 2403 are configured to implement beam forming. The digital processing devices 2403 send and receive signals to and from the AFE electronic system 2401 that functions, for example, as a beamformer transmitter and/or receiver. In an embodiment, the communication protocol implemented between the digital processing devices 2403 and the AFE electronic system 2401 is low voltage differential signaling (LVDS) via a serial peripheral interface (SPI). The digital processing devices 2403 perform multiple functions comprising, for example, capture of diagnostic examination data such as ultrasound image data, sampling of the diagnostic examination data, digital filtering, image processing, compression of the diagnostic examination data if the speed of data transmission is below universal serial bus (USB) 3.0 speed, demodulation and summation of channel signals, etc. The digital processing devices 2403 transmit, for example, USB 3.0 signals 2406 to the connector hub interface 2002 of the diagnosis control unit 101 exemplarily illustrated in FIG. 20, via the spring contact connectors 118 of the attachment unit 115 with the ultrasound device 141, thereby allowing the ultrasound device 141 to communicate with a local user device 2505 connected to the multipurpose diagnostic examination apparatus 100 via the connector interface 123 exemplarily illustrated in FIG. 20.

The printed circuit board (PCB) 143 of the ultrasound device 141 comprises a spring contact connector circuitry 2407 comprising spring contact connector elements 2407a, 2407b, 2407c, 2407d, 2407e, 2407f, 2407g, 2407h, and 2407i. The spring contact connector element 2407a receives a power control signal of, for example, about 5 V and 500 mA from the bottom connector element 123b of the connector interface 123 exemplarily illustrated in FIG. 13C, for activating the ultrasound device 141. The spring contact connector element 2407b provides a ground connection to the ultrasound device 141. The spring contact connector elements 2407c, 2407d, and 2407e are connected to the spring contact connector elements 2102c, 2102d, and 2102e of the spring contact connector circuitry 2102 respectively, as exemplarily illustrated in FIG. 24, to allow operable communication between the light emitting diodes (LEDs) 125 and the ultrasound device 141 connected to the attachment unit 115 of the multipurpose diagnostic examination apparatus 100 exemplarily illustrated in FIGS. 13A-13H.

When the attachment unit 115 with the ultrasound device 141 is connected to the diagnosis control unit 101, the spring contact connector elements 2407f, 2407g, 2407h, and 2407i of the attachment unit 115 connect to the connector pad circuitry 2014 of the diagnosis control unit 101 exemplarily illustrated in FIG. 20, for allowing electronic communication between the ultrasound device 141 connected to the front end 115a of the attachment unit 115 and the diagnosis control unit 101. That is, the spring contact connector elements 2407f, 2407g, 2407h, and 2407i contact the connector pad elements 2014k, 2014l, 2014m, and 2014n of the connector pad circuitry 2014 of the diagnosis control unit 101 respectively, exemplarily illustrated in FIG. 20. On activation of the trigger elements 103 and 104, the spring contact connector element 2407f transmits a communication signal or an action control signal received from the microcontroller 2004 of the diagnosis control unit 101 exemplarily illustrated in FIG. 20, to the digital processing devices 2403 of the ultrasound device 141 for activating zoom functionality. The spring contact connector elements 2407g and 2407h transmit universal serial bus (USB) 3.0 signals 2406, for example, D−_c and D+_c communication signals to the connector hub interface 2002 of the diagnosis control unit 101 exemplarily illustrated in FIG. 20, which in turn transmits the USB 3.0 signals 2406 to the connector interface 123 exemplarily illustrated in FIG. 20. The connector interface 123 transmits the USB 3.0 signals 2406 received via the spring contact connector elements 2407g and 2407h of the ultrasound device 141 to the local user device 2505 connected to the multipurpose diagnostic examination apparatus 100 via the connector interface 123 of the multipurpose diagnostic examination apparatus 100. The digital signal processor 2404 transmits a high acknowledge signal to the microcontroller 2004 of the diagnosis control unit 101 via the spring contact connector element 2407i.

FIG. 25 exemplarily illustrates a system 2500 for facilitating medical imaging and remote diagnostic examinations. The system 2500 disclosed herein comprises the medical diagnostic examination system 2506 accessible on one or more user devices, for example, a local user device 2505, a remote user device 2511, etc., and the multipurpose diagnostic examination apparatus 100. The local user device 2505 is, for example, an external computer operably connected to the multipurpose diagnostic examination apparatus 100 using, for example, a universal serial bus (USB) 3.0 cable via the connector interface 123 connected to, for example, a universal serial bus (USB) 3.0 connector hub interface 2002 of the diagnosis control unit 101 exemplarily illustrated in FIG. 20. The local user device 2505 or the remote user device 2511 is an electronic device, for example, a personal computer, a tablet computing device, a mobile computer, a portable computing device, a laptop, a touch centric device, a workstation, a client device, a portable electronic device, a network enabled computing device, an interactive network enabled communication device, any other suitable computing equipment, and combinations of multiple pieces of computing equipment, etc.

The multipurpose diagnostic examination apparatus 100 communicates with the medical diagnostic examination system 2506 on the local user device 2505 via the connector interface 123 of the multipurpose diagnostic examination apparatus 100. The medical diagnostic examination system 2506 on the local user device 2505 of a user, for example, a medical assistant communicates with the medical diagnostic examination system 2506 accessible on the remote user device 2511 of a user, for example, a doctor via the communication network 2509. The communication network 2509 is, for example, the internet, an intranet, a wired network, a wireless network, a network that implements Wi-Fi® of Wi-Fi Alliance Corporation, an ultra-wideband communication network (UWB), a communication network that implements ZigBee® of ZigBee Alliance Corporation, a general packet radio service (GPRS) network, a mobile telecommunication network such as a global system for mobile (GSM) communications network, a code division multiple access (CDMA) network, a third generation (3G) mobile communication network, a fourth generation (4G) mobile communication network, a long-term evolution (LTE) mobile communication network, etc., a local area network, a wide area network, an internet connection network, etc., or a network formed from any combination of these networks.

The medical diagnostic examination system 2506 comprises a medical diagnostic examination application 2508 configured as a software application for facilitating medical imaging and remote diagnostic examinations. In an embodiment, the medical diagnostic examination application 2508 is configured as downloadable software which is operable with multiple operation systems comprising, for example, Windows® XP, 7, 8/8.1, etc., of Microsoft corporation, the Mac operating system (OS) of Apple Inc., the Linux® operating system, the Android operating system of Google Inc., etc. The medical diagnostic examination system 2506 is accessible to users, for example, through a broad spectrum of technologies and devices such as personal computers with access to the internet, tablet computing devices, etc. In an embodiment, the medical diagnostic examination system 2506 is implemented in a cloud computing environment. The medical diagnostic examination system 2506 is a cloud computing based platform compliant with Health Insurance Portability and Accountability Act (HIPAA) standards and implemented as a service for facilitating medical imaging and remote diagnostic examinations. The medical diagnostic examination system 2506 is developed using, for example, the Google App engine cloud infrastructure of Google Inc., Amazon Web Services® of Amazon Technologies, Inc., the Amazon elastic compute cloud EC2® web service of Amazon Technologies, Inc., the Google® Cloud platform of Google Inc., the Microsoft® Cloud platform of Microsoft Corporation, etc., configured to comply with the HIPAA standards.

In an embodiment, the diagnostic image data and the diagnostic examination data recorded by the image capture device 106 and the medical diagnostic device 2504, for example, the otoscope device 119 exemplarily illustrated in FIGS. 5A-5L, or an ophthalmoscope device (not shown), or the stethoscope device 134 exemplarily illustrated in FIGS. 11A-11G, or the dermatoscope device 131 exemplarily illustrated in FIG. 8, or the ultrasound device 141 exemplarily illustrated in FIGS. 13A-13H, or an endoscope device (not shown), etc., are configured to be uploaded and stored on one or more servers comprising a dedicated server, for example, the data management server 2510 and a server in the cloud computing environment. In this embodiment, the servers are Health Insurance Portability and Accountability Act (HIPAA) compliant servers. In another embodiment, the medical diagnostic examination system 2506 stores the processed diagnostic image data and the diagnostic examination data in a local memory, for example, a universal serial bus (USB) flash memory, a solid state drive (SSD) memory, a hard disk drive (HDD) memory storage, etc., of the local user device 2505. In this embodiment, the stored diagnostic image data is automatically or manually uploaded to a HIPAA compliant dedicated server or a HIPAA compliant server in the cloud computing environment. In another embodiment, the captured diagnostic image data is uploaded directly from a local memory of the image capture device 106 of the multipurpose diagnostic examination apparatus 100 to a HIPAA compliant dedicated server or a HIPAA compliant server in the cloud computing environment. In this embodiment, the local memory of the image capture device 106 is, for example, a HIPAA compliant 256 bit hardware based encrypted flash drive.

The multipurpose diagnostic examination apparatus 100 comprises the diagnosis control unit 101, the image capture device 106, and the attachment unit 115 as disclosed in the detailed description of FIGS. 1A-14M. The diagnosis control unit 101 comprises the microcontroller 2004 configured to execute computer program instructions defined by modules, for example, 2501, 2502, 2503, etc., of the multipurpose diagnostic examination apparatus 100. The modules of the multipurpose diagnostic examination apparatus 100 comprise a detection module 2501, a data communication module 2502, and an action management module 2503. The detection module 2501 detects an operable connection of the image capture device 106 and/or a medical diagnostic device 2504, for example, a stethoscope device 134 exemplarily illustrated in FIGS. 10A-10B and FIGS. 11A-11G, to the diagnosis control unit 101 via the attachment unit 115 of the multipurpose diagnostic examination apparatus 100. The data communication module 2502 receives actuation signals from one or more trigger elements 102 positioned on a predefined section, for example, the upper section 101b of the diagnosis control unit 101. The action management module 2503 processes the received actuation signals to generate action control signals to indicate one or more actions to be performed by the image capture device 106 and/or the medical diagnostic device 2504.

In an embodiment, the action management module 2503 transmits the generated action control signals to the light emitting diodes (LEDs) 125 and the laser pointer 132 exemplarily illustrated in FIGS. 11A-11G and FIGS. 13A-13H, operably connected to the front section 115c of the attachment unit 115, or a predetermined section along the length of the attachment unit 115 such as on a section 115e proximal to the rear end 115b of the attachment unit 115, and/or on the upper section 101b of the diagnosis control unit 101 for illuminating and indicating one or more anatomical examination areas during medical imaging and remote diagnostic examinations. Consider an example where the light source, that is, the laser pointer 132 exemplarily illustrated in FIG. 9, points to the anatomical examination areas comprising, for example, a front or a back of a chest of a patient. In this example, a doctor using the remote user device 2511 that is in communication with the local user device 2505 over the communication network 2509, can remotely diagnose, that is, advise and/or indicate points of interest on the chest that during in medical imaging and diagnostic examinations, for example, during ultrasound and stethoscope diagnostic examinations.

In an embodiment where the medical diagnostic device 2504 is the stethoscope device 134 exemplarily illustrated in FIGS. 13A-13H, comprising the digital signal processor 2204 exemplarily illustrated in FIG. 22, the action management module 2503 generates and transmits action control signals to the digital signal processor 2204 of the stethoscope device 134 for actuating the stethoscope device 134 to perform the actions indicated by the generated action control signals. In another embodiment where the medical diagnostic device 2504 is the stethoscope device 134 comprising one or more microphones 2201 exemplarily illustrated in FIG. 22, the action management module 2503 generates and transmits action control signals to the digital signal processor 2204 of the stethoscope device 134 for actuating the microphones 2201 to receive diagnostic acoustic data from one or more anatomical examination areas. In an embodiment where the medical diagnostic device 2504 is the stethoscope device 134 comprising a touchscreen 135 exemplarily illustrated in FIG. 10A and FIG. 11G, the action management module 2503 generates and transmits action control signals to the digital signal processor 2204 of the stethoscope device 134 for actuating the touchscreen 135 to display information associated, for example, with diagnostic acoustic data received by the stethoscope device 134, the connection status of the stethoscope device 134 to the diagnosis control unit 101, the activation status of the stethoscope device 134, etc. In an embodiment where the medical diagnostic device 2504 is the stethoscope device 134 comprising the real time clock 2206 exemplarily illustrated in FIG. 22, the action management module 2503 generates and transmits action control signals to the digital signal processor 2204 of the stethoscope device 134 for actuating the real time clock 2206 to control recording of the diagnostic acoustic data by the stethoscope device 134 for a predefined time period.

In an embodiment where the medical diagnostic device 2504 is the ultrasound device 141 comprising an ultrasound digital signal processor 2404 exemplarily illustrated in FIG. 24, the action management module 2503 generates and transmits action control signals to the ultrasound digital signal processor 2404 of the ultrasound device 141 for actuating the ultrasound device 141 to perform the actions indicated by the generated action control signals. In an embodiment where the medical diagnostic device 2504 is the ultrasound device 141 comprising an interchangeable ultrasound probe 142 operably connected to the attachment unit 115 exemplarily illustrated in FIGS. 12A-12B and FIGS. 13A-13H, the action management module 2503 generates and transmits action control signals to the ultrasound digital signal processor 2404 of the ultrasound device 141 for actuating the interchangeable ultrasound probe 142 of the ultrasound device 141 to detect and receive ultrasonic sounds from one or more anatomical examination areas for diagnostic examinations.

The camera module 124 processes the diagnostic image data captured by the image capture device 106. The processed diagnostic image data from the camera module 124 and the diagnostic examination data of multiple formats received from the medical diagnostic device 2504 via the attachment unit 115 are transmitted to the medical diagnostic examination system 2506 accessible on the local user device 2505 via the connector interface 123 of the diagnosis control unit 101. In an embodiment, the medical diagnostic examination system 2506 on the local user device 2505 performs additional image processing on the diagnostic image data and the diagnostic examination data using image processing software. The medical diagnostic examination system 2506 on the local user device 2505 is in communication with the remote user device 2511 over the communication network 2509 to facilitate remote viewing, remote selection, and remote diagnostic examinations of multiple anatomical examination areas via the communication network 2509. In an embodiment, the data communication module 2502 transmits diagnostic data management signals to the medical diagnostic examination system 2506 accessible on the local user device 2505 via the connector interface 123 of the diagnosis control unit 101 for managing the transmitted diagnostic image data and the transmitted diagnostic examination data.

The medical diagnostic examination system 2506 comprises a non-transitory computer readable storage medium and at least one processor communicatively coupled to the non-transitory computer readable storage medium. As used herein, "non-transitory computer readable storage medium" refers to all computer readable media, for example, non-volatile media such as optical discs or magnetic disks, volatile media such as a register memory, a processor cache, etc., and transmission media such as wires that constitute a system bus coupled to the processor, except for a transitory, propagating signal. The non-transitory computer readable storage medium stores computer program instructions defined by modules, for example, 2508*a*, 2508*b*, etc., of the medical diagnostic examination application 2508. The processor is configured to execute the defined computer program instructions.

The medical diagnostic examination application 2508 comprises a data communication module 2508*a* and a diagnostic data management module 2508*b*. The data communication module 2508*a* receives the connection status of the image capture device 106 and/or the medical diagnostic device 2504 from the multipurpose diagnostic examination apparatus 100 via the connector interface 123 of the multipurpose diagnostic examination apparatus 100, based on the operable connection of the image capture device 106 and/or the medical diagnostic device 2504 to the diagnosis control unit 101. The medical diagnostic examination system 2506 provides a graphical diagnostic examination interface (GDEI) 2507. The GDEI 2507 is, for example, a display window, a webpage of a website hosted by the medical diagnostic examination system 2506, an online web interface, a web based downloadable application interface, a mobile based downloadable application interface, etc. The GDEI 2507 renders and indicates anatomical examination areas to be diagnostically examined using the multipurpose diagnostic examination apparatus 100 based on the received connection status of the image capture device 106 and/or the medical diagnostic device 2504 to the diagnosis control unit 101. The medical diagnostic examination system 2506 dynamically displays one or more of multiple interface elements on the anatomical examination areas rendered on the GDEI 2507.

The data communication module 2508*a* receives user inputs through the dynamically displayed interface elements on the graphical diagnostic examination interface (GDEI) 2507 for selectively activating the image capture device 106 and/or the medical diagnostic device 2504 for initiating recording of the diagnostic image data associated with the anatomical examination areas by the image capture device 106 and the diagnostic examination data associated with the anatomical examination areas by the medical diagnostic device 2504. The data communication module 2508*a* receives the processed diagnostic image data and the diagnostic examination data from the multipurpose diagnostic examination apparatus 100 based on the received user inputs.

In an embodiment, the diagnostic data management module 2508*b* manages the diagnostic image data and the diagnostic examination data received from the multipurpose diagnostic examination apparatus 100 via the connector interface 123 for performing remote diagnostic examinations based on the diagnostic data management signals received from the multipurpose diagnostic examination apparatus 100. The management of the received diagnostic image data and the received diagnostic examination data comprises, for example, storage of the received diagnostic image data and the received diagnostic examination data in the data management server 2510, deletion of the received diagnostic image data and the received diagnostic examination data from the data management server 2510, communication of the received diagnostic image data and the received diagnostic examination data with one or more remote user devices 2511 via the communication network 2509, etc.

The data management server 2510 comprises one or more databases 2510a for storing the diagnostic image data and the diagnostic examination data. The databases 2510a can be any storage area or medium that can be used for storing data and files and that complies with the Health Insurance Portability and Accountability Act (HIPAA) standards. The databases 2510a can be, for example, a structured query language (SQL) data store or a not only SQL (NoSQL) data store such as the Microsoft® SQL Server®, the Oracle® servers, the MySQL® database of MySQL AB Company, the mongoDB® of MongoDB, Inc., the Neo4j graph database of Neo Technology Corporation, the Cassandra database of the Apache Software Foundation, the HBase™ database of the Apache Software Foundation, etc. In an embodiment, the databases 2510a can also be locations on a file system. In another embodiment, the databases 2510a can be remotely accessed by the medical diagnostic examination system 2506 via the communication network 2509. In another embodiment, the databases 2510a are configured as cloud based databases implemented in a cloud computing environment, where computing resources are delivered as a service over the communication network 2509.

The diagnostic data management module 2508b dynamically converts the received diagnostic image data and the received diagnostic examination data to digital diagnostic image data and digital diagnostic examination data of multiple formats. The graphical diagnostic examination interface (GDEI) 2507 renders the digital diagnostic image data and the digital diagnostic examination data for facilitating medical imaging and remote diagnostic examinations. In an embodiment, the GDEI 2507 dynamically displays an updated status of diagnostic examination data based on subsequent diagnostic image data and subsequent diagnostic examination data received from the multipurpose diagnostic examination apparatus 100.

Figure 26:
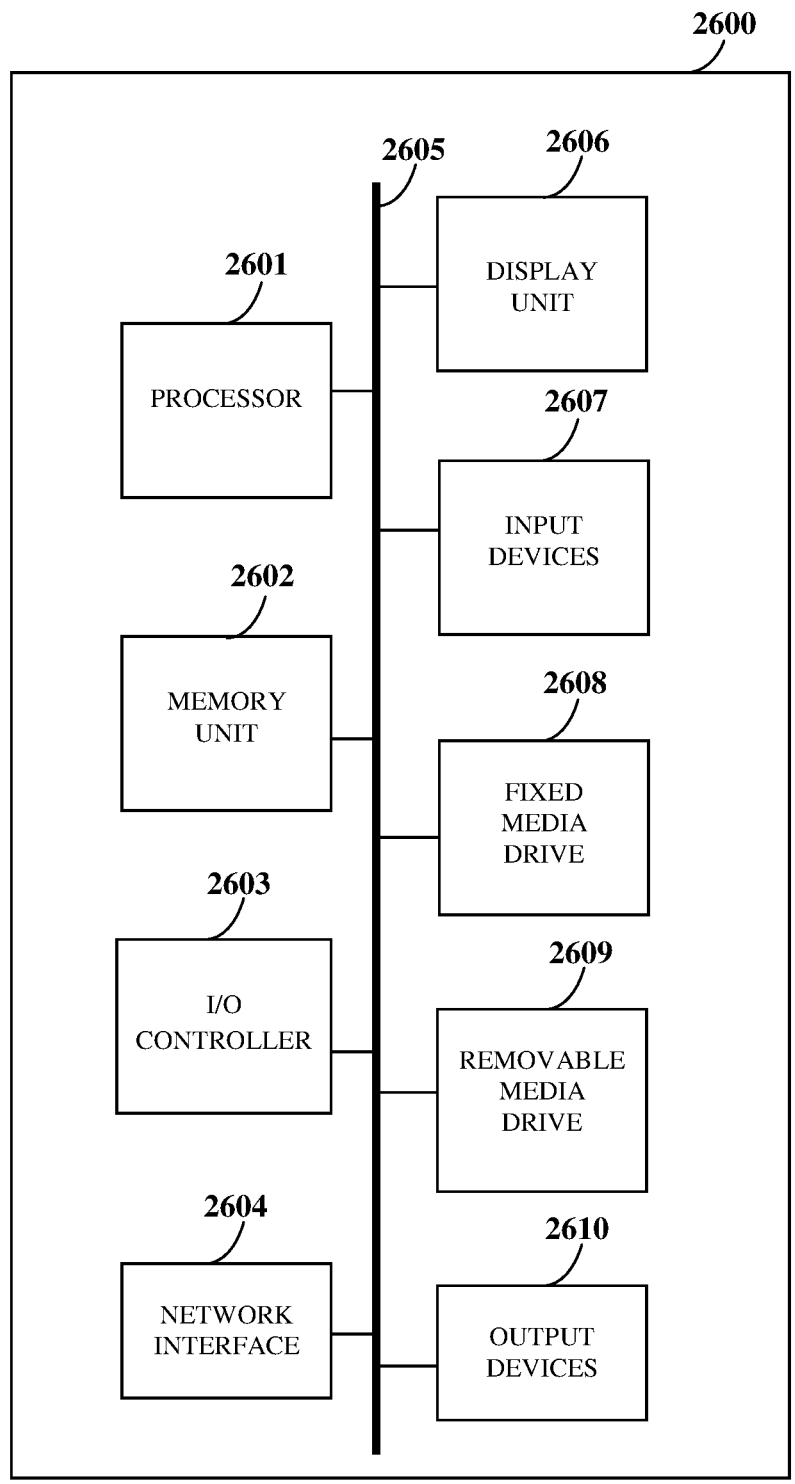
FIG. 26 exemplarily illustrates the hardware architecture of the medical diagnostic examination system employed for facilitating medical imaging and remote diagnostic examinations.

FIG. 26 exemplarily illustrates the hardware architecture 2600 of the medical diagnostic examination system 2506 exemplarily illustrated in FIG. 25, employed for facilitating medical imaging and remote diagnostic examinations. The medical diagnostic examination system 2506 is a computer system that is programmable using a high level computer programming language. The medical diagnostic examination system 2506 may be implemented using programmed and purposeful hardware. The medical diagnostic examination system 2506 communicates with a remote user device 2511 via a communication network 2509, for example, a short range network or a long range network.

As exemplarily illustrated in FIG. 26, the hardware architecture 2600 of the medical diagnostic examination system 2506 comprises a processor 2601, a non-transitory computer readable storage medium such as a memory unit 2602 for storing programs and data, an input/output (I/O) controller 2603, a network interface 2604, a data bus 2605, a display unit 2606, input devices 2607, a fixed media drive 2608 such as a hard drive, a removable media drive 2609 for receiving removable media, output devices 2610, etc. The processor 2601 refers to any one or more microprocessors, central processing unit (CPU) devices, finite state machines, computers, microcontrollers, digital signal processors, logic, a logic device, an electronic circuit, an application specific integrated circuit (ASIC), a field-programmable gate array (FPGA), a chip, etc., or any combination thereof, capable of executing computer programs or a series of commands, instructions, or state transitions. The processor 2601 may also be implemented as a processor set comprising, for example, a general purpose microprocessor and a math or graphics co-processor. The processor 2601 is selected, for example, from the Intel® processors such as the Itanium® microprocessor or the Pentium® processors, Advanced Micro Devices (AMD®) processors such as the Athlon® processor, UltraSPARC® processors, microSPARC® processors, Hp® processors, International Business Machines (IBM®) processors such as the PowerPC® microprocessor, the MIPS® reduced instruction set computer (RISC) processor of MIPS Technologies, Inc., RISC based computer processors of ARM Holdings, Motorola® processors, Qualcomm® processors, etc. The medical diagnostic examination system 2506 disclosed herein is not limited to employing a processor 2601. The medical diagnostic examination system 2506 may also employ a controller or a microcontroller. The processor 2601 executes the modules, for example, 2508a, 2508b, etc., of the medical diagnostic examination system 2506.

The memory unit 2602 is used for storing programs, applications, and data. For example, the data communication module 2508a, the diagnostic data management module 2508b, etc., of the medical diagnostic examination system 2506 are stored in the memory unit 2602. The memory unit 2602 is, for example, a random access memory (RAM) or another type of dynamic storage device that stores information and instructions for execution by the processor 2601. The memory unit 2602 also stores temporary variables and other intermediate information used during execution of the instructions by the processor 2601. The medical diagnostic examination system 2506 further comprises a read only memory (ROM) or another type of static storage device that stores static information and instructions for the processor 2601. The I/O controller 2603 controls input actions and output actions performed by the medical diagnostic examination system 2506.

The network interface 2604 enables connection of the medical diagnostic examination system 2506 to the communication network 2509. In an embodiment, the network interface 2604 is provided as an interface card also referred to as a line card. The network interface 2604 comprises, for example, one or more of an infrared (IR) interface, an interface implementing Wi-Fi® of Wi-Fi Alliance Corporation, a universal serial bus (USB) interface, a FireWire® interface of Apple Inc., an Ethernet interface, a frame relay interface, a cable interface, a digital subscriber line (DSL) interface, a token ring interface, a peripheral controller interconnect (PCI) interface, a local area network (LAN) interface, a wide area network (WAN) interface, interfaces using serial protocols, interfaces using parallel protocols, and Ethernet communication interfaces, asynchronous transfer mode (ATM) interfaces, a high speed serial interface (HSSI), a fiber distributed data interface (FDDI), interfaces based on transmission control protocol (TCP)/internet protocol (IP), interfaces based on wireless communications technology such as satellite technology, radio frequency (RF) technology, near field communication, etc. The data bus 2605 permits communications between the modules, for example, 2508a, 2508b, etc., of the medical diagnostic examination system 2506.

The display unit 2606, via the graphical diagnostic examination interface (GDEI) 2507, displays information, display interfaces, user interface elements such as text fields, checkboxes, text boxes, windows, etc., for allowing a user, for example, a medical assistant to enter patient information comprising, for example, personal information, a registration number of the patient, etc., for allowing viewing of medical diagnosis reports that help in reviewing medical history of the patient, etc. The display unit 2606 comprises, for example, a liquid crystal display, a plasma display, an organic light emitting diode (OLED) based display, etc. The input devices 2607 are used for inputting data into the medical diagnostic examination system 2506. Users, for example, medical assistants use the input devices 2607 to provide inputs to the medical diagnostic examination system 2506. For example, a medical assistant may enter a patient's personal information, a time of medically examining the patient, a name for an audio file comprising diagnostic acoustic data recorded by the multipurpose diagnostic examination apparatus 100, etc., using the input devices 2607. The input devices 2607 are, for example, a keyboard such as an alphanumeric keyboard, a joystick, a pointing device such as a computer mouse, a touch pad, a light pen, a digital pen, a microphone for providing voice input, a digital camera, a physical button, a touch sensitive display device, a track ball, a pointing stick, any device capable of sensing a tactile input, etc.

Computer applications and programs are used for operating the medical diagnostic examination system 2506. The programs are loaded onto the fixed media drive 2608 and into the memory unit 2602 via the removable media drive 2609. In an embodiment, the computer applications and programs may be loaded directly via the communication network 2509. Computer applications and programs are executed by double clicking a related icon displayed on the display unit 2606 using one of the input devices 2607. The output devices 2610 output the results of operations performed by the medical diagnostic examination system 2506. For example, the medical diagnostic examination system 2506 provides customized medical reports to users using the output devices 2610. The medical diagnostic examination system 2506 displays the generated medical reports using the output devices 2610.

The processor 2601 executes an operating system, for example, the Linux® operating system, the Unix® operating system, any version of the Microsoft® Windows® operating system, the Mac OS of Apple Inc., the IBM® OS/2, VxWorks® of Wind River Systems, Inc., QNX Neutrino® developed by QNX Software Systems Ltd., the Palm OS®, the Solaris operating system developed by Sun Microsystems, Inc., the Android operating system, the Windows Phone® operating system of Microsoft Corporation, the BlackBerry® operating system of Blackberry Limited, the iOS operating system of Apple Inc., the Symbian® operating system of Symbian Foundation Limited, etc. The medical diagnostic examination system 2506 employs the operating system for performing multiple tasks. The operating system is responsible for management and coordination of activities and sharing of resources of the medical diagnostic examination system 2506. The operating system further manages security of the medical diagnostic examination system 2506, peripheral devices connected to the medical diagnostic examination system 2506, and network connections. The operating system employed on the medical diagnostic examination system 2506 recognizes, for example, inputs provided by the users using one of the input devices 2607, the output display, files, and directories stored locally on the fixed media drive 2608. The operating system on the medical diagnostic examination system 2506 executes different programs using the processor 2601. The processor 2601 and the operating system together define a computer platform for which application programs in high level programming languages are written.

The processor 2601 of the medical diagnostic examination system 2506 retrieves instructions defined by the data communication module 2508a, the diagnostic data management module 2508b, etc., of the medical diagnostic examination system 2506 for performing respective functions disclosed in the detailed description of FIG. 25. The processor 2601 retrieves instructions for executing the modules, for example, 2508a, 2508b, etc., of the medical diagnostic examination system 2506 from the memory unit 2602. A program counter determines the location of the instructions in the memory unit 2602. The program counter stores a number that identifies the current position in the program of each of the modules, for example, 2508a, 2508b, etc., of the medical diagnostic examination system 2506. The instructions fetched by the processor 2601 from the memory unit 2602 after being processed are decoded. The instructions are stored in an instruction register in the processor 2601. After processing and decoding, the processor 2601 executes the instructions, thereby performing one or more processes defined by those instructions.

At the time of execution, the instructions stored in the instruction register are examined to determine the operations to be performed. The processor 2601 then performs the specified operations. The operations comprise arithmetic operations and logic operations. The operating system performs multiple routines for performing a number of tasks required to assign the input devices 2607, the output devices 2610, and memory for execution of the modules, for example, 2508a, 2508b, etc., of the medical diagnostic examination system 2506. The tasks performed by the operating system comprise, for example, assigning memory to the modules, for example, 2508a, 2508b, etc., of the medical diagnostic examination system 2506, and to data used by the medical diagnostic examination system 2506, moving data between the memory unit 2602 and disk units, and handling input/output operations. The operating system performs the tasks on request by the operations and after performing the tasks, the operating system transfers the execution control back to the processor 2601. The processor 2601 continues the execution to obtain one or more outputs. The outputs of the execution of the modules, for example, 2508a, 2508b, etc., of the medical diagnostic examination system 2506 are displayed to the user on the display unit 2606.

For purposes of illustration, the detailed description refers to the medical diagnostic examination system 2506 being run locally on a single computer system; however the scope of the computer implemented method and system 2500 disclosed herein is not limited to the medical diagnostic examination system 2506 being run locally on a single computer system via the operating system and the processor 2601, but may be extended to run remotely over the communication network 2509 by employing a web browser and a remote server, a mobile phone, or other electronic devices. One or more portions of the medical diagnostic examination system 2506 may be distributed across one or more computer systems (not shown) coupled to the communication network 2509.

Computer program codes comprising computer executable instructions are embodied on the non-transitory computer readable storage medium. The processor 2601 of the medical diagnostic examination system 2506 retrieves these computer executable instructions and executes them. When the computer executable instructions are executed by the processor 2601, the computer executable instructions cause the processor 2601 to perform the steps of the computer implemented method for facilitating medical imaging and remote diagnostic examinations.

FIGS. 27A-27I exemplarily illustrate screenshots of the graphical diagnostic examination interface (GDEI) 2507 provided by the medical diagnostic examination system 2506 for performing remote diagnostic examinations. During a diagnostic examination, a medical assistant logs into the medical diagnostic examination system 2506 on his/her local user device 2505 exemplarily illustrated in FIG. 25, via the GDEI 2507 of the medical diagnostic examination system 2506. The medical assistant plugs in the multipurpose diagnostic examination apparatus 100 exemplarily illustrated in FIG. 3, or FIGS. 5A-5E, or FIG. 8, or FIGS. 11A-11H, or FIGS. 13A-13G, or FIG. 14A-14F, to the medical diagnostic examination system 2506 via the connector interface 123 of the multipurpose diagnostic examination apparatus 100 using, for example, a universal serial bus (USB) 3.0 cable. The multipurpose diagnostic examination apparatus 100 operates with the local user device 2505 that implements the application programming interface and drivers of the medical diagnostic examination system 2506. The medical diagnostic examination system 2506 allows monitoring and recording of diagnostic examination data comprising, for example, images, audio files, etc.

Figure 27A:
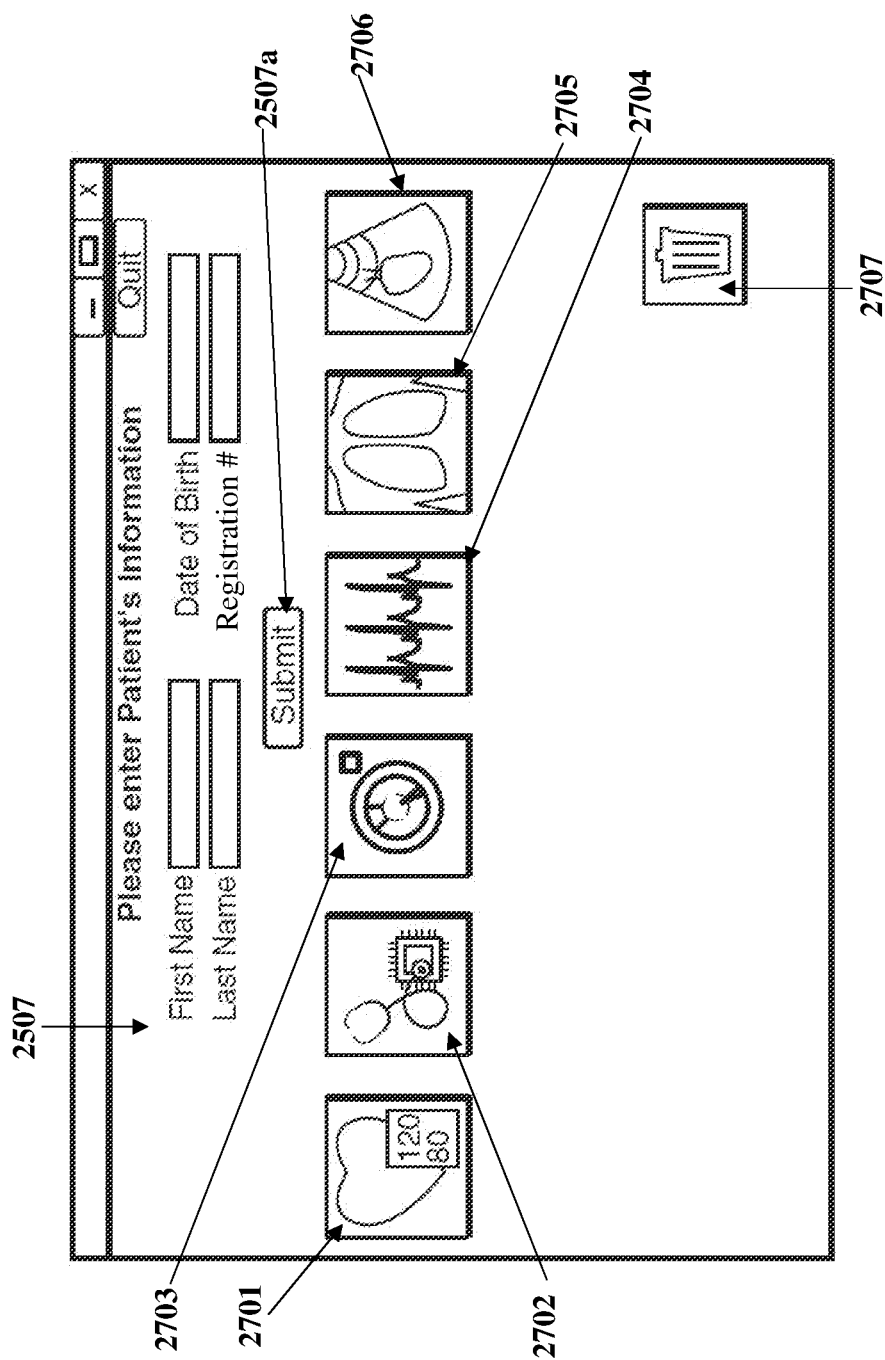
FIGS. 27A-27I exemplarily illustrate screenshots of the graphical diagnostic examination interface provided by the medical diagnostic examination system for performing remote diagnostic examinations.

FIG. 27A exemplarily illustrates a home interface provided by the graphical diagnostic examination interface (GDEI) 2507 of the medical diagnostic examination system 2506 exemplarily illustrated in FIG. 25. The home interface is displayed when the medical diagnostic examination system 2506 is loaded on the local user device 2505 exemplarily illustrated in FIG. 25. The home interface displays options for performing diagnostic examinations as exemplarily illustrated in FIG. 27A. The medical assistant can select one of the interface elements, for example, 2701, 2702, 2703, 2704, 2705, 2706, or 2707 on the GDEI 2507 for performing diagnostic examinations. For example, if the medical assistant wants to use the multipurpose diagnostic examination apparatus 100 with the stethoscope device 134 exemplarily illustrated in FIGS. 11A-11G, then the medical assistant can select the interface element 2702 depicting a stethoscope on the GDEI 2507 as exemplarily illustrated in FIG. 27A. If the medical assistant wants to measure blood pressure or a pulse of a patient, the medical assistant can select the interface element 2701 depicted as a "heart" on the GDEI 2507. In another example, the medical assistant can also select the interface elements 2704 and 2705 on the GDEI 2507 to initiate recording of an electrocardiogram and to perform an lung examination respectively. If the medical assistant selects the interface element 2701 depicted as a "heart" on the GDEI 2507, the medical diagnostic examination system 2506 displays another interface on the GDEI 2507 as exemplarily illustrated in FIG. 27B.

Figure 27B:
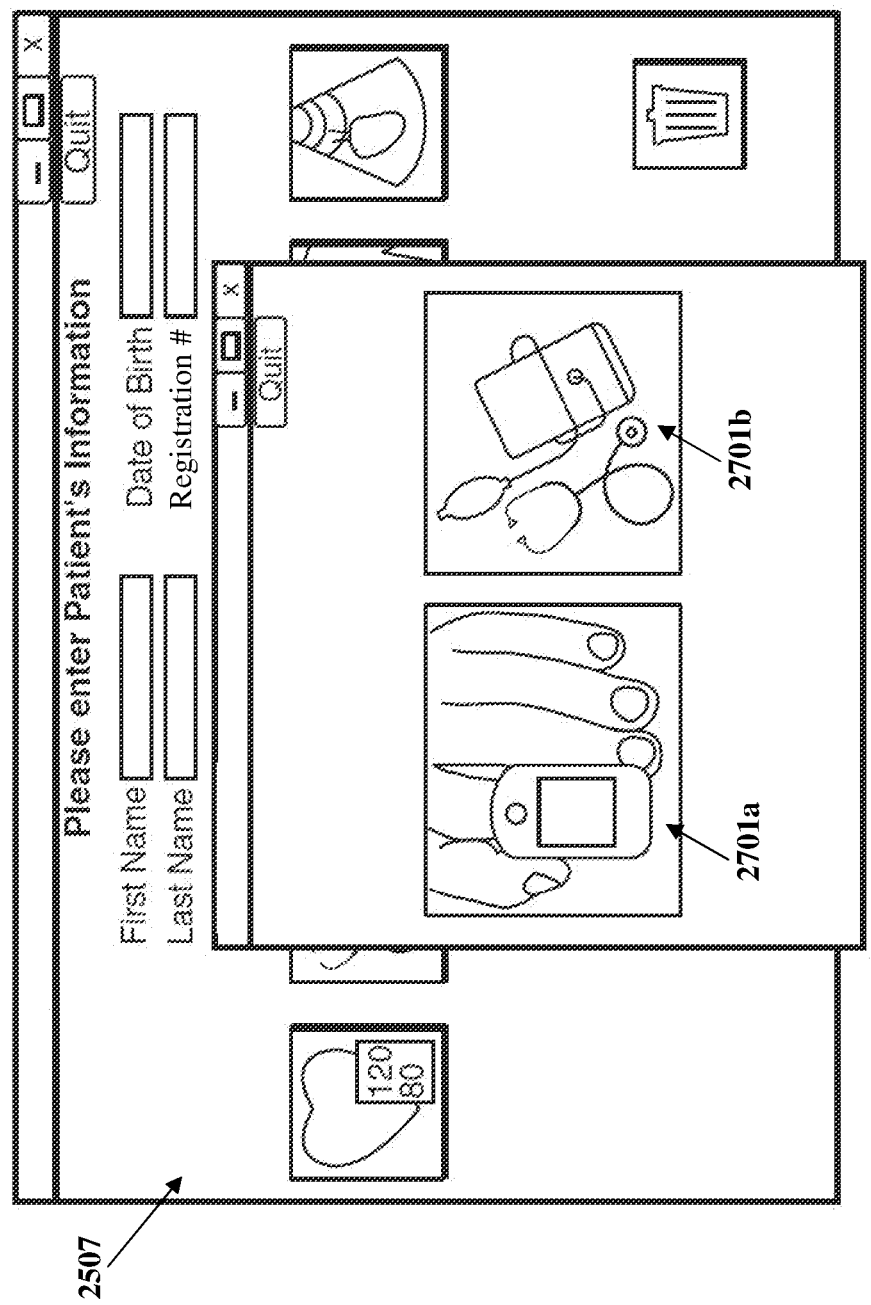

FIG. 27B exemplarily illustrates an interface displaying a pulse oximeter icon 2701a and a blood pressure icon 2701b on the GDEI 2507. If the medical assistant selects or clicks on the pulse oximeter icon 2701a on the GDEI 2507, the medical diagnostic examination system 2506 exemplarily illustrated in FIG. 25, activates the application programming interface (API) for a pulse oximeter window and displays a date output from a pulse oximeter (not shown) as long as the pulse oximeter is clamped on to the patient's fingertip. If the medical assistant selects or clicks on the blood pressure icon 2701b on the GDEI 2507, the medical diagnostic examination system 2506 activates the API for a blood pressure window and displays a date output from a blood pressure meter (not shown) as long as the blood pressure meter is tied around the patient's wrist.

Figure 27C:
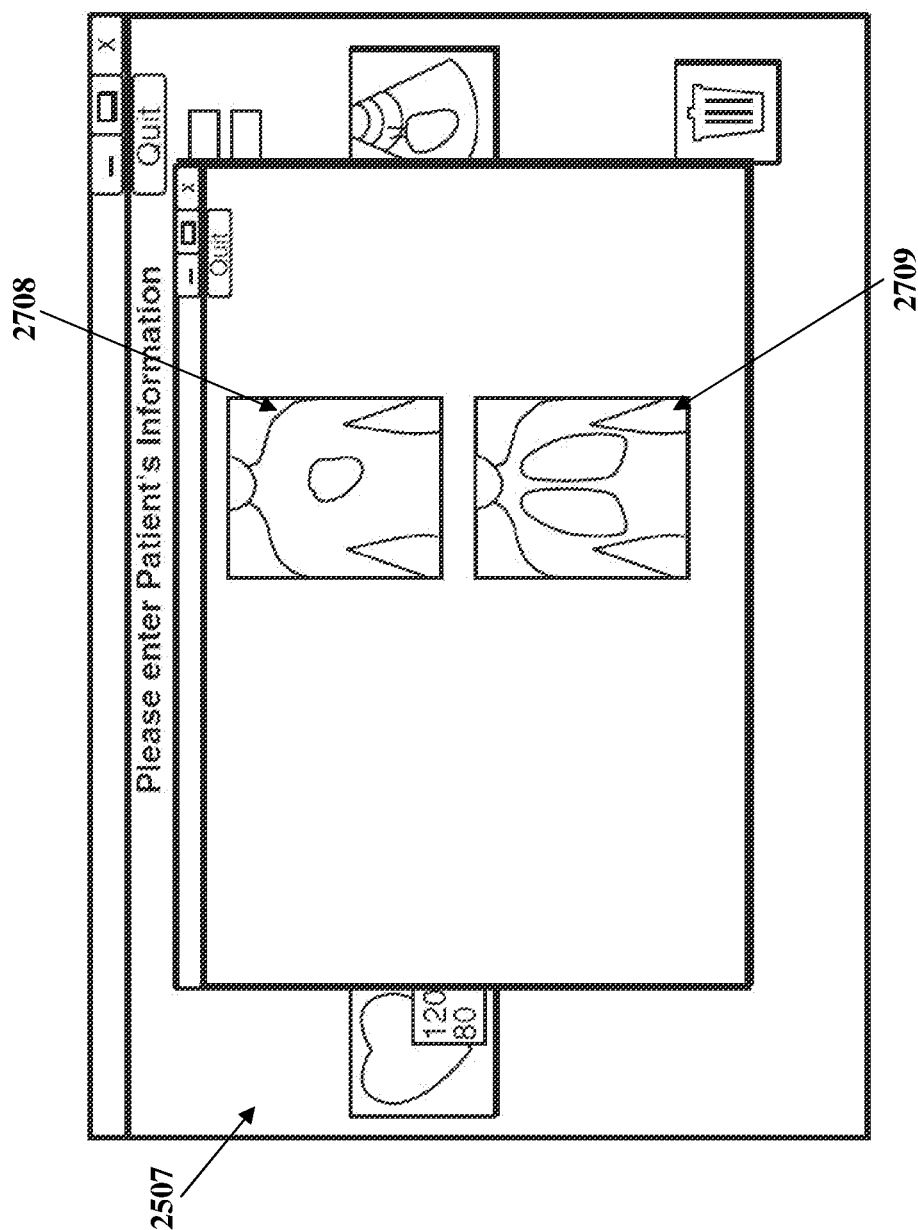

FIG. 27C exemplarily illustrates an anatomical examination area selection window displayed on the graphical diagnostic examination interface (GDEI) 2507 when the medical assistant selects the stethoscope interface element 2702 on the home interface exemplarily illustrated in FIG. 27A. As exemplarily illustrated in FIG. 27C, the GDEI 2507 displays options of anatomical examination areas that can be examined using the stethoscope device 134, for example, a heart option 2708 and a lung option 2709. The medical assistant can select the heart option 2708 on the GDEI 2507 to use the multipurpose diagnostic examination apparatus 100 with the stethoscope device 134 for recording diagnostic acoustic data of the patient's heart and for performing a diagnostic heart examination. The medical assistant can select the lung option 2709 on the GDEI 2507 to use the multipurpose diagnostic examination apparatus 100 with the stethoscope device 134 for recording diagnostic acoustic data of the patient's lungs and for performing a diagnostic lung examination. If the medical assistant selects the heart option 2708 on the GDEI 2507 exemplarily illustrated in FIG. 27C, the medical diagnostic examination system 2506 exemplarily illustrated in FIG. 25, displays another interface that indicates anatomical examination areas comprising, for example, an aortic area, a pulmonary area, Erb's point, a tricuspid area, a mitral area, etc., of the patient's heart on the GDEI 2507 as exemplarily illustrated in FIGS. 27D-27E.

Figure 27D:
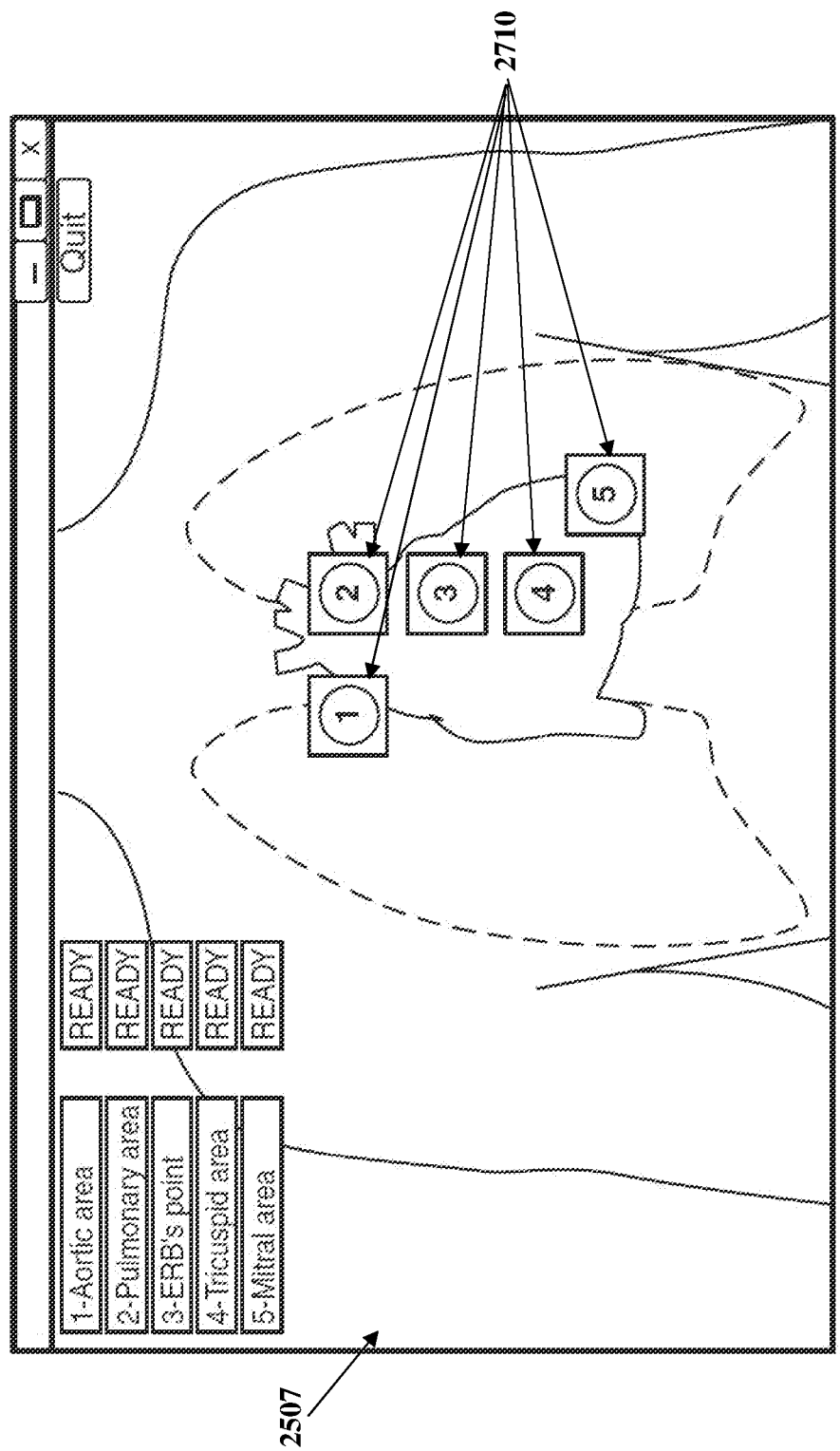
Figure 27E:
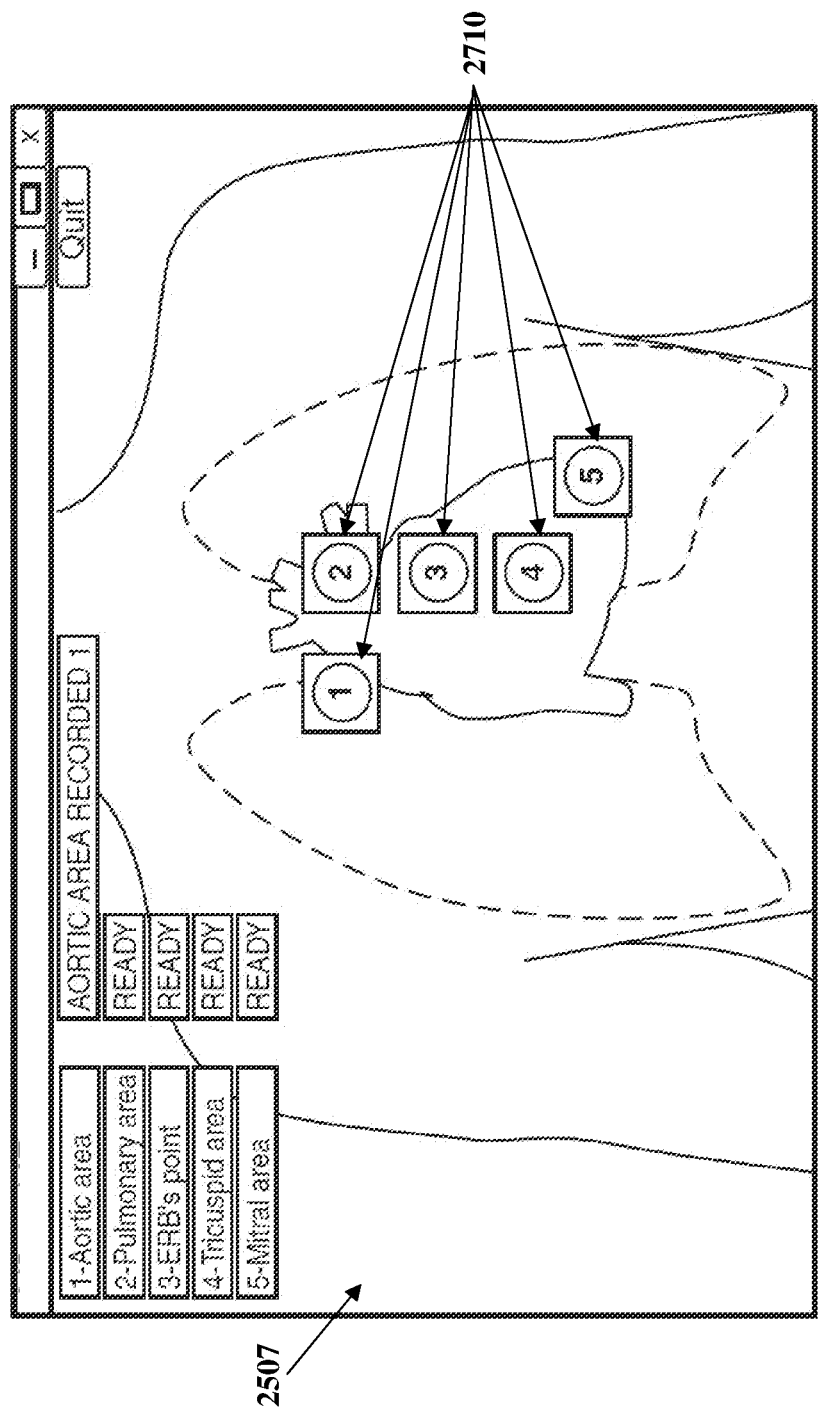

FIGS. 27D-27E exemplarily illustrate the graphical diagnostic examination interface (GDEI) 2507 displaying anatomical examination areas of the patient's heart with interface elements 2710, for example, buttons labeled "1", "2", "3", "4", and "5". The interface elements 2710 correspond to the anatomical examination areas and can be activated to select the anatomical examination areas. As exemplarily illustrated in FIGS. 27D-27E, the interface element "1" corresponds to the aortic area of the patient's heart, the interface element "2" corresponds to the pulmonary area of the patient's heart, the interface element "3" corresponds to Erb's point of the patient's heart, the interface element "4" corresponds to the tricuspid area of the patient's heart, and the interface element "5" corresponds to the mitral area of the patient's heart. To listen to the heart sounds, the medical assistant positions the multipurpose diagnostic examination apparatus 100 with the stethoscope device 134 exemplarily illustrated in FIGS. 11A-11G, on the patient's chest, and then the medical assistant along with the doctor can activate the interface elements 2710 on the GDEI 2507 exemplarily illustrated in FIG. 27D, to listen to the heart sounds from the selected anatomical examination areas of the patient's heart.

The medical diagnostic examination system 2506 exemplarily illustrated in FIG. 25, in communication with the multipurpose diagnostic examination apparatus 100 with the stethoscope device 134, records diagnostic acoustic data from a selected anatomical examination area of the patient's heart, for example, for about 10 seconds. By clicking on any one of the interface elements 2710 on the GDEI 2507 exemplarily illustrated in FIG. 27D, for example, via a touchscreen interface of the local user device 2505 exemplarily illustrated in FIG. 25, for example, a computer comprising a Windows® 8 operating system, the medical diagnostic examination system 2506 automatically creates an audio file, for example, a .WAV file in a waveform (WAV) audio file format. The created audio file contains the diagnostic acoustic data obtained from the heart sounds of the selected anatomical examination area of the patient's heart and can be used for creating a medical history record for the patient. The medical diagnostic examination system 2506 stores the created audio file in the data management server 2510.

The status of recording of the diagnostic acoustic data automatically changes on the graphical diagnostic examination interface (GDEI) 2507, when the medical assistant clicks on another one of the interface elements 2710. That is, the status of recording of the diagnostic acoustic data automatically changes based on each subsequent recording, for example, from "Ready" to "Recorded". The medical diagnostic examination system 2506 also displays the number of times the diagnostic acoustic data from the selected heart area is recorded, on the GDEI 2507. For example, prior to recording, the medical diagnostic examination system 2506 displays the status of recording of the diagnostic acoustic data of all the anatomical examination areas as "Ready" on the GDEI 2507 as exemplarily illustrated in FIG. 27D. Consider an example where the medical assistant clicks on the interface element "1" on the GDEI 2507. On receiving the click on the interface element "1" via the GDEI 2507, the medical diagnostic examination system 2506 receives and records diagnostic acoustic data of the aortic area, through the multipurpose diagnostic examination apparatus 100. After recording the diagnostic acoustic data of the aortic area for about 10 seconds, the medical assistant clicks on the interface element "2" on the GDEI 2507 to initiate recording of diagnostic acoustic data of the pulmonary area. On receiving the click on the interface element "2" via the GDEI 2507, the medical diagnostic examination system 2506 immediately changes the status of recording of the diagnostic acoustic data of the aortic area from "Ready" to "Aortic area recorded_1" on the GDEI 2507 and initiates recording of the diagnostic acoustic data of the pulmonary area. If the medical assistant clicks on the interface element "1" on the GDEI 2507 a second time, instead of clicking on the interface element "2", the medical diagnostic examination system 2506 records the diagnostic acoustic data of the aortic area a second time and changes the status from "Aortic Area Recorded_1" to "Aortic Area Recorded_2" on the GDEI 2507 after completion of the recording, for indicating the second time dynamic recording of the diagnostic acoustic data from the aortic area. A doctor can request the medical assistant to select a particular anatomical examination area displayed on the GDEI 2507, and through the image capture device 106 of the multipurpose diagnostic examination apparatus 100, the doctor is assured that the correct anatomical examination area is selected for remote diagnostic examination. If the medical assistant clicks on any of the interface elements 2710 on the GDEI 2507, the medical diagnostic examination system 2506 starts receiving diagnostic acoustic data from the multipurpose diagnostic examination apparatus 100.

Figure 27F:
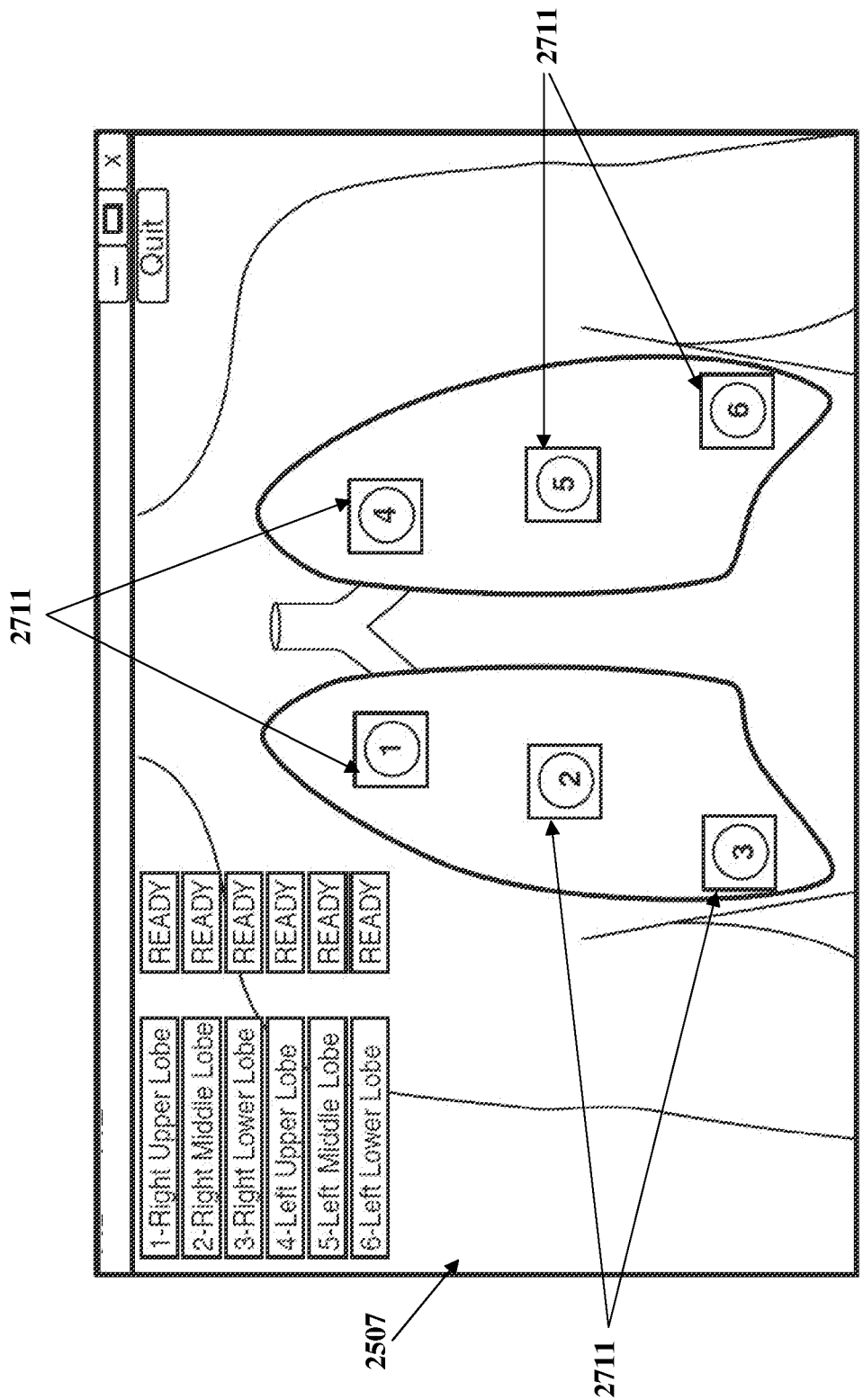
Figure 27G:
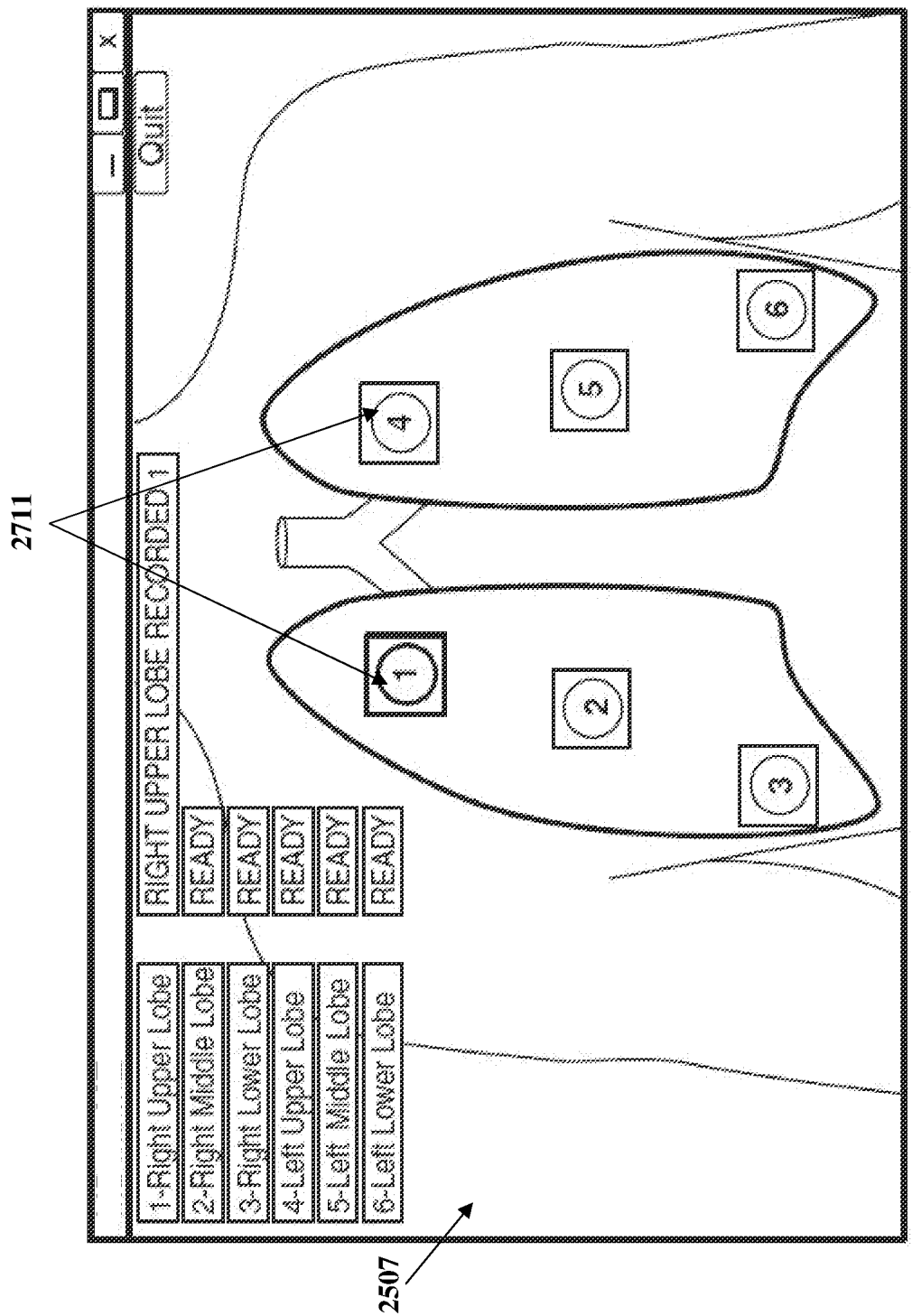

If the medical assistant selects the lung option 2709 on the graphical diagnostic examination interface (GDEI) 2507 exemplarily illustrated in FIG. 27C, the medical diagnostic examination system 2506 displays another interface that indicates anatomical examination areas comprising, for example, a right upper lobe, a right middle lobe, a right lower lobe, a left upper lobe, a left middle lobe, and a left lower lobe on the GDEI 2507 as exemplarily illustrated in FIGS. 27F-27G.

FIGS. 27F-27G exemplarily illustrate the graphical diagnostic examination interface (GDEI) 2507 displaying anatomical examination areas of the patient's lungs with interface elements 2711, for example, buttons labeled "1", "2", "3", "4", "5", and "6". The interface elements 2711 correspond to the anatomical examination areas and can be activated to select the anatomical examination areas. As exemplarily illustrated in FIGS. 27F-27G, the interface element "1" corresponds to the right upper lobe of the patient's lung, the interface element "2" corresponds to the right middle lobe of the patient's lung, the interface element "3" corresponds to the right lower lobe of the patient's lung, the interface element "4" corresponds to the left upper lobe of the patient's lung, the interface element "5" corresponds to the left middle lobe of the patient's lung, and the interface element "6" corresponds to the left lower lobe of the patient's lung. To listen to the lung sounds, the medical assistant positions the multipurpose diagnostic examination apparatus 100 with the stethoscope device 134 exemplarily illustrated in FIGS. 11A-11G, on the patient's chest, and then the medical assistant along with the doctor can activate the interface elements 2711 on the GDEI 2507 exemplarily illustrated in FIG. 27F, to remotely listen to lung sounds from the selected main lung areas of the patient's lungs.

The medical diagnostic examination system 2506 exemplarily illustrated in FIG. 25, in communication with the multipurpose diagnostic examination apparatus 100 with the stethoscope device 134, records diagnostic acoustic data from a selected lung area of the patient's lungs, for example, for about 10 seconds. By clicking on any one of the interface elements 2711 exemplarily illustrated in FIG. 27D, the medical diagnostic examination system 2506 automatically creates an audio file, for example, a .WAV file. The created audio file contains the diagnostic acoustic data obtained from the lung sounds of the selected lung area of the patient's lungs and can be used for creating a medical history record for the patient. The medical diagnostic examination system 2506 stores the created audio file in the data management server 2510.

The status of recording of the diagnostic acoustic data automatically changes on the graphical diagnostic examination interface (GDEI) 2507, when the medical assistant clicks on another one of the interface elements 2711. That is, the status of recording of the diagnostic acoustic data automatically changes based on each subsequent recording, for example, from "Ready" to "Recorded". The medical diagnostic examination system 2506 also displays the number of times the diagnostic acoustic data from the selected lung area is recorded, on the GDEI 2507. For example, prior to recording, the medical diagnostic examination system 2506 displays the status of recording of the diagnostic acoustic data of all the lung areas as "Ready" on the GDEI 2507 as exemplarily illustrated in FIG. 27F. Consider an example where the medical assistant clicks on the interface element "1" on the GDEI 2507. On receiving the click on the interface element "1" via the GDEI 2507, the medical diagnostic examination system 2506 receives and records diagnostic acoustic data of the right upper lobe, through the multipurpose diagnostic examination apparatus 100. After recording the diagnostic acoustic data of the aortic area for about 10 seconds, the medical assistant clicks on the interface element "2" on the GDEI 2507 to initiate recording of diagnostic acoustic data of the right middle lobe. On receiving the click on the interface element "2" via the GDEI 2507, the medical diagnostic examination system 2506 immediately changes the status of recording of the diagnostic acoustic data of the right upper lobe from "Ready" to "Right Upper Lobe Recorded_1" on the GDEI 2507 and initiates recording of the diagnostic acoustic data of the right middle lobe. If the medical assistant clicks on the interface element "1" on the GDEI 2507 a second time, instead of clicking on the interface element "2", the medical diagnostic examination system 2506 records the diagnostic acoustic data of the right upper lobe a second time and changes the status from "Right Upper Lobe Recorded_1" to "Right Upper Lobe Recorded_2" on the GDEI 2507 after completion of the recording, for indicating the second time dynamic recording of the diagnostic acoustic data from the right upper lobe.

The medical assistant can add the stethoscope device 134 exemplarily illustrated in FIGS. 11A-11G, or the ultrasound device 141 exemplarily illustrated in FIGS. 13A-13H to the attachment unit 115 of the multipurpose diagnostic examination apparatus 100, so that the multipurpose diagnostic examination apparatus 100 becomes an image capture device 106 and a stethoscope device 134 or an image capture device 106 and an ultrasound device 141. The multipurpose diagnostic examination apparatus 100 allows a doctor to perform a complete virtual examination to remotely ensure that correct anatomical examination areas are selected as indicated by the laser pointer 132 of the multipurpose diagnostic examination apparatus 100. By using the laser pointer 132, a doctor can remotely view points on the patient's body that should be considered for diagnostic examination using the multipurpose diagnostic examination apparatus 100. For example, if the doctor wishes to verify heart function, he/she should listen to five points on the heart as exemplarily illustrated in FIGS. 27D-27E. The length of the attachment unit 115 is of a sufficient length to facilitate a proper view of the patient's body via the image capture device 106 of the multipurpose diagnostic examination apparatus 100.

Figure 27H:
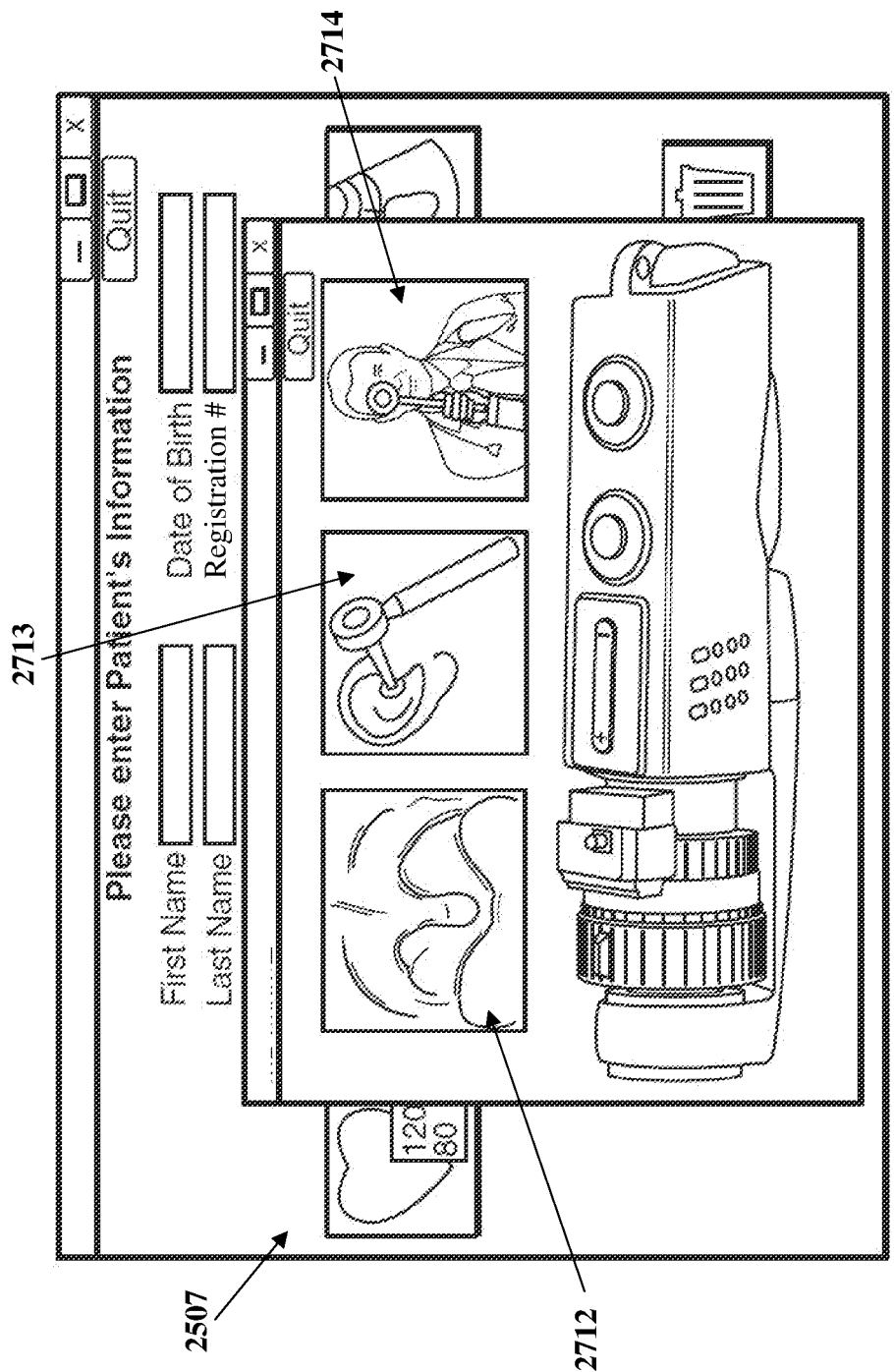

FIG. 27H exemplarily illustrates an interface displayed on the graphical diagnostic examination interface (GDEI) 2507, when the medical assistant clicks on the camera interface element 2703 on the GDEI 2507 exemplarily illustrated in FIG. 27A. The medical assistant can select an interface element, for example, 2712, 2713, or 2714 on the GDEI 2507, if he/she wants to perform a throat examination, an otoscopy, or a dermatoscopy respectively.

Figure 27I:
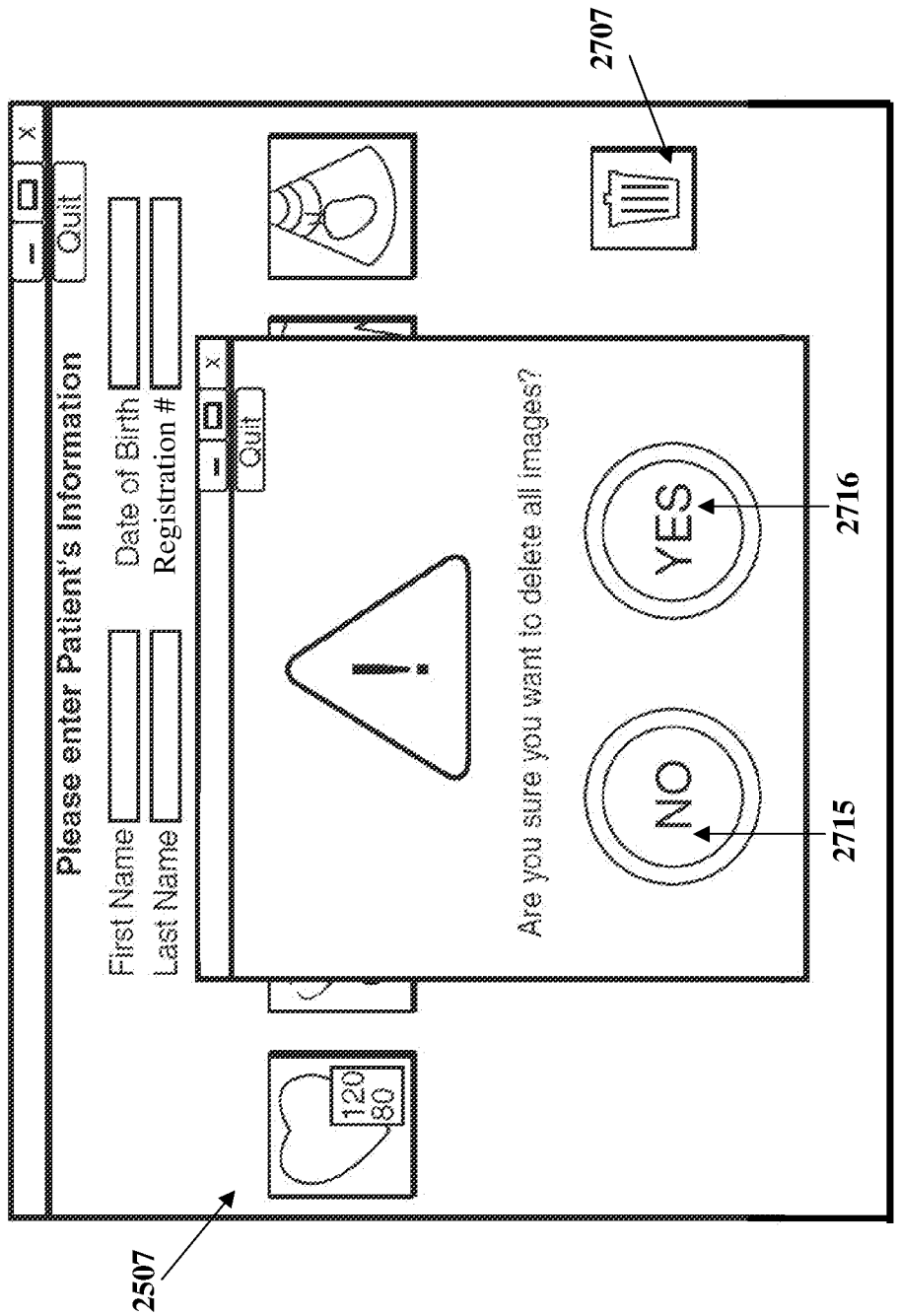

FIG. 27I exemplarily illustrates a window displayed on the graphical diagnostic examination interface (GDEI) 2507, when the medical assistant clicks a delete interface element 2707 on the GDEI 2507 exemplarily illustrated in FIG. 27A. The medical assistant can select the delete interface element 2707 if he/she wishes to delete diagnostic image data and diagnostic examination data received from the multipurpose diagnostic examination apparatus 100 via the connector interface 123 of the multipurpose diagnostic examination apparatus 100. The medical diagnostic examination system 2506 exemplarily illustrated in FIG. 25, prompts the medical assistant to confirm the action of deleting the diagnostic image data and the diagnostic examination data by clicking on a "yes" button 2716 or a "no" button 2715 displayed in the window on the GDEI 2507.

Figure 28:
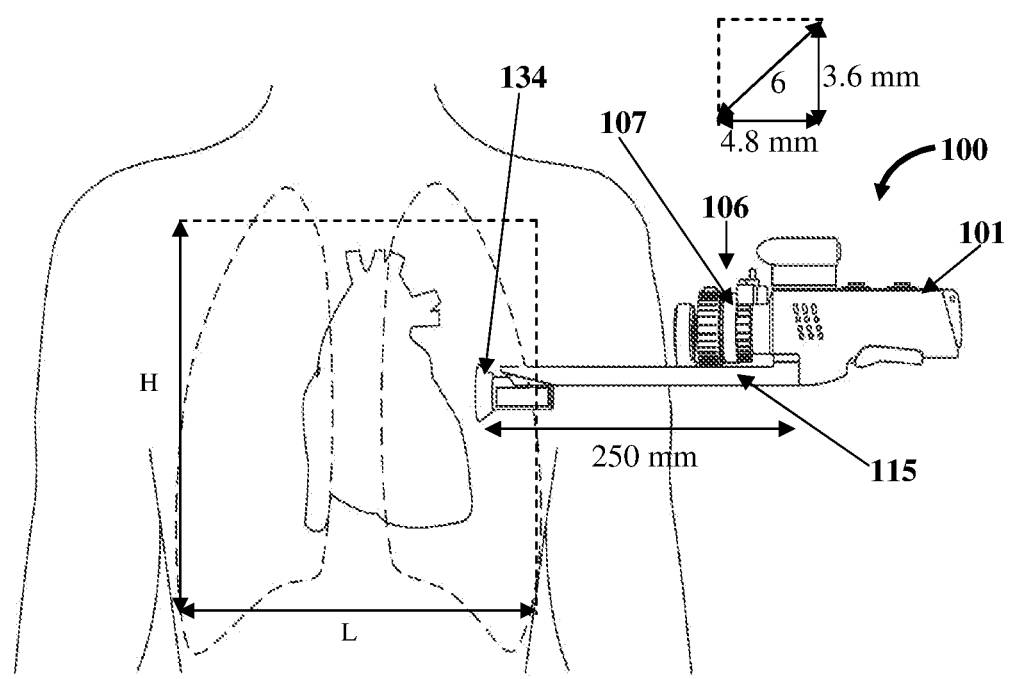
FIG. 28 exemplarily illustrates determination of a length of the attachment unit based on optical parameters of the image capture device.

FIG. 28 exemplarily illustrates determination of a length of the attachment unit 115 based on optical parameters of the image capture device 106. In an embodiment, the attachment unit 115 of the multipurpose diagnostic examination apparatus 100 is of a predetermined length to ensure that a doctor can remotely view a patient's front chest area or back chest area through the image capture device 106. The length of the attachment unit 115 comprising the stethoscope device 134 or the ultrasound device 141 exemplarily illustrated in FIGS. 12A-12B, is calculated to select a correct optical lens 107 for the image capture device 106 that matches focal length requirements for the attachment unit 115. The image capture device 106 comprises, for example, a ⅓" complementary metal-oxide-semiconductor (CMOS) image sensor (not shown). The size of the CMOS image sensor is, for example, 3.6 mm×4.8 mm. The focal length of the optical lens 107 is calculated based on the formulae disclosed below:

$$\frac{\text{Subject Distance(mm)} \times 4.8 \text{ mm}}{\text{Subject height}} = \text{Focal Length}$$

$$\frac{\text{Subject Distance(mm)} \times 3.6 \text{ mm}}{\text{Subject length}} = \text{Focal Length}$$

Based on experiments and testing conducted using the above formulae, the length of the attachment unit 115 for designing an image capture device 106 with a stethoscope device 134 or an image capture device 106 with an ultrasound device 141 is about 250 mm. Therefore, the doctor's viewing area of a patient's front chest or back chest is, for example, in average about 350 mm×300 mm. The focal length of the optical lens 107 of the image capture device 106 can be adjusted in a range of, for example, about 2 mm to about 8 mm $$\frac{\text{Subject Distance(mm)} \times 4.8 \text{ mm}}{\text{Focal Length (mm)}} =$$
$$\text{Subject height (mm)} \rightarrow \frac{250 \times 4.8}{2} = 600 \text{ mm}$$

$$\frac{\text{Subject Distance(mm)} \times 3.6 \text{ mm}}{\text{Subject length}} = \text{Focal Length} \rightarrow \frac{250 \times 3.6}{2} = 450 \text{ mm}$$

Based on the calculations disclosed above, a doctor can view a bigger examination area, for example, a height of about 600 mm of a patient's chest or back area. For improving the accuracy of the calculations, a thickness of the optical lens 107 and a Lensmaker's equation can be considered.

Figure 29A:
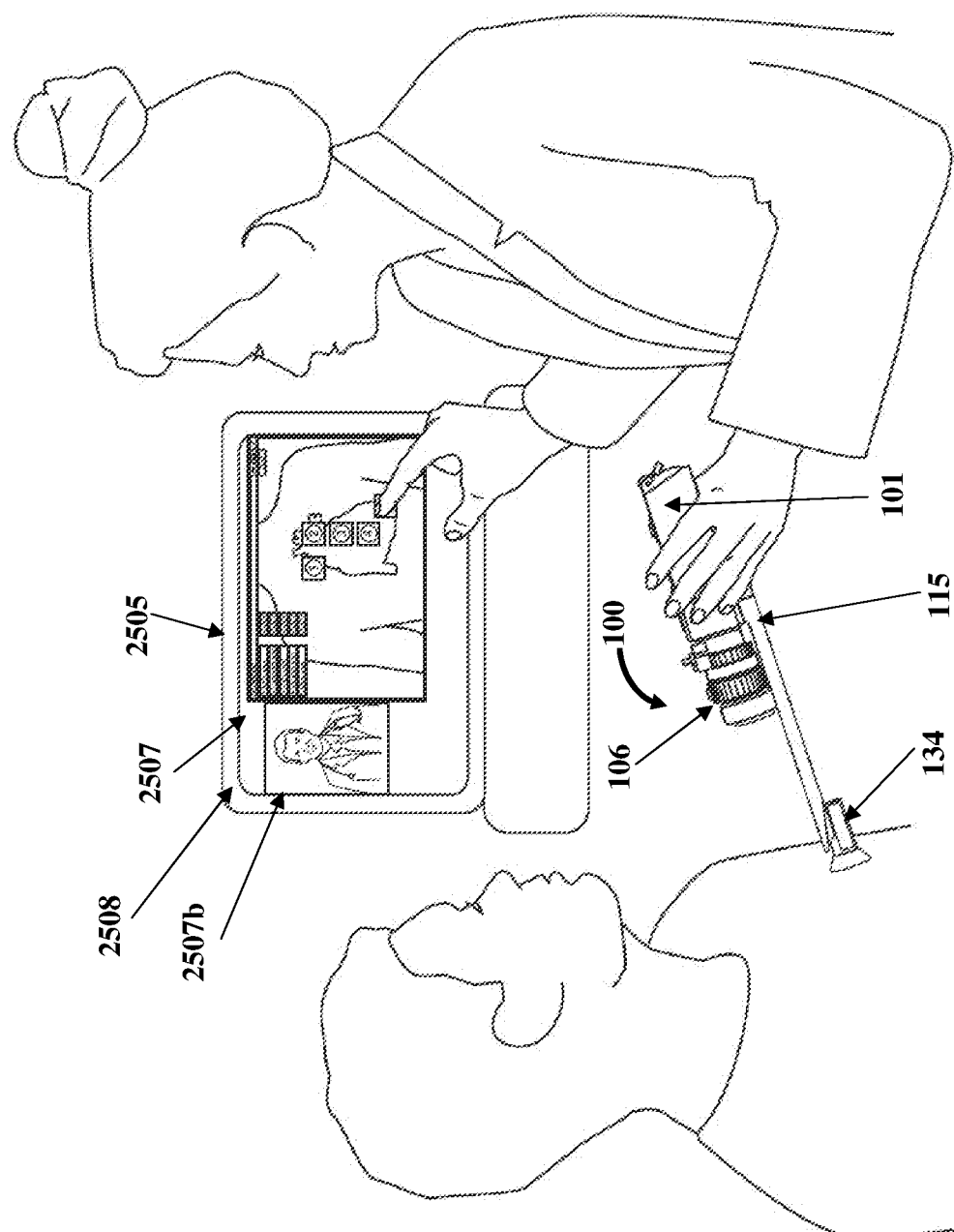
FIGS. 29A-29B exemplarily illustrate implementations of different embodiments of the multipurpose diagnostic examination apparatus with the stethoscope device, and the medical diagnostic examination system accessible on a local user device or a remote user device for medical imaging and remote diagnostic examinations.
Figure 29B:
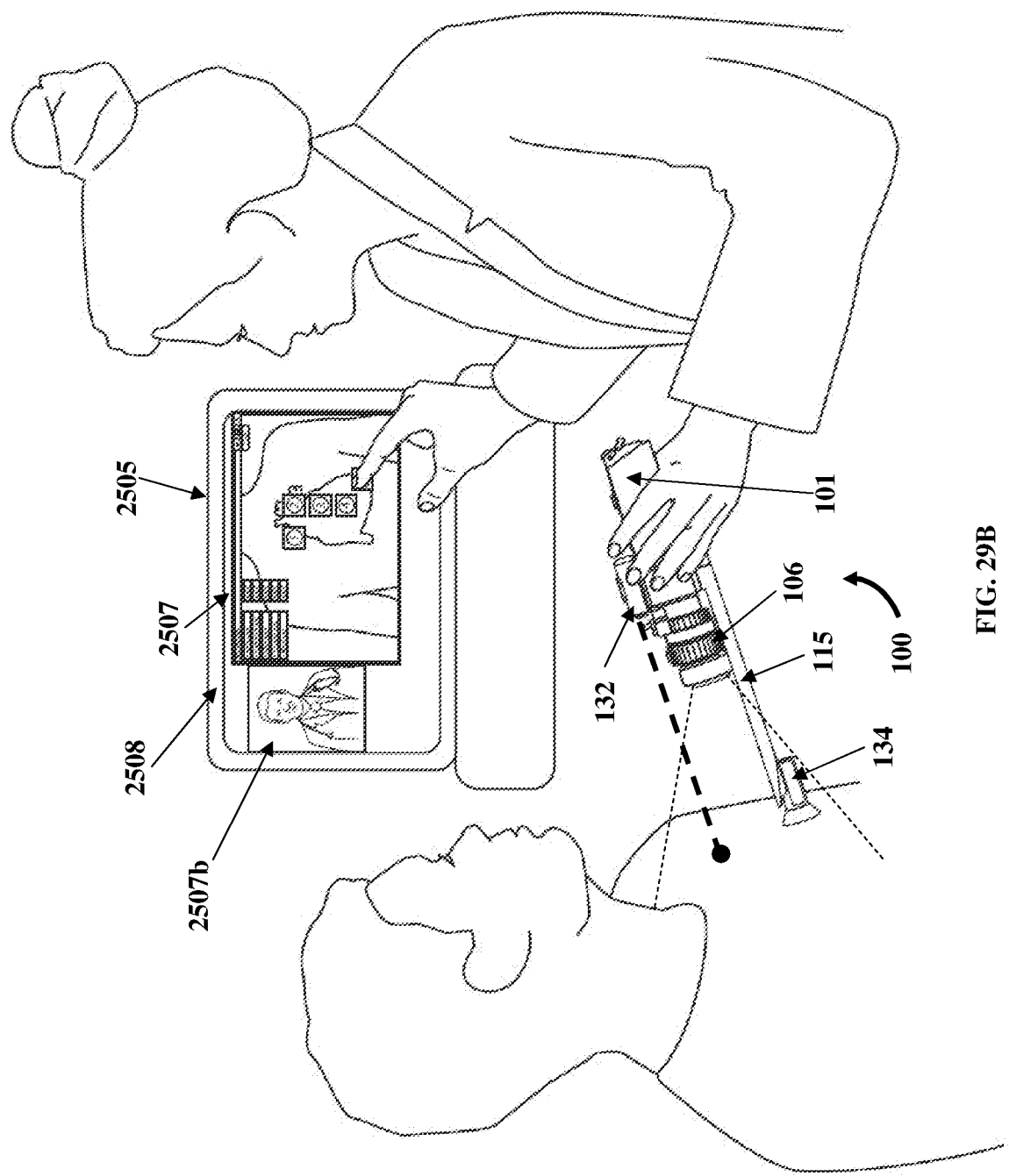

FIGS. 29A-29B exemplarily illustrate implementations of different embodiments of the multipurpose diagnostic examination apparatus 100 with the stethoscope device 134, and the medical diagnostic examination system 2506 accessible on a local user device 2505 or a remote user device 2511 exemplarily illustrated in FIG. 25, for medical imaging and remote diagnostic examinations. Consider an example where a nurse uses the multipurpose diagnostic examination apparatus 100 with the stethoscope device 134 connected to the attachment unit 115 to transmit diagnostic acoustic data from a patient's heart area to a doctor via the medical diagnostic examination system 2506. The nurse logs in to the medical diagnostic examination system 2506 and invites the doctor to a video session via the graphical diagnostic examination interface (GDEI) 2507 of the medical diagnostic examination system 2506 as exemplarily illustrated in FIG. 29A.

The doctor logged in to the medical diagnostic examination system 2506 via the GDEI 2507 on his/her remote user device 2511, for example, a laptop can view anatomical examination areas on the patient's body selected by the nurse via medical imaging facilitated by the image capture device 106 of the multipurpose diagnostic examination apparatus 100, in a doctor's view window 2507b on the GDEI 2507. This view window 2507b is activated when the nurse selects a screen sharing mode on his/her local user device 2505 or when the multipurpose diagnostic examination apparatus 100 is recognized as a web camera on the doctor's remote user device 2511. The nurse views the doctor in the doctor's view window 2507b on the GDEI 2507 that shows the doctor's image as recorded by the doctor's web camera in real time. The nurse and the doctor both use web cameras that work with the Health Insurance Portability and Accountability Act (HIPAA) compliant GDEI 2507. Thus, the doctor can view in real time the patient and the diagnostic reports of the patient. Similarly, the nurse views the doctor in real time on the nurse's local user device 2505.

The first step is to allow the doctor to select points on the patient's chest. In an embodiment, the nurse can attach a light source, for example, the laser pointer 132 to the upper section 101*b* of the diagnosis control unit 101 of the multipurpose diagnostic examination apparatus 100 as exemplarily illustrated in FIG. 29B. In this embodiment, the nurse can point the laser pointer 132 on the chest area of the patient, and the doctor can direct the nurse to point where he/she requires. The stethoscope device 134 on the multipurpose diagnostic examination apparatus 100 touches the selected point to allow the doctor to receive real time diagnostic acoustic data, that is, heart sounds. If the doctor wants to listen to lung sounds, the nurse points on the patient's back and the doctor selects a point on the patient's back. The stethoscope device 134 on the multipurpose diagnostic examination apparatus 100 touches the selected point to allow the doctor to receive real time diagnostic acoustic data, that is, lung sounds. The doctor can verify the anatomical examination areas selected by the nurse for retrieving diagnostic acoustic data comprising audio signals via the stethoscope device 134 of the multipurpose diagnostic examination apparatus 100. For example, the medical diagnostic examination system 2506 displays five interface elements 2710 corresponding to five anatomical examination areas of the patient's heart area on the graphical diagnostic examination interface (GDEI) 2507 as exemplarily illustrated in FIGS. 27D-27E and FIGS. 29A-29B. The nurse places the stethoscope device 134 on the patient's body based on those five anatomical examination areas. Based on diagnostic image data transmitted to the medical diagnostic examination system 2506 accessible on the doctor's laptop via the communication network 2509, the doctor can view and verify that the nurse is collecting diagnostic acoustic data from correct anatomical examination areas. Hence, the method disclosed herein allows a complete virtual diagnostic examination, for example, of heart, lungs, bowel, etc., by using the multipurpose diagnostic examination apparatus 100 with the stethoscope device 134, in communication with the medical diagnostic examination system 2506.

In an embodiment, if the doctor wishes to receive ultrasound data, the nurse can connect the attachment unit 115 with the ultrasound device 141 exemplarily illustrated in FIGS. 12A-12B, and the image capture device 106 to the diagnosis control unit 101, and then the nurse can proceed in the same way as is disclosed above. By using the graphical diagnostic examination interface (GDEI) 2507 of the medical diagnostic examination system 2506, a doctor can remotely view a patient's body and anatomical examination areas, for example, heart areas. The medical diagnostic examination system 2506 provides the application programming interface (API) in a sharing mode to provide a real time camera output for enabling the doctor to perform remote diagnostic examinations and monitor diagnostic examination data in real time.

Figure 30:
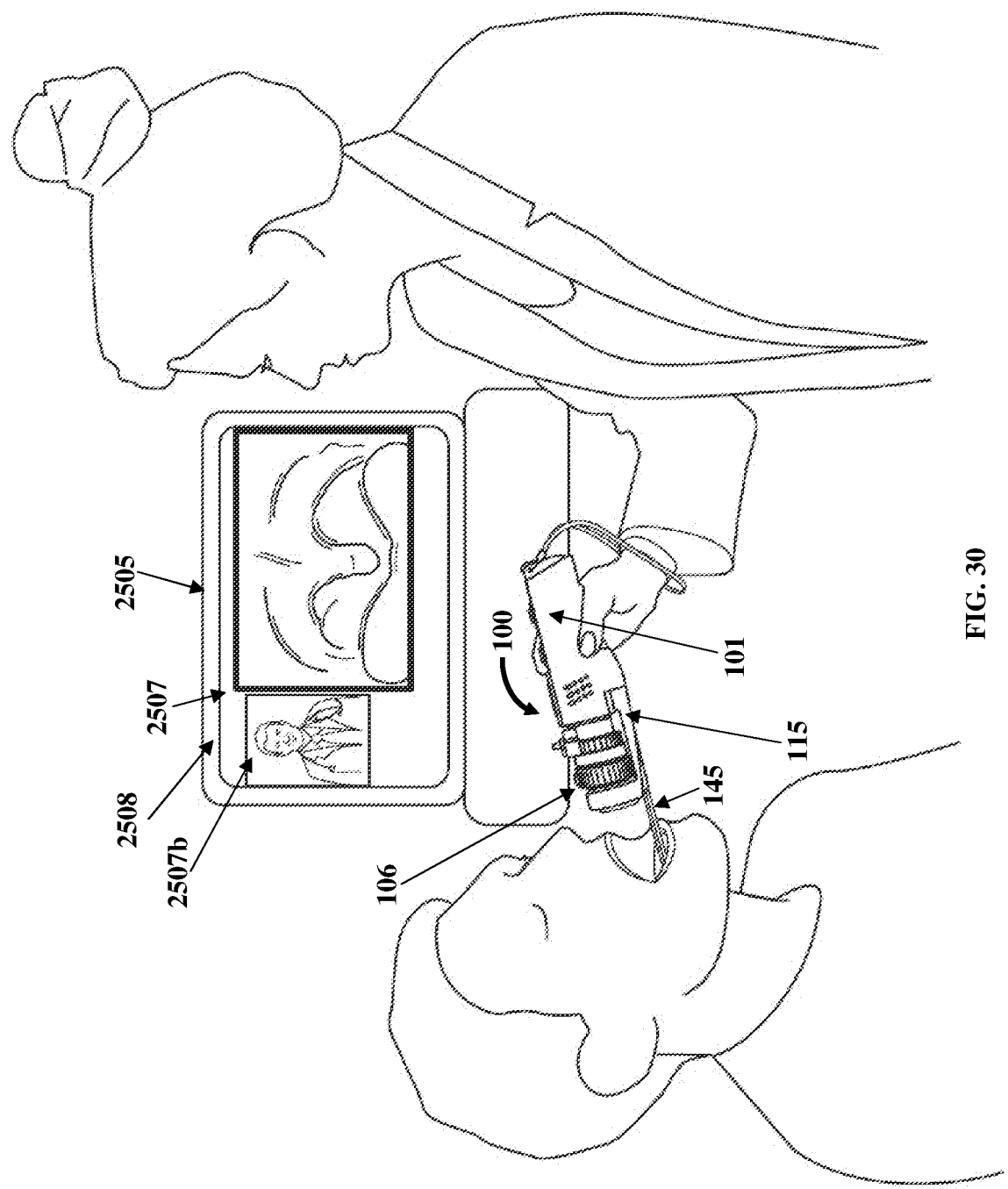
FIG. 30 exemplarily illustrates an implementation of another embodiment of the multipurpose diagnostic examination apparatus with the diagnostic assistance element, and the medical diagnostic examination system accessible on a local user device or a remote user device for medical imaging and remote diagnostic examinations.

FIG. 30 exemplarily illustrates an implementation of another embodiment of the multipurpose diagnostic examination apparatus 100 with the diagnostic assistance element 145, and the medical diagnostic examination system 2506 accessible on a local user device 2505 or a remote user device 2511 exemplarily illustrated in FIG. 25, for medical imaging and remote diagnostic examinations. A nurse inserts the diagnosis assistance element 145, for example, a tongue depressor into the supplementary attachment slot 146 of the attachment unit 115 of the multipurpose diagnostic examination apparatus 100 exemplarily illustrated in FIG. 14B, and plugs in the multipurpose diagnostic examination apparatus 100 to a local user device 2505 that deploys the medical diagnostic examination system 2506. The image capture device 106 of the multipurpose diagnostic examination apparatus 100 facilitates medical imaging during remote diagnostic examination. The nurse invites a doctor to a video session via the graphical diagnostic examination interface (GDEI) 2507 of the medical diagnostic examination system 2506. The nurse inserts the diagnosis assistance element 145 into a patient's mouth to access the patient's throat. The image capture device 106 captures images or records a video of the patient's throat and transmits the captured diagnostic image data to the camera module 124 exemplarily illustrated in FIG. 14G. The camera module 124 processes the captured diagnostic image data and transmits the processed diagnostic image data to the medical diagnostic examination system 2506 accessible on the local user device 2505 via the connector interface 123 exemplarily illustrated in FIG. 14G. The medical diagnostic examination system 2506 transmits the processed diagnostic image data to the doctor's remote user device 2511 via the communication network 2509 to allow the doctor to remotely perform a throat examination of the patient. The doctor logged in to the medical diagnostic examination system 2506 via the GDEI 2507 on his/her remote user device 2511 exemplarily illustrated in FIG. 25, can view the patient's throat via medical imaging facilitated by the image capture device 106 of the multipurpose diagnostic examination apparatus 100, in a doctor's view window 2507*b* on the GDEI 2507.

It will be readily apparent that the various methods, algorithms, and computer programs disclosed herein may be implemented on computer readable media appropriately programmed for computing devices. As used herein, "computer readable media" refers to non-transitory computer readable media that participate in providing data, for example, instructions that may be read by a computer, a processor, or a similar device. Non-transitory computer readable media comprise all computer readable media, for example, non-volatile media, volatile media, and transmission media, except for a transitory, propagating signal. Non-volatile media comprise, for example, optical discs or magnetic disks and other persistent memory volatile media including a dynamic random access memory (DRAM), which typically constitutes a main memory. Volatile media comprise, for example, a register memory, a processor cache, a random access memory (RAM), etc. Transmission media comprise, for example, coaxial cables, copper wire, fiber optic cables, modems, etc., including wires that constitute a system bus coupled to a processor, etc. Common forms of computer readable media comprise, for example, a floppy disk, a flexible disk, a hard disk, magnetic tape, a laser disc, a Blu-ray Disc® of the Blu-ray Disc Association, any magnetic medium, a compact disc-read only memory (CD-ROM), a digital versatile disc (DVD), any optical medium, a flash memory card, punch cards, paper tape, any other physical medium with patterns of holes, a random access memory (RAM), a programmable read only memory (PROM), an erasable programmable read only memory (EPROM), an electrically erasable programmable read only memory (EEPROM), a flash memory, any other memory chip or cartridge, or any other medium from which a computer can read.

The computer programs that implement the methods and algorithms disclosed herein may be stored and transmitted using a variety of media, for example, the computer readable media in a number of manners. In an embodiment, hardwired circuitry or custom hardware may be used in place of, or in combination with, software instructions for implementation of the processes of various embodiments. Therefore, the embodiments are not limited to any specific combination of hardware and software. In general, the computer program codes comprising computer executable instructions may be implemented in any programming language. Examples of programming languages that can be used comprise C, C++, Visual C++, C#, Java®, JavaScript®, Fortran, Ruby, Perl®, Python®, Visual Basic®, hypertext preprocessor (PHP), Microsoft®.NET etc. Other object-oriented, functional, scripting, and/or logical programming languages may also be used. The computer program codes or software programs may be stored on or in one or more mediums as object code. Various aspects of the method and the system 2500 exemplarily illustrated in FIG. 25, disclosed herein may be implemented in a non-programmed environment comprising documents created, for example, in a hypertext markup language (HTML), an extensible markup language (XML), or other format that render aspects of the graphical diagnostic examination interface (GDEI) 2507 exemplarily illustrated in FIG. 25, or perform other functions, when viewed in a visual area or a window of a browser program. Various aspects of the method and the system 2500 disclosed herein may be implemented as programmed elements, or non-programmed elements, or any suitable combination thereof. The computer program product disclosed herein comprises one or more computer program codes for implementing the processes of various embodiments.

Where databases are described such as the databases 2510a exemplarily illustrated in FIG. 25, it will be understood by one of ordinary skill in the art that (i) alternative database structures to those described may be readily employed, and (ii) other memory structures besides databases may be readily employed. Any illustrations or descriptions of any sample databases disclosed herein are illustrative arrangements for stored representations of information. Any number of other arrangements may be employed besides those suggested by tables illustrated in the drawings or elsewhere. Similarly, any illustrated entries of the databases represent exemplary information only; one of ordinary skill in the art will understand that the number and content of the entries can be different from those disclosed herein. Further, despite any depiction of the databases as tables, other formats including relational databases, object-based models, and/or distributed databases may be used to store and manipulate the data types disclosed herein. Likewise, object methods or behaviors of a database can be used to implement various processes such as those disclosed herein. In addition, the databases may, in a known manner, be stored locally or remotely from a device that accesses data in such a database. In embodiments where there are multiple databases in the system 2500, the databases may be integrated to communicate with each other for enabling simultaneous updates of data linked across the databases, when there are any updates to the data in one of the databases.

The method and the system 2500 disclosed herein can be configured to work in a network environment comprising one or more computers that are in communication with one or more devices via the communication network 2509 exemplarily illustrated in FIG. 25. The computers may communicate with the devices directly or indirectly, via a wired medium or a wireless medium such as the Internet, a local area network (LAN), a wide area network (WAN) or the Ethernet, a token ring, or via any appropriate communications mediums or combination of communications mediums. Each of the devices comprises processors, examples of which are disclosed above, that are adapted to communicate with the computers. In an embodiment, each of the computers is equipped with a network communication device, for example, a network interface card, a modem, or other network connection device suitable for connecting to the communication network 2509. Each of the computers and the devices executes an operating system, examples of which are disclosed above. While the operating system may differ depending on the type of computer, the operating system provides the appropriate communications protocols to establish communication links with the communication network 2509. Any number and type of machines may be in communication with the computers.

The method and the system 2500 disclosed herein are not limited to a particular computer system platform, processor, operating system, or network. One or more aspects of the method and the system 2500 disclosed herein may be distributed among one or more computer systems, for example, servers configured to provide one or more services to one or more client computers, or to perform a complete task in a distributed system. For example, one or more aspects of the method and the system 2500 disclosed herein may be performed on a client-server system that comprises components distributed among one or more server systems that perform multiple functions according to various embodiments. These components comprise, for example, executable, intermediate, or interpreted code, which communicate over a communication network 2509 using a communication protocol. The method and the system 2500 disclosed herein are not limited to be executable on any particular system or group of systems, and is not limited to any particular distributed architecture, network, or communication protocol.

The foregoing examples have been provided merely for the purpose of explanation and are in no way to be construed as limiting of the method, the medical diagnostic examination system 2506 exemplarily illustrated in FIG. 25, and the multipurpose diagnostic examination apparatus 100 exemplarily illustrated in FIGS. 1A-14M, disclosed herein. While the method, the medical diagnostic examination system 2506, and the multipurpose diagnostic examination apparatus 100 have been described with reference to various embodiments, it is understood that the words, which have been used herein, are words of description and illustration, rather than words of limitation. Further, although the method, the medical diagnostic examination system 2506, and the multipurpose diagnostic examination apparatus 100 have been described herein with reference to particular means, materials, and embodiments, the method, the medical diagnostic examination system 2506, and the multipurpose diagnostic examination apparatus 100 are not intended to be limited to the particulars disclosed herein; rather, the method, the medical diagnostic examination system 2506, and the multipurpose diagnostic examination apparatus 100 extend to all functionally equivalent structures, methods and uses, such as are within the scope of the appended claims. Those skilled in the art, having the benefit of the teachings of this specification, may effect numerous modifications thereto and changes may be made without departing from the scope and spirit of the method, the medical diagnostic examination system 2506, and the multipurpose diagnostic examination apparatus 100 disclosed herein in their aspects.

We claim:

1. A hand-held multipurpose diagnostic examination apparatus, comprising:
    a diagnosis control unit configured to communicate with a medical diagnostic examination system, wherein said medical diagnostic examination system is configured as a software application on a local user device, wherein said medical diagnostic examination system is accessible to said multipurpose diagnostic examination apparatus via a connector interface configured at a rear section of said diagnosis control unit of said multipurpose diagnostic examination apparatus, wherein said diagnosis control unit comprises a custom-built printed circuit board with a microcontroller, in operable communication with a plurality of trigger elements positioned on a predefined section of said diagnosis control unit, and wherein said diagnosis control unit of said hand-held multipurpose diagnostic examination apparatus is a custom-built unit;
    an attachment unit mounted to a connector slot configured at a front end of said diagnosis control unit, wherein said attachment unit comprises a receptacle, wherein an image capture device is mounted to a camera module positioned at a front section of said diagnosis control unit and supported within said receptacle of said attachment unit, wherein length of said attachment unit is configured based on a focal length of an optical lens of said image capture device and an anatomical examination area, and wherein said attachment unit is configured to mount one of a plurality of medical diagnostic devices interchangeably to said diagnosis control unit;
    said microcontroller of said diagnosis control unit configured to detect said image capture device and type of said one of said medical diagnostic devices mounted on said diagnosis control unit;
    said microcontroller of said diagnosis control unit further configured to receive actuation signals from one or more of said trigger elements positioned on a predefined section of said diagnosis control unit;
    said microcontroller of said diagnosis control unit further configured to process said received actuation signals to generate action control signals, wherein said action control signals are configured to indicate one or more actions to be performed by said image capture device and said one of said medical diagnostic devices;
    said camera module of said diagnosis control unit configured to process diagnostic image data captured by said image capture device; and
    said microcontroller of said diagnosis control unit further configured to facilitate transmission of said processed diagnostic image data from said camera module and diagnostic examination data of a plurality of formats from said one of said medical diagnostic devices to said medical diagnostic examination system, wherein said connector interface is in communication with said camera module and said one of said medical diagnostic devices via said attachment unit to receive and transmit said processed diagnostic image data and said diagnostic examination data to said medical diagnostic examination system, and wherein said medical diagnostic examination system on said local user device is in communication with a remote user device over a fiber network to facilitate remote viewing, remote selection, and said remote diagnostic examinations of a plurality of anatomical examination areas of a patient via said fiber network.

2. The hand-held multipurpose diagnostic examination apparatus of claim 1, wherein said microcontroller of said diagnosis control unit is further configured to transmit diagnostic data management signals to said medical diagnostic examination system accessible on said local user device via said connector interface of said diagnosis control unit for managing said processed diagnostic image data and said diagnostic examination data.

3. The hand-held multipurpose diagnostic examination apparatus of claim 1, wherein said actuation signals are generated by one of an activation of said one or more of said trigger elements at a same time and an activation of said one or more of said trigger elements in series.

4. The hand-held multipurpose diagnostic examination apparatus of claim 1, wherein said connector interface of said diagnosis control unit is configured to allow electronic communication between the multipurpose diagnostic examination apparatus and said medical diagnostic examination system accessible on said local user device for said medical imaging and said diagnostic examinations, wherein said connector interface comprises at least two connector elements, wherein a first of said at least two connector elements is configured to allow communication of said processed diagnostic image data from said camera module and said diagnostic examination data from said one of said medical diagnostic devices to said medical diagnostic examination system, and wherein a second of said at least two connector elements is configured to allow a serial data communication between said microcontroller of said diagnosis control unit and said medical diagnostic examination system for controlling operations of one or more of said image capture device and said one of said medical diagnostic devices for said medical imaging and said diagnostic examinations.

5. The hand-held multipurpose diagnostic examination apparatus of claim 1, wherein said connector interface of said diagnosis control unit is selected from the group consisting of a universal serial bus 3.0 connector interface, a hardware connector interface, and combinations thereof.

6. The hand-held multipurpose diagnostic examination apparatus of claim 1, wherein said connector interface of said diagnosis control unit is a universal serial bus 3.0 connector interface configured to allow uncompressed, high speed, and high quality serial data communication between said diagnosis control unit and said medical diagnostic examination system.

7. The hand-held multipurpose diagnostic examination apparatus of claim 1, wherein said microcontroller is further configured to generate and transmit action control signals to one or more of a plurality of light sources operably connected to one or more of a front section of said attachment unit, a predefined section along a length of said attachment unit, and an upper section of said diagnosis control unit, for illuminating and indicating one or more of said anatomical examination areas of said patient during said medical imaging and said remote diagnostic examinations, and wherein said illuminated and indicated one or more of said anatomical examination areas of said patient are viewed and selected remotely on said remote user device via said fiber network for said remote diagnostic examinations.

8. The hand-held multipurpose diagnostic examination apparatus of claim 1, further comprising spring contact connectors positioned on a rear section of said attachment unit, wherein said spring contact connectors are configured to allow electrical communication of light sources operably connected to one of a front section of said attachment unit and a predefined section along a length of said attachment unit, and said one of said medical diagnostic devices operably connected to said attachment unit, with said microcontroller of said diagnosis control unit.

9. The hand-held multipurpose diagnostic examination apparatus of claim 1, wherein said connector slot of said diagnosis control unit comprises connector pads configured to engage with spring contact connectors positioned on a rear section of said attachment unit to allow electrical communication of one or more of: one of a plurality of light sources operably connected to one of a front section of said attachment unit and a predefined section along a length of said attachment unit, and said one of said medical diagnostic devices operably connected to said attachment unit, with said microcontroller of said diagnosis control unit.

10. The hand-held multipurpose diagnostic examination apparatus of claim 1, wherein said one of said medical diagnostic devices is a stethoscope device, and wherein said microcontroller of said diagnosis control unit is further configured to transmit said generated action control signals to a digital signal processor of said stethoscope device for actuating said stethoscope device to perform said one or more actions indicated by said generated action control signals.

11. The hand-held multipurpose diagnostic examination apparatus of claim 1, wherein said one of said medical diagnostic devices is a stethoscope device comprising one or more microphones, and wherein said microcontroller of said diagnosis control unit is further configured to transmit said generated action control signals to a digital signal processor of said stethoscope device for actuating said one or more microphones to receive diagnostic acoustic data from one or more of said anatomical examination areas of said patient.

12. The hand-held multipurpose diagnostic examination apparatus of claim 1, wherein said one of said medical diagnostic devices is a stethoscope device comprising a touchscreen, and wherein said microcontroller of said diagnosis control unit is further configured to transmit said generated action control signals to a digital signal processor of said stethoscope device for actuating said touchscreen to display information associated with one or more of diagnostic acoustic data received by said stethoscope device, a connection status of said stethoscope device to said diagnosis control unit, and an activation status of said stethoscope device.

13. The hand-held multipurpose diagnostic examination apparatus of claim 1, wherein said one of said medical diagnostic devices is a stethoscope device comprising a real time clock, and wherein said microcontroller of said diagnosis control unit is further configured to transmit said generated action control signals to a digital signal processor of said stethoscope device for actuating said real time clock to control recording of diagnostic acoustic data by said stethoscope device for a predefined time period.

14. The hand-held multipurpose diagnostic examination apparatus of claim 1, wherein said one of said medical diagnostic devices is an ultrasound device, and wherein said microcontroller of said diagnosis control unit is further configured to transmit said generated action control signals to an ultrasound processor of said ultrasound device for actuating said ultrasound device to perform said one or more actions indicated by said generated action control signals.

15. The hand-held multipurpose diagnostic examination apparatus of claim 1, wherein said one of said medical diagnostic devices is an ultrasound device comprising one of a plurality of interchangeable ultrasound probes operably connected to said attachment unit, and wherein said microcontroller of said diagnosis control unit is further configured to transmit said generated action control signals to an ultrasound processor of said ultrasound device for actuating said one of said interchangeable ultrasound probes of said ultrasound device to detect and receive ultrasonic sounds from one or more of said anatomical examination areas of said patient for said diagnostic examinations.

16. The hand-held multipurpose diagnostic examination apparatus of claim 1, further comprising a supplementary attachment slot positioned on a lower section of said attachment unit, wherein said supplementary attachment slot is configured to interchangeably accommodate a diagnosis assistance element for facilitating said diagnostic examinations, and wherein said diagnosis assistance element is a tongue depressor of a predefined length.

17. The hand-held multipurpose diagnostic examination apparatus of claim 1, wherein said one or more actions to be performed by said image capture device and said one of said medical diagnostic devices comprise one or more of power control of said image capture device and said medical diagnostic devices, power control of one or more of a plurality of light sources operably connected to one of a front section of said attachment unit, a predefined section along a length of said attachment unit, and an upper section of said diagnosis control unit, said capture of said diagnostic image data by said image capture device, recording of said diagnostic examination data by said one of said medical diagnostic devices, wherein said diagnostic examination data comprises audio data, video data, image data, and any combination thereof, recording of said diagnostic image data and said diagnostic examination data for a predefined time period, managing storage of said diagnostic image data and said diagnostic examination data, managing deletion of said stored diagnostic image data and said stored diagnostic examination data, light generation and brightness control by said one or more of said light sources, image scaling by said image capture device, audio volume control, creation of audio files in a plurality of audio file formats, and any combination thereof.

18. The hand-held multipurpose diagnostic examination apparatus of claim 1, wherein said medical diagnostic devices comprise a stethoscope device, an ultrasound device, an otoscope device, an ophthalmoscope device, a dermatoscope device, an endoscope device, and any combination thereof.

19. The hand-held multipurpose diagnostic examination apparatus of claim 1, wherein said diagnostic image data and said diagnostic examination data from one of said image capture device and said local user device are configured to be uploaded to and stored on one or more servers comprising a dedicated server and a server in a cloud computing environment, and wherein said one or more servers are health insurance portability and accountability act compliant servers.

* * * * *